United States Patent
Devasthale et al.

(10) Patent No.: US 9,974,778 B2
(45) Date of Patent: May 22, 2018

(54) SUBSTITUTED PYRIDINONES AS MGAT2 INHIBITORS

(71) Applicant: BRISTOL-MYERS SQUIBB COMPANY, Princeton, NJ (US)

(72) Inventors: Pratik Devasthale, Plainsboro, NJ (US); Fang Moore, Bensalem, PA (US); James Mignone, Hamilton, NJ (US); Wei Wang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days. days.

(21) Appl. No.: 15/316,853

(22) PCT Filed: Jun. 10, 2015

(86) PCT No.: PCT/US2015/035054
§ 371 (c)(1),
(2) Date: Dec. 7, 2016

(87) PCT Pub. No.: WO2015/191681
PCT Pub. Date: Dec. 17, 2015

(65) Prior Publication Data
US 2017/0114054 A1   Apr. 27, 2017

Related U.S. Application Data

(60) Provisional application No. 62/010,685, filed on Jun. 11, 2014.

(51) Int. Cl.
| | | |
|---|---|---|
| *A61K 31/4418* | (2006.01) | |
| *C07D 417/04* | (2006.01) | |
| *C07D 417/14* | (2006.01) | |
| *C07D 409/14* | (2006.01) | |
| *C07D 213/82* | (2006.01) | |
| *C07D 413/04* | (2006.01) | |
| *A61K 31/4439* | (2006.01) | |
| *C07D 401/04* | (2006.01) | |
| *C07D 213/80* | (2006.01) | |
| *C07D 409/04* | (2006.01) | |
| *C07D 401/12* | (2006.01) | |
| *A61K 31/444* | (2006.01) | |
| *C07D 401/14* | (2006.01) | |
| *C07D 413/12* | (2006.01) | |
| *A61K 45/06* | (2006.01) | |
| *C07D 213/74* | (2006.01) | |
| *C07D 405/04* | (2006.01) | |
| *A61K 31/4412* | (2006.01) | |

(52) U.S. Cl.
CPC ........ *A61K 31/4418* (2013.01); *A61K 31/444* (2013.01); *A61K 31/4412* (2013.01); *A61K 31/4439* (2013.01); *A61K 45/06* (2013.01); *C07D 213/74* (2013.01); *C07D 213/80* (2013.01); *C07D 213/82* (2013.01); *C07D 401/04* (2013.01); *C07D 401/12* (2013.01); *C07D 401/14* (2013.01); *C07D 405/04* (2013.01); *C07D 409/04* (2013.01); *C07D 409/14* (2013.01); *C07D 413/04* (2013.01); *C07D 413/12* (2013.01); *C07D 417/04* (2013.01); *C07D 417/14* (2013.01)

(58) Field of Classification Search
CPC ............ A61K 31/4418; A61K 31/4439; A61K 31/444; A61K 31/4412; C07D 417/04
USPC ........................................................ 514/335
See application file for complete search history.

(56) References Cited

U.S. PATENT DOCUMENTS

| | | |
|---|---|---|
| 5,614,492 A | 3/1997 | Habener |
| 8,791,091 B2 | 7/2014 | Turdi et al. |
| 9,187,424 B1 | 11/2015 | Turdi et al. |
| 9,365,558 B2 | 6/2016 | Ahmad et al. |
| 9,663,466 B2 | 5/2017 | Turdi et al. |
| 9,688,656 B2 | 6/2017 | Ahmad |
| 9,701,672 B2 | 7/2017 | Meng et al. |
| 2016/0256445 A1 | 9/2016 | Ahmad et al. |

(Continued)

FOREIGN PATENT DOCUMENTS

| | | | |
|---|---|---|---|
| WO | WO2013/082345 A1 | 6/2013 | |
| WO | WO 2013082345 A1 * | 6/2013 | ........... A61K 31/675 |

(Continued)

OTHER PUBLICATIONS

Krohnke et al, Chem. Ber. (1970), vol. 103, pp. 322-324.*
Arbeeny, C. et al., "The Metabolic Syndrome: From Pathophysiology to Novel Treatment Strategies", Current Med. Chem.—Imm., Endoc. & Metab. Agents, vol. 1, pp. 1-24 (2001).
Elangbam, C.S., "Review Paper: Current Strategies in the development of Anti-obesity Drugs and Their Safety Concerns", Vet. Pathol., vol. 46, pp. 10-24 (2009).
Ford, E. et al., "Prevalence of the Metabolic Syndrome Among US Adults",JAMA, vol. 287(3), pp. 356-359 (2002).
Fyfe, M.C. T. et al., "Glucokinase Activators as Potential Antidiabetic Agents Possessing Superior Glucose-Lowering Efficacy", Drugs of the Future, vol. 34(8), pp. 641-653 (2009).

(Continued)

Primary Examiner — Craig D Ricci
Assistant Examiner — Janet L. Coppins
(74) Attorney, Agent, or Firm — Jing G. Sun

(57) ABSTRACT

The present invention provides compounds of Formula (I): or a stereoisomer, a tautomer, a pharmaceutically acceptable salt, a polymorph, or a solvate thereof, wherein all of the variables are as defined herein. These compounds are monoacylglycerol acyltransferase type 2 (MGAT2) inhibitors which may be used as medicaments.

(I)

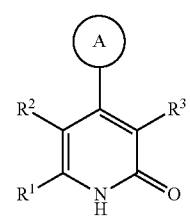

16 Claims, No Drawings

(56) References Cited

U.S. PATENT DOCUMENTS

| | | |
|---|---|---|
| 2017/0015648 A1 | 1/2017 | Ahmad |
| 2017/0015653 A1 | 1/2017 | Meng et al. |

FOREIGN PATENT DOCUMENTS

| | | | |
|---|---|---|---|
| WO | WO2014/193884 A1 | 12/2014 | |
| WO | WO-2014193884 A1 * | 12/2014 | ........... C07D 417/04 |
| WO | WO2015/134699 A1 | 9/2015 | |
| WO | WO2015/134701 A1 | 9/2015 | |

OTHER PUBLICATIONS

Jones, Dan., "Novel pharmacotherapies for obesity poised to enter market", Nature Reviews/Drug Discovery, vol. 8, pp. 833-834.
Melnikova, Irena et al., "Anti-obesity therapies", Nature Review/Drug Discovery, vol. 5, pp. 369-370 (2006).
Mizuno, Cassia et al., "Type 2 Diabetes and Oral Antihyperglycemic Drugs", Current Medicinal Chemistry, vol. 15, pp. 61-74 (2008).
Mohler, Michael et al., "Recent and Emerging Anti-Diabetes Targets", Medicinal Research Reviews, vol. 29(1), pp. 125-195 (2009).
Obici, Silvana, "Minireview: Molecular Targets for Obesity Therapy in the Brain", Endocrinology, vol. 150(6), pp. 2512-2517 (2009).
Okawa, M. et al., "Role of GMAT2 and DGAT1 in the release of gut peptides after triglyceride ingestion", Biochemical and Biophysical Research Communications, vol. 390, pp. 377-381 (2009).
Yen, Chi-Liang Eric et al., "Deficiency of the intestinal enzyme acyl CoA: monoacylglycerol acyltransferase-2 protects mice from metabolic disorders induced by high0fat feeding", Nature Medicine< vol. 15(4), pp. 442-446 (2009).
Zhong, Yong-Li et al., "Practical and efficient synthesis of N-halo compounds", Tetrahedron Letters, vol. 46, pp. 1099-1101 (2005).
U.S. Appl. No. 15/488,642, filed Apr. 17, 2017, Turdi et al.
U.S. Appl. No. 15/602,515, filed May 23, 2017, Ahmad.
U.S. Appl. No. 15/617,079, filed Jun. 8, 2017, Meng et al.
U.S. Appl. No. 15/618,182, filed Jun. 9, 2017, Ahmad et al.
Abdalla, M. et al., "Synthesis and Reaction of 3-CYANO 2-(1H)-Pyridones", Pakistan J. Scientific and Industrial Research, vol. 20(3), pp. 139-149 (1977).
Ammar, Y.A. et al., "Cyanoacetanilides Intermediates in Heterocyclic Synthesis. Part 1: A Facile Synthesis of Polysubstituted and Condensed Pyridones", J. of the Chinese Chemical Society, vol. 51, pp. 975-981 (2004).
El-Deek, et al., "Studies on pyridines. I. Synthesis and reactions of 3-acetyl-(3,4-dichlorophenyl)-2-(1H)pyridines", Revue Roumaine de chimie, vol. 26(4), pp. 647-653 (1981).
El-Nagdy, et al., "Studies on the condensation of 1,3-diarylpropen-1-one with ethyl cyanoacetate", Revue Roumaine de chimie, vol. 34(9-10), pp. 1979-1985 (1989).
Kohler, E.P. et al., "Some Delta Ketonic Nitriles and Their Relation to cyclic compounds", J. of the American Chemical Society, vol. 44, pp. 2536-2556 (1922).
Li, Weiwei et al., "A facile solid-phase synthesis of 3,4,6-trisubstituted-2-pyridones using sodium benzenesulfinate as a traceless linker", Tetrahedron Letters, vol. 45, pp. 6545-6547 (2004).
Plati, John T. et al., "Aromatization of N-Substituted Piperidine compounds", J. of Organic Chemistry, vol. 15, pp. 1165-1171 (1950).
Ried, et al., "The use of cyanoacetic acid hydrazide for the preparation of nitrogen heterocyclics. I. A simple synthesis of N-amino-α-pyridinones", Chemische Berichte, vol. 90, pp. 2841-2848 (1957).
Sammour, et al., "Reactions with 3-cyano- and 3-acetyl-2(H)-pyridones", United Arab Republic J. of Chemistry, vol. 14(3), pp. 213-223 (1971).
Stockel, Richard F., "Isomeric diketopiperazines", Textile Research Journal, vol. 14(5), pp. 433-434 (1875).
CAS Registry No. 1226405-63-5 (May 30, 2010).
CAS Registry No. 1226342-42-2 (May 30, 2010).
CAS Registry No. 1226336-88-4 (May 30, 2010).
CAS Registry No. 1226298-41-4 (May 30, 2010).
CAS Registry No. 1226283-66-4 (May 30, 2010).
CAS Registry No. 1226227-38-8 (May 30, 2010).
CAS Registry No. 1226199-62-7 (May 30, 2010).
CAS Registry No. 1226197-38-1 (May 30, 2010).
CAS Registry No. 1226172-69-5 (May 30, 2010).
CAS Registry No. 1226168-42-8 (May 30, 2010).
CAS Registry No. 1226123-09-6 (May 30, 2010).
CAS Registry No. 1226063-92-8 (May 30, 2010).
CAS Registry No. 1226056-56-9 (May 30, 2010).
CAS Registry No. 1225963-28-9 (May 30, 2010).
CAS Registry No. 1225924-10-6 (May 30, 2010).
CAS Registry No. 1225826-75-4 (May 30, 2010).
CAS Registry No. 1225820-32-5 (May 30, 2010).
CAS Registry No. 1225801-72-8 (May 30, 2010).
CAS Registry No. 1225720-87-5 (May 30, 2010).
CAS Registry No. 1225714-02-2 (May 30, 2010).
CAS Registry No. 1225579-25-8 (May 28, 2010).
CAS Registry No. 1225556-82-0 (May 28, 2010).
CAS Registry No. 1225548-36-6 (May 28, 2010).
CAS Registry No. 1225548-32-2 (May 28, 2010).
CAS Registry No. 1225511-30-7 (May 28, 2010).
CAS Registry No. 1225490-76-5 (May 28, 2010).
CAS Registry No. 846597-27-1 (Mar. 22, 2005).
CAS Registry Report, 9 pages, Compounds 1-27.
Kroehnke, F. et al., "Pyridone synthesis by the J. Thesing method", Chemische Berichte, vol. 103(1), pp. 322-324 (1970).

* cited by examiner

SUBSTITUTED PYRIDINONES AS MGAT2 INHIBITORS

CROSS-REFERENCE TO RELATED APPLICATIONS

This application is a 371 of International Application No. PCT/US2015/035054 filed on Jun. 10, 2015, which claims priority benefit of U.S. Provisional Application Ser. No. 62/010,685, filed Jun. 11, 2014, each of which is fully incorporated herein by reference.

FIELD OF THE INVENTION

The present invention provides novel substituted pyridinone compounds, and their analogues thereof, which are MGAT2 inhibitors, compositions containing them, and methods of using them, for example, for the treatment of diabetes, obesity, dyslipidemia and related conditions.

BACKGROUND OF THE INVENTION

The prevalence of obesity and diabetes is increasing at an alarming rate. According to WHO, in 2008, 70% of the U.S. adult population was overweight, and among them 33% were obese. Parallel to the explosive number of people becoming overweight and obese, in 2008, it was estimated that 12.3% of the U.S. population had elevated blood glucose [http://www.who.int/diabetes/facts/en/]. The obesity/diabetes epidemic is not unique to the U.S. According to WHO (Fact Sheet No. 312, September 2012), 347 million people worldwide have diabetes. Treating obesity and improving glycemic control effectively and safely remain major challenges for modern medicine.

Monoacylglycerol acyltransferase 2 (MGAT2) has emerged as an attractive target for the treatment of obesity and type II diabetes [Yen, C. L. et al., *Nat. Med.*, 15(4):442-446 (2009)]. MGAT2 is highly and selectively expressed in the small intestine where it exerts a pivotal role in the monoacylglycerol-pathway for the absorption of dietary fat. When dietary fat is ingested, pancreatic lipase digests triglycerides into free fatty acids and 2-monoacylglycerol, which are absorbed by intestinal epithelial enterocytes. Once inside enterocytes, free fatty acids and 2-monoacylglycerol are used as building blocks to resynthesize triglycerides by two sequential acylation steps; first by MGAT and then by DGAT enzyme reactions. Triglycerides are then incorporated into chylomicrons and secreted into lymph to be utilized as an energy supply for the body. MGAT2 knockout mice exhibit a healthy metabolic phenotype and show resistance to high-fat diet induced obesity, improvement in insulin sensitivity and decreased fat accumulation in liver and adipose tissue. In addition, genetic deletion of MGAT2 produces mice with increased levels of GLP-1 [Yen, C. L. et al., *Nat. Med.*, 15(4):442-446 (2009)]. Taken together, these data show that MGAT2 inhibitors hold promise to treat metabolic disorders such as obesity, type II diabetes and dyslipidemia.

SUMMARY OF THE INVENTION

The present invention provides substituted pyridinone compounds, and their analogues thereof, which are useful as MGAT2 inhibitors, including stereoisomers, tautomers, pharmaceutically acceptable salts, polymorphs, or solvates thereof.

The present invention also provides processes and intermediates for making the compounds of the present invention or stereoisomers, tautomers, pharmaceutically acceptable salts, polymorphs, or solvates thereof.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The compounds of the invention may be used in the treatment of multiple diseases or disorders associated with MGAT2, such as diabetes, obesity, dyslipidemia and related conditions, such as microvascular and macrovascular complications associated with diabetes, cardiovascular diseases, Metabolic Syndrome and its component conditions, disorders of glucose and lipid metabolism and other maladies.

The compounds of the invention may be used in therapy.

The compounds of the invention may be used for the manufacture of a medicament for the treatment of multiple diseases or disorders associated with MGAT2.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

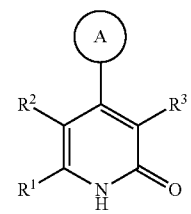

or a stereoisomer, a tautomer, a pharmaceutically acceptable salt, a polymorph, or a solvate thereof, wherein:

ring A is independently phenyl, tetrahydronaphthalenyl, or a 5- to 10-membered heteroaryl comprising carbon atoms and 1-4 heteroatoms selected from N, $NR^e$, O and S; wherein said phenyl, tetrahydronaphthalenyl, and heteroaryl are substituted with 0-1 $R^6$ and 0-3 $R^7$;

$R^1$ is independently selected from: $-(CH_2)_m-C_{3-6}$ carbocycle substituted with 0-2 $R^b$ and 0-2 $R^g$), $-(CH_2)_m$-(5- to 6-membered heteroaryl comprising carbon atoms and 1-4 heteroatoms selected from N, $NR^e$, O and S; wherein said heteroaryl is substituted with 0-1 $R^b$ and 0-2 $R^g$), and a $C_{1-12}$ hydrocarbon chain substituted with 0-3 $R^a$; wherein said hydrocarbon chain may be straight or branched, saturated or unsaturated;

R² is independently selected from: H, halogen, $C_{3-4}$ cycloalkyl, phenyl substituted with 0-2 $R^h$, and $C_{1-12}$ hydrocarbon chain substituted with 0-3 $R^a$; wherein said hydrocarbon chain may be straight or branched, saturated or unsaturated;

R³ is independently selected from: H, $CO_2H$, —$(CH_2)_n$—X—$(CH_2)_mR^4$, —$CONHSO_2R^i$, —$NHCOX_1SO_2R^i$, a 5- to 6-membered heterocycle comprising carbon atoms and 1-4 heteroatoms selected from N, $NR^e$, O, and S; wherein said heterocycle is substituted with 0-2 $R^d$;

X is independently selected from: CONH and NHCO;

$X_1$ is independently $C_{1-4}$ hydrocarbon chain optionally substituted with $C_{1-4}$ alkyl or $C_{3-4}$ cycloalkyl;

R⁴ is independently selected from: $C_{3-6}$ cycloalkyl substituted with 0-2 $R^d$, $C_{3-6}$ cycloalkenyl substituted with 0-2 $R^d$, —$(CH_2)_m$-(phenyl substituted with 0-3 $R^d$), and a 5- to 6-membered heterocycle comprising carbon atoms and 1-4 heteroatoms selected from N, $NR^e$, O, and S; wherein said heterocycle is substituted with 0-2 $R^d$;

R⁶ is independently selected from: halogen, $C_{1-6}$ alkyl substituted with 0-2 $R^h$, $C_{1-4}$ alkoxy, $C_{1-4}$ haloalkyl, $C_{1-4}$ haloalkoxy, —$(CH_2)_m$—$C_{3-6}$ cycloalkyl, —$(CH_2)_m$—$NR^fR^i$, CN, $OR^i$, $SR^i$, and a 4- to 6-membered heterocycle comprising carbon atoms and 1-4 heteroatoms selected from N, $NR^e$, O, and S;

R⁷ is independently selected from: halogen, $C_{1-4}$ alkyl, $C_{1-4}$ alkoxy, $C_{1-4}$ haloalkyl, and $C_{1-4}$ haloalkoxy;

$R^a$ is, at each occurrence, independently selected from: halogen, OH, $C_{1-6}$ alkoxy, $C_{1-6}$ haloalkyl, $C_{1-6}$ haloalkoxy, $N(C_{1-4}$ alkyl$)_2$, and —$(CH_2)N$—$(X)_t$—$R^c$;

$R^b$ is, at each occurrence, independently selected from: halogen, OH, $C_{1-10}$ alkyl, $C_{2-8}$ alkenyl, $C_{1-10}$alkoxy, $C_{1-10}$ haloalkyl, $C_{1-10}$ haloalkoxy, $C_{1-10}$ alkylthio, $C_{1-10}$ haloalkylthio, $N(C_{1-4}$ alkyl$)_2$, —$CONH(C_{4-20}$ alkyl$)$, —$CONH(C_{4-20}$ haloalkyl$)$, —$O(CH_2)_sO(C_{1-6}$ alkyl$)$, —$O(CH_2)_sO(C_{1-6}$ haloalkyl$)$, —(CH=CH)($C_{3-6}$ cycloalkyl), $R^c$, and —$(CH_2)_n$—$(O)_t$—$(CH_2)_mR^c$;

$R^c$ is, at each occurrence, independently selected from: $C_{3-6}$ cycloalkyl substituted with 0-2 $R^d$, $C_{4-8}$ cycloalkenyl substituted with 0-2 $R^d$, phenyl substituted with 0-3 $R^d$, and a 5- to 6-membered heterocycle comprising carbon atoms and 1-4 heteroatoms selected from N, $NR^e$, O, and S; wherein said heterocycle is substituted with 0-2 $R^d$;

$R^d$ is, at each occurrence, independently selected from: =O, halogen, OH, CN, $NO_2$, $C_{1-4}$ alkyl, $C_{1-4}$ alkoxy, $C_{1-4}$ haloalkyl, $C_{1-4}$ haloalkoxy, tetrazolyl, OBn and phenyl;

$R^e$ is, at each occurrence, independently selected from: H, $C_{1-8}$ alkyl, $C_{1-8}$ haloalkyl, —$(CH_2)_n$—$C_{3-6}$ carbocycle, $CO(C_{1-4}$ alkyl$)$ and COBn;

$R^f$ is, at each occurrence, independently selected from: H and $C_{1-4}$ alkyl;

$R^g$ is independently selected from: halogen, OH, $C_{1-4}$ alkyl, $C_{1-4}$ alkoxy, $C_{1-4}$ haloalkyl, and $C_{1-4}$ haloalkoxy;

$R^h$ is independently selected from: halogen, $C_{1-4}$ alkoxy, $C_{1-4}$ haloalkoxy, and $C_{1-12}$ hydrocarbon chain substituted with 0-3 $R^a$; wherein said hydrocarbon chain may be straight or branched, saturated or unsaturated;

$R^i$ is, at each occurrence, independently selected from: $C_{1-4}$ alkyl, $C_{3-4}$ cycloalkyl and phenyl;

n, at each occurrence, is independently 0 or 1;
m, at each occurrence, is independently 0, 1, 2, 3, or 4;
s, at each occurrence, is independently 1, 2, or 3; and
t, at each occurrence, is independently 0 or 1;

provided that:
i) when R¹ is methyl, phenyl, 4-halo-Ph, or 3,4-diCl-Ph, then R³ is other than $CO_2H$;
ii) when ring A is phenyl, then R¹ is other than thienyl; or
iii) when ring A is phenyl or 4-OMe-Ph, then R¹ is other than phenyl or 4-Me-Ph;

and the following compounds are excluded:

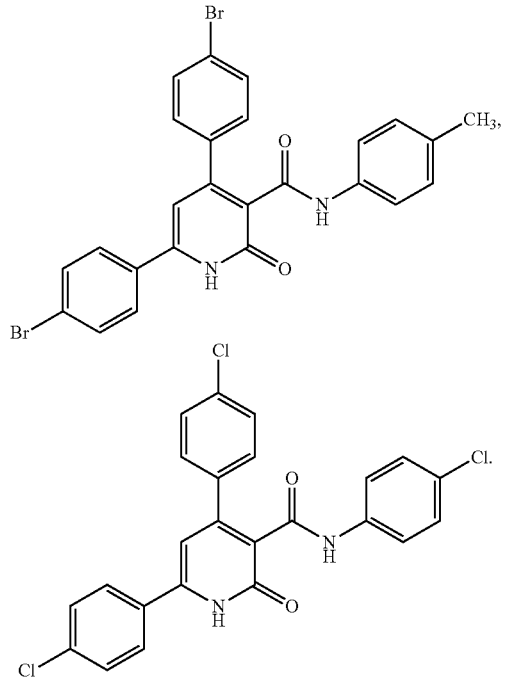

In a second aspect, the present invention includes a compound of Formula (I), or a stereoisomer, a tautomer, a pharmaceutically acceptable salt, a polymorph, or a solvate thereof, within the scope of the first aspect, wherein:

R¹ is independently selected from: —$(CH_2)_m$—$(C_{3-6}$ carbocycle substituted with 1 $R^b$ and 0-2 $R^g$), —$(CH_2)_m$-heteroaryl substituted with 0-1 $R^b$ and 0-1 $R^g$, wherein said heteroaryl is selected from: pyridyl, furanyl, thienyl, 1-$R^e$-pyrrolyl, oxazolyl, thiazolyl, and 1-$R^e$-pyrazolyl), and a $C_{1-12}$ hydrocarbon chain substituted with 0-1 $R^a$; wherein said hydrocarbon chain may be straight or branched, saturated or unsaturated).

In a third aspect, the present invention includes a compound of Formula (I) or a stereoisomer, a tautomer, a pharmaceutically acceptable salt, a polymorph, or a solvate thereof, within the scope of any of the above aspects, wherein:

ring A is independently tetrahydronaphthalenyl, phenyl substituted with 0-1 $R^6$ and 0-1 $R^7$, or a heteroaryl substituted with 0-1 $R^6$; wherein said heteroaryl is selected from: furanyl, thienyl, 1-$R^e$-pyrrolyl, thiazolyl, 1-$R^e$-pyrazolyl, and benzothienyl;

R¹ is independently selected from: $C_{3-6}$ cycloalkyl substituted 0-1 $R^g$, $C_{5-6}$ cycloalkenyl substituted 0-1 $R^g$, phenyl substituted with 1 $R^b$ and 0-1 $R^g$, and a heteroaryl substituted with 0-1 $R^b$ and 0-1 $R^g$, wherein said heteroaryl is selected from: oxazolyl, thiazolyl, and 1-$R^e$-pyrazolyl;

R² is independently selected from: H, halogen, $C_{1-4}$ alkyl, $C_{2-4}$ alkenyl, $C_{1-4}$ alkoxy, and phenyl substituted with 0-1 $C_{1-6}$ alkyl;

R³ is independently selected from: tetrazolyl, tetrazolone, —NHCO(tetrazolyl), —CONH(pyridyl), —$CONH(C_{3-6}$ cycloalkyl), —CONH(phenyl substituted with 0-1 $R^d$), —$CONHSO_2(C_{1-4}$ alkyl), —$CONHSO_2(C_{3-6}$ cycloalkyl), —CONHSO$_2$ (isoxazolyl substituted with 0-1 C$_{1-4}$ alkyl), and —CONHSO$_2$N(C$_{1-4}$ alkyl)$_2$;

R$^6$ is independently selected from: C$_{1-4}$ alkyl, C$_{1-4}$ alkoxy, C$_{1-4}$ haloalkoxy, N(C$_{1-4}$ alkyl)$_2$, and —(CH$_2$)$_{1-4}$(C$_{3-6}$ cycloalkyl);

R$^7$ is independently selected from: halogen and C$_{1-4}$ alkyl;

R$^b$ is independently selected from: C$_{1-6}$ alkyl, C$_{2-6}$ alkenyl, C$_{1-6}$ alkoxy, C$_{1-8}$ haloalkyl, C$_{1-8}$ haloalkoxy, —CONH(CH$_2$)$_{6-20}$H, C$_{3-6}$ cycloalkyl substituted with 0-2 C$_{1-4}$ alkyl, C$_{4-8}$ cycloalkenyl substituted with 0-2 C$_{1-4}$ alkyl, —(O)$_t$—(CH$_2$)$_m$(C$_{3-6}$ cycloalkyl), —(CH=CH)(C$_{3-6}$ cycloalkyl), Ph, Bn, phenoxy, benzoxy, pyrimidinyl, pyrazinyl and —O-pyrimidinyl;

R$^d$ is, at each occurrence, independently selected from: halogen, C$_{1-4}$ alkyl, C$_{1-4}$ alkoxy, C$_{1-4}$ haloalkyl, and C$_{1-4}$ haloalkoxy;

R$^e$ is independently selected from: H, C$_{1-6}$ alkyl, C$_{1-8}$ haloalkyl, and —(CH$_2$)$_n$—(C$_{3-6}$ cycloalkyl); and R$^g$ is independently selected from: halogen, OH, C$_{1-4}$ alkyl and C$_{1-4}$ alkoxy;

provided that: when ring A is phenyl or 4-OMe-Ph, then R$^1$ is other than phenyl or 4-Me-Ph; and the following compounds are excluded:

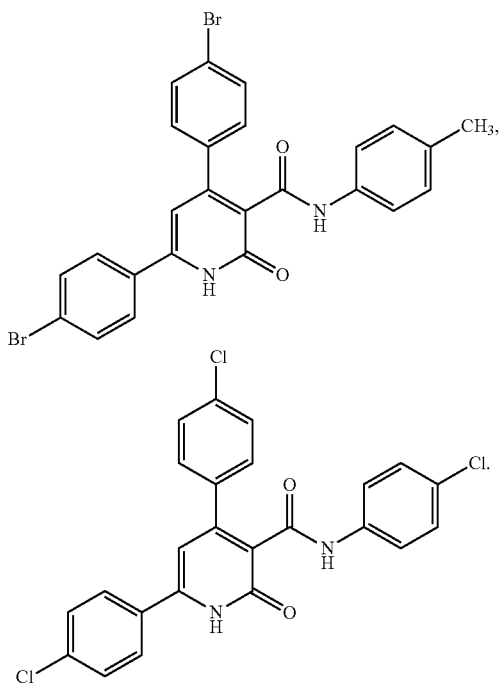

In a fourth aspect, the present invention includes a compound of Formula (I) or a stereoisomer, a tautomer, a pharmaceutically acceptable salt, a polymorph, or a solvate thereof, within the scope of any of the above aspects, wherein:

ring A is independently selected from: phenyl substituted with 0-1 R$^6$ and 0-1 R$^7$,

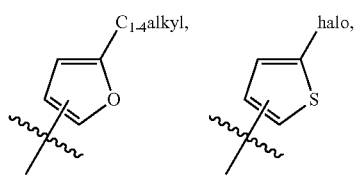
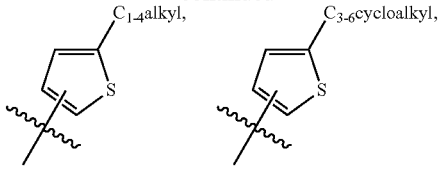
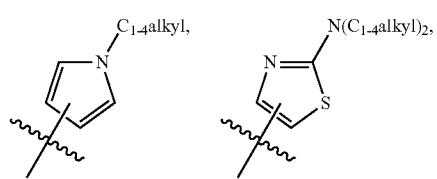
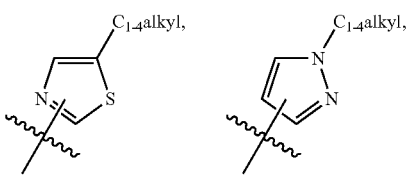
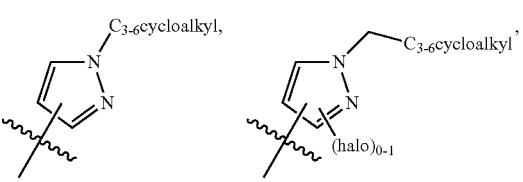
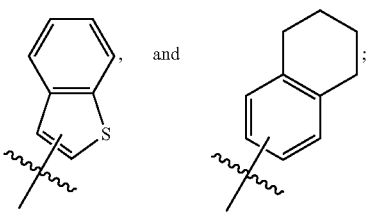

R$^1$ is independently selected from: C$_{3-6}$ cycloalkyl, C$_{5-6}$ cycloalkenyl, 1-halo-C$_{3-6}$ cycloalkyl, 1-OH—C$_{3-6}$ cycloalkyl, 4-R$^b$-Ph, 1-(—(CH$_2$)$_{1-6}$CF$_3$)-pyrazol-4-yl, 1-(—(CH$_2$)$_{1-6}$CF$_3$)-thiazol-2-yl, and 2-Ph-5-C$_{1-4}$ alkyl-oxazol-4-yl;

R$^2$ is independently selected from: H, halogen, C$_{1-4}$ alkyl, C$_{2-4}$ alkenyl, C$_{1-4}$ alkoxy, and phenyl substituted with 0-1 C$_{1-6}$ alkyl;

R$^3$ is independently selected from: tetrazolyl, tetrazolone, —NHCO(tetrazolyl), —CONH(C$_{3-6}$ cycloalkyl), —CONHPh, —CONH(4-C$_{1-4}$ alkoxy-Ph), —CONH(4-C$_{1-4}$ haloalkoxy-Ph), —CONH(pyrid-3-yl), —CONHSO$_2$(C$_{1-4}$ alkyl), —CONHSO$_2$(C$_{3-6}$ cycloalkyl), —CONHSO$_2$ (isoxazolyl substituted with 0-1 C$_{1-4}$ alkyl), and —CONHSO$_2$N(C$_{1-4}$ alkyl)$_2$;

R$^6$ is independently selected from: C$_{1-4}$ alkyl, C$_{1-4}$ alkoxy, C$_{1-4}$ haloalkoxy, N(C$_{1-4}$ alkyl)$_2$, and —(CH$_2$)$_{1-4}$(C$_{3-6}$ cycloalkyl);

R$^7$ is independently selected from: halogen and C$_{1-4}$ alkyl; and

R$^b$ is independently selected from: C$_{2-6}$ alkyl, C$_{2-6}$ alkenyl, —(CH$_2$)$_{1-6}$CF$_3$, —O(CH$_2$)$_{1-6}$CF$_3$, —(O)$_{0-1}$—

$-(CH_2)_{1-4}(C_{3-6}$ cycloalkyl), $-(CH=CH)(C_{3-6}$ cycloalkyl), $C_{3-6}$ cycloalkyl substituted with 0-2 $C_{1-4}$ alkyl, $C_{5-6}$ cycloalkenyl substituted with 0-2 $C_{1-4}$ alkyl, and Bn.

In a fifth aspect, the present invention includes a compound of Formula (I) or a stereoisomer, a tautomer, a pharmaceutically acceptable salt, a polymorph, or a solvate thereof, within the scope of any of the above first to third aspects, wherein:

ring A is independently phenyl substituted with 0-1 $R^6$ and 0-1 $R^7$;

$R^1$ is independently selected from: $C_{3-6}$ cycloalkyl substituted 0-1 $R^g$, $C_{5-6}$ cycloalkenyl substituted 0-1 $R^g$, phenyl substituted with 1 $R^b$ and 0-1 $R^g$, 1-($-(CH_2)_{1-6}CF_3$)-pyrazol-4-yl, 1-($-(CH_2)_{1-6}CF_3$)-thiazol-2-yl, and 2-Ph-5-$C_{1-4}$ alkyl-oxazol-4-yl;

$R^2$ is independently selected from: H, halogen, $C_{1-4}$ alkyl, $C_{2-4}$ alkenyl, $C_{1-4}$ alkoxy, and phenyl substituted with 0-1 $C_{1-6}$ alkyl;

$R^3$ is independently selected from: tetrazolyl, tetrazolone, $-CONH(pyridyl)$, and $-CONH(phenyl$ substituted with 0-1 $C_{1-4}$ alkoxy);

$R^6$ is independently selected from: $C_{1-4}$ alkyl, $N(C_{1-4}$ alkyl$)_2$, and $C_{3-6}$ cycloalkyl;

$R^7$ is independently selected from: halogen and $C_{1-4}$ alkyl;

$R^b$ is independently selected from: $C_{1-6}$ alkyl, $C_{2-6}$ alkenyl, $C_{1-6}$ alkoxy, $C_{1-8}$ haloalkyl, $C_{1-8}$ haloalkoxy, $-CONH(CH_2)_{6-20}H$, $C_{3-6}$ cycloalkyl, $C_{4-8}$ cycloalkenyl, $-O(CH_2)_m(C_{3-6}$ cycloalkyl), $-(CH=CH)(C_{3-6}$ cycloalkyl), Ph, Bn, phenoxy, and benzoxy; and $R^g$ is independently selected from: halogen, OH, $C_{1-4}$ alkyl and $C_{1-4}$ alkoxy;

provided that: when ring A is phenyl or 4-OMe-Ph, then $R^1$ is other than phenyl or 4-Me-Ph;

and the following compounds are excluded:

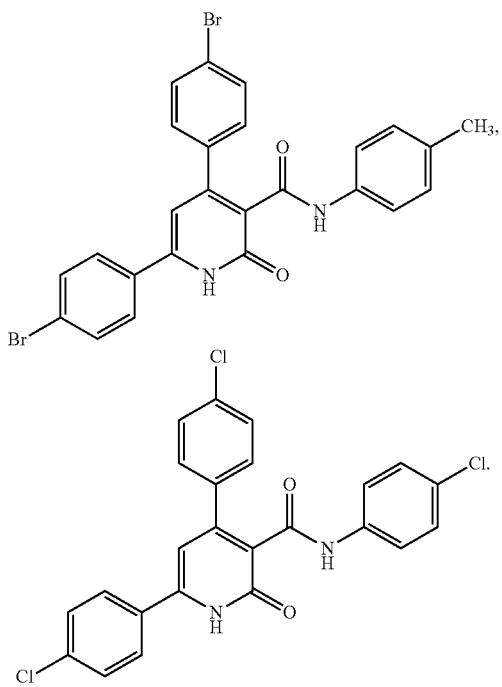

In a sixth aspect, the present invention includes a compound of Formula (I), or a stereoisomer, a tautomer, a pharmaceutically acceptable salt, a polymorph, a solvate or a hydrate thereof, within the scope of any of the above aspects, wherein:

$R^1$ is

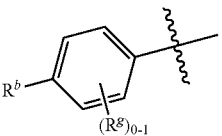

In a seventh aspect, the present invention provides a compound selected from the exemplified examples or a stereoisomer, a tautomer, a pharmaceutically acceptable salt, a polymorph, a solvate or a hydrate thereof.

In another aspect, the present invention provides a compound selected from any subset list of compounds or a single compound from the exemplified examples within the scope of any of the above aspects.

In another embodiment, the compounds of the present invention have hMGAT2 $IC_{50}$ values ≤1 µM, using the MGAT2 LCMS assay.

In another embodiment, the compounds of the present invention have hMGAT2 $IC_{50}$ values ≤0.5 µM, using the MGAT2 LCMS assay.

In another embodiment, the compounds of the present invention have hMGAT2 $IC_{50}$ values ≤0.1 µM, using the MGAT2 LCMS assay.

II. Other Embodiments of the Invention

In another embodiment, the present invention provides a composition comprising at least one of the compounds of the present invention or a stereoisomer, a tautomer, a pharmaceutically acceptable salt, a polymorph, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, a polymorph, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, a polymorph, or a solvate thereof.

In another embodiment, the present invention provides a process for making a compound of the present invention or a stereoisomer, a tautomer, a pharmaceutically acceptable salt, a polymorph, or a solvate thereof.

In another embodiment, the present invention provides an intermediate for making a compound of the present invention or a stereoisomer, a tautomer, a pharmaceutically acceptable salt, a polymorph, or a solvate thereof.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example a member selected from saxagliptin, sitagliptin, vildagliptin and alogliptin).

In another embodiment, the present invention provides a method for the treatment of multiple diseases or disorders associated with MGAT2, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the MGAT2 that can be prevented, modulated, or treated according to the present invention include, but are not limited to, diabetes, hyperglycemia, impaired glucose tolerance, gestational diabetes, insulin resistance, hyperinsulinemia, nonalcoholic fatty liver disease (NAFLD) including nonalcoholic steatohepatitis (NASH), retinopathy, neuropathy, nephropathy, atherosclerosis and its sequelae, myocardial ischemia, stroke, Metabolic Syndrome, hypertension, obesity, dyslipidemia, dyslipidemia, hyperlipidemia, hypertriglyceridemia, hypercholesterolemia, low high-density lipoprotein (HDL), high low-density lipoprotein (LDL), non-cardiac ischemia, lipid disorders, and glaucoma.

In another embodiment, the present invention provides a method for the treatment of diabetes, hyperglycemia, gestational diabetes, obesity, dyslipidemia, and hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with MGAT2.

In another embodiment, the present invention also provides the use of a compound of the present invention for the manufacture of a medicament for the treatment of multiple diseases or disorders associated with MGAT2.

In another embodiment, the present invention provides a method for the treatment of multiple diseases or disorders associated with MGAT2, comprising administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with MGAT2.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the MGAT2 inhibitor of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the MGAT2 inhibitor of the present invention include, but are not limited to, insulin secretagogues or insulin sensitizers, other MGAT2 inhibitors, or other antidiabetic agents. These agents include, but are not limited to, dipeptidyl peptidase IV (DP4) inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR40 receptor modulators (e.g., TAK-875), GPR119 receptor modulators (for example, MBX-2952, PSN821, and APD597), sodium-glucose transporter-2 (SGLT2) inhibitors (for example, dapagliflozin, canagliflozin and remagliflozin), 11b-HSD-1 inhibitors (for example MK-0736, BI35585, BMS-823778, and LY2523199), amylin analogs such as pramlintide, and/or insulin.

The MGAT2 inhibitor of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compounds of the present invention may also be employed in combination with an agonist of the glucagon-like peptide-1 receptor (GLP-1 R), such as exenatide, liraglutide, GPR-1(1-36) amide, GLP-1

(7-36) amide, GLP-1(7-37), which may be administered via injection, intranasal, or by transdermal or buccal devices.

The MGAT2 inhibitor of the present invention may also be optionally employed in combination with one or more other types of therapeutic agents, such as DGAT inhibitors, LDL lowering drugs such as statins (inhibitors of HMG CoA reductase) or inhibitors of cholesterol absorption, modulators of PCSK9, drugs that increase HDL such as CETP inhibitors.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, Fourth Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers, (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
Ag$_2$CO$_3$ silver carbonate
AgOAc silver acetate
CDCl$_3$ deutero-chloroform
CHCl$_3$ chloroform
cDNA complementary DNA
DCC N,N'-dicyclohexylcarbodiimide
DIAD diisopropyl azodicarboxylate
DMA dimethylamine
DME dimethylether
DMF dimethyl formamide
DMSO dimethyl sulfoxide
DMAP 4-dimethylaminopyridine
DAST (diethylamino)sulfur trifluoride
EDTA ethylenediaminetetraacetic acid
EtOAc ethyl acetate
Et$_2$O diethyl ether
AlCl$_3$ aluminum chloride
Boc tert-butyloxycarbonyl
CAN ceric ammonium nitrate
CH$_2$Cl$_2$ dichloromethane
CH$_3$CN or ACN acetonitrile
Cs$_2$CO$_3$ cesium carbonate
HCl hydrochloric acid
H$_2$SO$_4$ sulfuric acid
K$_2$CO$_3$ potassium carbonate
KCN potassium cyanide
mCPBA or m-CPBA meta-chloroperbenzoic acid
NIS N-iodosuccinimide
Pd/C palladium on carbon
PhSO$_2$Cl benzenesulfonyl chloride
i-Pr$_2$NEt diisopropylethylamine
PS polystyrene
SFC Supercritical Fluid Chromatography
SiO$_2$ silica oxide
SnCl$_2$ tin(II) chloride
TBAT tetrabutylammonium triphenydifluorosilicate
TEA triethylamine
TFA trifluoroacetic acid
THF tetrahydrofuran
KOAc potassium acetate
MgSO$_4$ magnesium sulfate
NaCl sodium chloride
NaH sodium hydride
NaHCO$_3$ sodium bicarbonate
NaOH sodium hydroxide
Na$_2$SO$_3$ sodium sulfite
Na$_2$SO$_4$ sodium sulfate
NH$_3$ ammonia
NH$_4$Cl ammonium chloride
NH$_4$OH ammonium hydroxide
LG leaving group
Pd$_2$dba$_3$ tris(dibenzylideneacetone)dipalladium(0)
SELECTFLUOR® N-fluoro-N'-methyl-triethylenediamine bis(tetrafluoroborate)

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear herein-after and in the working examples. Protection and deprotection in the processes below may be carried out by procedures generally known in the art (see, for example, Greene, T. W. et al., *Protecting Groups in Organic Synthesis*, Fourth Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. Sixth Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

For example, compounds of Formula (I), where $R^2$=H and $R^3$=tetrazole, can be made according to Scheme 1. Ketones 1a and aldehyde 1b undergoes Aldol condensation to afford enone 1c. Treatment of enone 1c and 2-cyanoacetamide with t-BuOK gives cyanopyridone 1d. [3+2] cycloaddition of azide (TMSN$_3$ or NaN$_3$) to cyano group in 1d affords Formula (I). Alternatively, formula (I) can be synthesized by reacting enone 1c with tetrazoloacetamide 1e in the presence of FeCl$_3$ and propionic acid.

Scheme 1

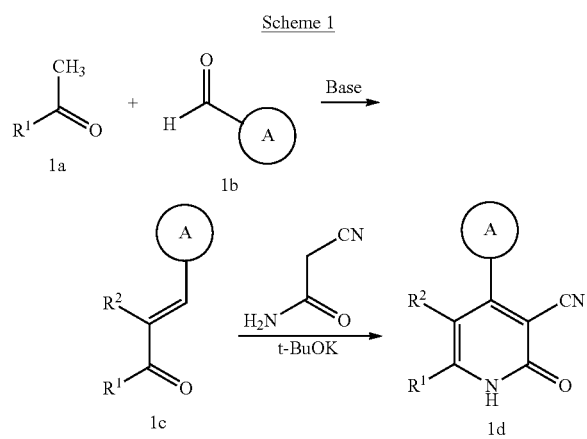

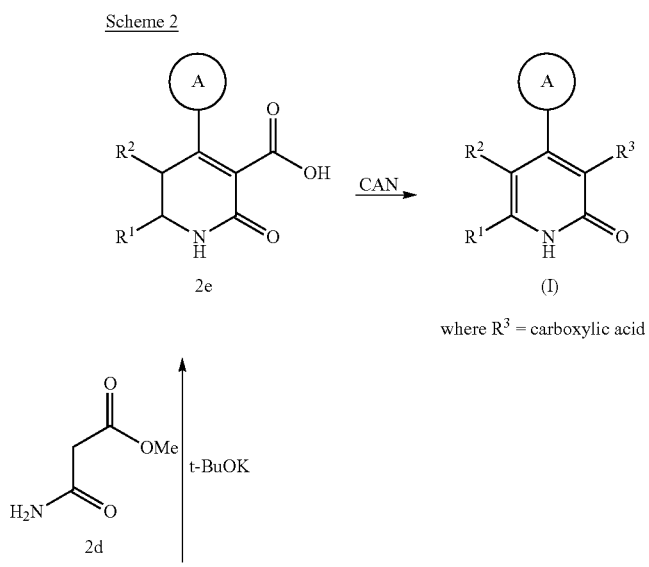

Compounds of Formula (I), where $R^2$=H and $R^3$=carboxamide, carboxylic acid and acyl sulfonamide, may be made according to Scheme 2. Reaction of enone 1c and acetamide 2b in the presence of tBuOK affords compounds of Formula (I) containing an aryl carboxamide at $R^3$. Alternatively, compounds of Formula (I) containing an aryl carboxamide at $R^3$ can be synthesized by treating enone 1c and cyanoamide 2c with FeCl$_3$ and propionic acid. Additionally, reaction of enone 1c and methyl 3-amino-3-oxopropanoate 2d in the presence of tBuOK provides dihydropyridone carboxylic acid 2e. CAN-mediated oxidation of 2e gives compounds of Formula (I) containing a carboxylic acid at $R^3$. In a similar way, dihydropyridone sulfonamide 2h can be made by reacting enone 1c and sulfonylmalonamide 2g with tBuOK. Subsequent CAN-mediated oxidation of dihydropyridone acyl sulfonamide 2h gives compounds of Formula (I) containing an acyl sulfonamide at $R^3$.

Scheme 2

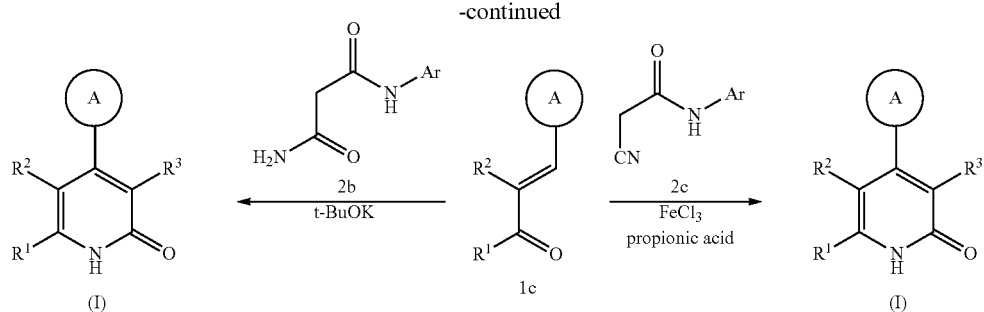

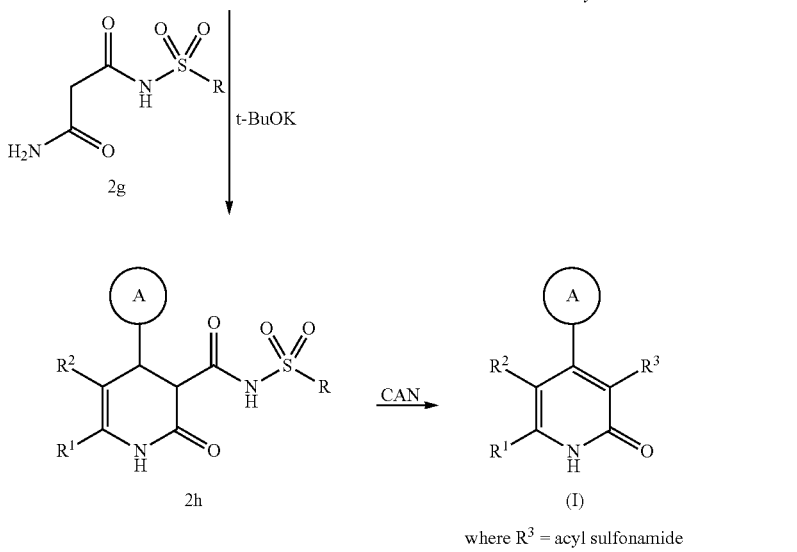

Alternatively, compounds of Formula (I), where $R^2$=H, can be made according to Scheme 3. Condensation of aldehyde 3a and sulfinamide 3b provides imine 3c. Imine 3c is alkylated with ketone 3d in the presence of KHMDS in THF at −78° C. to ambient temperature to provide ketone 3e. Subsequently, ketone 3e is deprotected using HCl in a suitable solvent such as MeOH to provide 3-amino ketone 3f. Other conditions to remove the t-butylsulfinyl group may be employed as determined by those skilled in the art. β-Amino ketone 3f is acylated with carboxylic acid 3g using DCC in THF to give β-ketoamide 3h. Cyclization of β-ketoamide 3h in the presence of a base such as NaOEt in EtOH at 90° C. yields Formula (I).

Scheme 3

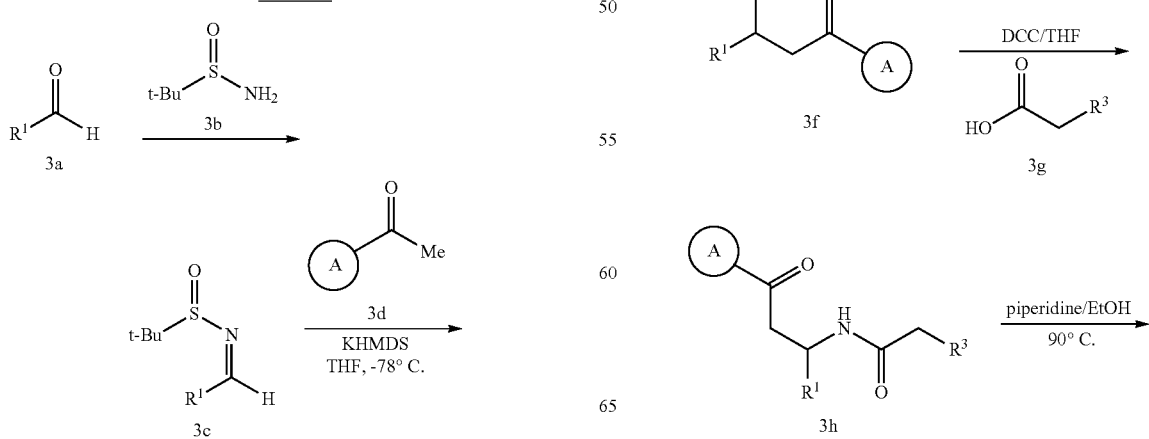

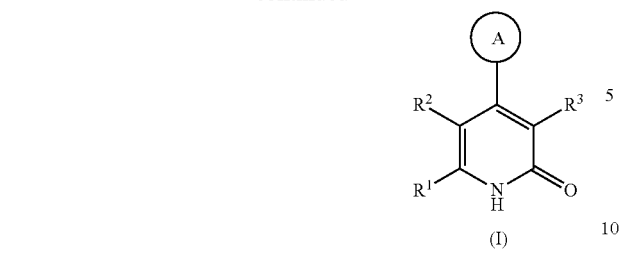

Compounds of Formula (I), where $R^2$=halogen, alkyl and alkenyl, may be made according to Scheme 4. Pyridone 4a, which is prepared according to Scheme 1, 2, or 3, can be halogenated by using halogenating agent, such as NBS, NCS, NIS, or SELECTFLUOR® to provide compounds of Formula (I). When $R^2$=Br in Formula (I), it can react with various boronic reagents/stannyl reagents through Suzuki or Stille type of cross coupling reaction to generate compounds of Formula (I) where $R^2$=alkyl or alkenyl. The choices of boronic/stannyl reagents, catalysts, ligands, bases, solvents and temperatures are well documented in the literature and can be selected appropriately by those skilled in the art.

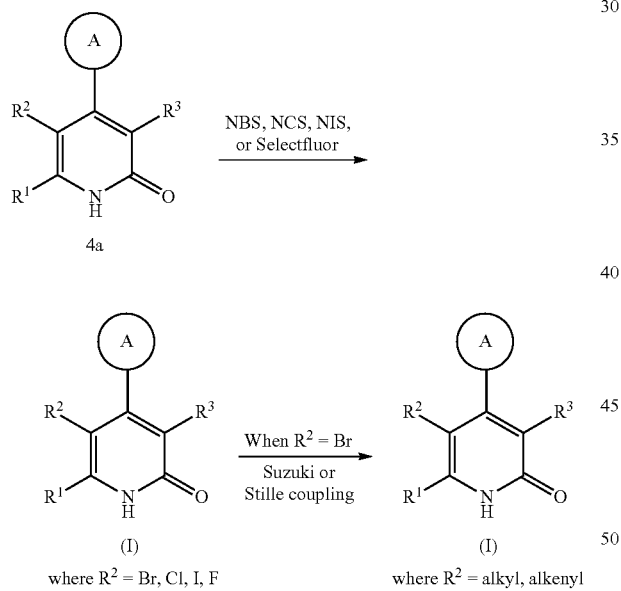

Alternatively, compounds of Formula (I), where $R^2$=F, may be made according to Scheme 5. Difluorosilylenol 5b can be obtained by treating trifluoroketone 5a with Mg and TMSCl in THF at 0° C. Subsequent addition of difluorosilylenol 5b to imine 5c in the presence of TBAT in THF at ambient temperature affords ketone 5d. Ketone 5d is deprotected using HCl in a suitable solvent such as MeOH to provide amino ketone 5e. Other conditions to remove the t-butylsulfinyl group may be employed as determined by those skilled in the art. Amino ketone 5e is acylated with acyl chloride 5f to give amide 5g. Cyclization of β-ketoamide 5g in the presence of piperidine in EtOH at 50° C. yields compounds of Formula (I).

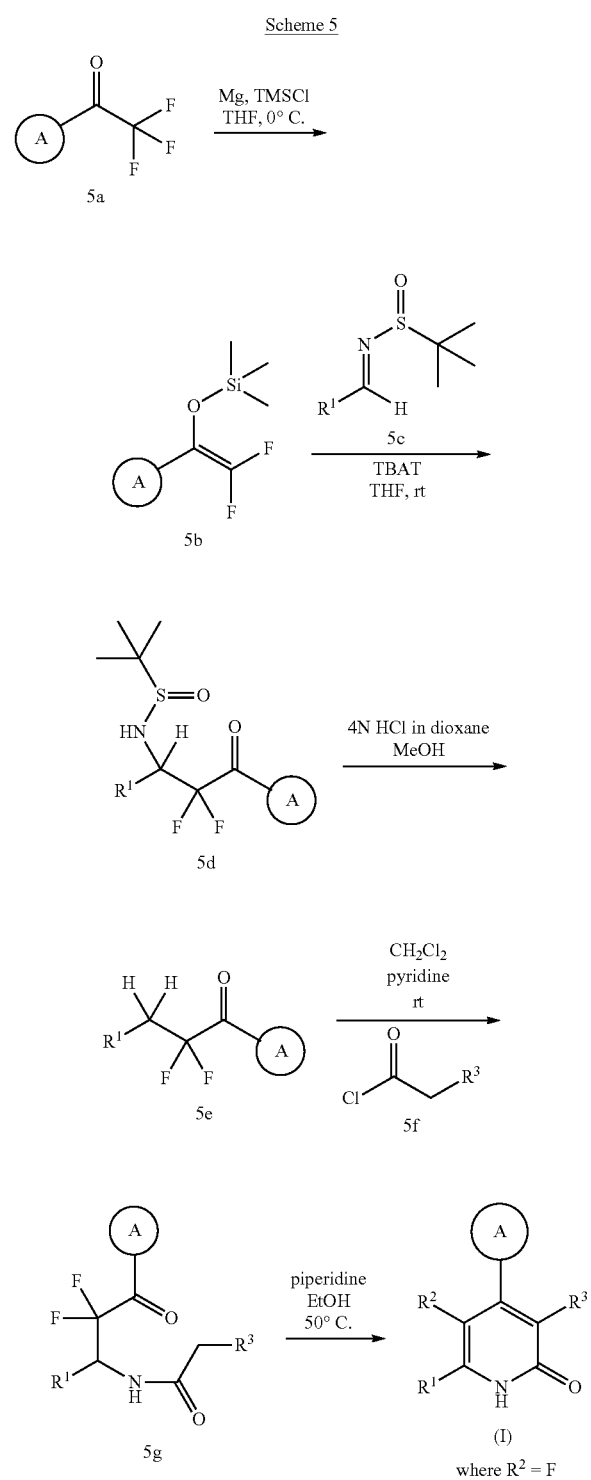

Compounds of Formula (I), where $R^2$=H, may be made according to Scheme 6. Elimination of dihydropyridone 6a (compound 6a can be prepared according to WO 13/082345) in the presence of a base, such as NaOEt, in the solvent such as THF under microwave condition or conventional heating at temperature such as 180° C. provides Formula (I). Other conditions to eliminate trifluoromethyl group may be employed as determined by those skilled in the art.

Scheme 6

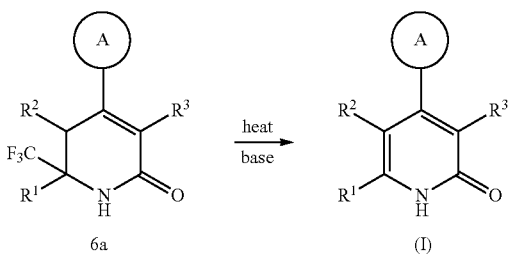

Compounds of Formula (I), where $R^2=H$ and $R^3=$—NHCOR, may be made according to Scheme 7. Pyridone 7a can be synthesized by reacting enone 1c and 2-acetamidoacetamide with base such as $Cs_2CO_3$ in DMF. Bromination of pyridone 7a gives bromo pyridone 7b. Subsequently, methylation of pyridone by using MeI generates methoxy pyridine 7c. Cu-catalyzed amination of bromo pyridine 7c affords amide 7d. The choices of catalysts, ligands, bases, solvents and temperatures are well documented in the literature and can be selected appropriately by those skilled in the art. Further demethylation of methoxy pyridine 7d gives formula (I).

Scheme 7

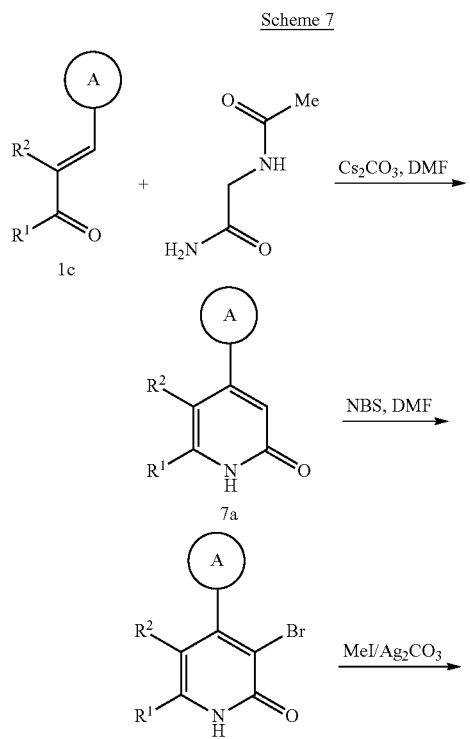

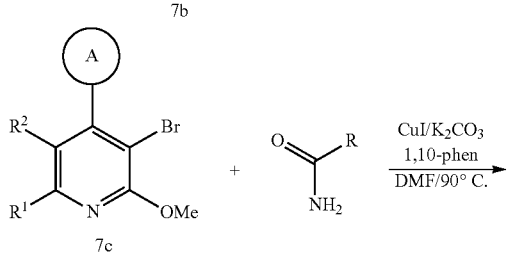

Alternatively, compounds of Formula (I), where $R^2=H$ and $R^3=$—NHCOR, may be made according to Scheme 8. 1,4-addition of 8a to enone 1c in the presence of the base such as NaOtBu affords amide 8b. Subsequent cyclization of 8b in the presence of $FeCl_3$ and acetic acid gives formula (I).

Scheme 8

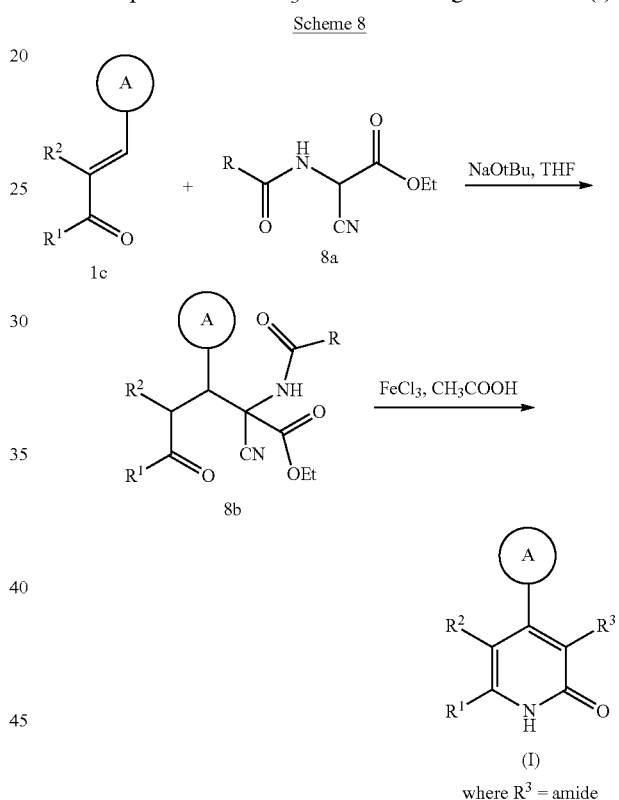

Compounds of formula (I) can also be made according to Scheme 9. Compound 9f can be obtained as described in the earlier schemes. Chlorination of 9f with NaOCl, followed by treatment with a base such as DBU, affords formula (I) after removal of any protecting groups employed on $R^1$, $R^2$, or $R^3$.

Scheme 9

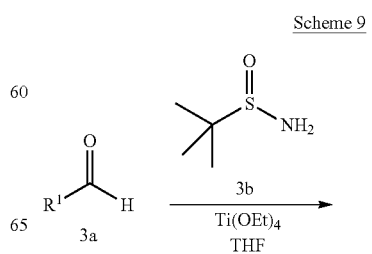

-continued

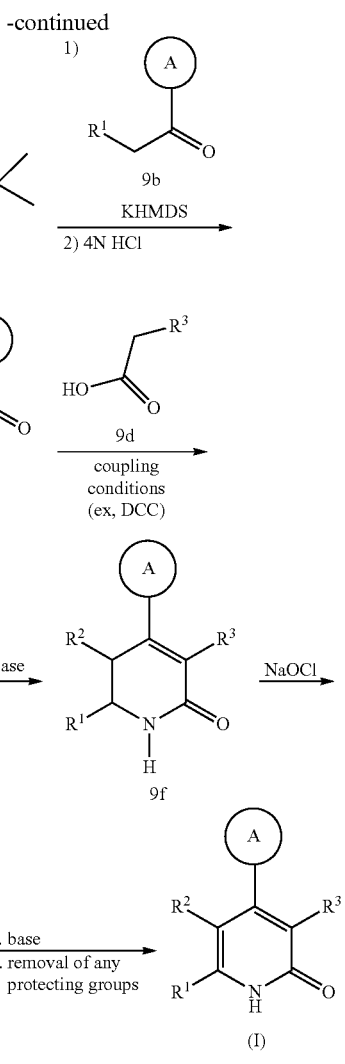

IV. Biology

In mammals, there are two triglyceride synthesis pathways: glycerol-3-phosphate pathway and monoacylglycerol pathway. The former is mainly responsible for energy storage in the peripheral tissues such as fat, liver, skeletal muscle; the latter is essential for the dietary fat absorption which takes place in the small intestine. When dietary fat is ingested, pancreatic lipase digests triglycerides into free fatty acids and 2-monoacylglycerol, which are absorbed by intestinal epithelial enterocytes. Once inside enterocytes, free fatty acids and 2-monoacylglycerol are used as building blocks to resynthesize triglycerides by two sequential acylation steps; first by MGAT and then by DGAT enzyme reactions. Triglycerides are then incorporated into chylomicrons and secreted into lymph to be utilized as an energy supply for the body.

Monoacylglycerol acyltransferase 2 (MGAT2) is a membrane-bound acyltransferase that belongs to diacylglycerol acyltransferase 2 (DGAT2) gene family. It is highly and selectively expressed in the small intestine. Genetic deletion of MGAT2 in mice decreased the rate of absorption for the orally ingested triglycerides, indicating that MGAT2 plays an important role for the intestinal MGAT/DGAT pathway [Yen, C. L. et al., Nat. Med., 15(4):442-446 (2009); Okawa, M. et al., Biochem. Biophys. Res. Commun., 390(3):377-381 (2009)]. When chronically challenged with a high fat diet, in contrast to wild type mice that became obese, MGAT2 knockout mice resisted the impact of high-fat feeding and had a lower body weight, less adiposity, and less hepatic fat accumulation. In contrast to hyperinsulinemic wild type mice after high-fat challenge, MGAT2 deletion normalizes the insulin level and decreased fasting glucose. In the glucose tolerance test, they also had an improved glucose excursion. Consistent with their improved glycemic profile, MGAT2 knockout mice also had an increased level of GLP-1, an incretin gut hormone that profoundly impacts glucose metabolism [Yen, C. L. et al., Nat. Med., 15(4):442-446 (2009)]. Taken together, it is expected that inhibition of MGAT2 through pharmacological intervention would provide the same benefit as demonstrated in the knock-out mice, e.g., resistance to weight gain, or conversely, reduction in fat body mass. In addition, MGAT2 inhibition would lead to an improved insulin sensitivity and glucose metabolism which either leads to a decrease in the incidence of Type II diabetes, or a treatment of diabetic condition.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a MGAT2 inhibitor. Exemplary subjects include human beings of any age with risk factors for metabolic disease. Common risk factors include, but are not limited to, age, sex, weight, family history, or signs of insulin resistance such as acanthosis nigricans, hypertension, dyslipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit MGAT2 and/or to prevent or treat the disorders listed herein. When applied to a combination, the term refers to combined amounts of the active ingredients that result in the preventive or therapeutic effect, whether administered in combination, serially, or simultaneously.

A. Assay Methods

MGAT LCMS Assay

The MGAT enzyme reactions were performed in Corning FALCON® 96-well polypropylene plates, in a total volume of 60 μL of 50 mM potassium phosphate buffer pH 7.4, containing a final concentration of 100 μM 2-oleoylglycerol, 15 μM oleoyl-coenzyme A and 0.0013 μg/μL Human or Mouse MGAT-2 or 0.0026 μg/μL Rat recombinant MGAT-2 membranes expressed in Sf9 cells. Assay plates were run through a fully automated robotics system and shaken for 5 seconds every minute for a total 10 minutes. The reactions were then quenched with 120 μL of ice cold methanol containing 1 μg/mL 1,2-distearoyl-rac-glycerol as the internal standard. Plates were shaken for 2 minutes and spun down to remove protein precipitation. After the spin, samples were transferred to LC/MS compatible PCR plates. For LC/MS analysis, a ThermoFisher Surveyor pump, utilizing a Waters SYMMETRY® C8, 50×2.1 mm column, was used for the chromatography of enzyme products. The buffer system consists of 0.1% formic acid in water with a mobile phase consisting 0.1% formic acid in methanol. The shallow gradient is 90-100% mobile phase in 0.2 min with a total run time of 2.3 min. The first 0.5 minutes of each injection was diverted to waste to eliminate the presence of Phosphate buffer in the enzymatic reaction. The column was run at 0.6 mL/min and a temperature of 65° C. Mass spectrometry analysis of the samples was performed on a ThermoFisher Quantum Triple quad utilizing APCI (+) as the mode of ionization. Data was acquired in Single Ion Monitoring (SIM) mode analyzing Diolein=m/z 603.6 (PRODUCT) and 1,2-distearoyl-rac-glycerol (IS)=m/z 607.6. The ratio of Diolein to internal standard (Peak Area Ratio) is utilized to calculate $IC_{50}$ values.

The exemplified Examples disclosed below were tested in the MGAT2 in vitro assays described above and were found having MGAT2 inhibitory activity. Table 1 below lists human MGAT2 $IC_{50}$ values measured for the following examples.

TABLE 1

| Example No. | h-MGAT LCMS $IC_{50}$ (nM) |
|---|---|
| 1 | 25 |
| 2 | 30 |
| 3 | 19 |
| 4 | 5 |
| 5 | 21 |
| 6 | 79 |
| 7 | 9 |
| 8 | 50 |
| 9 | 293 |
| 10 | 17 |
| 11 | 461 |
| 12 | 56 |
| 13 | 21 |
| 14 | 100 |
| 15 | 5 |
| 16 | 80 |
| 17 | 298 |
| 18 | 232 |
| 19 | 100 |
| 20 | 5 |
| 21 | 21 |
| 22 | 252 |
| 23 | 24 |
| 24 | 39 |
| 25 | 72 |
| 26 | 82 |
| 27 | 86 |
| 28 | 137 |
| 29 | 144 |
| 30 | 150 |
| 31 | 178 |
| 32 | 193 |
| 33 | 218 |
| 34 | 223 |
| 35 | 288 |
| 36 | 311 |
| 37 | 543 |
| 38 | 1248 |
| 39 | 139 |
| 40 | 390 |
| 41 | 36 |
| 42 | 395 |
| 43 | 2 |
| 44 | 6 |
| 45 | 9 |
| 46 | 27 |
| 47 | 29 |
| 48 | 40 |
| 49 | 44 |
| 50 | 109 |
| 51 | 417 |
| 52 | 3 |
| 53 | 267 |
| 54 | 127 |
| 55 | 27 |
| 56 | 29 |
| 57 | 30 |
| 58 | 575 |
| 59 | 6 |
| 60 | 8 |
| 61 | 139 |
| 62 | 188 |
| 63 | 17 |
| 64 | 5 |
| 65 | 172 |
| 66 | 61 |
| 67 | 2 |
| 68 | 673 |
| 69 | 220 |
| 70 | 97 |
| 71 | 15 |
| 72 | 9 |
| 73 | 148 |
| 74 | 255 |
| 75 | 24 |
| 76 | 87 |
| 77 | 143 |
| 78 | 106 |
| 79 | 198 |
| 80 | 168 |
| 81 | 256 |
| 82 | 1 |
| 83 | 32 |
| 84 | 1 |
| 85 | 7 |
| 86 | 27 |
| 87 | 10 |
| 88 | 56 |
| 89 | 24 |
| 90 | 2 |
| 91 | 17 |
| 92 | 59 |

TABLE 1-continued

| Example No. | h-MGAT LCMS IC$_{50}$ (nM) |
|---|---|
| 93 | 21 |
| 94 | 355 |
| 95 | 17 |
| 96 | 1 |
| 97 | 153 |
| 98 | 332 |
| 99 | 16 |
| 100 | 14 |
| 101 | 7 |
| 102 | 1 |
| 103 | 26 |
| 104 | 84 |
| 105 | 23 |
| 106 | 2 |
| 107 | 99 |
| 108 | 14 |
| 109 | 130 |
| 110 | 43 |
| 111 | 2 |
| 112 | 17 |
| 113 | 7 |
| 114 | 14 |
| 115 | 38 |
| 116 | 17 |
| 117 | 29 |
| 118 | 19 |
| 119 | 10 |
| 120 | 45 |
| 121 | 11 |
| 122 | 27 |
| 123 | 11 |
| 124 | 129 |
| 125 | 2 |
| 126 | 43 |
| 127 | 8 |
| 128 | 83 |
| 129 | 51 |
| 130 | 4 |
| 131 | 7 |
| 132 | 14 |
| 133 | 2 |
| 134 | 3 |
| 135 | 5 |
| 136 | 5 |
| 137 | 5 |
| 138 | 13 |
| 139 | 4 |
| 140 | 30 |
| 141 | 7 |
| 142 | 4 |
| 143 | 52 |
| 144 | 24 |
| 145 | 10 |
| 146 | 29 |
| 147 | 7 |
| 148 | 0.8 |
| 149 | 52 |
| 150 | Not tested |
| 151 | 0.3 |
| 152 | 23 |
| 153 | 49 |
| 154 | 2 |
| 155 | 3 |
| 156 | 143 |
| 157 | 46 |
| 158 | 6 |
| 159 | 38 |
| 160 | 12 |
| 161 | 76 |
| 162 | 1966 |
| 163 | 69 |
| 164 | 55 |
| 165 | 420 |
| 166 | 70 |
| 167 | 39 |
| 168 | 373 |
| 169 | 9 |
| 170 | 17 |
| 171 | 6 |
| 172 | 26 |
| 173 | 57 |

The compounds of the present invention possess activity as inhibitors of MGAT2, and, therefore, may be used in the treatment of diseases associated with MGAT2 activity. Via modulation of MGAT2, the compounds of the present invention may preferably be employed to modulate, either enhance or decrease the production/secretion of insulin and/or gut hormones, such as GLP-1, GIP, CCK, PYY, PP, Amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, lipid disorders, PCOS, and glaucoma.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other MGAT2 inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, appetite suppressants, treatments for heart failure, and treatments for peripheral arterial disease.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the MGAT2 inhibitor of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other MGAT2 inhibitors, or other antidiabetic agents. These agents include, but are not limited to, dipeptidyl peptidase IV (DP4) inhibitors (for example, sitagliptin, saxagliptin, alogliptin, vildagliptin and the like), biguanides (for example, metformin, phenformin and the like), sulfonyl ureas (for example, glyburide, glimepiride, glipizide and the like), glucosidase inhibitors (for example, acarbose, miglitol, and the like), PPARγ agonists such as thiazolidinediones (for example, rosiglitazone, pioglitazone, and the like), PPAR α/γ dual agonists (for example, muraglitazar, tesaglitazar, aleglitazar, and the like), glucokinase activators (as described in Fyfe, M. C. T. et al., *Drugs of the Future,* 34(8):641-653 (2009) and incorporated herein by reference), GPR40 receptor modulators, GPR119 receptor modulators (MBX-2952, PSN821, APD597 and the like), SGLT2 inhibitors (dapagliflozin, canagliflozin, remagliflozin and the like), amylin analogs such as pramlintide, and/or insulin. Reviews of current and emerging therapies for the treatment of diabetes can be found in: Mohler, M. L. et al., *Medicinal Research Reviews,* 29(1):125-195 (2009), and Mizuno, C. S. et al., *Current Medicinal Chemistry,* 15:61-74 (2008).

The compounds of the present invention may also be optionally employed in combination with agents for treating complication of diabetes. These agents include PKC inhibitors and/or AGE inhibitors.

The compounds of the present invention may also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery,* 5:369-370 (2006); Jones, D., *Nature Reviews: Drug Discovery,* 8:833-834 (2009); Obici, S., *Endocrinology,* 150(6):2512-2517 (2009); and Elangbam, C. S., *Vet. Pathol.,* 46(1):10-24 (2009).

The compounds of the present invention may also be optionally employed in combination with one or more other types of therapeutic agents, such as DGAT inhibitors, LDL lowering drugs such as statins (inhibitors of HMG CoA reductase) or inhibitors of cholesterol absorption, modulators of PCSK9, drugs increase HDL such as CETP inhibitors.

The above other therapeutic agents, when employed in combination with the compounds of the present invention may be used, for example, in those amounts indicated in the Physicians' Desk Reference, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the MGAT2 enzyme. Such compounds may be provided in a commercial kit, for example, for use in pharmaceutical research involving MGAT2 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving MGAT2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of multiple diseases or disorders associated with MGAT2 (as defined previously). In another embodiment, the package insert states that the pharmaceutical composition can be used in combination (as defined previously) with a second therapeutic agent for the treatment of multiple diseases or disorders associated with MGAT2. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS, Preparatory/Analytical HPLC, and Chiral Separation Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desolvation Gas: Nitrogen; Desolvation Temp. 250° C.; Ion Source Temp: 120° C.; Positive Electrospray conditions) using the following methods:

Linear Gradient of 0% to 100% solvent B over 2 min, with 1 minute hold at 100% B, or Linear Gradient of 0% to 100% solvent B over 4 min, with 1 minute hold at 100% B; UV visualization at 220 nm;

Column: PHENOMENEX® Luna C18 (2) 30 mm×4.6 mm; 5μ particle (heated to Temp. 40° C.);

Flow rate: 1.0 mL/min (2 min gradient) or 0.8 mL/min (4 min gradient);

Solvent A: 10% ACN, 90% water, 0.1% TFA; or, 10% MeOH, 90% water, 0.1% TFA; and

Solvent B: 90% ACN, 10% water, 0.1% TFA; or, 90% MeOH, 10% water, 0.1% TFA.

Preparatory HPLC (unless otherwise noted) was performed on a Shimadzu SCL-10A liquid chromatograph with a linear gradient of 20-100% Solvent B over 10 to 30 min, with either a 2 to 5 min hold at 100% Solvent B as determined by on skilled in the art;

UV visualization at 220 nm;

Column: PHENOMENEX® Luna Axia 5μ C18 30×100 mm;

Flow rate: 20 mL/min;

Solvent A: 10% ACN, 90% water, 0.1% TFA; or 10% MeOH, 90% water, 0.1% TFA; and

Solvent B: 90% ACN, 10% water, 0.1% TFA; or 90% MeOH, 10% water, 0.1% TFA.

NMR Employed in Characterization of Examples $^1$H NMR spectra (unless otherwise noted) were obtained with JEOL® or Bruker FOURIER® transform spectrometers operating at 400 MHz or 500 MHz. 1H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Microwave instrumentation employed in heating reactions.

BIOTAGE® Initiator 2.5, maximum power 400 W, reaction volume range 0.2-10 mL. Reactions are run in sealed pressure vessels specially manufactured for this instrument.

Intermediate 1

1-(4-(4,4,4-Trifluorobutoxy)phenyl)ethanone

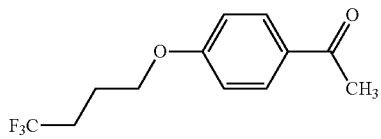

Intermediate 1. 1-(4-(4,4,4-Trifluorobutoxy)phenyl)ethanone: To a solution of 1-(4-hydroxyphenyl)ethanone (3.6 g, 26.4 mmol) and 4,4,4-trifluorobutan-1-ol (3.73 g, 29.1 mmol) in $CH_2Cl_2$ (66.1 mL) cooled to 0° C. was added triphenylphosphine (7.63 g, 29.1 mmol). The reaction was stirred for 30 min, then DIAD (5.66 mL, 29.1 mmol) was added. The reaction was stirred at 0° C. for another 30 min, then warmed to rt and stirred overnight. The reaction was evaporated in vacuo. The residue was purified by chromatography to give the product as a white solid (3.55 g, 52%). $^1$H NMR (400 MHz, $CDCl_3$) δ 8.07-7.82 (m, 2H), 7.02-6.83 (m, 2H), 4.09 (t, J=6.1 Hz, 2H), 2.65-2.50 (m, 3H), 2.42-2.23 (m, 2H), 2.17-1.96 (m, 2H).

Intermediate 2

5-Cyclopropylthiophene-2-carbaldehyde

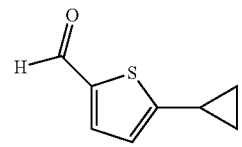

Intermediate 2. 5-Cyclopropylthiophene-2-carbaldehyde: A sealed reaction vial was charged with palladium(II) acetate (9.19 mg, 0.041 mmol), butyldi-1-adamantylphosphine (0.022 g, 0.061 mmol), potassium cyclopropyl trifluoroborate (0.306 g, 2.067 mmol) and $Cs_2CO_3$ (2.000 g, 6.14 mmol). The vessel was purged and back filled with Ar. A solution of 5-chlorothiophene-2-carbaldehyde (0.3 g, 2.046 mmol) in a mixture of toluene (degassed) (8.0 mL) and water (degassed) (0.800 mL) was added and the reaction mixture stirred at 100° C. The reaction mixture was heated at this temperature overnight. The reaction mixture was cooled to rt, diluted with water and extracted with DCM. The combined organic layers were washed with brine, dried over anhydrous $Na_2SO_4$, filtered and concentrated. The crude product was purified by chromatography to yield Intermediate 2 (156 mg, 50%) as a yellow oil. $^1$H NMR (400 MHz, $CDCl_3$) δ 9.77 (s, 1H), 7.57 (d, J=3.7 Hz, 1H), 6.86 (dd, J=3.9, 0.6 Hz, 1H), 2.16 (s, 1H), 1.36-1.23 (m, 2H), 0.91-0.79 (m, 2H).

Intermediate 3

(S,E)-2-Methyl-N-(4-(4,4,4-trifluorobutoxy)benzylidene)propane-2-sulfinamide

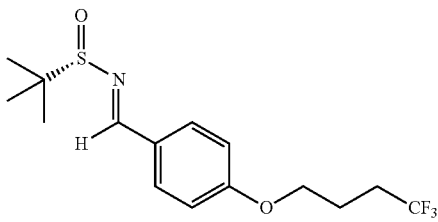 [SMILES: CC(C)(C)[S@](=O)/N=C/c1ccc(OCCCC(F)(F)F)cc1]

Intermediate 3A. 4-(4,4,4-Trifluorobutoxy)benzaldehyde: To a solution of 4-hydroxybenzaldehyde (20 g, 164 mmol) and 4,4,4-trifluorobutan-1-ol (25 g, 195 mmol) in anhydrous $CH_2Cl_2$ (500 mL) at 0° C. under Ar was added a solution of $PPh_3$ (51.5 g, 196 mmol) in $CH_2Cl_2$ (200 mL) over 15 min, and then DIAD (36.4 g, 180 mmol) in anhydrous $CH_2Cl_2$ (150 mL) was added dropwise. The mixture was stirred at 0° C. for 0.5 h. The reaction was warmed to rt and stirred for another 3 h. The solvent was removed in vacuo and the residue was triturated with $CH_2Cl_2$ three times to remove insoluble solids. The combined $CH_2Cl_2$ portions were concentrated and the residue was purified by silica gel chromatography to provide Intermediate 3A (27 g, 71%) as a light brown oil. LCMS Anal. Calc'd for $C_{11}H_{11}F_3O_2$ 232.20. found [M+H] 233.0.

Intermediate 3: To a solution of Intermediate 3A (510 mg, 2.196 mmol) and (S)-2-methylpropane-2-sulfinamide (532 mg, 4.39 mmol) in THF (8 mL) was added tetraethoxytitanium (1.842 mL, 8.79 mmol) at rt and the resulting mixture was stirred at rt for 3 h. After 3 h reaction, solvent was evaporated to afford a pale yellow oil which was dissolved in EtOAc (50 mL) and then 1 M citric acid solution (10 mL) was added. The resulting mixture was stirred for 5 min and filtered through a bed of CELITE®. The white precipitate was rinsed with EtOAc. The combined EtOAc solution was washed with brine, dried with $Na_2SO_4$, and evaporated in vacuo to give the crude product as a pale yellow oil. Purification by flash chromatography yielded intermediate 3 (640 mg, 87%) as a white solid. MS(ESI) m/z: 336.0 $(M+H)^+$.

Intermediate 4

3-(4-Methoxyphenylamino)-3-oxopropanoic acid

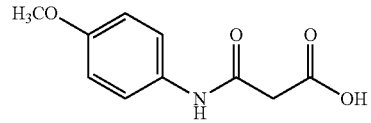 [SMILES: COc1ccc(NC(=O)CC(=O)O)cc1]

Intermediate 4A. Benzyl 3-(4-methoxyphenylamino)-3-oxopropanoate: To a solution of monobenzyl malonate (12.2 g, 63.1 mmol) and DMF (90 μL) in anhydrous $CH_2Cl_2$ (100 mL) at 0° C. was added 2 M oxalyl chloride (35 mL, 70 mmol) in $CH_2Cl_2$. The reaction was stirred at 0° C. for 30 min, then at rt for 2.5 h. The solvent was removed in vacuo to provide freshly prepared acid chloride. This was dissolved in anhydrous $CH_2Cl_2$ (50 mL) and added dropwise to a solution of 4-methoxyaniline (7.76 g, 63 mmol) in anhydrous $CH_2Cl_2$ (50 mL) at 0° C. followed by the addition of pyridine (5.35 mL, 66.2 mmol). The reaction was stirred at 0° C. for 0.5 h, then at rt overnight. The reaction was washed with water and sat'd aq NaCl, dried over anhydrous $MgSO_4$, filtered and concentrated. The residue was triturated with $EtOAc/CH_2Cl_2$ to yield the first batch of Intermediate 6A as a light brown solid (6.95 g). The supernatant was evaporated and the residue was purified by silica gel chromatography (eluted with EtOAc in hexanes) to provide a second batch of Intermediate 6A as a light brown solid (7.4 g). The combined yield was 14.4 g (76%). LCMS Anal. Calc'd for $C_{17}H_{18}N_2O_3$ 298.34. found [M+H]300.2.

Intermediate 4: To a solution of Intermediate 4A (14.4 g, 4.8 mmol) in 10:1 EtOAc/MeOH (220 mL) was added 10% Pd/C (250 mg). The reaction mixture was stirred vigorously under an atmosphere of hydrogen (40 psi) for 2 h. More 10% Pd/C (250 mg) was added and the reaction was stirred under 50 psi hydrogen for another 1 h. Additional 10% Pd/C (500 mg) was added and the reaction was stirred under 50 psi hydrogen for an additional 1 h. The reaction was filtered through a pad of CELITE® and the filtrate was concentrated in vacuo to yield Intermediate 4 (11.1 g, 96%) as an off-white solid. LCMS Anal. Calc'd for $C_{10}H_{11}NO_4$ 209.20. found [M+H] 210.1.

Intermediate 5

$N^1$-(Cyclopropylsulfonyl)malonamide

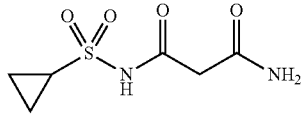 [SMILES: NC(=O)CC(=O)NS(=O)(=O)C1CC1]

Intermediate 5A. Benzyl 3-(cyclopropanesulfonamido)-3-oxopropanoate: Intermediate 5A was prepared by the similar procedure according to Intermediate 4A. $^1$H NMR (400 MHz, $CDCl_3$) δ 7.53-7.31 (m, 5H), 5.22 (s, 2H), 3.50 (s, 2H), 3.07-2.81 (m, 1H), 1.45-1.34 (m, 2H), 1.15-1.02 (m, 2H).

Intermediate 5: A mixture of Intermediate 5A (900 mg, 3.03 mmol) in ammonia (15 mL, 7 N in MeOH) was irradiated at 110° C. for 45 min in a microwave reactor. The solvent was evaporated to give an oily residue. The product was then used for the next step without further purification. MS(ESI) m/z: 207.1 (M+H)+.

Intermediate 6

2-(5-Oxo-4-((2-(trimethylsilyl)ethoxy)methyl)-4,5-dihydro-1H-tetrazol-1-yl)acetic acid

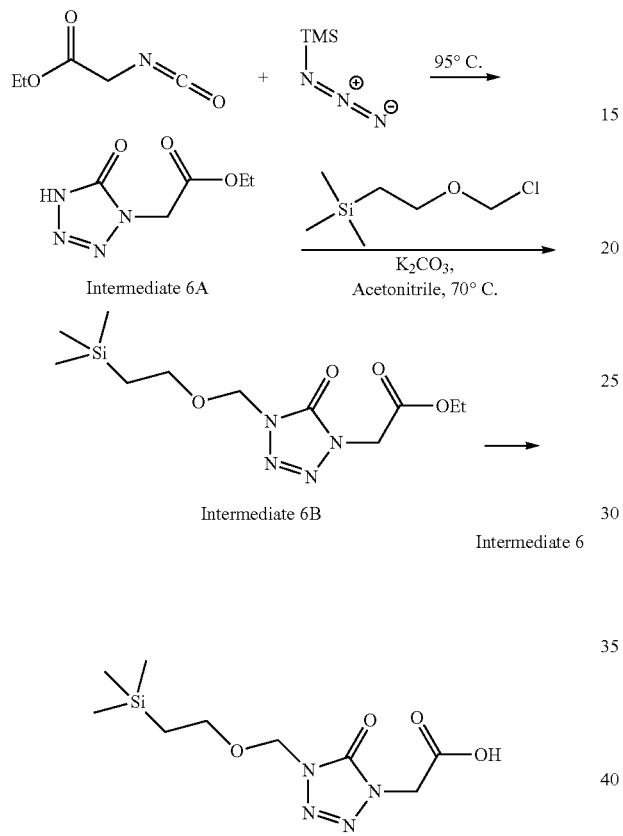

Intermediate 6A. Ethyl 2-(5-oxo-4,5-dihydro-1H-tetrazol-1-yl)acetate: Azidotrimethylsilane (7.06 mL, 53.4 mmol) and ethyl 2-isocyanatoacetate (2.65 mL, 23.24 mmol) were charged into a sealed tube that was equipped with a magnetic stirrer and the reaction mixture was stirred at 95° C. overnight. The reaction mixture was loaded onto an 120 g ISCO column and purified by flash chromatography (0-20% DCM/MeOH) to yield Intermediate 6A (3.84 g, 96%) as a white solid.

Intermediate 6B. Ethyl 2-(5-oxo-4-((2-(trimethylsilyl)ethoxy)methyl)-4,5-dihydro-1H-tetrazol-1-yl)acetate: Intermediate 6A (2.63 g, 15.28 mmol) was dissolved in acetonitrile (75 mL) in a 200 mL 1-necked pear-shaped flask that was equipped with a magnetic stirrer, a reflux condenser and an Ar inlet. K2CO3 (4.22 g, 30.6 mmol) and SEM-Cl (3.52 mL, 19.86 mmol) were added and the reaction mixture was stirred at 70° C. overnight. The reaction mixture was filtered and the filter cake was washed with EtOAc. The filtrate concentrated under vacuum and the residue was dissolved in a minimal amount of DCM and purified by flash chromatography (0-100% EtOAc:hexanes) to give Intermediate 6B (3.61 g, 78%) as an oil.

Intermediate 6. 2-(5-Oxo-4-((2-(trimethylsilyl)ethoxy)methyl)-4,5-dihydro-1H-tetrazol-1-yl)acetic acid: To a solution of Intermediate 6B (1 g, 3.31 mmol) in THF (2 mL) was added 1N NaOH (9.92 mL, 9.92 mmol). The reaction was stirred at RT for 1 h. The mixture was acidified with 1N HCl and extracted with EtOAc. The organic layer was washed with brine, dried over MgSO4, filtered, and concentrated to yield Intermediate 6 (844 mg, 93%). $^1$H NMR (400 MHz, CDCl3) δ 5.34 (s, 2H), 4.81 (s, 2H), 3.70 (dd, J=7.70, 8.58 Hz, 2H), 0.92-1.01 (m, 2H), 0.01 (s, 9H).

Example 1

4-(5-Cyclopropylthiophen-2-yl)-3-1H-tetrazol-5-yl)-6-(4-(4,4,4-trifluorobutoxy)phenyl)-6-(trifluoromethyl)-5,6-dihydropyridin-2(1H)-one

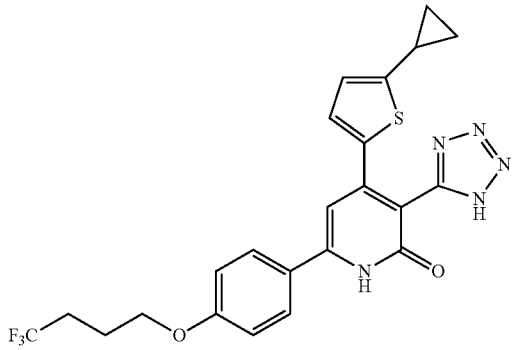 [SMILES: O=c1[nH]c(-c2ccc(OCCCC(F)(F)F)cc2)cc(-c2ccc(C3CC3)s2)c1-c1nnn[nH]1]

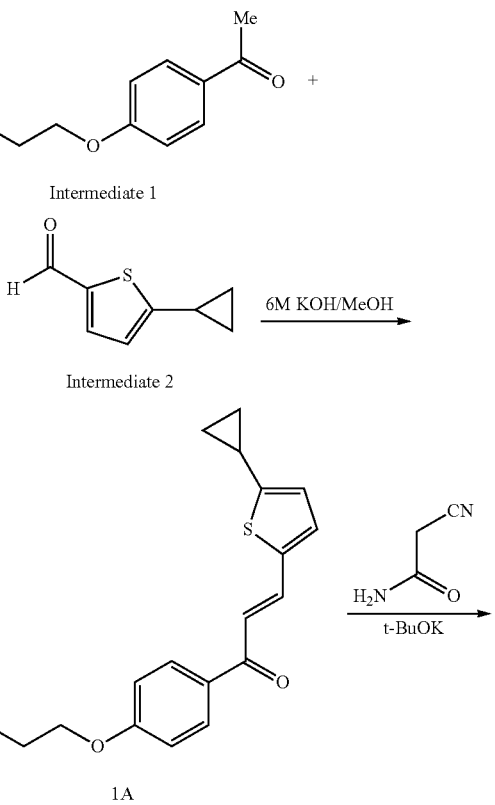

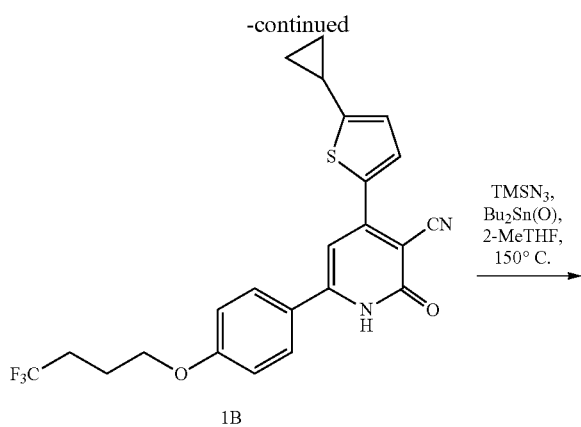

1B

Example 1

1A. (E)-3-(5-Cyclopropylthiophen-2-yl)-1-(4-(4,4,4-trifluorobutoxy)phenyl) prop-2-en-1-one: To a solution of Intermediate 1 (250 mg, 1.015 mmol) and Intermediate 2 (155 mg, 1.015 mmol) in MeOH (20 mL) at rt was added KOH (1.33 g, 23.71 mmol) and water (3 mL). The mixture was stirred at rt overnight. The mixture was filtered and dried under suction to yield 1A (225 mg, 58%) as a solid. MS(ESI) m/z: 381.1 (M+H)$^+$.

1B. 4-(5-Cyclopropylthiophen-2-yl)-2-oxo-6-(4-(4,4,4-trifluorobutoxy) phenyl)-1,2-dihydropyridine-3-carbonitrile: To a solution of 1A (20 mg, 0.053 mmol) and 2-cyanoacetamide (4.86 mg, 0.058 mmol) in DMSO (0.5 mL) at rt was added potassium tert-butoxide (23.60 mg, 0.210 mmol). The reaction mixture was allowed to stir for 0.4 h and then 5 mL H$_2$O and 4 drops of conc. HCl were added. The crude product was further purified by preparative HPLC to afford 1B as a yellow solid (12 mg, 51%). MS(ESI) m/z: 445.2 (M+H)$^+$.

Example 1: 1B (12 mg, 0.027 mmol) and dibutyltin oxide (3 mg, 0.012 mmol) were stirred in 2-Me-THF (1 mL) in a 10 mL microwave vial. TMSN$_3$ (8.96 μL, 0.067 mmol) was added and the reaction mixture was stirred at 150° C. in an oil bath overnight. The reaction was concentrated in vacuo to a brown oil that was dissolved in MeOH and purified by preparative HPLC to yield Example 1 (3.2 mg, 23%). MS(ESI) m/z: 488.1 (M+H)$^+$. $^1$H NMR (500 MHz, DMSO-d$_6$) δ 7.89 (d, J=8.3 Hz, 2H), 7.19 (d, J=3.6 Hz, 1H), 7.11 (d, J=8.8 Hz, 2H), 6.88 (br. s., 1H), 6.77 (d, J=3.9 Hz, 1H), 4.15 (t, J=6.2 Hz, 2H), 2.50-2.38 (m, 2H), 2.17-2.03 (m, 1H), 2.02-1.93 (m, 2H), 1.00 (dd, J=8.3, 2.2 Hz, 2H), 0.69-0.54 (m, 2H).

Example 2

N-(4-Methoxyphenyl)-2-oxo-4-(p-tolyl)-6-(4-(4,4,4-trifluorobutoxy)phenyl)-1,2-dihydropyridine-3-carboxamide

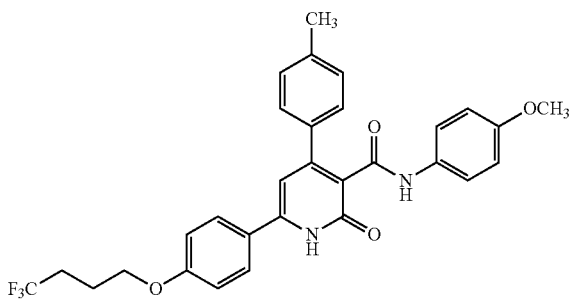 [SMILES: COc1ccc(NC(=O)c2c(-c3ccc(C)cc3)cc(-c3ccc(OCCCC(F)(F)F)cc3)[nH]c2=O)cc1]

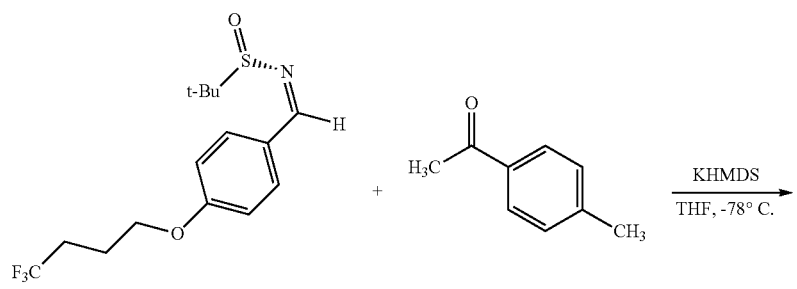

Intermediate 3

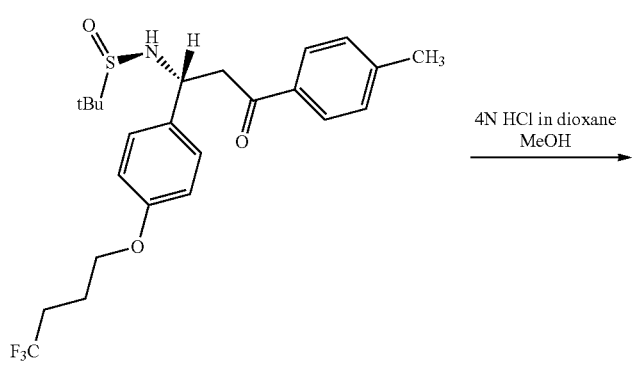

2A

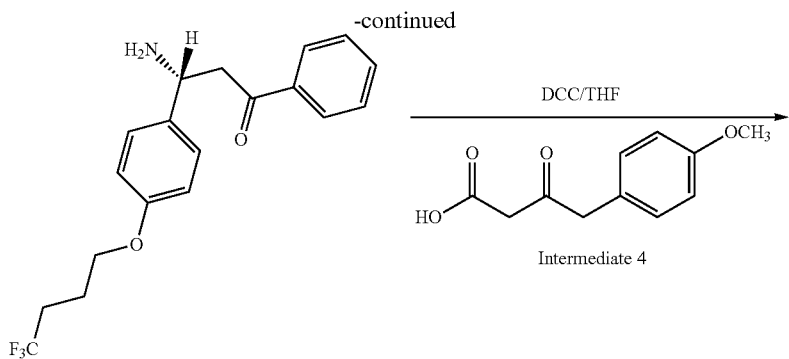

2B

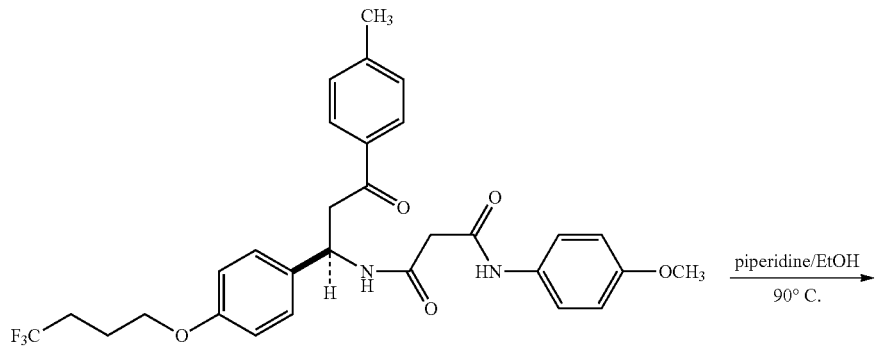

2C

Example 2

2A. (R)-2-Methyl-N—((S)-3-oxo-3-(p-tolyl)-1-(4-(4,4,4-trifluorobutoxy)phenyl) propyl)propane-2-sulfinamide: To a solution of 1-(p-tolyl)ethanone (126 mg, 0.939 mmol) in THF (2 mL) at −78° C. was added 1 M KHMDS in THF (0.939 mL, 0.939 mmol). The resulting mixture was stirred at this temperature for 20 min and Intermediate 3 (105 mg, 0.313 mmol) in THF (1 mL) was added. Stirring continued at −78° C. for an additional 40 min. The reaction mixture was quenched with sat aq. NH$_4$Cl (500 μL) and diluted with EtOAc (25 mL) and water (25 mL). The organic layer was washed with brine, dried (Na$_2$SO$_4$), filtered, and evaporated to yield the crude product. Purification by flash chromatography yielded 2A (127 mg, 86%) as a colorless oil. $^1$H NMR (500 MHz, CDCl$_3$) δ 7.83 (d, J=8.2 Hz, 2H), 7.33 (d, J=8.7 Hz, 1H), 7.25 (d, J=7.9 Hz, 2H), 6.88 (d, J=8.5 Hz, 2H), 4.92 (dt, J=8.2, 4.0 Hz, 1H), 4.83 (d, J=3.8 Hz, 1H), 4.02 (t, J=6.0 Hz, 2H), 3.54 (dd, J=17.2, 4.3 Hz, 1H), 3.41 (dd, J=17.1, 8.3 Hz, 1H), 2.41 (s, 3H), 2.38-2.26 (m, 2H), 2.09-2.01 (m, 2H), 1.23 (s, 9H).

2B. (R)-3-Amino-1-phenyl-3-(4-(4,4,4-trifluorobutoxy)phenyl)propan-1-one: To a solution of 2A (127 mg, 0.270 mmol) in MeOH (5 mL) at rt was added a solution of 4 N HCl/dioxane (0.676 mL, 2.70 mmol) and the mixture stirred for 30 min. The mixture was evaporated to dryness to yield 2B as a white solid 2B which was used as such for the next step. MS(ESI) m/z: 366.0 (M+H)$^+$.

2C. (R)—N1-(4-Methoxyphenyl)-N3-(3-oxo-3-(p-tolyl)-1-(4-(4,4,4-trifluorobutoxy)phenyl)propyl)malonamide: To a suspension of 2B (49 mg, 0.134 mmol) and Intermediate 4 in THF (8 mL) was added DCC (83 mg, 0.402 mmol) and the mixture stirred at rt overnight. The mixture was diluted with EtOAc (30 mL), filtered, transferred to a sep funnel, washed with sat. aq. NaHCO$_3$ (25 mL), brine, dried (Na$_2$SO$_4$), filtered, and evaporated under reduced pressure to yield the crude product which as used as such for the next step. MS(ESI) m/z: 557.2 (M+H)$^+$.

Example 2: A mixture of 2C (75 mg, 0.134 mmol), piperidine (50 μL, 0.505 mmol) and EtOH (2 mL) were stirred in a sealed tube at 90° C. overnight. The crude product was purified by preparative HPLC to yield Example 2 (0.5 mg, 0.6%). MS(ESI) m/z: 537.3 (M+H)$^+$. $^1$H NMR (500 MHz, DMSO-d$_6$) δ 12.14 (s, 1H), 10.21 (s, 1H), 7.82 (s, 2H), 7.47 (dd, J=10.7, 8.3 Hz, 4H), 7.44-7.34 (m, 1H), 7.21 (d, J=7.9 Hz, 2H), 7.07 (d, J=8.6 Hz, 2H), 6.86 (d, J=9.0 Hz, 2H), 4.13 (t, J=6.3 Hz, 2H), 3.72 (s, 3H), 2.49-2.39 (m, 2H), 2.31 (s, 3H), 1.98 (dq, J=13.1, 6.7 Hz, 2H).

Example 3

5-Fluoro-N-(4-methoxyphenyl)-2-oxo-4-(p-tolyl)-6-(4-(4,4,4-trifluorobutoxy)phenyl)-1,2-dihydropyridine-3-carboxamide

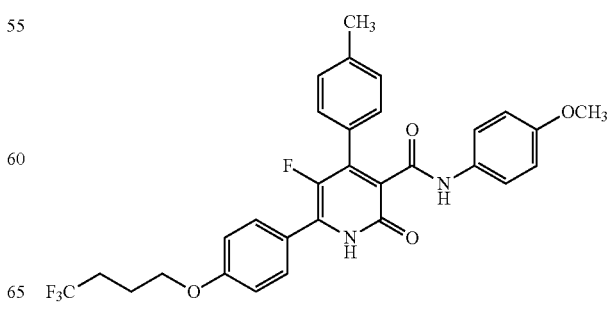

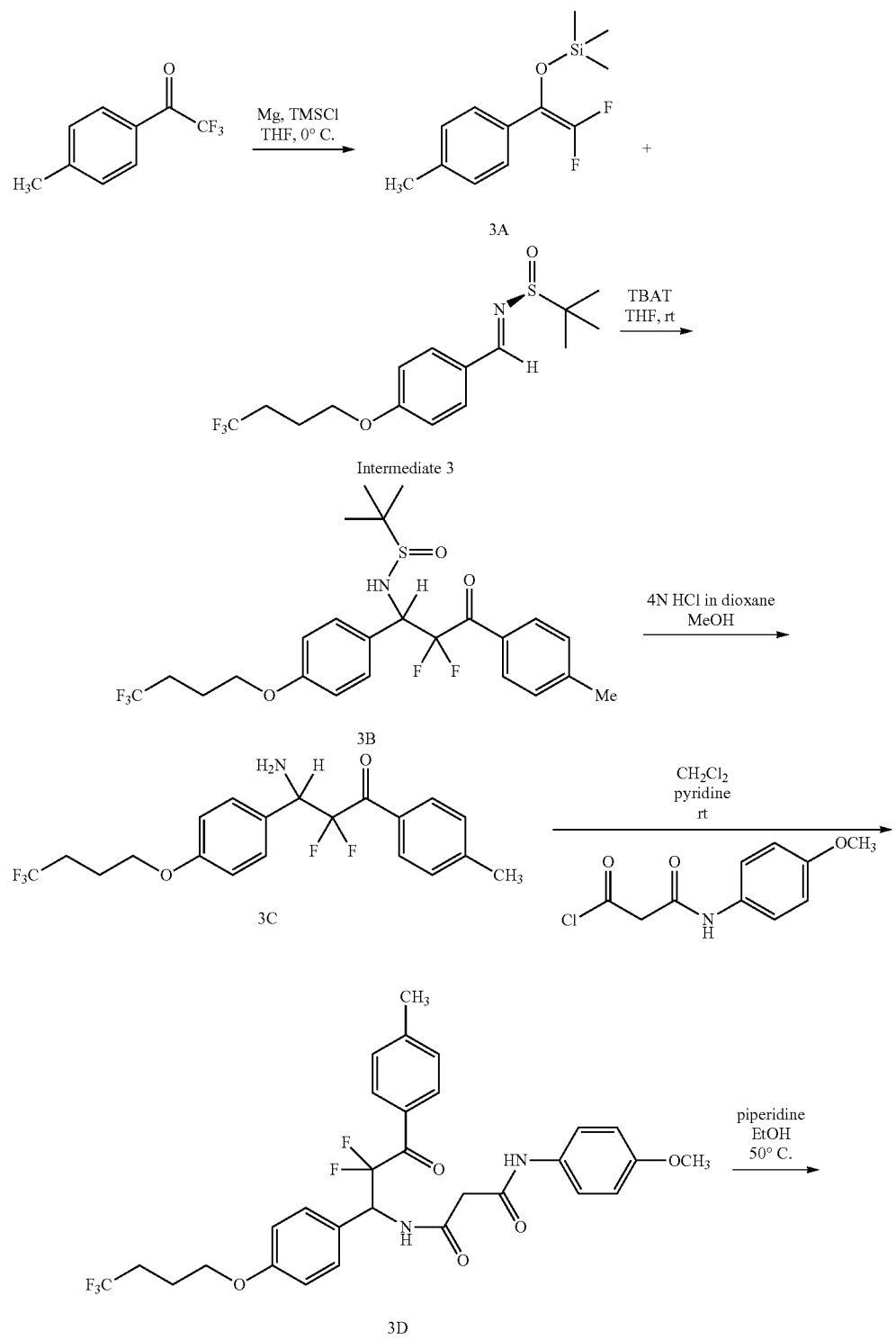

Example 3

3A. ((2,2-Difluoro-1-(p-tolyl)vinyl)oxy)trimethylsilane: Mg (0.775 g, 31.9 mmol) turnings were suspended in THF (80 mL) and trimethylchlorosilane (8.15 mL, 63.8 mmol) was added and the mixture was cooled to 0° C. 2,2,2-Trifluoro-1-(p-tolyl)ethanone (3 g, 15.95 mmol) was added dropwise and the reaction mixture stirred at 0° C. for 1 h. During the reaction the Mg metal became very shiny. The reaction was decanted and dried in vacuo. The residue was redissolved in hexanes, and the insoluble material removed by filtration. The hexanes were removed in vacuo to provide the product which was used in the next step without further purification. $^1$H NMR (500 MHz, CDCl$_3$) δ 7.38 (d, J=7.2

Hz, 2H), 7.18 (d, J=8.3 Hz, 2H), 2.37 (s, 3H), 0.19 (d, J=0.8 Hz, 9H); $^{19}$F NMR (471 MHz, CDCl$_3$) δ −100.7 (d, J=68.7 Hz), −112.3 (d, J=70.1 Hz).

3B. N-(2,2-Difluoro-3-oxo-3-(p-tolyl)-1-(4-(4,4,4-trifluorobutoxy)phenyl) propyl)-2-methylpropane-2-sulfinamide: To a solution of 3A (100 mg, 0.298 mmol) and ((2,2-difluoro-1-(p-tolyl)vinyl)oxy)trimethylsilane (217 mg, 0.894 mmol) in THF (0.5 mL) was added TBAT (241 mg, 0.447 mmol) in THF (2.5 mL). The reaction was stirred at rt. The reaction was quenched with brine and diluted with EtOAc. The layers were separated and the organic layer dried over Na$_2$SO$_4$, filtered and evaporated to dryness. The product was purified by chromatography to give 3B. MS(ESI) m/z: 506.2 (M+H)$^+$.

3C. 3-Amino-2,2-difluoro-1-(p-tolyl)-3-(4-(4,4,4-trifluorobutoxy)phenyl) propan-1-one: A solution of 3B (6.8 mg, 0.013 mmol) and 4M HCl (0.034 mL, 0.135 mmol) in dioxane and MeOH (0.5 mL) was stirred at rt. The reaction was completed in 1 h. The solvent was evaporated and the crude product was used without purification. MS(ESI) m/z: 402.1 (M+H)$^+$.

3D. N$^1$-(2,2-Difluoro-3-oxo-3-(p-tolyl)-1-(4-(4,4,4-trifluorobutoxy)phenyl) propyl)-N$^3$-(4-methoxyphenyl)malonamide: Formation of the acid chloride: Intermediate 4 (20 mg, 0.096 mmol) was dissolved in CH$_2$Cl$_2$ (0.4 mL). Oxalyl chloride (13 mg, 0.105 mmol, 9 μL) followed by a drop of anhydrous DMF were added. The reaction was stirred at rt for 30 min, then 0.2 mL was transferred to a flask containing 3C (5.4 mg, 0.013 mmol), pyridine (5.44 μl, 0.067 mmol) in CH$_2$Cl$_2$ (0.1 mL). The reaction was stirred at rt. After 1.5 h, the reaction was completed. The solvent was evaporated and the crude product was used without purification. MS(ESI) m/z: 593.2 (M+H)$^+$.

Example 3: 3D (7.97 mg, 0.013 mmol) and piperidine (0.030 mL, 0.303 mmol) in EtOH (1.1 mL) were stirred at 50° C. for 4 days. The reaction mixture was purified by preparative HPLC to afford Example 3 (1.3 mg, 17%). $^1$H NMR (500 MHz, 1:1 CDCl$_3$: CD$_3$OD) δ 8.57 (d, J=8.0 Hz, 2H), 8.13 (d, J=9.1 Hz, 4H), 8.01-7.93 (m, 2H), 7.84-7.77 (m, 2H), 7.57 (d, J=9.1 Hz, 2H), 4.90-4.83 (m, 2H), 4.57 (s, 3H), 3.24-3.11 (m, 2H), 3.11 (s, 2H), 2.84-2.71 (m, 2H). MS(ESI) m/z: 555.2 (M+H)$^+$.

Example 4

N-(4-Methoxyphenyl)-6-(5-methyl-2-phenyloxazol-4-yl)-2-oxo-4-(p-tolyl)-1,2-dihydropyridine-3-carboxamide

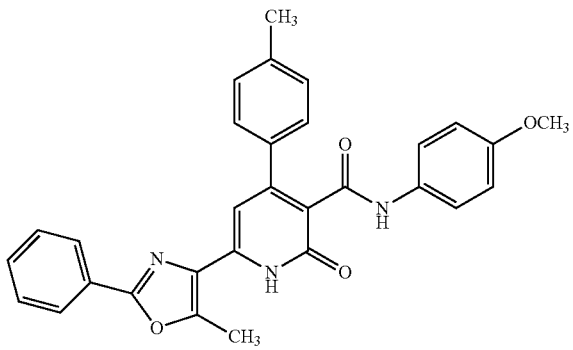 [SMILES: COc1ccc(NC(=O)c2c(-c3ccc(C)cc3)cc(-c3nc(-c4ccccc4)oc3C)[nH]c2=O)cc1]

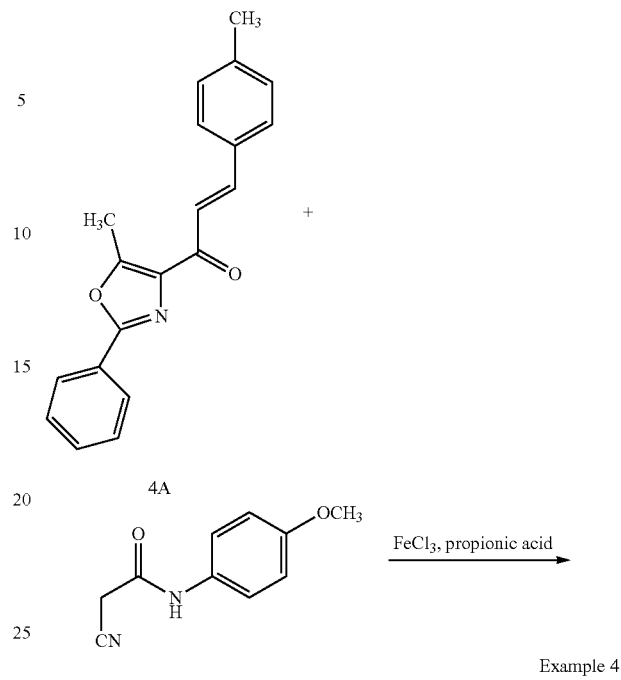

4A. (E)-1-(5-Methyl-2-phenyloxazol-4-yl)-3-(p-tolyl)prop-2-en-1-one: 4A was prepared to according to the procedure for 1A. $^1$H NMR (400 MHz, CDCl$_3$) δ 8.08-8.13 (m, 2H), 7.88 (d, J=2.42 Hz, 2H), 7.63 (d, J=8.14 Hz, 2H), 7.48-7.51 (m, 3H), 7.24 (d, J=7.92 Hz, 2H), 2.80 (s, 3H), 2.41 (s, 3H).

Example 4: The mixture of 4A (30 mg, 0.099 mmol), 2-cyano-N-(4-methoxyphenyl)acetamide (18.81 mg, 0.099 mmol), and ferric chloride (48.1 mg, 0.297 mmol) in propionic acid (0.5 mL) was heated at 140° C. for 2 h. The crude mixture was purified by preparative HPLC to afford Example 4 (19 mg, 37%). MS(ESI) m/z: 492.2 (M+H)$^+$. $^1$H NMR (500 MHz, DMSO-d$_6$) δ 10.21 (s, 1H), 8.00-8.05 (m, 2H), 7.52-7.59 (m, 3H), 7.46 (t, J=8.12 Hz, 4H), 7.23 (d, J=7.98 Hz, 2H), 6.85 (d, J=9.08 Hz, 2H), 6.52 (br. s., 1H), 3.71 (s, 3H), 2.78 (br. s., 3H), 2.31 (s, 3H).

Example 5

N-(4-Ethoxyphenyl)-2-oxo-4-(p-tolyl)-6-(4-(4,4,4-trifluorobutoxy)phenyl)-1,2-dihydropyridine-3-carboxamide

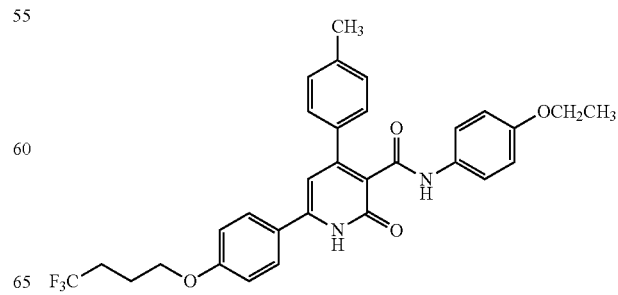

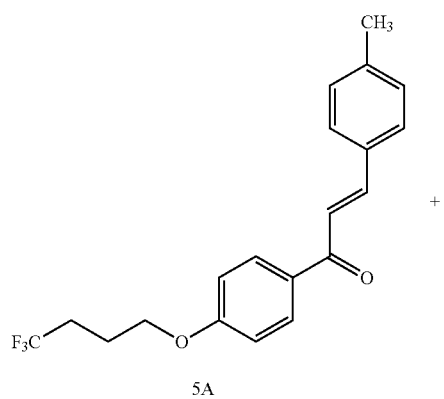

5A

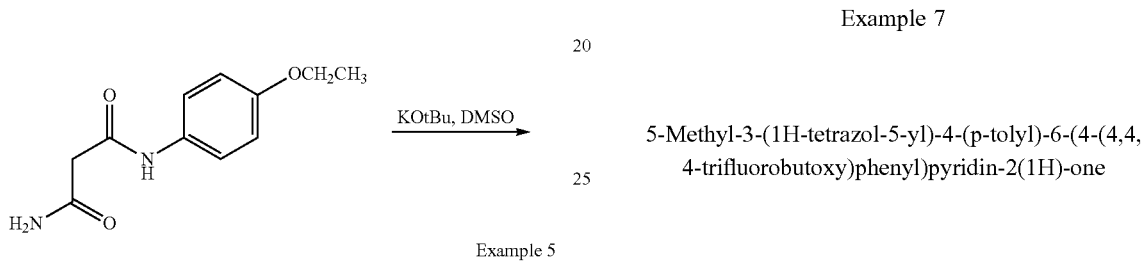

Example 5

5A. (E)-3-(p-Tolyl)-1-(4-(4,4,4-trifluorobutoxy)phenyl)prop-2-en-1-one: 5A was prepared to according to Example 1A. MS(ESI) m/z: 349.3 (M+H)+.

Example 5: To a solution of 5A (500 mg, 1.435 mmol) in DMSO (8 mL) at rt was added potassium tert-butoxide (644 mg, 5.74 mmol). The reaction was stirred at rt in open air for 4 h. The reaction was diluted with water and acidified with 1 N HCl. The solid was collected by filtration and dried to yield Example 5 (480 mg, 61%). MS(ESI) m/z: 551.5 (M+H)+. $^1$H NMR (400 MHz, CDCl$_3$) δ 7.72 (d, J=8.58 Hz, 2H), 7.39 (d, J=8.36 Hz, 2H), 7.29-7.32 (m, 2H), 7.23 (s, 2H), 6.89 (d, J=8.80 Hz, 2H), 6.78 (d, J=9.02 Hz, 2H), 6.62 (s, 1H), 3.99 (q, J=6.97 Hz, 2H), 3.80 (t, J=7.15 Hz, 2H), 2.42 (s, 3H), 2.22-2.35 (m, 2H), 1.97-2.06 (m, 2H), 1.39 (t, J=6.93 Hz, 3H).

Example 6

5-Bromo-3-(1H-tetrazol-5-yl)-4-(p-tolyl)-6-(4-(4,4,4-trifluorobutoxy)phenyl)pyridin-2(1H)-one

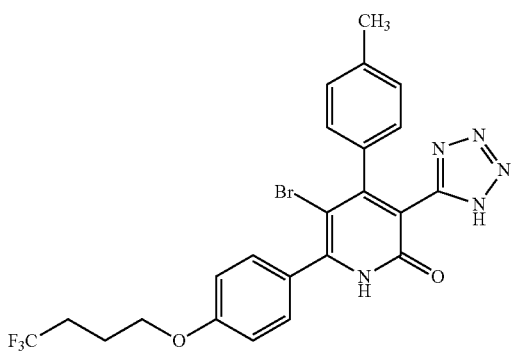

6A. 3-(1H-Tetrazol-5-yl)-4-(p-tolyl)-6-(4-(4,4,4-trifluorobutoxy)phenyl)pyridin-2(1H)-one: Intermediate 6A was prepared to according to Example 1. MS(ESI) m/z: 456.4 (M+H)+.

Example 6: To a solution of 6A (23 mg, 0.051 mmol) in DMF (1 mL) at rt was added NBS (8.99 mg, 0.051 mmol) in portions. The reaction was stirred at rt for 30 min and purified by preparative HPLC to yield Example 6 (19.2 mg, 70%). MS(ESI) m/z: 536.3 (M+H)+. $^1$H NMR (400 MHz, CD$_3$OD) δ 7.61 (d, J=8.80 Hz, 2H), 7.10-7.21 (m, 4H), 7.05 (d, J=7.92 Hz, 2H), 4.18 (t, J=6.05 Hz, 2H), 2.38-2.50 (m, 2H), 2.35 (s, 3H), 2.05-2.15 (m, 2H).

Example 7

5-Methyl-3-(1H-tetrazol-5-yl)-4-(p-tolyl)-6-(4-(4,4,4-trifluorobutoxy)phenyl)pyridin-2(1H)-one Example 7: To a microwave vial was added Example 6 (19 mg, 0.036 mmol), palladium(II) acetate (0.399 mg, 1.778 μmol), tri-o-tolylphosphine (1.136 mg, 3.73 μmol) and DMF (1 mL). The mixture was purged with Ar and tetramethylstannane (0.049 mL, 0.356 mmol) was added. The mixture was purged with Ar again and then sealed. The reaction was then stirred at 110° C. in microwave for 25 mins. Palladium(II) acetate (0.399 mg, 1.778 μmol) and tri-o-tolylphosphine (1.136 mg, 3.73 μmol) were added and purged with Ar. Tetramethylstannane (0.049 mL, 0.356 mmol) was added and the reaction was purged with Ar and sealed. The reaction was heated at 150 C under microwave conditions for 20 min. The mixture was diluted with 1 mL MeOH, filtered and purified by preparative HPLC to afford Example 7 (4.8 mg, 27%). MS(ESI) m/z: 470.2 (M+H)+. $^1$H NMR (500 MHz, DMSO-d$_6$) δ 7.45 (d, J=8.24 Hz, 2H), 7.09 (d, J=7.63 Hz, 2H), 7.06 (d, J=8.55 Hz, 2H), 6.95 (d, J=7.63 Hz, 2H), 4.09 (t, J=5.80 Hz, 2H), 2.33-2.46 (m, 2H), 2.23 (s, 3H), 1.87-2.01 (m, 2H), 1.64 (s, 3H).

Example 8

6-Cyclohexyl-4-(2-(dimethylamino)thiazol-5-yl)-N-(4-ethoxyphenyl)-2-oxo-1,2-dihydropyridine-3-carboxamide

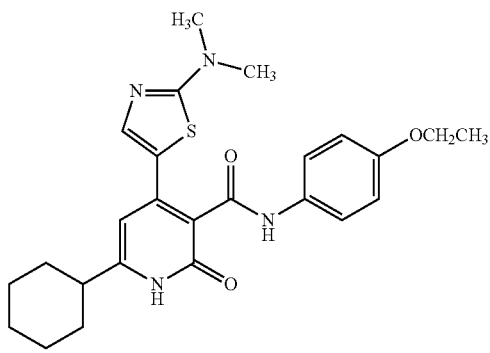 [SMILES: CCOc1ccc(NC(=O)c2c(-c3cnc(N(C)C)s3)cc(C3CCCCC3)[nH]c2=O)cc1]

and

Example 9

4-(2-(Dimethylamino)thiazol-5-yl)-N-(4-ethoxyphenyl)-6-(1-hydroxycyclohexyl)-2-oxo-1,2-dihydropyridine-3-carboxamide

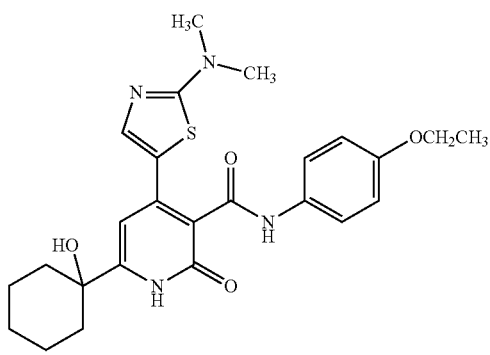 [SMILES: CCOc1ccc(NC(=O)c2c(-c3cnc(N(C)C)s3)cc(C3(O)CCCCC3)[nH]c2=O)cc1]

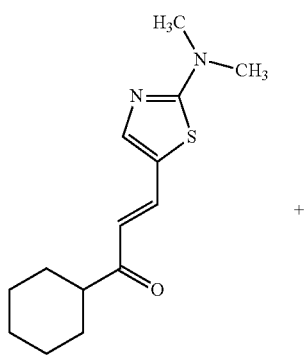

8A

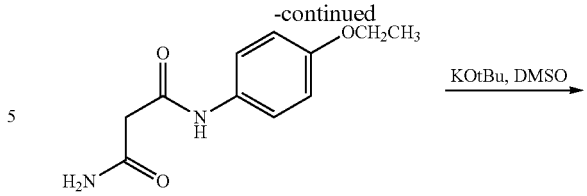

Example 8 + Example 9

8A. (E)-1-Cyclohexyl-3-(2-(dimethylamino)thiazol-5-yl)prop-2-en-1-one: 8A was prepared according to Example 1A. $^1$H NMR (400 MHz, CDCl$_3$) δ 7.62 (d, J=15.19 Hz, 1H), 7.42 (s, 1H), 6.17 (d, J=15.19 Hz, 1H), 3.18 (s, 6H), 2.50-2.60 (m, 1H), 1.78-1.92 (m, 4H), 1.70 (d, J=10.78 Hz, 1H), 1.18-1.48 (m, 5H).

Example 8 and Example 9: To a solution of 8A (30 mg, 0.113 mmol) and N$^1$-(4-ethoxyphenyl)malonamide (25.2 mg, 0.113 mmol) in DMSO (1 mL) at rt was added potassium tert-butoxide (50.9 mg, 0.454 mmol). The reaction was stirred at rt for 3 h. The reaction was neutralized with 1 N HCl, filtered and purified by preparative HPLC to afford Example 8 (2.7 mg, 5%) and Example 9 (9.1 mg, 16%).

Example 8: MS(ESI) m/z: 467.2 (M+H)$^+$. $^1$H NMR (500 MHz, DMSO-d$_6$) δ 10.23 (s, 1H), 7.63 (s, 1H), 7.55 (d, J=8.85 Hz, 2H), 6.87 (d, J=8.85 Hz, 2H), 6.17 (s, 1H), 3.98 (q, J=6.71 Hz, 2H), 3.00 (s, 4H), 1.79 (br. s., 3H), 1.67 (d, J=11.29 Hz, 1H), 1.44-1.57 (m, 3H), 1.16-1.38 (m, 7H).

Example 9: MS(ESI) m/z: 483.2 (M+H)+. $^1$H NMR (500 MHz, DMSO-d$_6$) δ 10.27 (s, 1H), 7.59 (s, 1H), 7.56 (d, J=8.85 Hz, 2H), 6.88 (d, J=8.85 Hz, 2H), 6.44 (br. s., 1H), 3.98 (q, J=6.82 Hz, 2H), 3.01 (s, 6H), 1.82-1.93 (m, 2H), 1.40-1.73 (m, 8H), 1.31 (t, J=6.87 Hz, 3H).

Example 10

4-(2-(Dimethylamino)thiazol-5-yl)-N-(4-ethoxyphenyl)-6-(1-fluorocyclohexyl)-2-oxo-1,2-dihydropyridine-3-carboxamide

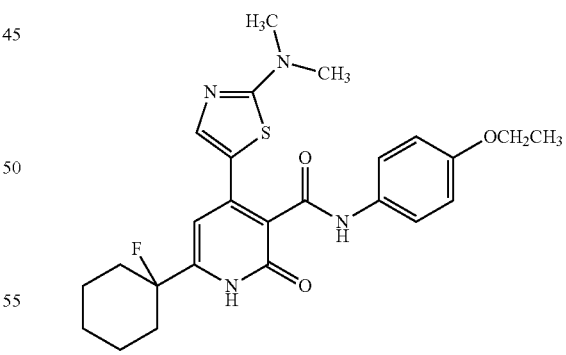

Example 10: To a solution of Example 9 (6.94 mg, 0.014 mmol) in dry DCM (2 mL) under Ar at 0° C. was added DAST (2.85 μL, 0.022 mmol) dropwise. The reaction was stirred at 0° C. for 1 h. LCMS indicated completion of the reaction. The reaction was concentrated. The residue was dissolved in DMF/MeOH, filtered and purified by preparative HPLC to afford Example 10 (3 mg, 42%). MS(ESI) m/z: 485.2 (M+H)$^+$. $^1$H NMR (500 MHz, DMSO-d$_6$) δ 10.30 (s, 1H), 7.64 (s, 1H), 7.52 (d, J=8.55 Hz, 2H), 6.87 (d, J=8.55

Hz, 2H), 6.45 (br. s., 1H), 3.97 (q, J=6.82 Hz, 2H), 2.99 (s, 6H), 1.81-2.08 (m, 4H), 1.47-1.71 (m, 5H), 1.29 (t, J=6.87 Hz, 3H), 1.25-1.38 (m, 1H).

Example 11

4-(4-(tert-Butyl)phenyl)-2-oxo-6-(4-(4,4,4-trifluorobutoxy)phenyl)-1,2-dihydropyridine-3-carboxylic acid 11A. (E)-3-(4-(tert-Butyl)phenyl)-1-(4-(4,4,4-trifluorobutoxy)phenyl)prop-2-en-1-one: 11A was prepared according to Example 1A. $^1$H NMR (400 MHz, CDCl$_3$) δ 8.03 (d, J=8.8 Hz, 2H), 7.80 (d, J=15.6 Hz, 1H), 7.59 (d, J=8.1 Hz, 2H), 7.50 (d, J=15.6 Hz, 1H), 7.44 (d, J=8.4 Hz, 2H), 6.97 (d, J=8.8 Hz, 2H), 4.11 (t, J=6.1 Hz, 2H), 2.47-2.25 (m, 2H), 2.10 (dd, J=9.5, 6.4 Hz, 2H), 1.43-1.29 (m, 9H).

11B. 4-(4-(tert-Butyl)phenyl)-2-oxo-6-(4-(4,4,4-trifluorobutoxy)phenyl)-1,2,5,6-tetrahydropyridine-3-carboxylic acid: A solution of 11A (150 mg, 0.384 mmol) and methyl 3-amino-3-oxopropanoate (49.5 mg, 0.423 mmol) in DMSO (5 mL) at rt was bubbled with air for 5 min. Potassium tert-butoxide (172 mg, 1.537 mmol) was added. The reaction mixture was allowed to stir for 20 min. H$_2$O (5 mL) and 4 drops of conc. HCl was added. The solid was collected to give the product as yellow solid. The crude product was purified by preparative HPLC to afford 11B (20 mg, 11%). MS(ESI) m/z: 476.2 (M+H)$^+$.

Example 11: To a solution of 11B (20 mg, 0.042 mmol) in acetonitrile (1 mL) was added CAN (23.06 mg, 0.042 mmol) in water (0.2 mL). The resulting mixture was stirred for 20 min. The crude product was purified by preparative HPLC to afford Example 11 (2 mg, 10%). MS(ESI) m/z: 476.2 (M+H)$^+$. $^1$H NMR (400 MHz, CD$_3$OD δ 7.87-7.72 (m, 2H), 7.56-7.46 (m, 2H), 7.44-7.32 (m, 2H), 7.19-7.05 (m, 2H), 6.70 (s, 1H), 4.17 (t, J=6.1 Hz, 2H), 2.52-2.32 (m, 2H), 2.19-2.02 (m, 2H), 1.39 (s, 9H).

Example 12

4-(4-(tert-Butyl)phenyl)-N-(cyclopropylsulfonyl)-2-oxo-6-(4-(4,4,4-trifluorobutoxy)phenyl)-1,2-dihydropyridine-3-carboxamide

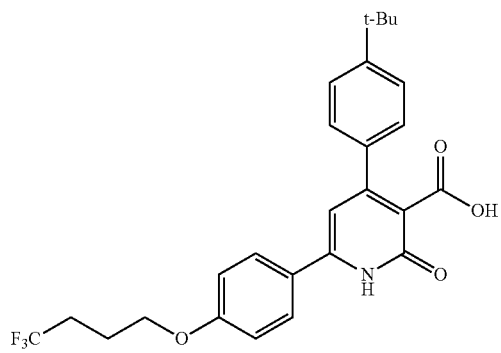 [SMILES: CC(C)(C)c1ccc(-c2cc(-c3ccc(OCCCC(F)(F)F)cc3)[nH]c(=O)c2C(=O)O)cc1]
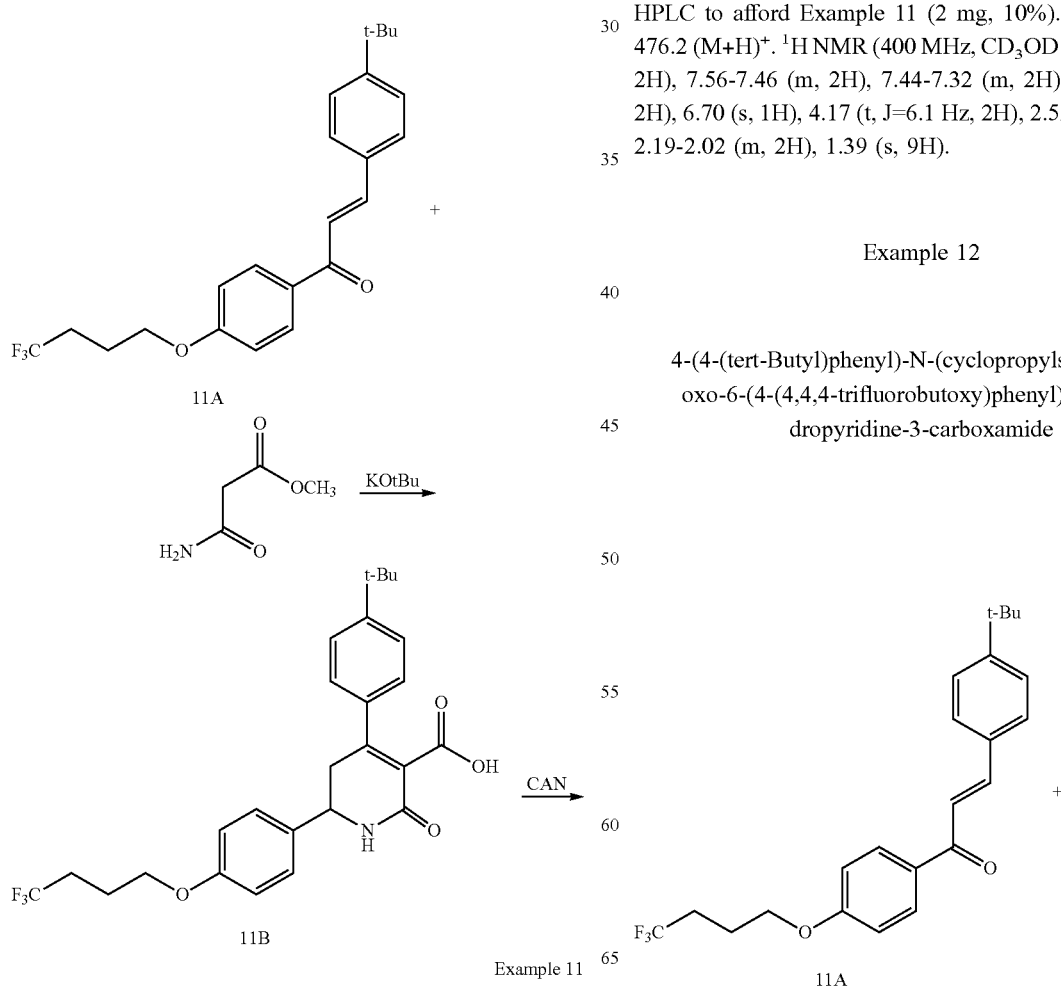

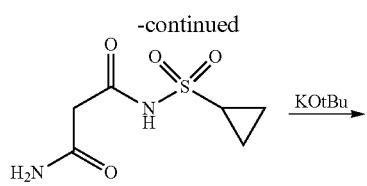

Intermediate 5

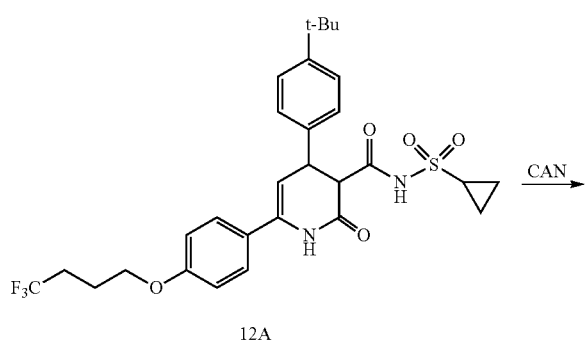

12A

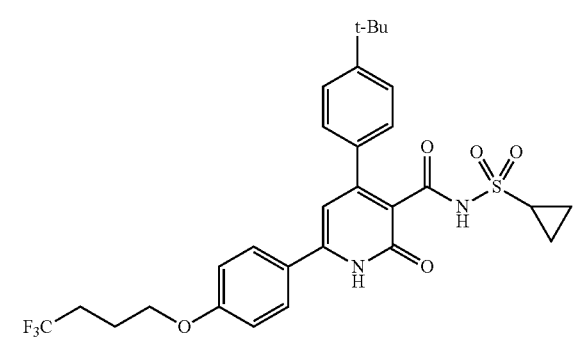 [SMILES: CC(C)(C)c1ccc(-c2cc(-c3ccc(OCCCC(F)(F)F)cc3)[nH]c(=O)c2C(=O)NS(=O)(=O)C2CC2)cc1]

12A. 4-(4-(tert-Butyl)phenyl)-N-(cyclopropylsulfonyl)-2-oxo-6-(4-(4,4,4-trifluorobutoxy)phenyl)-1,2,3,4-tetrahydropyridine-3-carboxamide: To a solution of 11A (85 mg, 0.218 mmol) and Intermediate 5 (45 mg, 0.218 mmol) in DMSO (1 mL) at rt was added potassium tert-butoxide (98 mg, 0.871 mmol). The reaction mixture was allowed to stir for 1.5 h. H₂O (5 mL) and 4 drops of conc. HCl were added. Solid was collected to give the product as yellow solid. The crude product was purified by preparative HPLC to afford 12A (5 mg, 4%). MS(ESI) m/z: 579.3 (M+H)⁺.

Example 12: To a solution of 12A (5 mg, 8.64 μmol) in acetonitrile (0.8 mL) was added CAN (4.74 mg, 8.64 μmol) in water (0.2 mL). The resulting mixture was stirred at rt for 10 min. The crude product was purified by preparative HPLC to afford Example 12 (0.9 mg, 17%). MS(ESI) m/z: 579.3 (M+H)⁺. ¹H NMR (400 MHz, CD₃OD) δ 7.80-7.70 (m, 2H), 7.59-7.51 (m, 2H), 7.49-7.43 (m, 2H), 7.17-7.08 (m, 2H), 6.65 (bs, 1H), 4.17 (t, J=6.1 Hz, 2H), 2.90-2.83 (m, 1H), 2.59-2.28 (m, 2H), 2.20-2.00 (m, 2H), 1.38 (s, 9H). 1.23-1.15 (m, 2H), 1.14-0.96 (m, 2H).

Example 13

3-(1H-Tetrazol-5-yl)-4-(p-tolyl)-6-(4-(4,4,4-trifluorobutoxy)phenyl)pyridin-2(1H)-one

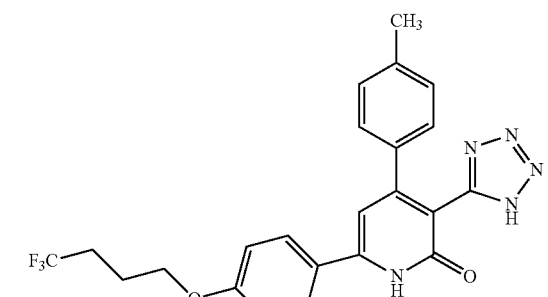

13A

Example 13

Example 13: 13A (17 mg, 0.032 mmol, prepared according to WO 13/082345) and sodium ethoxide (41.9 mg, 0.129 mmol) were stirred in EtOH (2 mL) in a microwave vial. The reaction mixture was stirred and irradiated under microwave reactor at 180° C. for 25 min. The crude mixture was purified by preparative HPLC to yield Example 13 (4.3 mg, 29%). MS(ESI) m/z: 456.5 (M+H)⁺. ¹H NMR (400 MHz, CD₃OD) δ 7.85-7.77 (m, 2H), 7.25-7.06 (m, 6H), 6.75 (s, 1H), 4.17 (t, J=6.1 Hz, 2H), 2.50-2.38 (m, 2H), 2.36 (s, 3H), 2.22-2.00 (m, 2H).

Example 14

N-(2-Oxo-6-(4-pentylphenyl)-4-(p-tolyl)-1,2-dihydropyridin-3-yl)benzamide

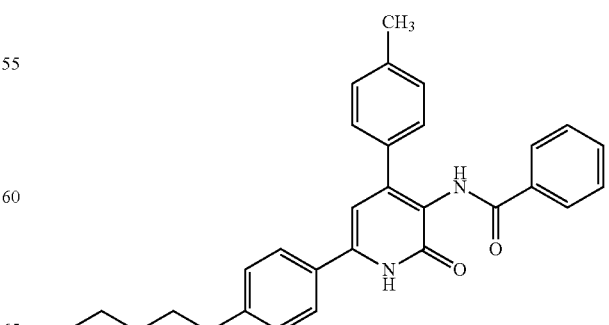

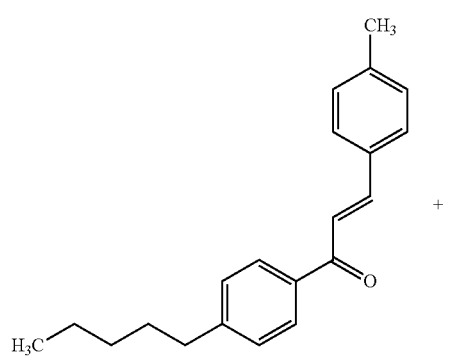

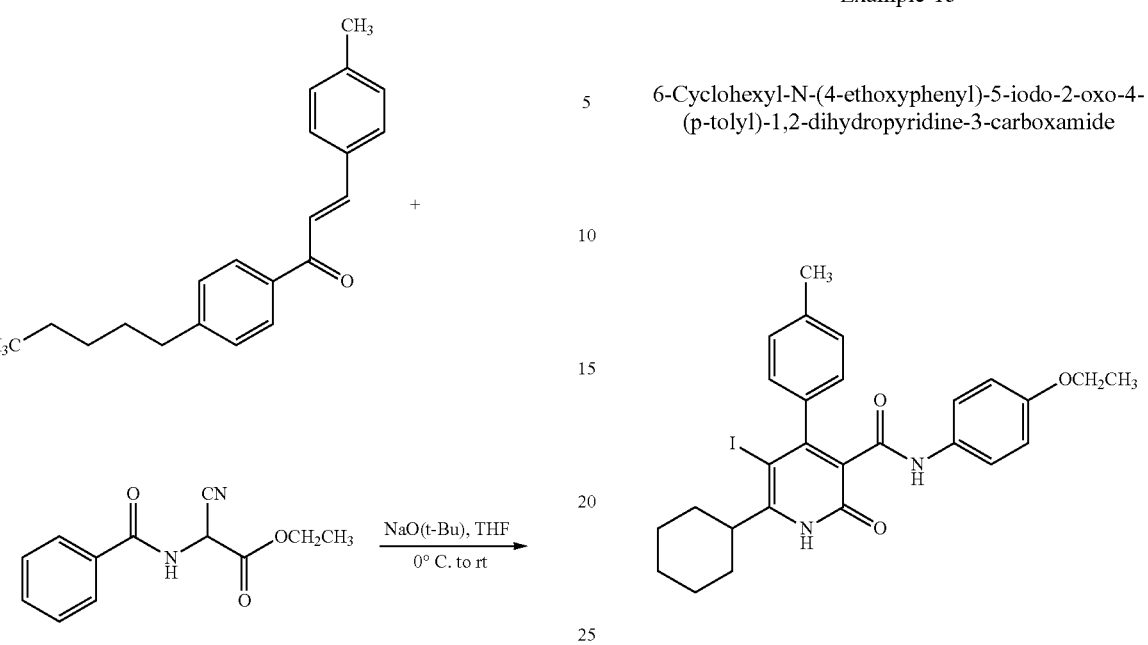

Example 15

6-Cyclohexyl-N-(4-ethoxyphenyl)-5-iodo-2-oxo-4-(p-tolyl)-1,2-dihydropyridine-3-carboxamide Example 15: To a suspension of Example 28 (30 mg, 0.070 mmol) in DMF (1 mL) at rt was added NIS (23.5 mg, 0.105 mmol). The reaction was heated to 130° C. under microwave conditions for 30 min. The reaction was diluted with MeOH (1 mL), filtered, and purified by preparative HPLC to yield Example 15 (20 mg, 49% yield). $^1$H NMR (400 MHz, CDCl$_3$) δ 9.35 (br. s., 1H), 7.18-7.27 (m, 4H), 7.05 (d, J=7.70 Hz, 2H), 6.75 (d, J=8.58 Hz, 2H), 3.91-4.02 (m, 2H), 3.21 (t, J=11.88 Hz, 1H), 2.41 (s, 3H), 1.80-1.98 (m, 4H), 1.51-1.73 (m, 4H), 1.37 (t, J=6.82 Hz, 3H), 1.17-1.45 (m, 2H). MS(ESI) m/z: 557.1 (M+H)$^+$.

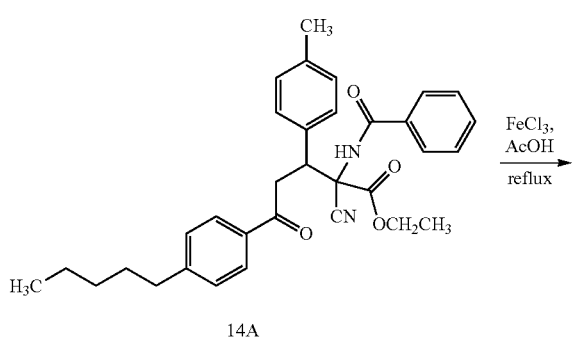

14A

Example 14

14A. Ethyl 2-benzamido-2-cyano-5-oxo-5-(4-pentylphenyl)-3-(p-tolyl) pentanoate: To a solution of ethyl 2-benzamido-2-cyanoacetate (27 mg, 0.12 mmol) and (E)-1-(4-pentylphenyl)-3-(p-tolyl)prop-2-en-1-one (34 mg, 0.12 mmol) in THF (3 mL) at 0° C. was added sodium tert-butoxide (0.559 mg, 5.81 µmol). The reaction was warmed to rt and stirred overnight. The mixture was concentrated and purified by preparative HPLC to yield 14A (22 mg, 36%). MS(ESI) m/z: 525.6 (M+H)$^+$.

Example 14: A mixture of 14A (22 mg, 0.042 mmol) and ferric chloride (14 mg, 0.084 mmol) in acetic acid (1 mL) was refluxed for 4 h. The crude product was purified by preparative HPLC to give Example 14 (4.4 mg, 22%). $^1$H NMR (500 MHz, DMSO-d$_6$) δ 9.47 (s, 1H), 7.80 (d, J=7.32 Hz, 2H), 7.70 (d, J=7.93 Hz, 2H), 7.49-7.58 (m, 1H), 7.38-7.48 (m, 4H), 7.29 (d, J=7.93 Hz, 2H), 7.17 (d, J=7.93 Hz, 2H), 6.54 (br. s., 1H), 2.59 (t, J=7.48 Hz, 2H), 2.25 (s, 3H), 1.47-1.60 (m, 2H), 1.27 (br. s., 4H), 0.84 (t, J=6.71 Hz, 3H). MS(ESI) m/z: 451.3 (M+H)$^+$.

Example 16

N-(2-Oxo-4-(p-tolyl)-6-(4-(4,4,4-trifluorobutoxy)phenyl)-1,2-dihydropyridin-3-yl)-2H-tetrazole-5-carboxamide

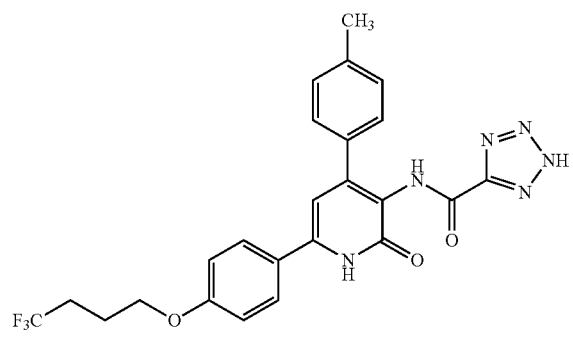 [SMILES: Cc1ccc(-c2cc(-c3ccc(OCCCC(F)(F)F)cc3)[nH]c(=O)c2NC(=O)c2nn[nH]n2)cc1]

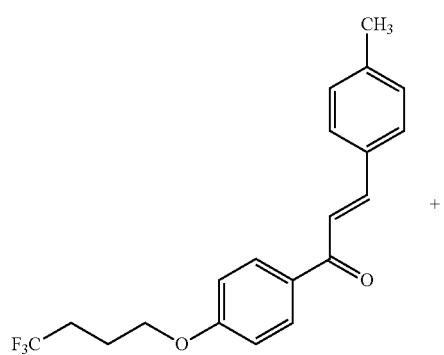

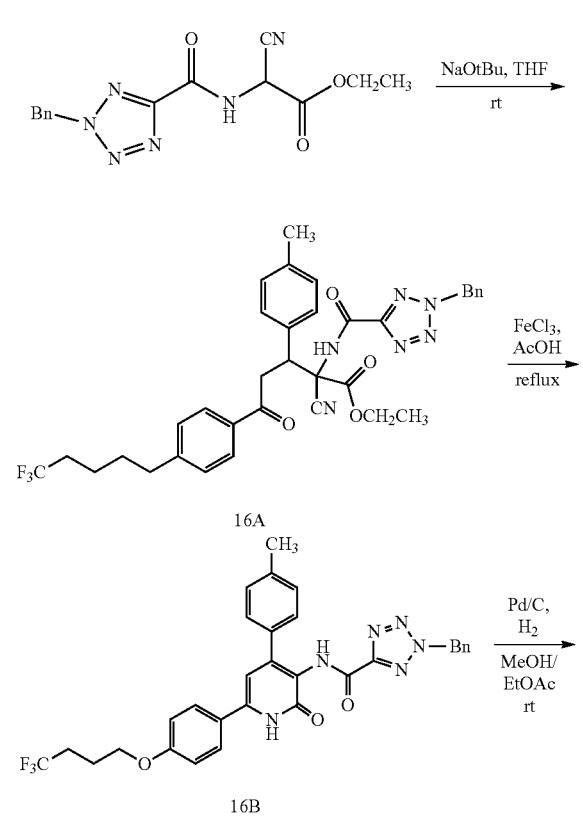

Example 16

16A. Ethyl 2-(2-benzyl-2H-tetrazole-5-carboxamido)-2-cyano-5-oxo-3-(p-tolyl)-5-(4-(4,4,4-trifluorobutoxy)phenyl)pentanoate: To a solution of 5A (80 mg, 0.23 mmol) and ethyl 2-(2-benzyl-2H-tetrazole-5-carboxamido)-2-cyanoacetate (72 mg, 0.23 mmol) in THF (3 mL) at rt was added sodium tert-butoxide (1.1 mg, 0.011 mmol). The reaction was stirred overnight. The mixture was concentrated and purified by preparative HPLC to yield 16A (10 mg, 7%). MS(ESI) m/z: 663.5 (M+H)$^+$.

16B. 2-Benzyl-N-(2-oxo-4-(p-tolyl)-6-(4-(4,4,4-trifluorobutoxy)phenyl)-1,2-dihydropyridin-3-yl)-2H-tetrazole-5-carboxamide: A mixture of 16A (10 mg, 0.015 mmol) and ferric chloride (4.9 mg, 0.030 mmol) in acetic acid (0.5 mL) was refluxed for 2 h. The reaction was cooled to rt, diluted with MeOH, filtered, and purified by preparative HPLC to yield 16B (3 mg, 34%). MS(ESI) m/z: 589.4 (M+H)$^+$.

Example 16: To a solution of 16B (3 mg, 5 μmol) in MeOH (5 mL) and EtOAc (1 mL) was added Pd/C (5.4 mg, 5.1 μmol). The reaction was charged with a H$_2$ balloon and stirred at rt for 1 h. The mixture was filtered through CELITE® and concentrated. The residue was purified by preparative HPLC to yield Example 16 (0.9 mg, 34%). $^1$H NMR (400 MHz, DMSO-d$_6$) δ 12.15 (br. s., 1H), 10.21 (br. s., 1H), 7.81 (br. s., 2H), 7.49 (d, J=7.92 Hz, 2H), 7.21 (d, J=8.14 Hz, 2H), 7.07 (d, J=8.80 Hz, 2H), 6.48 (br. s., 1H), 4.13 (t, J=6.27 Hz, 2H), 2.40-2.47 (m, 2H), 2.31 (s, 3H), 1.92-2.03 (m, 2H). MS(ESI) m/z: 499.4 (M+H)$^+$.

Example 17

5-Fluoro-3-(1H-tetrazol-5-yl)-4-(p-tolyl)-6-(4-(4,4,4-trifluorobutoxy)phenyl)pyridin-2(1H)-one

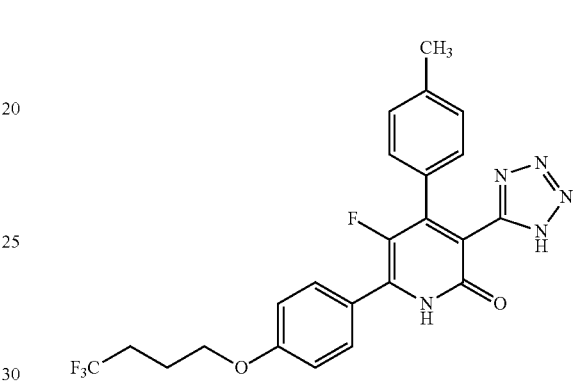

Example 17: To a solution of 6A (37 mg, 0.081 mmol) in DMF (0.5 mL) was added SELECTFLUOR® (31 mg, 0.088 mmol). The mixture was heated to 110° C. under microwave irradiation for 20 min. The mixture was diluted with MeOH and purified by preparative HPLC to give Example 17 (3.9 mg, 10%). $^1$H NMR (500 MHz, DMSO-d$_6$) δ 7.85 (br. s., 2H), 7.04-7.19 (m, 6H), 4.13 (t, J=5.95 Hz, 2H), 2.45 (dd, J=11.29, 16.48 Hz, 2H), 2.29 (s, 3H), 1.91-2.05 (m, 2H). MS(ESI) m/z: 474.2 (M+H)$^+$.

Example 18

6-(4-(4,4-Dimethylcyclohexyl)phenyl)-3-(2H-tetrazol-5-yl)-4-(p-tolyl)pyridin-2(1H)-one

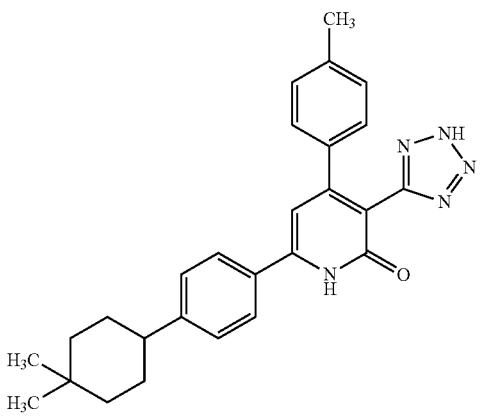 [SMILES: Cc1ccc(-c2cc(-c3ccc(C4CCC(C)(C)CC4)cc3)[nH]c(=O)c2-c2nn[nH]n2)cc1]

Example 18: A mixture of Example 86 (7.2 mg, 0.016 mmol) and Pd/C (10 mg, 9.40 μmol) in MeOH (10 mL) was hydrogenated overnight under stirring at 1 atm. The reaction mixture was then filtered and concentrated. The residue was purified by preparative HPLC to give Example 18 (4.8 mg, 66%). ¹H NMR (500 MHz, DMSO-d$_6$) δ 7.82 (d, J=7.8 Hz, 2H), 7.41 (d, J=7.8 Hz, 2H), 7.15-7.06 (m, 4H), 6.73 (s, 1H), 2.28 (s, 3H), 1.67-1.60 (m, 4H), 1.51-1.44 (m, 2H), 1.37-1.31 (m, 2H), 0.99 (s, 3H), 0.95 (s, 3H). MS(ESI) m/z: 440.5 (M+H)⁺.

Example 19

5-Chloro-3-(1H-tetrazol-5-yl)-4-(p-tolyl)-6-(4-(4,4,4-trifluorobutoxy)phenyl)pyridin-2(1H)-one

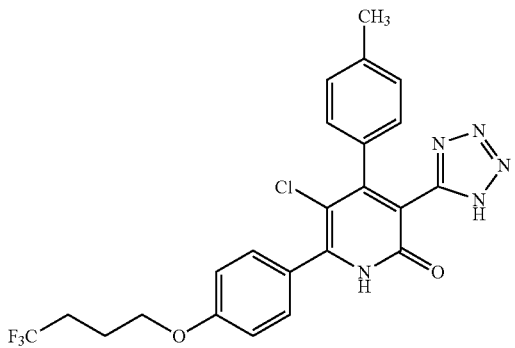 [SMILES: Cc1ccc(-c2c(Cl)c(-c3ccc(OCCCC(F)(F)F)cc3)[nH]c(=O)c2-c2nnn[nH]2)cc1]

Example 19: To a solution of 6A (32 mg, 0.070 mmol) in DMF (1 mL) was added NCS (14.1 mg, 0.105 mmol). The reaction was heated at 110° C. under microwave conditions for 30 min. The mixture was diluted with MeOH, filtered, and purified by preparative HPLC to give Example 19 (11.6 mg, 33%). ¹H NMR (500 MHz, DMSO-d$_6$) δ 7.61 (d, J=8.24 Hz, 2H), 7.12 (d, J=7.63 Hz, 2H), 7.08 (d, J=8.24 Hz, 2H), 7.01 (d, J=7.63 Hz, 2H), 4.12 (t, J=5.95 Hz, 2H), 2.38-2.47 (m, 2H), 2.26 (s, 3H), 1.90-2.01 (m, 2H). MS(ESI) m/z: 490.1 (M+H)⁺.

Example 20

4-(5-Ethylthiophen-2-yl)-6-(2-fluoro-4-(4,4,4-trifluorobutoxy)phenyl)-3-(2H-tetrazol-5-yl)pyridin-2(1H)-one

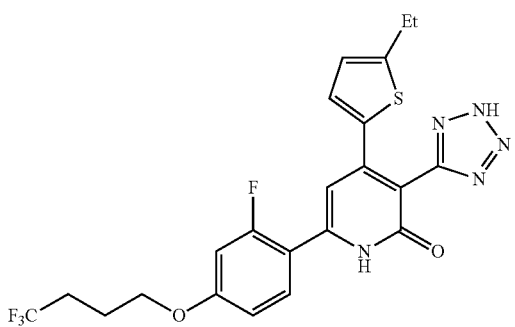 [SMILES: CCc1ccc(-c2cc(-c3ccc(OCCCC(F)(F)F)cc3F)[nH]c(=O)c2-c2nn[nH]n2)s1]

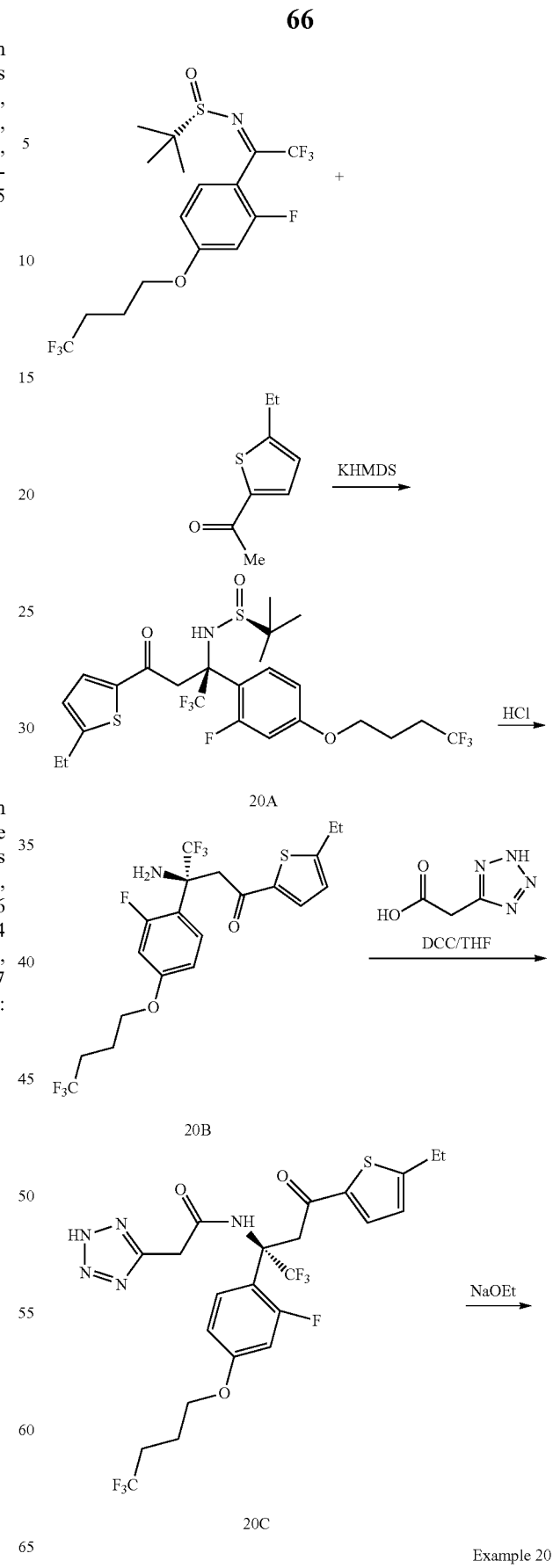

20A. (S)—N—((S)-4-(5-Ethylthiophen-2-yl)-1,1,1-trifluoro-2-(2-fluoro-4-(4,4,4-trifluorobutoxy)phenyl)-4-oxobutan-2-yl)-2-methylpropane-2-sulfinamide: A 1 M solution of KHMDS in THF (0.36 mL, 0.36 mmol) was added to a solution of 1-(5-ethylthiophen-2-yl)ethanone (54.9 mg, 0.356 mmol) in THF (3 mL) at −78° C. and the reaction mixture was stirred for 30 min. Then, a solution of (S,E)-2-methyl-N-(2,2,2-trifluoro-1-(2-fluoro-4-(4,4,4-trifluorobutoxy)phenyl)ethylidene)propane-2-sulfinamide (100 mg, 0.237 mmol) in THF (1.5 mL) was added and the reaction mixture was stirred at −78° C. for 1 h. The reaction was quenched with water, diluted with EtOAc, washed with brine, dried (MgSO$_4$), and concentrated. The crude was purified using silica gel chromatography to give 20A (101 mg, 74%). MS(ESI) m/z: 576.4 (M+H)$^+$.

20B. (S)-3-Amino-1-(5-ethylthiophen-2-yl)-4,4,4-trifluoro-3-(2-fluoro-4-(4,4,4-trifluorobutoxy)phenyl)butan-1-one: A solution of 20A (101 mg, 0.175 mmol) and 4 M HCl in dioxane (0.22 mL, 0.88 mmol) in MeOH (2 mL) was stirred at rt for 45 min and concentrated. The crude material was diluted with DCM, washed with sat. NaHCO$_3$, dried (MgSO$_4$), and concentrated to give 20B (83 mg, 100%) as a clear oil. MS(ESI) m/z: 472.4 (M+H)$^+$.

20C. (S)—N-(4-(5-Ethylthiophen-2-yl)-1,1,1-trifluoro-2-(2-fluoro-4-(4,4,4-trifluorobutoxy)phenyl)-4-oxobutan-2-yl)-2-(2H-tetrazol-5-yl)acetamide: To a solution of 20C (33 mg, 0.070 mmol) and 2-(2H-tetrazol-5-yl)acetic acid (35.9 mg, 0.280 mmol) in THF (3 mL) at 0° C. was added DCC (57.8 mg, 0.280 mmol). The resulting mixture was stirred at rt for 2 days. The solvent was evaporated and the crude mixture was taken up in EtOAc and washed with saturated NaHCO$_3$, 1 N HCl and brine. Drying (MgSO$_4$) and removal of solvent afforded a brown oil. The crude material was purified by preparative HPLC to give 20C (28 mg, 69%).

Example 20: A mixture of 20C (28 mg, 0.048 mmol) and sodium ethoxide (62.4 mg, 0.193 mmol) (21% in EtOH) in EtOH (4 mL) was heated at 180° C. for 25 min in a microwave reactor. A drop of 4 M HCl in dioxane was added and the solvent was evaporated. The crude product was dissolved in DMF and purified by preparative HPLC to give Example 20 (6.5 mg, 27%). $^1$H NMR (500 MHz, DMSO-d$_6$) δ 7.67 (t, J=8.9 Hz, 1H), 7.13-6.99 (m, 2H), 6.95 (d, J=8.6 Hz, 1H), 6.80 (d, J=3.7 Hz, 1H), 6.75 (s, 1H), 4.15 (t, J=6.3 Hz, 2H), 2.72 (q, J=7.6 Hz, 2H), 2.49-2.36 (m, 2H), 2.13-1.87 (m, 2H), 1.15 (t, J=7.5 Hz, 3H). MS(ESI) m/z: 494.3 (M+H)$^+$.

Example 21

4-(5-Ethylthiophen-2-yl)-N-(methylsulfonyl)-2-oxo-6-(4-(4,4,4-trifluorobutoxy)phenyl)-1,2-dihydropyridine-3-carboxamide

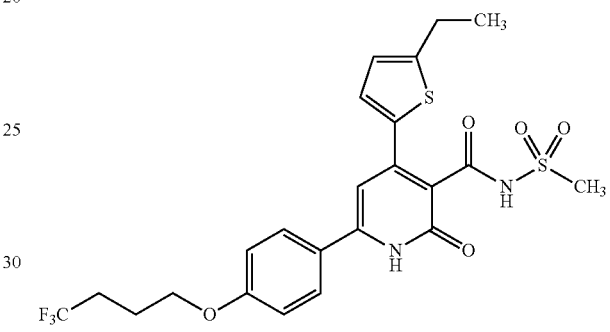

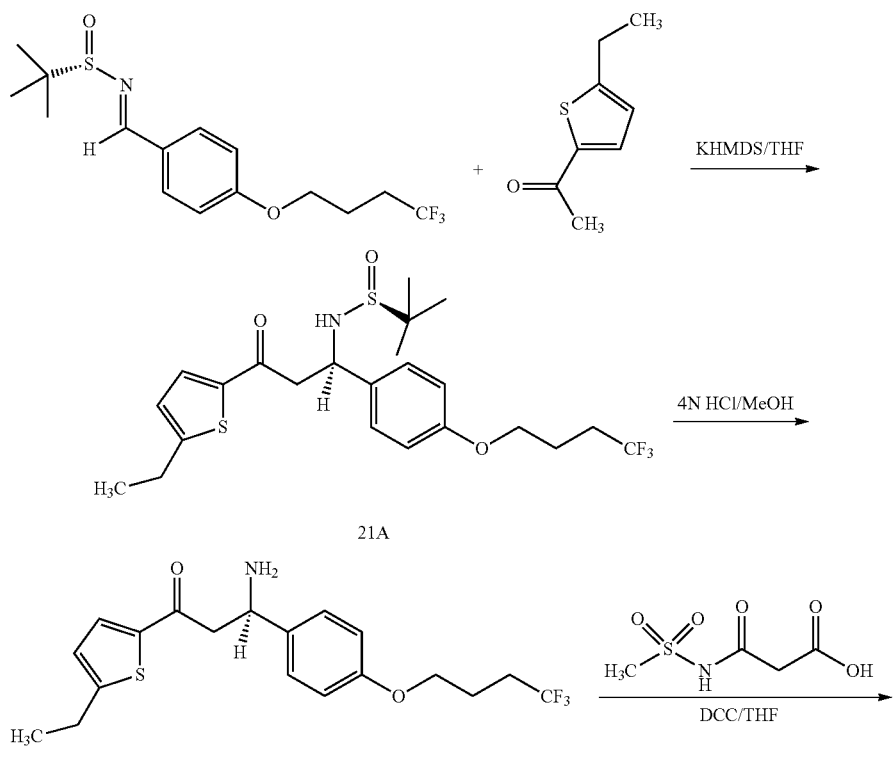

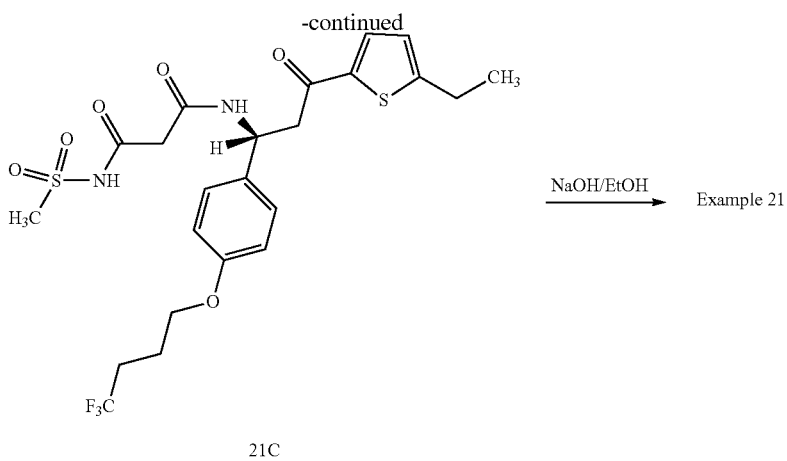

21C 21C was prepared in a manner analogous to Example 20 above.

Example 21. A solution of NaOEt (21% in EtOH) (0.112 mL, 0.301 mmol) was added to a solution of 21C (33 mg, 0.060 mmol) in EtOH (1 mL) and stirred at rt for 1 h. LCMS indicated no reaction. More NaOEt (21% in EtOH) (0.112 mL, 0.301 mmol) was added and the reaction was heated at 60° C. The mixture was concentrated, dissolved in DCM (1 mL) and TFA (0.5 mL) was added. The resulting mixture was stirred for 1 h. The mixture was purified by preparative HPLC (PHENOMENEX® Luna Axia 5μ C18 30×100 mm; 10 min gradient from 25% A: 75% B to 0% A: 100% B (A=90% H$_2$O/10% MeOH+0.1% TFA); (B=90% MeOH/10% H$_2$O+0.1% TFA); detection at 220 nm) to yield Example 21 (2.2 mg, 7%). $^1$H NMR (500 MHz, DMSO-d$_6$) δ 7.79 (d, J=8.24 Hz, 2H), 7.38 (d, J=3.66 Hz, 1H), 7.07 (d, J=8.85 Hz, 2H), 6.93 (d, J=3.36 Hz, 1H), 6.65 (br. s., 1H), 4.12 (t, J=6.10 Hz, 2H), 2.86 (q, J=7.32 Hz, 2H), 2.50 (br. s., 3H), 2.36-2.48 (m, 2H), 1.89-2.01 (m, 2H), 1.26 (t, J=7.48 Hz, 3H). MS(ESI) m/z: 529.2 (M+H)$^+$.

Example 22

6-(2-Chloro-4-(4,4,4-trifluorobutoxy)phenyl)-4-(5-ethylthiophen-2-yl)-3-(5-oxo-4,5-dihydro-1H-tetrazol-1-yl)pyridin-2(1H)-one

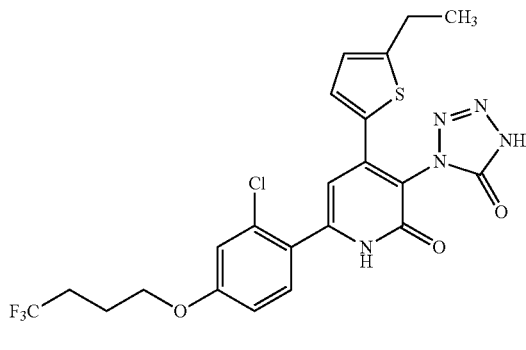 [SMILES: CCc1ccc(-c2cc(-c3ccc(OCCCC(F)(F)F)cc3Cl)[nH]c(=O)c2-n2nn[nH]c2=O)s1]

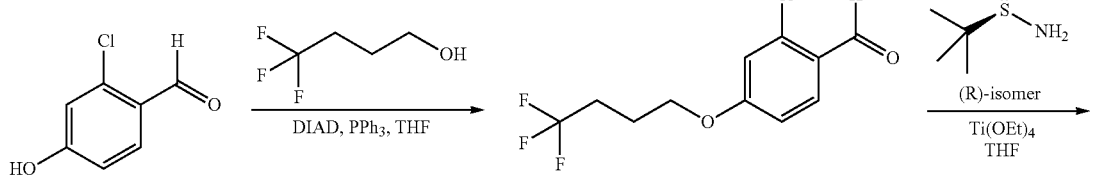

22A

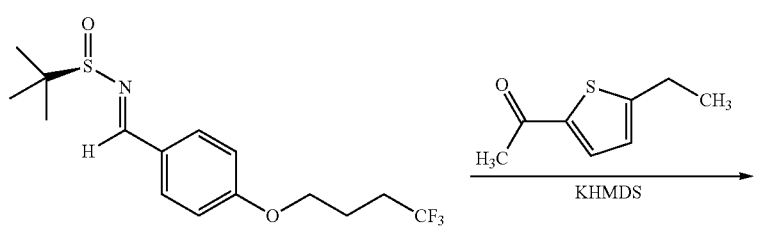

22B

-continued
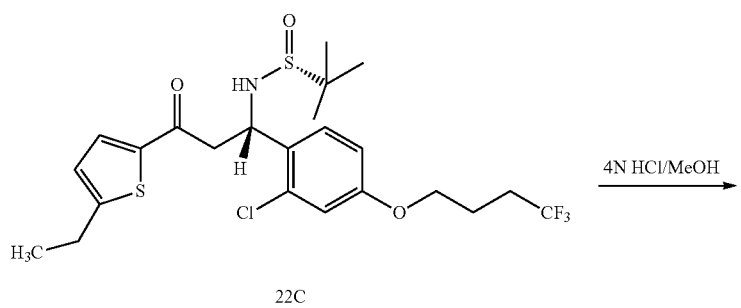
22C
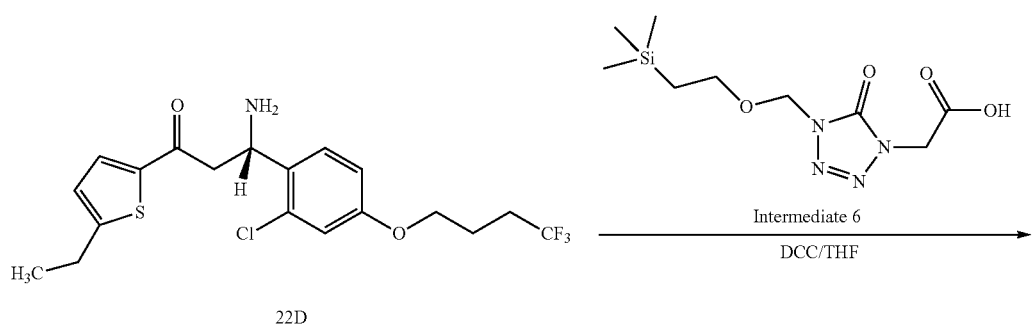
22D
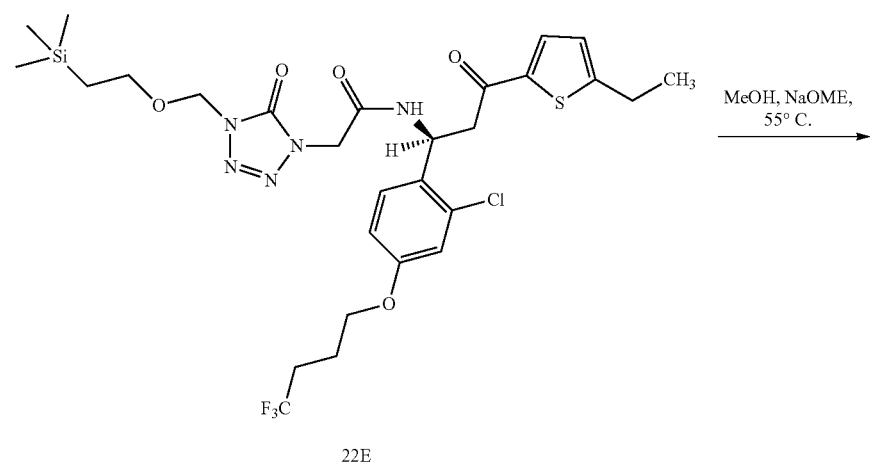
22E
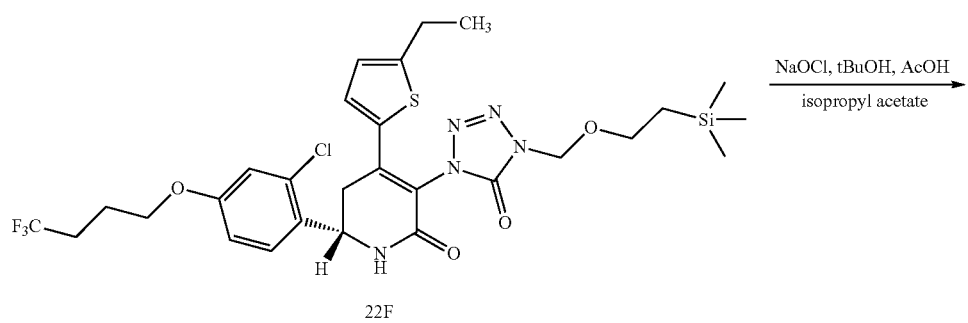
22F

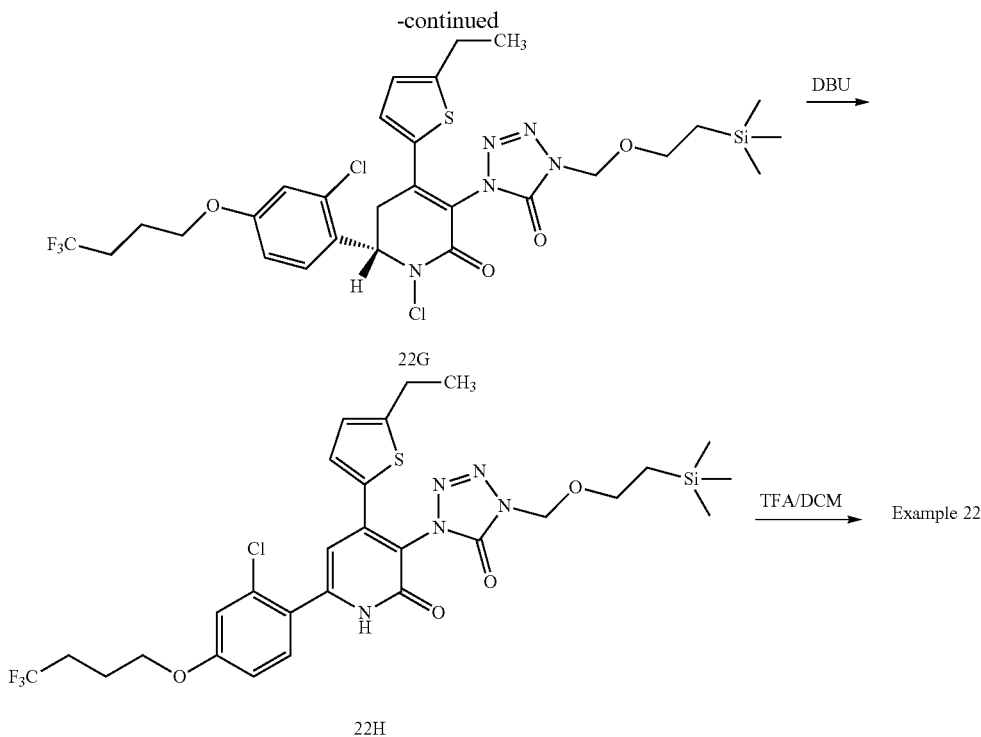

22A. 2-Chloro-4-(4,4,4-trifluorobutoxy)benzaldehyde: To a solution of 2-chloro-4-hydroxybenzaldehyde (1 g, 6.39 mmol), 4,4,4-trifluorobutan-1-ol (1.029 mL, 9.58 mmol) and DIAD (1.863 mL, 9.58 mmol) in THF (15 mL) was added Ph$_3$P (2.51 g, 9.58 mmol) and the reaction mixture stirred at RT overnight. The solvent was removed in vacuo to yield a crude yellow oil. Hexanes (100 mL) were added and the mixture was allowed to stand at RT for a few hours while solids appeared (Ph$_3$PO). The mixture was filtered and washed with hexanes. The filtrate was concentrated and purified by flash chromatography (220 g silica, 0 to 30% EtOAc-hexanes) to yield 21A (1 g, 59%). LCMS, [M+H]$^+$=267.0. $^1$H NMR (500 MHz, CDCl$_3$) δ 10.35 (d, J=0.55 Hz, 1H), 7.91 (d, J=8.80 Hz, 1H), 6.94 (d, J=2.48 Hz, 1H), 6.86-6.91 (m, 1H), 4.11 (t, J=5.91 Hz, 2H), 2.27-2.40 (m, 2H), 2.07-2.14 (m, 2H).

22B. (R,E)-N-(2-Chloro-4-(4,4,4-trifluorobutoxy)benzylidene)-2-methylpropane-2-sulfinamide: To a solution of 22A (250 mg, 0.938 mmol) and (R)-2-methylpropane-2-sulfinamide (114 mg, 0.938 mmol) in THF (8 mL) was added tetraethoxytitanium (0.786 mL, 3.75 mmol) at RT and the resulting mixture was stirred at RT for 2 h. The reaction was diluted with EtOAc and 1M citric acid solution was added to the reaction mixture. A large amount of white precipitate was formed. The resulting mixture was stirred for 20 min and filtered through a bed of CELITE®. The white precipitate was rinsed with EtOAc. The combined EtOAc solution was washed with brine, dried with Na$_2$SO$_4$, and evaporated in vacuo to give the crude product which was purified by flash chromatography (12 g, 0% to 100% EtOAc-Hexanes) to yield 22B (270 mg, 78%). LCMS, [M+H]$^+$=370.0. $^1$H NMR (400 MHz, CDCl$_3$) δ 8.95 (s, 1H), 8.03 (d, J=8.80 Hz, 1H), 6.95 (d, J=2.42 Hz, 1H), 6.83-6.91 (m, 1H), 4.08 (t, J=6.05 Hz, 2H), 2.25-2.40 (m, 2H), 2.06-2.15 (m, 2H), 1.27 (s, 9H).

22C. (R)—N—((S)-1-(2-Chloro-4-(4,4,4-trifluorobutoxy)phenyl)-3-(5-ethylthiophen-2-yl)-3-oxopropyl)-2-methylpropane-2-sulfinamide: Potassium bis(trimethylsilyl)amide (1.095 mL, 1.095 mmol) was added at −78° C. to a solution of 1-(5-ethylthiophen-2-yl)ethanone (169 mg, 1.095 mmol) in THF (3 mL) and stirred for 30 min. A solution of 22B (270 mg, 0.730 mmol) in THF (1.5 mL) was then added and stirred at −78° C. for 1 h. The reaction mixture was quenched with water, diluted with EtOAc, washed with brine, dried (MgSO$_4$), and concentrated. The crude product was purified using ISCO flash chromatography (silica gel/hexanes/ethyl acetate 100:0 to 50:50 gradient) to give 22C (272 mg, 71%). LCMS, [M+H]$^+$=524.3. $^1$H NMR (400 MHz, CDCl$_3$) δ 7.53 (d, J=3.96 Hz, 1H), 7.40 (d, J=8.80 Hz, 1H), 6.90 (d, J=2.42 Hz, 1H), 6.74-6.84 (m, 2H), 5.26 (td, J=4.73, 7.48 Hz, 1H), 5.10 (d, J=5.06 Hz, 1H), 3.99 (t, J=5.94 Hz, 2H), 3.43-3.56 (m, 1H), 3.28-3.39 (m, 1H), 2.86 (q, J=7.48 Hz, 2H), 2.22-2.38 (m, 2H), 1.96-2.11 (m, 2H), 1.31 (t, J=7.48 Hz, 3H), 1.24 (s, 9H).

22D. (S)-3-Amino-3-(2-chloro-4-(4,4,4-trifluorobutoxy)phenyl)-1-(5-ethylthiophen-2-yl)propan-1-one: A solution of 22C (272 mg, 0.519 mmol) and 4M HCl in dioxane (0.649 mL, 2.60 mmol) in MeOH (2 mL) was stirred at RT for 45 min and then concentrated. The mixture was diluted with DCM and the resulting suspension was washed with sat. NaHCO$_3$, brine, and concentrated to give 22D (180 mg, 83%) as a white solid. LCMS, [M+H]$^+$=420.0. $^1$H NMR (400 MHz, CDCl$_3$) δ 7.68 (d, J=8.58 Hz, 1H), 7.58 (d, J=3.74 Hz, 1H), 6.92 (d, J=2.64 Hz, 1H), 6.86 (dd, J=2.64, 8.58 Hz, 1H), 6.83 (d, J=3.74 Hz, 1H), 5.04 (dd, J=4.07, 8.69 Hz, 1H), 4.01 (t, J=5.94 Hz, 2H), 3.26-3.44 (m, 2H), 2.88 (q, J=7.41 Hz, 2H), 2.24-2.40 (m, 2H), 1.98-2.12 (m, 2H), 1.33 (t, J=7.48 Hz, 3H).

22E. (S)—N-(1-(2-Chloro-4-(4,4,4-trifluorobutoxy)phenyl)-3-(5-ethylthiophen-2-yl)-3-oxopropyl)-2-(5-oxo-4-((2-(trimethylsilyl)ethoxy)methyl)-4,5-dihydro-1H-tetrazol-1- yl)acetamide: To a mixture of 22D (100 mg, 0.238 mmol) and Intermediate 6 (98 mg, 0.357 mmol) in THF (3 mL) was added DCC (147 mg, 0.714 mmol). The resulting mixture was stirred at RT overnight. The mixture was filtered through CELITE® and rinsed with EtOAc. The filtrate was concentrated and purified by flash chromatography (0-100% EtOAc:hexanes) to yield 22E (143 mg, 89%) as a white solid. LCMS, [M+H]⁺=676.2.

22F. (S)-6-(2-Chloro-4-(4,4,4-trifluorobutoxy)phenyl)-4-(5-ethylthiophen-2-yl)-3-(5-oxo-4-((2-(trimethylsilyl)ethoxy)methyl)-4,5-dihydro-1H-tetrazol-1-yl)-5,6-dihydro-pyridin-2(1H)-one: 22E (140 mg, 0.207 mmol) was dissolved in MeOH (5 mL) in a 10 mL 1-neck pear-shaped flask that was equipped with a magnetic stirrer. NaOMe (25% in MeOH, 0.206 mL, 0.828 mmol) was added and the reaction mixture was stirred at 55° C. for 1 h. LCMS indicated ~20% of desired product formation. The reaction mixture was heated at 55° C. for another hour and HPLC indicated no major change. A few drops of conc. HCl were added and the mixture was concentrated and purified by preparative HPLC (PHENOMENEX® Luna Axia 5µ C18 30×100 mm; 10 min gradient from 15% A: 85% B to 0% A: 100% B (A=90% H₂O/10% MeOH+0.1% TFA); (B=90% MeOH/10% H₂O+0.1% TFA); detection at 220 nm) to yield 22F (15 mg, 11%). LCMS, [M+H]⁺=658.1. ¹H NMR (400 MHz, CD₃OD) δ 7.52 (d, J=8.58 Hz, 1H), 7.40 (dd, J=3.96, 8.14 Hz, 1H), 7.06 (dd, J=2.42, 6.60 Hz, 1H), 6.98 (ddd, J=2.53, 6.49, 8.80 Hz, 1H), 6.88 (t, J=3.85 Hz, 1H), 5.42 (d, J=1.54 Hz, 2H), 5.32-5.41 (m, 1H), 4.03-4.11 (m, 2H), 3.74-3.84 (m, 2H), 3.50-3.61 (m, 1H), 3.28-3.37 (m, 1H), 2.81 (q, J=7.48 Hz, 2H), 2.26-2.43 (m, 2H), 1.96-2.07 (m, 2H), 1.24 (t, J=7.59 Hz, 3H), 0.97-1.07 (m, 2H), 0.03 (s, 9H).

22G. (S)-1-Chloro-6-(2-chloro-4-(4,4,4-trifluorobutoxy)phenyl)-4-(5-ethylthiophen-2-yl)-3-(5-oxo-4-((2-(trimethylsilyl)ethoxy)methyl)-4,5-dihydro-1H-tetrazol-1-yl)-5,6-dihydropyridin-2(1H)-one:

Reference: Zhong, Y-L. et al., *Tetrahedron Lett.*, 46:1099-1101 (2005).

To a solution of 22F (7 mg, 10.63 µmol) and t-BuOH (0.509 µl, 5.32 µmol) in isopropyl acetate (1 mL) at 0° C. was added HOAc (0.609 µL, 10.63 µmol) and NaOCl (0.656 µl, 10.63 µmol). The reaction was stirred for 2 d at RT. The reaction was concentrated and purified by preparative HPLC (PHENOMENEX® Luna Axia 5µ C18 30×100 mm; 10 min gradient from 15% A: 85% B to 0% A: 100% B (A=90% H₂O/10% MeOH+0.1% TFA); (B=90% MeOH/10% H₂O+0.1% TFA); detection at 220 nm) to yield 22G (4.6 mg, 62%). LCMS, [M+H]⁺=692.0. ¹H NMR (400 MHz, CD₃OD) δ 7.26-7.50 (m, 2H), 7.10 (dd, J=2.53, 9.13 Hz, 1H), 6.99 (ddd, J=2.64, 8.80, 16.95 Hz, 1H), 6.89 (dd, J=4.18, 5.28 Hz, 1H), 5.66 (q, J=6.38 Hz, 1H), 5.44 (d, J=2.20 Hz, 2H), 4.07 (q, J=5.87 Hz, 2H), 3.90 (ddd, J=6.49, 8.03, 17.39 Hz, 1H), 3.75-3.83 (m, 2H), 3.57 (ddd, J=5.94, 13.15, 17.44 Hz, 1H), 2.80 (q, J=7.48 Hz, 2H), 2.29-2.43 (m, 2H), 1.98-2.07 (m, 2H), 1.23 (dt, J=1.32, 7.48 Hz, 3H), 0.97-1.05 (m, 2H), 0.04 (s, 9H).

22H. 6-(2-Chloro-4-(4,4,4-trifluorobutoxy)phenyl)-4-(5-ethylthiophen-2-yl)-3-(5-oxo-4-((2-(trimethylsilyl)ethoxy)methyl)-4,5-dihydro-1H-tetrazol-1-yl)pyridin-2(1H)-one:
To a solution of 22G (4.6 mg, 6.64 µmol) in THF (1 mL) at RT was added DBU (1 M in THF, 0.020 mL, 0.020 mmol). The reaction was stirred at RT for 1 h. LCMS indicated complete reaction. 1 N HCl (1 mL) was added and the mixture was diluted with EtOAc. The organic layer was separated, washed with brine, dried over MgSO₄ and concentrated. The crude product (22H) was carried on to the next step without purification. LCMS, [M+H]⁺=656.1.

Example 22. 6-(2-Chloro-4-(4,4,4-trifluorobutoxy)phenyl)-4-(5-ethylthiophen-2-yl)-3-(5-oxo-4,5-dihydro-1H-tetrazol-1-yl)pyridin-2(1H)-one: To a solution of 22H (4.3 mg, 6.55 µmol) in DCM (0.5 mL) was added TFA (0.151 mL, 1.966 mmol) carefully. The reaction was stirred at RT for 1 h and concentrated. The residue was dissolved in MeOH, filtered and purified by preparative HPLC (PHENOMENEX® Luna Axia 5µ C18 30×100 mm; 10 min gradient from 35% A: 65% B to 0% A: 100% B (A=90% H₂O/10% MeOH+0.1% TFA); (B=90% MeOH/10% H₂O+0.1% TFA); detection at 220 nm) to yield Example 22 (1 mg, 28%). LCMS, [M+H]⁺=526.2. ¹H NMR (400 MHz, CD₃OD) δ 7.53 (d, J=8.58 Hz, 1H), 7.43 (d, J=3.74 Hz, 1H), 7.20 (d, J=2.42 Hz, 1H), 7.07 (dd, J=2.53, 8.69 Hz, 1H), 6.90 (d, J=3.96 Hz, 1H), 6.83 (s, 1H), 4.15 (t, J=6.05 Hz, 2H), 2.85 (q, J=7.78 Hz, 2H), 2.33-2.45 (m, 2H), 2.02-2.12 (m, 2H), 1.29 (t, J=7.48 Hz, 3H).

The Examples in the following Table 2 were prepared in similar manners as Example 1-21. ¹H NMR was measured at 500 MHz, DMSO-d₆, unless otherwise indicated.

TABLE 2

| Ex. No. | Structure and Name | Analytical Data | Method |
|---|---|---|---|
| 23 | 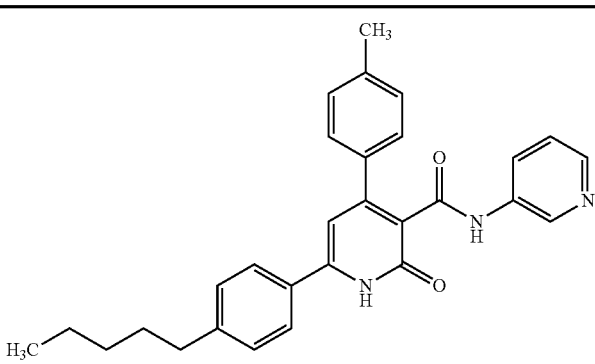<br>2-Oxo-6-(4-pentylphenyl)-N-(pyridin-3-yl)-4-(p-tolyl)-1,2-dihydropyridine-3-carboxamide | ¹H NMR: δ 10.65 (s, 1H), 8.69 (br. s, 1H), 8.25 (br. s., 1H), 7.99 (d, J = 8.24 Hz, 1H), 7.75 (d,. J = 7.63 Hz, 2H), 7.45 (d, J = 7.93 Hz, 2H), 7.36 (dd, J = 4.42, 8.09 Hz, 1H), 7.32 (d, J = 7.93 Hz, 2H), 7.21 (d, J = 7.93 Hz, 2H), 6.62 (br. s., 1H), 2.62 (t, J = 7.48 Hz, 2H), 2.28 (s, 3H), 1.50-1.66 (m, 2H), 1.29 (br. s., 5H), 0.85 (t, J = 6.87 Hz, 3H). MS(ESI) m/z: 452.2 (M + H)⁺. | Ex. 4 |

TABLE 2-continued

| Ex. No. | Structure and Name | Analytical Data | Method |
|---|---|---|---|
| 24 | 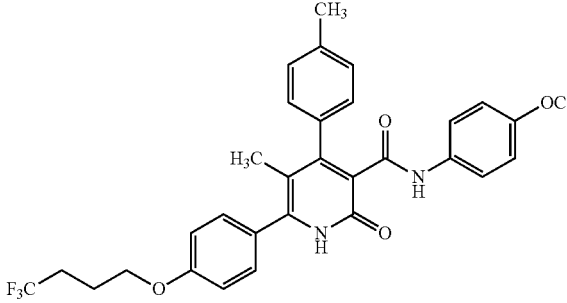<br>N-(4-Ethoxyphenyl)-5-methyl-2-oxo-4-(p-tolyl)-6-(4-(4,4,4-trifluorobutoxy)phenyl)-1,2-dihydropyridine-3-carboxamide | $^1$H NMR: δ 10.06 (s, 1H), 7.38 (d, J = 8.24 Hz, 2H), 7.31 (d, J = 8.85 Hz, 2H), 7.13-7.21 (m, 4H), 7.05 (d, J = 8.24 Hz, 2H), 6.77 (d, J = 8.54 Hz, 2H), 4.10 (t, J = 5.80 Hz, 2H), 3.93 (q, J = 6.92 Hz, 2H), 2.43 (dd, J = 11.14, 16.63 Hz, 2H), 2.27 (s, 3H), 1.91-2.00 (m, 2H), 1.60 (br. s., 3H), 1.27 (t, J = 6.87 Hz, 3H). MS(ESI) m/z: 564.2 (M + H)$^+$. | Ex. 7 |
| 25 | 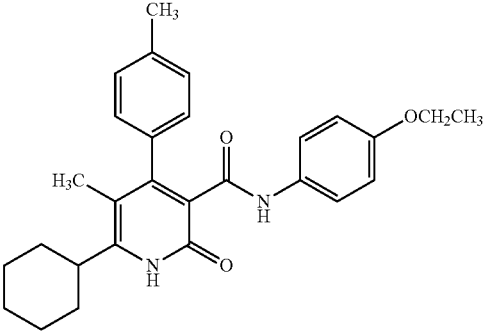 [SMILES: CCOc1ccc(NC(=O)c2c(-c3ccc(C)cc3)c(C)c(C3CCCCC3)[nH]c2=O)cc1]<br>6-Cyclohexyl-N-(4-ethoxyphenyl)-5-methyl-2-oxo-4-(p-tolyl)-1,2-dihydropyridine-3-carboxamide | $^1$H NMR: δ 9.95 (s, 1H), 7.28 (d, J = 8.85 Hz, 2H), 7.10-7.16 (m, 2H), 7.08 (d, J = 7.93 Hz, 2H), 6.75 (d, J = 8.85 Hz, 2H), 3.92 (q, J = 6.71 Hz, 2H), 2.81 (t, J = 11.90 Hz, 1H), 2.26 (s, 3H), 1.77 (d, J = 10.38 Hz, 4H), 1.70 (br. s., 3H), 1.55-1.67 (m, 3H), 1.20-1.39 (m, 6H). MS(ESI) m/z: 445.3 (M + H)$^+$. | Ex. 7 |
| 26 | 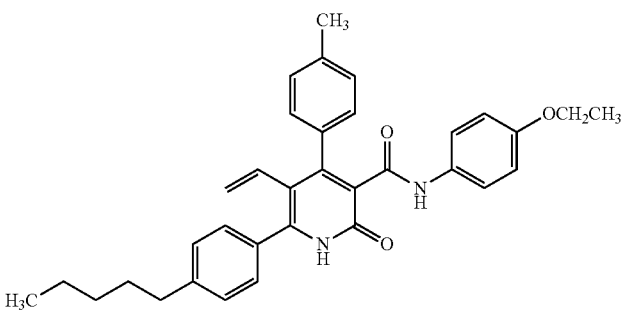 [SMILES: C=Cc1c(-c2ccc(CCCCC)cc2)[nH]c(=O)c(C(=O)Nc2ccc(OCC)cc2)c1-c1ccc(C)cc1]<br>N-(4-Ethoxyphenyl)-2-oxo-6-(4-pentylphenyl)-4-(p-tolyl)-5-vinyl-1,2-dihydropyridine-3-carboxamide | $^1$H NMR: δ 12.09 (br. s., 1H), 10.03 (s, 1H), 7.27-7.36 (m, 6H), 7.14 (q, J = 8.25 Hz, 4H), 6.78 (d, J = 9.08 Hz, 2H), 5.95 (br. s., 1H), 4.79 (d, J = 11.55 Hz, 1H), 4.29 (d, J = 18.71 Hz, 1H), 3.95 (q, J = 7.06 Hz, 2H), 2.60-2.66 (m, 2H), 2.26 (s, 3H), 1.60 (quin, J = 7.50 Hz, 2H), 1.26-1.36 (m, 7H), 0.88 (t, J = 7.02 Hz, 3H). MS(ESI) m/z: 521.3 (M + H)$^+$. | Ex. 7 |
| 27 | 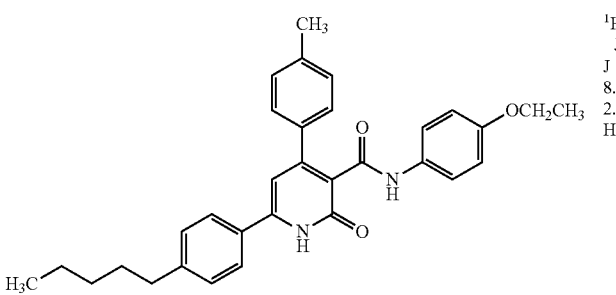<br>N-(4-Ethoxyphenyl)-2-oxo-6-(4-pentylphenyl)-4-(p-tolyl)-1,2-dihydropyridine-3-carboxamide | $^1$H NMR (400 MHz, CDCl$_3$) δ 10.45 (br. s., 1H), 7.67 (d, J = 7.92 Hz, 2H), 7.38 (d, J = 8.58 Hz, 2H), 7.32 (d, J = 7.92 Hz, 2H), 7.24 (d, J = 7.70 Hz, 4H), 6.78 (d, J = 8.58 Hz, 2H), 6.71 (s, 1H), 3.99 (q, J = 6.53 Hz, 2H), 2.53-2.61 (m, 2H), 2.41 (s, 3H), 1.57 (td, J = 7.43, 15.08 Hz, 2H), 1.39 (t, J = 6.93 Hz, 3H), 1.28-1.36 (m, 4H), 0.90 (t, J = 6.93 Hz, 3H). MS(ESI) m/z: 495.5 (M + H)$^+$. | Ex. 5 |

TABLE 2-continued

| Ex. No. | Structure and Name | Analytical Data | Method |
|---|---|---|---|
| 28 | 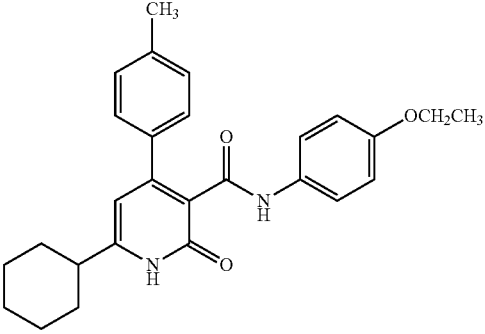 [SMILES: CCOc1ccc(NC(=O)c2c(-c3ccc(C)cc3)cc(C3CCCCC3)[nH]c2=O)cc1]<br>6-Cyclohexyl-N-(4-ethoxyphenyl)-2-oxo-4-(p-tolyl)-1,2-dihydropyridine-3-carboxamide | $^1$H NMR: δ 10.15 (s, 1H), 7.43 (d, J = 8.85 Hz, 2H), 7.39 (d, J = 8.24 Hz, 2H), 7.20 (d, J = 7.93 Hz, 2H), 6.83 (d, J = 8.85 Hz, 2H), 6.06 (s, 1H), 3.98 (q, J = 6.92 Hz, 2H), 2.30 (s, 3H), 1.75-1.90 (m, 4H), 1.69 (d, J = 11.90 Hz, 1H), 1.44-1.55 (m, 2H), 1.31 (t, J = 6.87 Hz, 3H), 1.00-1.35 (m, 4H). MS(ESI) m/z: 431.3 (M + H)$^+$. | Ex. 4 |
| 29 | 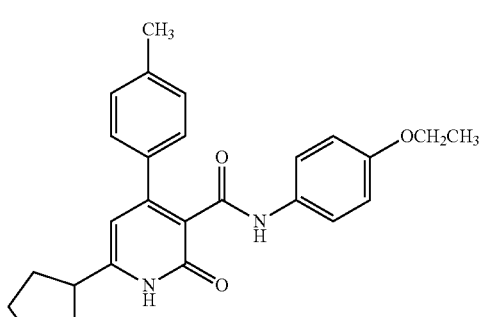<br>6-Cyclopentyl-N-(4-ethoxyphenyl)-2-oxo-4-(p-tolyl)-1,2-dihydropyridine-3-carboxamide | $^1$H NMR (400 MHz, CDCl$_3$) δ 9.78 (br. s., 1H), 7.41 (d, J = 8.80 Hz, 2H), 7.27-7.33 (m, 2H), 7.17-7.26 (m, 2H), 6.81 (d, J = 8.80 Hz, 2H), 6.42 (s, 1H), 3.99 (q, J = 7.12 Hz, 2H), 2.99-3.11 (m, 1H), 2.40 (s, 3H), 2.18 (br. s., 2H), 1.84 (br. s., 2H), 1.71 (br. s., 4H), 1.39 (t, J = 6.93 Hz, 3H). MS(ESI) m/z: 417.4 (M + H)$^+$. | Ex. 5 |
| 30 | 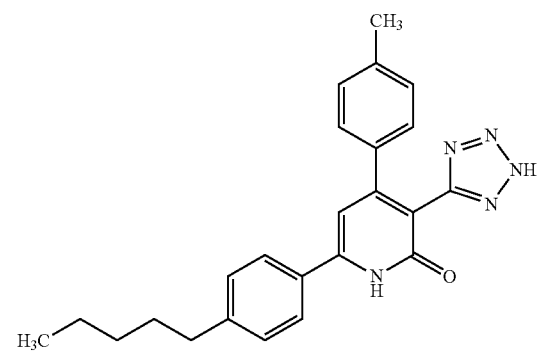 [SMILES: CCCCCc1ccc(-c2cc(-c3ccc(C)cc3)c(-c3nn[nH]n3)c(=O)[nH]2)cc1]<br>6-(4-Pentylphenyl)-3-(2H-tetrazol-5-yl)-4-(p-tolyl)pyridin-2(1H)-one | $^1$H NMR (400 MHz, CDCl$_3$) δ 11.79 (s, 1H), 7.68 (d, J = 7.26 Hz, 2H), 7.37 (d, J = 6.82 Hz, 2H), 7.18-7.30 (m, 4H), 6.78 (s, 1H), 2.70 (t, J = 7.26 Hz, 2H), 2.44 (s, 3H), 1.63-1.73 (m, J = 6.82 Hz, 2H), 1.36 (d, J = 3.30 Hz, 4H), 0.91 (t, J = 6.60 Hz, 3H). MS(ESI) m/z: 400.3 (M + H)$^+$. | Ex. 4 |
| 31 | 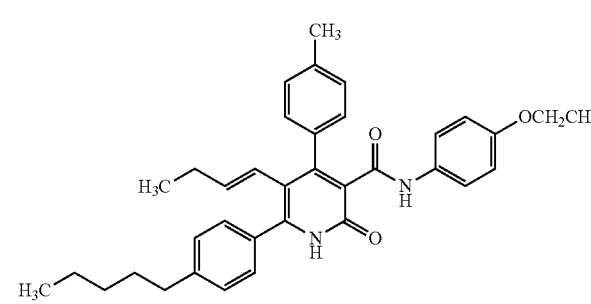<br>(E)-5-(But-1-en-1-yl)-N-(4-ethoxyphenyl)-2-oxo-6-(4-pentylphenyl)-4-(p-tolyl)-1,2-dihydropyridine-3-carboxamide | $^1$H NMR: δ 12.03 (br. s., 1H), 10.02 (s, 1H), 7.29-7.36 (m, 4H), 7.22-7.28 (m, 2H), 7.09-7.16 (m, 4H), 6.78 (d, J = 9.08 Hz, 2H), 5.55 (d, J = 15.96 Hz, 1H), 4.79 (td, J = 6.67, 15.82 Hz, 1H), 3.94 (q, J = 6.88 Hz, 2H), 2.61 (t, J = 7.57 Hz, 2H), 2.25 (s, 3H), 1.60 (sxt, J = 7.43 Hz, 4H), 1.23-1.35 (m, 7H), 0.86 (t, J = 6.88 Hz, 3H), 0.49 (t, J = 7.43 Hz, 3H). MS(ESI) m/z: 549.4 (M + H)$^+$. | Ex. 7 |

TABLE 2-continued

| Ex. No. | Structure and Name | Analytical Data | Method |
|---|---|---|---|
| 32 | 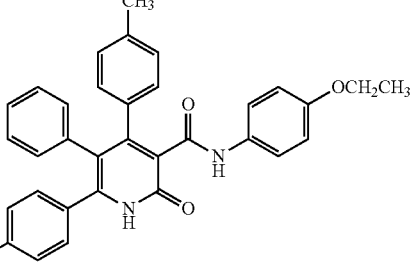<br>N-(4-Ethoxyphenyl)-2-oxo-6-(4-pentylphenyl)-5-phenyl-4-(p-tolyl)-1,2-dihydropyridine-3-carboxamide | $^1$H NMR: δ 10.07 (s, 1H), 7.33 (d, J = 8.85 Hz, 2H), 6.99-7.08 (m, 4H), 6.90-6.97 (m, 5H), 6.86 (d, J = 7.93 Hz, 2H), 6.71-6.80 (m, 4H), 3.94 (q, J = 7.02 Hz, 2H), 2.43-2.50 (m, 2H), 2.10 (s, 3H), 1.49 (quin, J = 7.48 Hz, 2H), 1.23-1.33 (m, 5H), 1.14-1.22 (m, 2H), 0.83 (t, J = 7.17 Hz, 3H). MS(ESI) m/z: 571.3 (M + H)$^+$. | Ex. 7 |
| 33 | 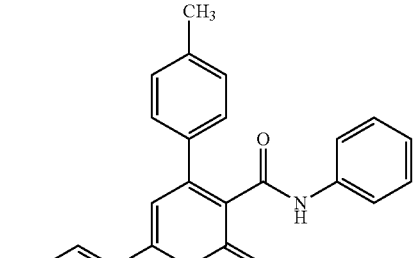<br>2-Oxo-6-(4-pentylphenyl)-N-phenyl-4-(p-tolyl)-1,2-dihydropyridine-3-carboxamide | $^1$H NMR: δ 12.20 (br. s., 1H), 10.36 (s, 1H), 7.77 (d, J = 6.60 Hz, 2H), 7.55 (d, J = 7.70 Hz, 2H), 7.48 (d, J = 7.98 Hz, 2H), 7.32 (d, J = 8.25 Hz, 2H), 7.27 (t, J = 7.84 Hz, 2H), 7.21 (d, J = 8.25 Hz, 2H), 7.03 (t, J = 7.29 Hz, 1H), 6.61 (br. s., 1H), 2.63 (t, J = 7.70 Hz, 2H), 2.30 (s, 3H), 1.60 (quin, J = 7.50 Hz, 2H), 1.26-1.37 (m, 4H), 0.87 (t, J = 7.02 Hz, 3H). MS(ESI) m/z: 451.2 (M + H)$^+$. | Ex. 4 |
| 34 | 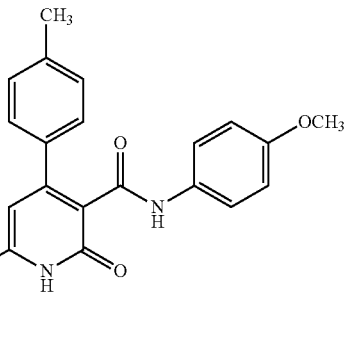<br>6-Cyclohexyl-N-(4-methoxyphenyl)-2-oxo-4-(p-tolyl)-1,2-dihydropyridine-3-carboxamide | $^1$H NMR: δ 10.13 (s, 1H), 7.43 (d, J = 9.08 Hz, 2H), 7.37 (d, J = 8.25 Hz, 2H), 7.17 (d, J = 7.98 Hz, 2H), 6.82 (d, J = 9.08 Hz, 2H), 6.03 (br. s., 1H), 3.70 (s, 3H), 2.28 (s, 3H), 1.74-1.88 (m, 4H), 1.67 (d, J = 12.38 Hz, 1H), 1.43-1.56 (m, 2H), 1.13-1.35 (m, 4H). MS(ESI) m/z: 417.3 (M + H)$^+$. | Ex. 4 |
| 35 | 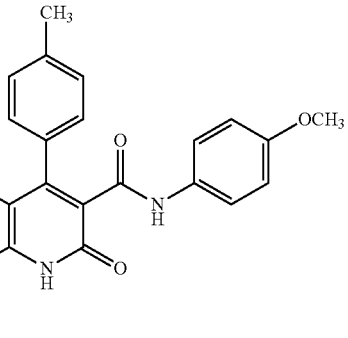<br>5-Chloro-6-cyclohexyl-N-(4-methoxyphenyl)-2-oxo-4-(p-tolyl)-1,2-dihydropyridine-3-carboxamide | $^1$H NMR: δ 10.11 (br. s., 1H), 7.27 (d, J = 8.54 Hz, 2H), 7.15 (s, 4H), 6.77 (d, J = 8.85 Hz, 2H), 3.93 (q, J = 6.82 Hz, 2H), 3.10 (br. s., 1H), 2.26 (s, 3H), 1.61-1.86 (m, 7H), 1.18-1.40 (m, 6H). MS(ESI) m/z: 465.2 (M + H)$^+$. | Ex. 6 |

TABLE 2-continued

| Ex. No. | Structure and Name | Analytical Data | Method |
|---|---|---|---|
| 36 | 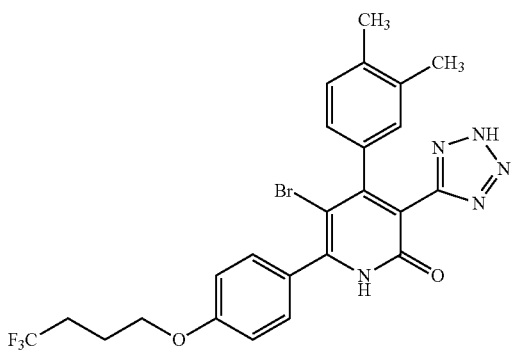 [SMILES: Cc1ccc(-c2c(Br)c(-c3ccc(OCCCC(F)(F)F)cc3)[nH]c(=O)c2-c2nn[nH]n2)cc1C]<br>5-Bromo-4-(3,4-dimethylphenyl)-3-(2H-tetrazol-5-yl)-6-(4-(4,4,4-trifluorobutoxy)phenyl)pyridin-2(1H)-one | $^1$H NMR (500 MHz, CD$_3$OD) δ 7.60 (d, J = 8.80 Hz, 2H), 7.14 (d, J = 8.80 Hz, 2H), 7.09 (d, J = 7.70 Hz, 1H), 6.94 (s, 1H), 6.86 (d, J = 7.70 Hz, 1H), 4.18 (t, J = 6.05 Hz, 2H), 2.38-2.49 (m, 2H), 2.26 (s, 3H), 2.24 (s, 3H), 2.06-2.14 (m, 2H). MS(ESI) m/z: 550.2 (M + H)$^+$. | Ex. 6 |
| 37 | 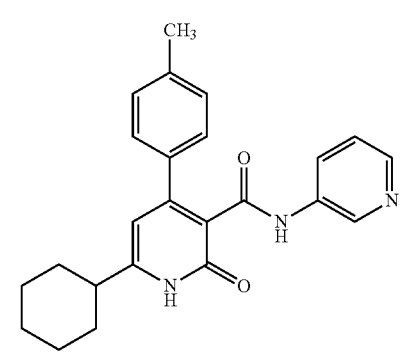 [SMILES: Cc1ccc(-c2cc(C3CCCCC3)[nH]c(=O)c2C(=O)Nc2cccnc2)cc1]<br>6-Cyclohexyl-2-oxo-N-(pyridin-3-yl)-4-(p-tolyl)-1,2-dihydropyridine-3-carboxamide | $^1$H NMR: δ 11.99 (br. s., 1H), 10.63 (s, 1H), 8.72 (d, J = 1.93 Hz, 1H), 8.27 (d, J = 4.68 Hz, 1H), 7.93-8.04 (m, 1H), 7.31-7.41 (m, 3H), 7.19 (d, J = 7.98 Hz, 2H), 6.01-6.17 (m, 1H), 2.28 (s, 3H), 1.75-1.88 (m, 4H), 1.67 (d, J = 12.10 Hz, 1H), 1.43-1.56 (m, 2H), 1.15-1.36 (m, 4H). MS(ESI) m/z: 388.2 (M + H)$^+$. | Ex. 4 |
| 38 | 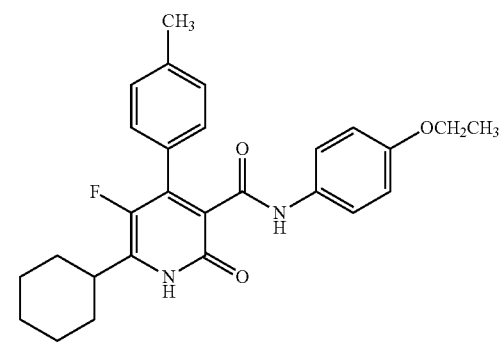 [SMILES: CCOc1ccc(NC(=O)c2c(-c3ccc(C)cc3)c(F)c(C3CCCCC3)[nH]c2=O)cc1]<br>6-Cyclohexyl-N-(4-ethoxyphenyl)-5-fluoro-2-oxo-4-(p-tolyl)-1,2-dihydropyridine-3-carboxamide | $^1$H NMR: (400 MHz, DMSO-d$_6$) δ 10.15 (s, 1H), 7.35 (d, J = 9.02 Hz, 2H), 7.29 (d, J = 7.92 Hz, 2H), 7.19 (d, J = 8.14 Hz, 2H), 6.80 (d, J = 9.24 Hz, 2H), 3.95 (q, J = 7.04 Hz, 2H), 2.89 (br. s., 1H), 2.29 (s, 3H), 1.61-1.88 (m, 7H), 1.28 (t, J = 7.04 Hz, 3H), 1.19-1.60 (m, 3H). MS(ESI) m/z: 449.2 (M + H)$^+$. | Ex. 6 |

TABLE 2-continued

| Ex. No. | Structure and Name | Analytical Data | Method |
|---|---|---|---|
| 39 | 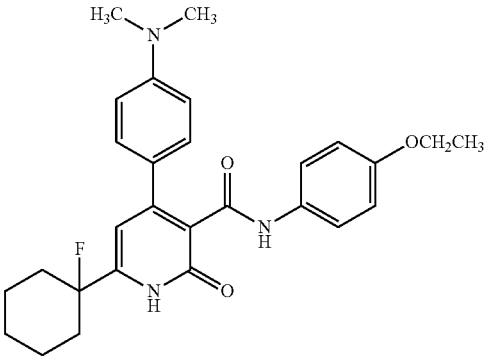 [SMILES: CCOc1ccc(NC(=O)c2c(-c3ccc(N(C)C)cc3)cc(C3(F)CCCCC3)[nH]c2=O)cc1]<br>4-(4-(Dimethylamino)phenyl)-N-(4-ethoxyphenyl)-6-(1-fluorocyclohexyl)-2-oxo-1,2-dihydropyridine-3-carboxamide | $^1$H NMR: δ 10.10 (s, 1H), 7.45 (d, J = 8.75 Hz, 2H), 7.40 (d, J = 8.75 Hz, 2H), 6.82 (d, J = 8.75 Hz, 2H), 6.68 (d, J = 8.75 Hz, 2H), 6.30 (br. s., 1H), 3.95 (q, J = 6.73 Hz, 2H), 2.89 (s, 6H), 1.94-2.12 (m, 2H), 1.84-1.93 (m, 2H), 1.52-1.71 (m, 5H), 1.31-1.39 (m, 1H), 1.28 (t, J = 6.90 Hz, 3H). MS(ESI) m/z: 478.3 (M + H)$^+$. | Ex. 10 |
| 40 | 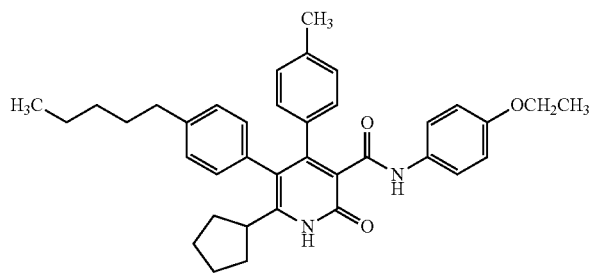 [SMILES: CCCCCc1ccc(-c2c(C3CCCC3)[nH]c(=O)c(C(=O)Nc3ccc(OCC)cc3)c2-c2ccc(C)cc2)cc1]<br>6-Cyclopentyl-N-(4-ethoxyphenyl)-2-oxo-5-(4-pentylphenyl)-4-(p-tolyl)-1,2-dihydropyridine-3-carboxamide | $^1$HNMR: δ 10.01 (s, 1H), 7.31 (d, J = 9.09 Hz, 2H), 6.96 (d, J = 7.74 Hz, 2H), 6.85-6.90 (m, 2H), 6.79-6.84 (m, 4H), 6.76 (d, J = 9.09 Hz, 2H), 3.92 (q, J = 6.96 Hz, 2H), 2.63 (br. s., 1H), 2.45 (t, J = 7.40 Hz, 2H), 2.07 (s, 3H), 1.64-1.87 (m, 6H), 1.46 (quin, J = 7.32 Hz, 2H), 1.36 (br. s., 2H), 1.18-1.30 (m, 5H), 1.04-1.13 (m, 2H), 0.80 (t, J = 7.24 Hz, 3H). MS(ESI) m/z: 563.4 (M + H)$^+$. | Ex. 7 |
| 41 | 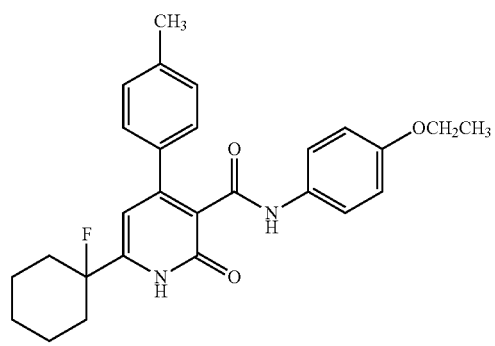 [SMILES: CCOc1ccc(NC(=O)c2c(-c3ccc(C)cc3)cc(C3(F)CCCCC3)[nH]c2=O)cc1]<br>N-(4-Ethoxyphenyl)-6-(1-fluorocyclohexyl)-2-oxo-4-(p-tolyl)-1,2-dihydropyridine-3-carboxamide | $^1$H NMR: δ 10.14 (s, 1H), 7.41 (dd, J = 5.78, 8.25 Hz, 4H), 7.20 (d, J = 7.98 Hz, 2H), 6.82 (d, J = 9.08 Hz, 2H), 3.96 (q, J = 1.15 Hz, 2H), 2.29 (s, 3H), 1.96-2.14 (m, 2H), 1.85-1.95 (m, 2H), 1.52-1.73 (m, 6H), 1.29 (t, J = 7.02 Hz, 3H), 1.22-1.37 (m, 1H). MS(ESI) m/z: 449.3 (M + H)$^+$. | Ex. 10 |
| 42 | 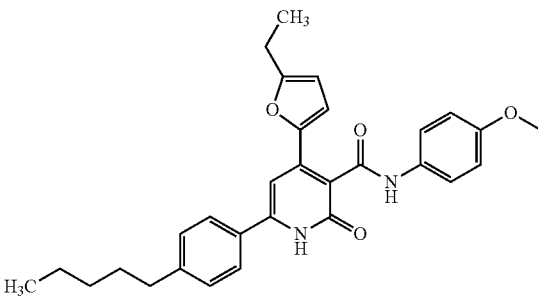<br>N-(4-Ethoxyphenyl)-4-(5-ethylfuran-2-yl)-2-oxo-6-(4-pentylphenyl)-1,2-dihydropyridine-3-carboxamide | $^1$H NMR: δ 10.16 (s, 1H), 7.71 (d, J = 7.02 Hz, 2H), 7.59 (d, J = 8.24 Hz, 2H), 7.33 (d, J = 7.63 Hz, 2H), 7.05 (br. s., 1H), 6.88 (d, J = 7.93 Hz, 2H), 6.73-6.92 (m, 1H), 6.26 (br. s., 1H), 3.99 (q, J = 6.71 Hz, 2H), 2.63 (t, J = 7.17 Hz, 2H), 1.51-1.66 (m, 2H), 1.18-1.38 (m, 9H), 1.03 (t, J = 7.48 Hz, 3H), 0.86 (t, J = 6.26 Hz, 3H). MS(ESI) m/z: 499.3 (M + H)$^+$. | Ex. 5 |

TABLE 2-continued

| Ex. No. | Structure and Name | Analytical Data | Method |
|---|---|---|---|
| 43 | 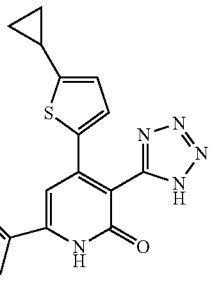<br>4-(5-Cyclopropylthiophen-2-yl)-3-(1H-tetrazol-5-yl)-6-(4-((6,6,6-trifluorohexyl)oxy)phenyl)pyridin-2(1H)-one | $^1$H NMR: δ 12.25 (s, 1H), 7.86 (d, J = 8.3 Hz, 2H), 7.17 (d, J = 4.0 Hz, 1H), 7.14-7.04 (m, 2H), 6.84 (bs, 1H), 6.77 (d, J = 3.8 Hz, 1H), 4.08 (t, J = 6.4 Hz, 2H), 2.39-2.19 (m, 2H), 2.15-1.97 (m, 1H), 1.79 (p, J = 6.6 Hz, 2H), 1.71-1.44 (m, 4H), 1.08-0.90 (m, 2H), 0.74-0.54 (m, 2H). MS(ESI) m/z: 516.2 (M + H)$^+$. | Ex. 1 |
| 44 | 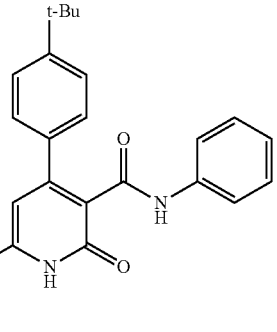<br>4-(4-(tert-Butyl)phenyl)-2-oxo-N-phenyl-6-(4-(4,4,4-trifluorobutoxy)phenyl)-1,2-dihydropyridine-3-carboxamide | $^1$H NMR: δ 12.18 (s, 1H), 10.40 (s, 1H), 7.84 (d, J = 8.2 Hz, 2H), 7.60-7.50 (m, 5H), 7.47-7.40 (m, 2H), 7.28 (t, J = 7.8 Hz, 2H), 7.06 (d, J = 8.7 Hz, 2H), 6.62 (bs, 1H), 4.12 (t, J = 6.3 Hz, 2H), 2.49-2.38 (m, 2H), 2.06-1.87 (m, 2H), 1.27 (s, 9H). MS(ESI) m/z: 549.4 (M + H)$^+$. | Ex. 4 |
| 45 | 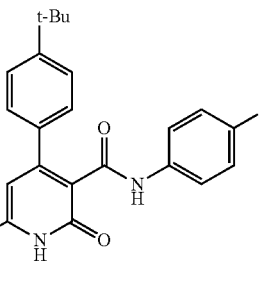<br>4-(4-(tert-Butyl)phenyl)-N-(4-ethoxyphenyl)-2-oxo-6-(4-(4,4,4-trifluorobutoxy)phenyl)-1,2-dihydropyridine-3-carboxamide | 1H NMR: δ 12.15 (s, 1H), 10.23 (s, 1H), 7.84 (s, 2H), 7.54 (d, J = 8.3 Hz, 2H), 7.48-7.41 (m, 4H), 7.10-7.05 (m, 2H), 6.88-6.83 (m, 2H), 6.53 (bs, 1H), 4.14 (t, J = 6.2 Hz, 2H), 3.99 (q, J = 7.0 Hz, 2H), 2.50-2.36 (m, 2H), 2.04-1.92 (m, 2H), 1.32 (t, J = 6.9 Hz, 3H), 1.29 (s, 9H). MS(ESI) m/z: 593.3 (M + H)$^+$. | Ex. 5 |
| 46 | 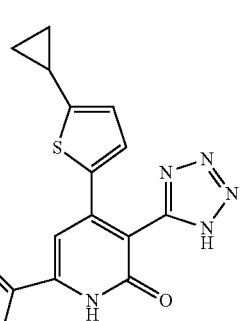<br>4-(5-Cyclopropylthiophen-2-yl)-3-1H-tetrazol-5-yl)-6-(4-((5,5,5-trifluoropentyl)oxy)phenyl)pyridin-2(1H)-one | $^1$H NMR (400 MHz, CD$_3$OD) δ 7.77 (d, J = 8.5 Hz, 2H), 7.14 (d, J = 8.8 Hz, 2H), 6.98 (d, J = 3.8 Hz, 1H), 6.90 (s, 1H), 6.74 (d, J = 3.8 Hz, 1H), 4.14 (t, J = 6.1 Hz, 2H), 2.29 (dd, J = 16.0, 11.1 Hz, 2H), 2.07 (d, J = 7.9 Hz, 1H), 2.02-1.87 (m, 2H), 1.87-1.74 (m, 2H), 1.11-1.00 (m, 2H), 0.76-0.62 (m, 2H). MS(ESI) m/z: 502.2 (M + H)$^+$. | Ex. 1 |

TABLE 2-continued

| Ex. No. | Structure and Name | Analytical Data | Method |
|---|---|---|---|
| 47 | 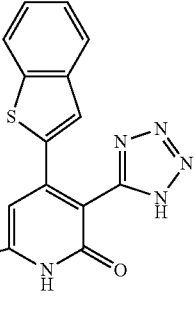<br>4-(Benzo[b]thiophen-2-yl)-3-(1H-tetrazol-5-yl)-6-(4-(4,4,4-trifluorobutoxy)phenyl)pyridin-2(1H)-one | $^1$H NMR (400 MHz, DMSO-d$_6$) δ 12.52 (s, 1H), 8.11-7.83 (m, 4H), 7.79 (s, 1H), 7.49-7.34 (m, 2H), 7.23-7.08 (m, 2H), 7.01 (s, 1H), 4.17 (t, J = 6.2 Hz, 2H), 2.51 (d, J = 2.0 Hz, 2H), 2.10-1.91 (m, 2H). MS(ESI) m/z: 498.1 (M + H)$^+$. | Ex. 1 |
| 48 | 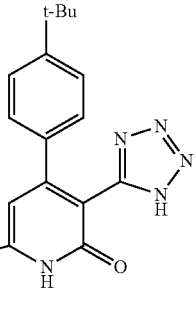<br>4-(4-(tert-Butyl)phenyl)-3-(1H-tetrazol-5-yl)-6-(4-(4,4,4-trifluorobutoxy)phenyl)pyridin-2(1H)-one | $^1$H NMR: δ 12.47 (s, 1H), 7.90 (d, J = 9.1 Hz, 2H), 7.43-7.29 (m, 2H), 7.15 (d, J = 8.3 Hz, 2H), 7.12-7.07 (m, 2H), 6.70 (bs, 1H), 4.15 (t, J = 6.2 Hz, 2H), 2.50-2.41 (m, 2H), 2.04-1.90 (m, 2H), 1.27 (s, 9H). MS(ESI) m/z: 498.2 (M + H)$^+$. | Ex. 1 |
| 49 | 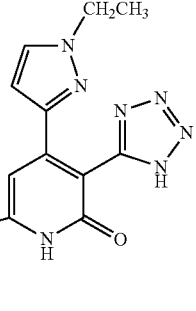<br>4-(1-Ethyl-1H-pyrazol-3-yl)-3-(1H-tetrazol-5-yl)-6-(4-(4,4,4-trifluorobutoxy)phenyl)pyridin-2(1H)-one | $^1$H NMR: δ 12.26 (s, 1H), 7.86 (d, J = 8.7 Hz, 2H), 7.70 (s, 1H), 7.12 (d, J = 8.3 Hz, 2H), 7.05 (bs, 1H), 5.86 (bs, 1H), 4.15 (t, J = 6.3 Hz, 2H), 4.05 (q, J = 7.4 Hz, 2H), 2.51-2.39 (m, 2H), 2.07-1.89 (m, 2H), 1.26 (t, J = 7.3 Hz, 3H). MS(ESI) m/z: 460.2 (M + H)$^+$. | Ex. 1 |
| 50 | 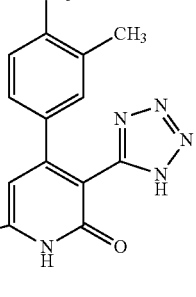<br>4-(3,4-Dimethylphenyl)-3-(1H-tetrazol-5-yl)-6-(4-(4,4,4-trifluorobutoxy)phenyl)pyridin-2(1H)-one | $^1$H NMR: δ 12.46 (s, 1H), 7.89 (d, J = 8.3 Hz, 2H), 7.18-6.99 (m, 4H), 6.82 (d, J = 7.8 Hz, 1H), 6.70 (bs, 1H), 4.15 (t, J = 6.2 Hz, 2H), 2.51-2.43 (m, 2H), 2.21 (s, 3H), 2.18 (s, 3H), 2.03-1.95 (m, 2H). MS(ESI) m/z: 470.1 (M + H)$^+$. | Ex. 1 |

TABLE 2-continued

| Ex. No. | Structure and Name | Analytical Data | Method |
|---|---|---|---|
| 51 | 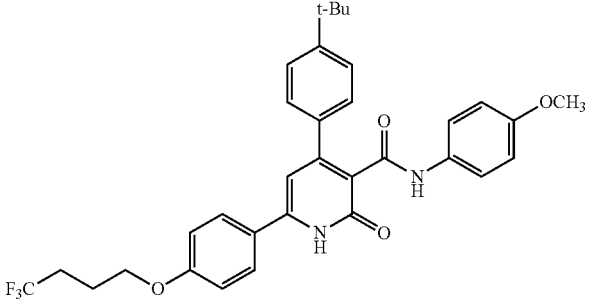<br>4-(4-(tert-Butyl)phenyl)-N-(4-methoxyphenyl)-2-oxo-6-(4-(4,4,4-trifluorobutoxy)phenyl)-1,2-dihydropyridine-3-carboxamide | $^1$H NMR: δ 10.25 (s, 1H), 7.85 (s, 2H), 7.54 (d, J = 8.2 Hz, 2H), 7.46 (dd, J = 10.5, 8.4 Hz, 4H), 7.08 (d, J = 8.4 Hz, 2H), 6.88 (d, J = 8.9 Hz, 2H), 6.59 (bs, 1H), 4.14 (t, J = 6.3 Hz, 2H), 3.74 (s, 3H), 2.51-2.40 (m, 2H), 2.05-1.95 (m, 2H), 1.30 (s, 9H). MS(ESI) m/z: 579.3 (M + H)$^+$. | Ex. 4 |
| 52 | 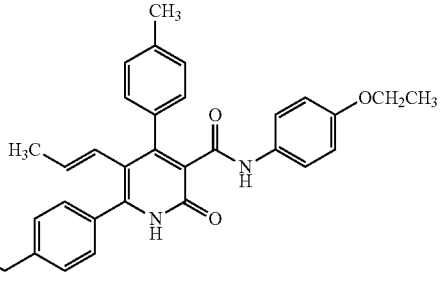<br>((E)-N-(4-Ethoxyphenyl)-2-oxo-6-(4-pentylphenyl)-5-(prop-1-en-1-yl)-4-(p-tolyl)-1,2-dihydropyridine-3-carboxamide | $^1$H NMR: δ 12.04 (br. s., 1H), 10.05 (s, 1H), 7.29-7.38 (m, 4H), 7.23 (d, J = 7.98 Hz, 2H), 7.10 (q, J = 8.25 Hz, 4H), 6.78 (d, J = 9.08 Hz, 2H), 5.73 (br. s., 1H), 5.13-5.21 (m, 1H), 3.94 (q, J = 7.06 Hz, 2H), 2.60 (t, J = 7.57 Hz, 2H), 2.24 (s, 3H), 1.58 (td, J = 7.43, 14.86 Hz, 2H), 1.21-1.35 (m, 7H), 0.97 (dd, J = 1.65, 6.88 Hz, 3H), 0.86 (t, J = 7.15 Hz, 3H). MS(ESI) m/z: 535.6 (M + H)$^+$. | Ex. 7 |
| 53 | 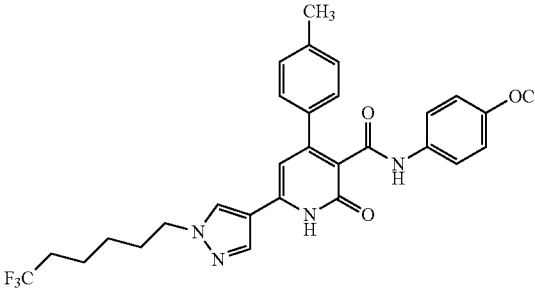<br>N-(4-Ethoxyphenyl)-2-oxo-4-(p-tolyl)-6-(1-(6,6,6-trifluorohexyl)-1H-pyrazol-4-yl)-1,2-dihydropyridine-3-carboxamide | 1H NMR: δ 10.17 (br. s., 1H), 8.46 (br. s., 1H), 8.15 (br. s., 1H), 7.39 (d, J = 7.63 Hz, 4H), 7.18 (d, J = 7.02 Hz, 2H), 6.81 (d, J = 7.93 Hz, 2H), 6.56 (br. s., 1H), 4.11 (br. s., 2H), 3.88-4.01 (m, 2H), 2.28 (br. s 3H), 2.19 (d, J = 7.63 Hz, 2H), 1.80 (br. s., 2H), 1.47 (d, J = 7.02 Hz, 2H), 1.18-1.37 (m, 5H). MS(ESI) m/z: 553.3 (M + H)$^+$. | Ex. 5 |
| 54 | 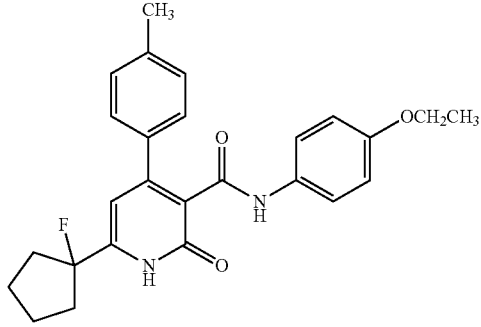 [SMILES: CCOc1ccc(NC(=O)c2c(-c3ccc(C)cc3)cc(C3(F)CCCC3)[nH]c2=O)cc1]<br>N-(4-Ethoxyphenyl)-6-(1-fluorocyclopentyl)-2-oxo-4-(p-tolyl)-1,2-dihydropyridine-3-carboxamide | $^1$H NMR: δ 11.71 (br. s., 1H), 10.16 (br. s., 1H), 7.35-7.49 (m, 4H), 7.20 (d, J = 7.98 Hz, 2H), 6.82 (d, J = 9.08 Hz, 2H), 6.45 (br. s., 1H), 3.96 (q, J = 6.97 Hz, 2H), 2.29 (s, 3H), 2.05-2.26 (m, 4H), 1.86 (d, J = 3.58 Hz, 4H), 1.29 (t, J = 7.02 Hz, 3H). MS(ESI) m/z: 435.2 (M + H)$^+$. | Ex. 10 |

TABLE 2-continued

| Ex. No. | Structure and Name | Analytical Data | Method |
|---|---|---|---|
| 55 | 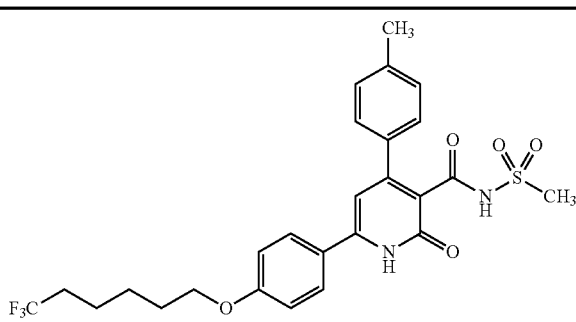<br>N-(Methylsulfonyl)-2-oxo-4-(p-tolyl)-6-(4-((6,6,6-trifluorohexyl)oxy)phenyl)-1,2-dihydropyridine-3-carboxamide | $^1$H NMR: δ 7.80 (d, J = 8.41 Hz, 2H), 7.35 (d, J = 7.74 Hz, 2H), 7.25 (d, J = 8.08 Hz, 2H), 7.03 (d, J = 8.75 Hz, 2H), 6.59 (br. s., 1H), 4.03 (t, J = 6.23 Hz, 2H), 3.10 (s, 3H), 2.33 (s, 3H), 2.18-2.29 (m, 2H), 1.70-1.80 (m, 2H), 1.42-1.59 (m, 4H). MS(ESI) m/z: 537.2 (M + H)$^+$. | Ex. 13 |
| 56 | 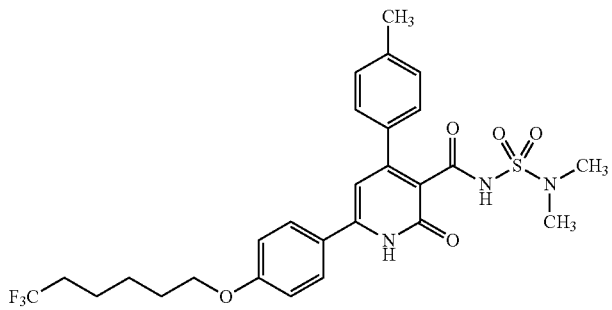 [SMILES: Cc1ccc(-c2cc(-c3ccc(OCCCCCC(F)(F)F)cc3)[nH]c(=O)c2C(=O)NS(=O)(=O)N(C)C)cc1]<br>N-(N,N-Dimethylsulfamoyl)-2-oxo-4-(p-tolyl)-6-(4-((6,6,6-trifluorohexyl)oxy)phenyl)-1,2-dihydropyridine-3-carboxamide | $^1$H NMR: δ 7.79 (d, J = 8.08 Hz, 2H), 7.38 (d, J = 7.74 Hz, 2H), 7.26 (d, J = 7.74 Hz, 2H), 7.03 (d, J = 8.41 Hz, 2H), 6.55 (br. s., 1H), 4.04 (t, J = 6.23 Hz, 2H), 2.70 (s, 6H), 2.35 (s, 3H), 2.19-2.31 (m, 2H), 1.69-1.80 (m, 2H), 1.45-1.61 (m, 4H). MS(ESI) m/z: 566.2 (M + H)$^+$. | Ex. 13 |
| 57 | 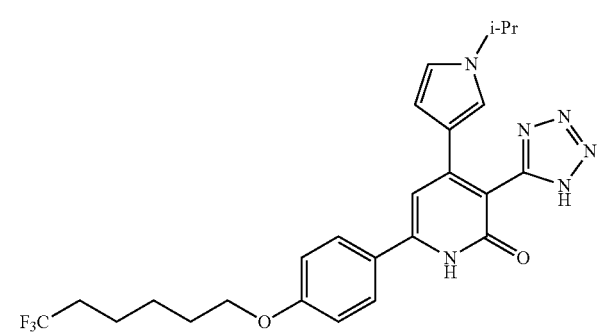 [SMILES: CC(C)n1ccc(-c2cc(-c3ccc(OCCCCCC(F)(F)F)cc3)[nH]c(=O)c2-c2nnn[nH]2)c1]<br>4-(1-Isopropyl-1H-pyrrol-3-yl)-3-(1H-tetrazol-5-yl)-6-(4-((6,6,6-trifluorohexyl)oxy)phenyl)pyridin-2(1H)-one | $^1$H NMR: δ 7.82 (d, J = 8.41 Hz, 2H), 7.12 (br. s., 1H), 7.05 (d, J = 8.75 Hz, 2H), 6.83 (br. s., 1H), 6.75 (br. s., 1H), 5.28 (br. s., 1H), 4.18 (td, J = 6.48, 13.30 Hz, 1H), 4.05 (t, J = 6.23 Hz, 2H), 2.17-2.36 (m, 2H), 1.69-1.83 (m, 2H), 1.43-1.63 (m, 4H), 1.30 (d, J = 6.73 Hz, 6H). MS(ESI) m/z: 501.2 (M + H)$^+$. | Ex. 13 |
| 58 | 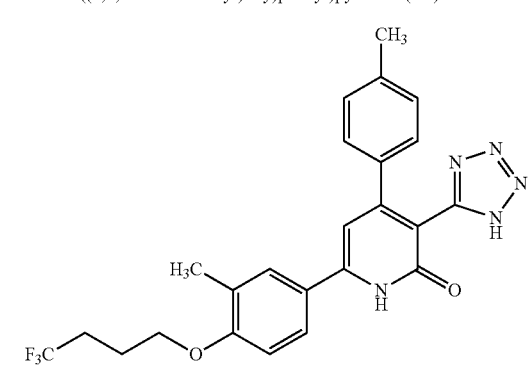<br>6-(3-Methyl-4-(4,4,4-trifluorobutoxy)phenyl)-3-(1H-tetrazol-5-yl)-4-(p-tolyl)pyridin-2(1H)-one | MS(ESI) m/z: 470.1 (M + H)$^+$. | Ex. 13 |

TABLE 2-continued

| Ex. No. | Sructure and Name | Analytical Data | Method |
|---|---|---|---|
| 59 | 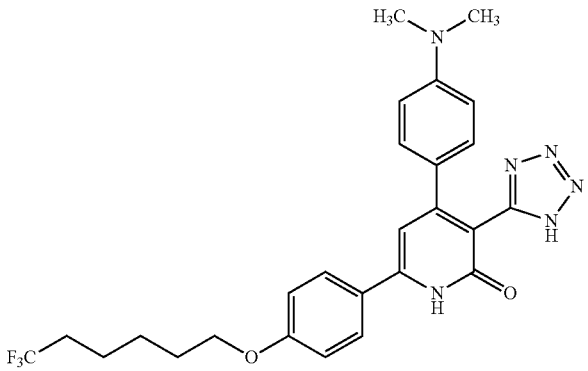 [SMILES: CN(C)c1ccc(-c2cc(-c3ccc(OCCCCCC(F)(F)F)cc3)[nH]c(=O)c2-c2nnn[nH]2)cc1]<br>4-(4-(Dimethylamino)phenyl)-3-(1H-tetrazol-5-yl)-6-(4-((6,6,6-trifluorohexyl)oxy)phenyl)pyridin-2(1H)-one | MS(ESI) m/z: 513.1 (M + H)+. | Ex. 13 |
| 60 | 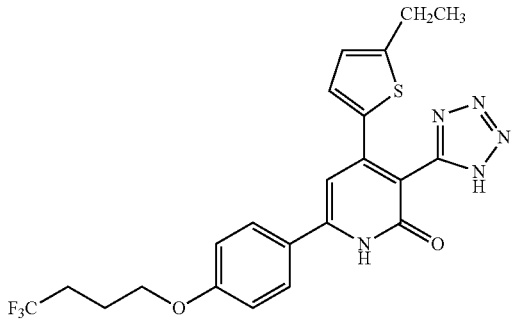 [SMILES: CCc1ccc(-c2cc(-c3ccc(OCCCC(F)(F)F)cc3)[nH]c(=O)c2-c2nnn[nH]2)s1]<br>4-(5-Ethylthiophen-2-yl)-3-(1H-tetrazol-5-yl)-6-(4-(4,4,4-trifluorobutoxy)phenyl)pyridin-2(1H)-one | $^1$H NMR: δ 7.86 (d, J = 8.41 Hz, 2H), 7.19 (d, J = 3.37 Hz, 1H), 7.09 (d, J = 8.75 Hz, 2H), 6.88 (br. s., 1H), 6.82 (d, J = 3.03 Hz, 1H), 4.13 (t, J = 5.89 Hz, 2H), 2.72 (q, J = 7.41 Hz, 2H), 2.45 (dd, J =11.11, 16.49 Hz, 2H), 1.88-2.04 (m, 2H), 1.15 (t, J = 7.57 Hz, 3H). MS(ESI) m/z: 476.2 (M + H)+. | Ex. 13 |
| 61 | 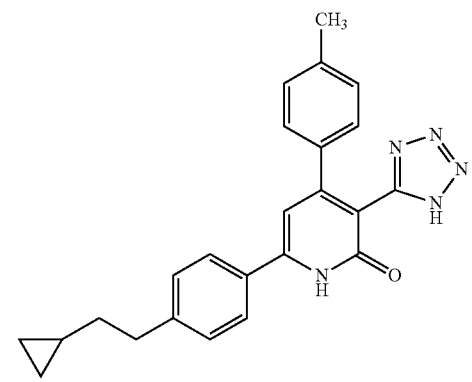 [SMILES: Cc1ccc(-c2cc(-c3ccc(CCC4CC4)cc3)[nH]c(=O)c2-c2nnn[nH]2)cc1]<br>6-(4-(2-Cyclopropylethyl)phenyl)-3-(1H-tetrazol-5-yl)-4-(p-tolyl)pyridin-2(1H)-one | $^1$H NMR: δ 7.80 (d, J = 7.74 Hz, 2H), 7.36 (d, J = 7.74 Hz, 2H), 7.10-7.17 (m, 2H), 7.00-7.10 (m, 2H), 6.71 (br. s., 1H), 2.73 (t, J = 7.57 Hz, 2H), 2.28 (s, 3H), 1.49 (q, J = 7.07 Hz, 2H), 0.70 (br. s., 1H), 0.40 (d, J = 7.07 Hz, 2H), 0.06 (d, J = 4.04 Hz, 2H). MS(ESI) m/z: 398.2 (M + H)+. | Ex. 13 |

TABLE 2-continued

| Ex. No. | Structure and Name | Analytical Data | Method |
|---|---|---|---|
| 62 | 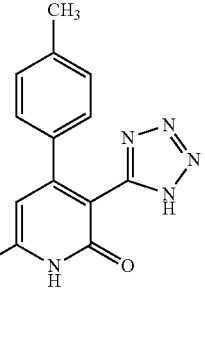<br>3-(1H-Tetrazol-5-yl)-4-(p-tolyl)-6-(5-(7,7,7-trifluoroheptyl)thiazol-2-yl)pyridin-2(1H)-one | $^1$H NMR: δ 7.74 (s, 1H), 7.48 (br. s., 1H), 7.13 (d, J = 7.74 Hz, 2H), 7.03 (d, J = 7.74 Hz, 2H), 2.88 (t, J = 7.24 Hz, 2H), 2.26 (s, 3H), 2.11-2.23 (m, 2H), 1.57-1.69 (m, 2H), 1.45 (br. s., 2H), 1.35 (br. s., 4H). MS(ESI) m/z: 489.2 (M + H)$^+$. | Ex. 13 |
| 63 | 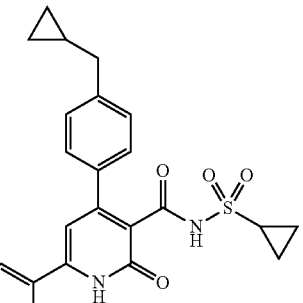<br>4-(4-(Cyclopropylmethyl)phenyl)-N-(cyclopropylsulfonyl)-2-oxo-6-(4-((6,6,6-trifluorohexyl)oxy)phenyl)-1,2-dihydropyridine-3-carboxamide | $^1$H NMR: δ 7.78 (d, J = 7.41 Hz, 2H), 7.38 (d, J = 7.40 Hz, 2H), 7.31 (d, J = 8.08 Hz, 2H), 7.02 (d, J = 8.75 Hz, 2H), 6.59 (br. s., 1H), 4.01 (t, J = 6.23 Hz, 2H), 2.22 (br. s., 2H), 1.68-1.78 (m, 2H), 1.50 (br. s., 6H), 1.10-1.26 (m, 1H), 0.96 (br. s., 5H), 0.38-0.48 (m, 2H), 0.11-0.22 (m, 2H). MS(ESI) m/z: 603.2 (M + H)$^+$. | Ex. 13 |
| 64 | 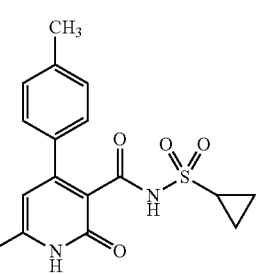<br>N-(Cyclopropylsulfonyl)-6-(2-fluoro-4-((6,6,6-trifluorohexyl)oxy)phenyl)-2-oxo-4-(p-tolyl)-1,2-dihydropyridine-3-carboxamide | $^1$H NMR: δ 12.33 (br. s., 1H), 12.18 (br. s., 1H), 7.62 (br. s., 1H), 7.37 (d, J = 8.25 Hz, 2H), 7.26 (d, J = 7.98 Hz, 2H), 6.98 (dd, J = 2.20, 12.93 Hz, 1H), 6.90 (dd, J = 2.34, 8.67 Hz, 1H), 6.42 (br. s., 1H), 4.06 (t, J = 6.46 Hz, 2H), 2.78-2.86 (m, 1H), 2.34 (s, 3H), 2.21-2.31 (m, 2H), 1.76 (quin, J = 6.88 Hz, 2H), 1.45-1.60 (m, 4H), 0.96-1.06 (m, 4H). MS(ESI) m/z: 581.5 (M + H)$^+$. | Ex. 13 |

TABLE 2-continued

| Ex. No. | Structure and Name | Analytical Data | Method |
|---|---|---|---|
| 65 | 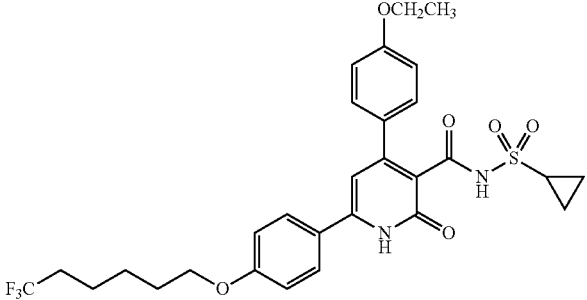 [SMILES: CCOc1ccc(-c2cc(-c3ccc(OCCCCCC(F)(F)F)cc3)[nH]c(=O)c2C(=O)NS(=O)(=O)C2CC2)cc1]<br>N-(Cyclopropylsulfonyl)-4-(4-methoxyphenyl)-2-oxo-6-(4-((6,6,6-trifluorohexyl)oxy(phenyl)-1,2-dihydropyridine-3-carboxamide | $^1$H NMR: δ 7.70 (d, J = 7.93 Hz, 2H), 7.42 (d, J = 7.63 Hz, 2H), 7.01 (d, J = 7.93 Hz, 2H), 6.96 (d, J = 8.55 Hz, 2H), 6.54 (br. s., 1H), 3.99 (br. s., 2H), 3.74 (s, 3H), 2.17 (br. s., 2H), 1.71 (br. s., 2H), 1.47 (d, J = 7.02 Hz, 4H), 1.20 (br. s., 1H), 0.93 (br. s., 4H). MS(ESI) m/z: 579.5 (M + H)$^+$. | Ex. 13 |
| 66 | 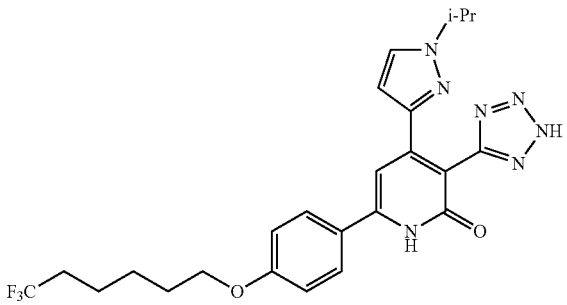 [SMILES: CC(C)n1ccc(-c2cc(-c3ccc(OCCCCCC(F)(F)F)cc3)[nH]c(=O)c2-c2nn[nH]n2)n1]<br>4-(1-Isopropyl-1H-pyrazol-3-yl)-3-(2H-tetrazol-5-yl)-6-(4-((6,6,6-trifluorohexyl)oxy(phenyl)pyridin-2(1H)-one | $^1$H NMR: δ 7.84 (d, J = 8.53 Hz, 2H), 7.71 (d, J = 2.48 Hz, 1H), 7.08 (d, J = 8.80 Hz, 2H), 7.04 (br. s., 1H), 6.06 (br. s., 1H), 4.37 (td, J = 6.71, 13.27 Hz, 1H), 4.07 (t, J = 6.33 Hz, 2H), 2.20-2.33 (m, 2H), 1.78 (quin, J = 6.81 Hz, 2H), 1.47-1.62 (m, 4H), 1.26 (d, J = 6.60 Hz, 6H). MS(ESI) m/z: 502.6 (M + H)$^+$. | Ex. 13 |
| 67 | 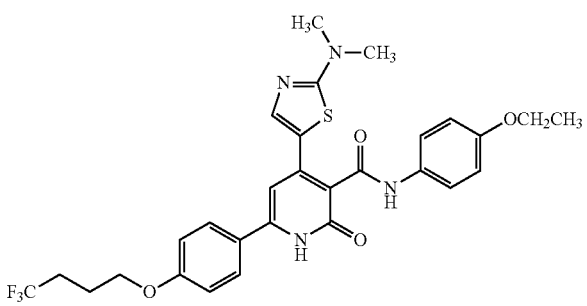 [SMILES: CCOc1ccc(NC(=O)c2c(-c3cnc(N(C)C)s3)cc(-c3ccc(OCCCC(F)(F)F)cc3)[nH]c2=O)cc1]<br>4-(2-(Dimethylamino)thiazol-5-yl)-N-(4-ethoxyphenyl)-2-oxo-6-(4-(4,4,4-trifluorobutoxy)phenyl)-1,2-dihydropyridine-3-carboxamide | $^1$H NMR: δ 10.32 (s, 1H), 7.68-7.84 (m, 3H), 7.58 (d, J = 8.55 Hz, 2H), 7.07 (d, J = 8.24 Hz, 2H), 6.91 (d, J = 8.54 Hz, 2H), 6.68 (br. s., 1H), 4.12 (t, J = 5.95 Hz, 2H), 4.01 (q, J = 6.71 Hz, 2H), 3.02 (s, 6H), 2.45 (dd, J = 10.53, 16.94 Hz, 2H), 1.92-2.03 (m, 2H), 1.32 (t, J = 6.87 Hz, 3H). MS(ESI) m/z: 587.5 (M + H)$^+$. | Ex. 8 |
| 68 | 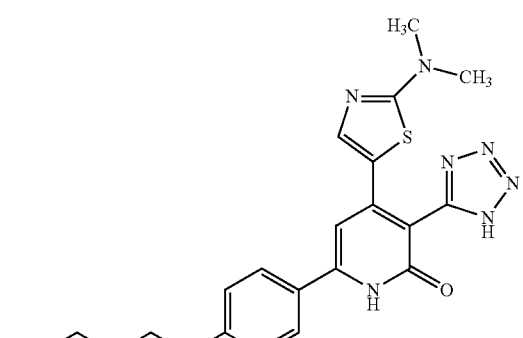<br>4-(2-(Dimethylamino)thiazol-5-yl)-3-(1H-tetrazol-5-yl)-6-(4-(4,4,4-trifluorobutoxy)phenyl)pyridin-2(1H)-one, TFA | $^1$H NMR: δ 7.86 (d, J = 8.53 Hz, 2H), 7.73 (br. s., 1H), 7.09 (d, J = 8.80 Hz, 2H), 6.90 (br. s., 1H), 4.14 (t, J = 6.05 Hz, 2H), 2.97 (s, 6H), 2.40-2.47 (m, 2H), 1.93-2.01 (m, 2H). MS(ESI) m/z: 492.5 (M + H)$^+$. | Ex. 1 |

TABLE 2-continued

| Ex. No. | Structure and Name | Analytical Data | Method |
|---|---|---|---|
| 69 | 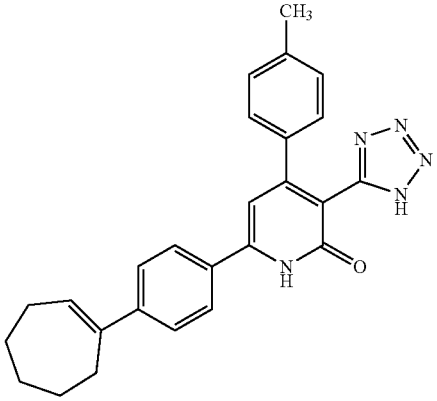 [SMILES: Cc1ccc(-c2cc(-c3ccc(C4=CCCCCC4)cc3)[nH]c(=O)c2-c2nnn[nH]2)cc1]<br>6-(4-(Cyclohept-1-en-1-yl)phenyl)-3-(1H-tetrazol-5-yl)-4-(p-tolyl)pyridin-2(1H)-one | $^1$H NMR (400 MHz, DMSO-$d_6$) δ 7.85 (br. s., 2H), 7.46 (d, J = 8.58 Hz, 2H), 7.11-7.19 (m, 2H), 7.03-7.11 (m, 2H), 6.69 (br. s., 1H), 6.25 (t, J = 6.71 Hz, 1H), 2.58-2.64 (m, 2H), 2.30-2.35 (m, 2H), 2.29 (s, 3H), 1.81 (d, J = 5.28 Hz, 2H), 1.62 (d, J = 4.84 Hz, 2H), 1.53 (br. s., 2H). MS(ESI) m/z: 424.5 (M + H)$^+$. | Ex. 13 |
| 70 | 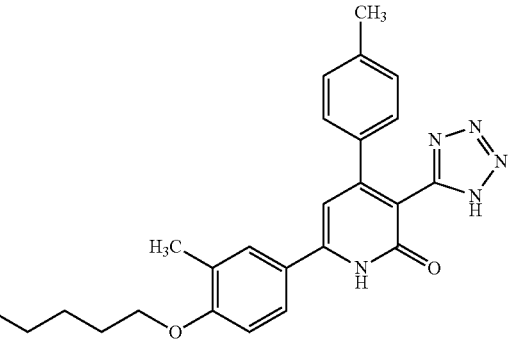<br>6-(3-Methyl-4-((6,6,6-trifluorohexyl)oxy)phenyl)-3-(1H-tetrazol-5-yl)-4-(p-tolyl)pyridin-2(1H)-one | $^1$H NMR: δ 7.64-7.74 (m, 2H), 7.09-7.14 (m, 2H), 6.99-7.07 (m, 3H), 6.65 (br. s., 1H), 4.04 (t, J = 6.26 Hz, 2H), 2.26 (s, 3H), 2.21-2.25 (m, 2H), 2.19 (s, 3H), 1.72-1.81 (m, 2H), 1.46-1.60 (m, 4H). MS(ESI) m/z: 498.5 (M + H)$^+$. | Ex. 13 |
| 71 | 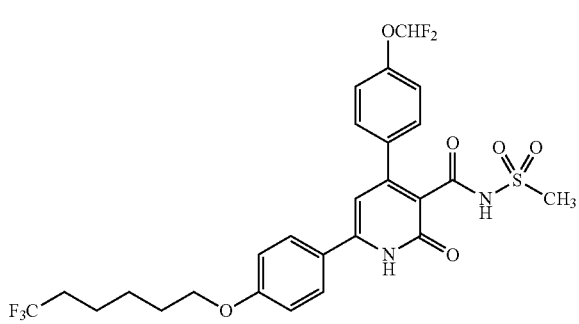 [SMILES: CS(=O)(=O)NC(=O)c1c(-c2ccc(OC(F)F)cc2)cc(-c2ccc(OCCCCCC(F)(F)F)cc2)[nH]c1=O]<br>4-(4-(Difluoromethoxy)phenyl)-N-(methylsulfonyl)-2-oxo-6-(4-((6,6,6-trifluorohexyl)oxy(phenyl)-1,2-dihydropyridine-3-carboxamide | $^1$H NMR: δ 7.86 (d, J = 8.6 Hz, 2H), 7.51 (d, J = 8.3 Hz, 2H), 7.32 (t, J = 73.9 Hz, 1H), 7.26 (d, J = 8.3 Hz, 2H), 7.05 (d, J = 8.5 Hz, 2H), 6.66 (s, 1H), 4.06 (t, J = 6.4 Hz, 2H), 3.14 (s, 3H), 2.43-2.06 (m, 2H), 1.92-1.68 (m, 2H), 1.69-1.44 (m, 4H). MS(ESI) m/z: 589.5 (M + H)$^+$. | Ex. 13 |

TABLE 2-continued

| Ex. No. | Structure and Name | Analytical Data | Method |
|---|---|---|---|
| 72 | 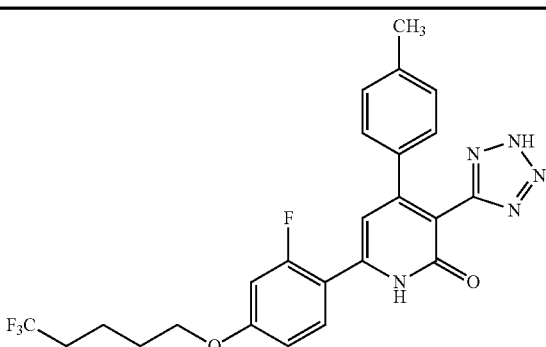<br>6-(2-Fluoro-4-((5,5,5-trifluoropentyl)oxy)phenyl)-3-(2H)-tetrazol-5-yl)-4-(p-tolyl)pyridin-2(1H)-one | $^1$H NMR: δ 7.64 (s, 1H), 7.10 (d, J = 7.8 Hz, 2H), 7.02 (d, J = 7.9 Hz, 2H), 6.98 (dd, J = 12.9, 2.4 Hz, 1H), 6.91 (dd, J = 8.8, 2.5 Hz, 1H), 6.51 (s, 1H), 4.07 (t, J = 6.3 Hz, 2H), 2.38-2.22 (m, 2H), 2.25 (s, 3H), 1.90-1.72 (m, 2H), 1.70-1.55 (m, 2H). MS(ESI) m/z: 488.6 (M + H)$^+$. | Ex. 13 |
| 73 | 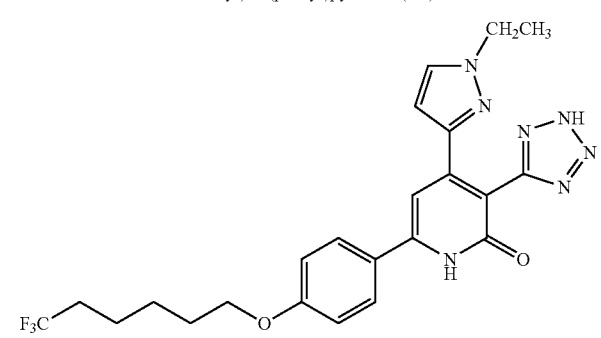<br>4-(1-Ethyl-1H-pyrazol-3-yl)-3-(2H-tetrazol-5-yl)-6-(4-((6,6,6-trifluorohexyl)oxy)phenyl)pyridin-2(1H)-one | $^1$H NMR: δ 7.88 (d, J = 8.3 Hz, 2H), 7.71 (d, J = 2.4 Hz, 1H), 7.21-7.08 (m, 3H), 5.83 (s, 1H), 4.21-4.02 (m, 4H), 2.43-2.15 (m, 2H), 1.93-1.71 (m, 2H), 1.70-1.49 (m, 4H), 1.33 (t, J = 7.3 Hz, 3H). MS(ESI) m/z: 488.6 (M + H)$^+$. | Ex. 13 |
| 74 | 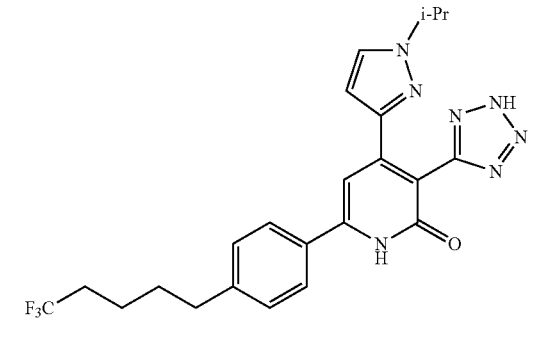 [SMILES: CC(C)n1ccc(-c2cc(-c3ccc(CCCCC(F)(F)F)cc3)[nH]c(=O)c2-c2nn[nH]n2)n1]<br>4-(1-Isopropyl-1H-pyrazol-3-yl)-3-(2H-tetrazol-5-yl)-6-(4-(5,5,5-trifluoropentyl)phenyl)pyridin-2(1H)-one | $^1$H NMR: δ 7.77 (d, J = 7.9 Hz, 2H), 7.66 (d, J = 2.4 Hz, 1H), 7.37 (d, J = 7.8 Hz, 2H), 7.06 (s, 1H), 5.97 (s, 1H), 4.49-4.28 (m, 1H), 2.68 (t, J = 7.6 Hz, 2H), 2.36-2.14 (m, 2H), 1.82-1.60 (m, 2H), 1.58-1.42 (m, 2H), 1.24 (d, J = 6.6 Hz, 6H). MS(ESI) m/z: 472.6 (M + H)$^+$. | Ex. 13 |
| 75 | 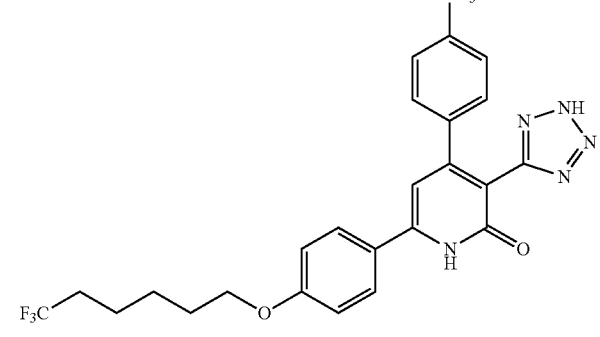<br>3-(2H-Tetrazol-5-yl)-4-(p-tolyl)-6-(4-((6,6,6-trifluorohexyl)oxy)phenyl)pyridin-2(1H)-one | 1H NMR: δ 7.91 (d, J = 8.4 Hz, 2H), 7.19 (d, J = 8.0 Hz, 2H), 7.17-7.11 (m, 4H), 6.75 (s, 1H), 4.12 (t, J = 6.3 Hz, 2H), 2.40-2.27 (m, 2H), 2.35 (s, 3H), 1.90-1.74 (m, 2H), 1.74-1.50 (m, 4H). MS(ESI) m/z: 484.6 (M + H)$^+$. | Ex. 13 |

| Ex. No. | Structure and Name | Analytical Data | Method |
|---|---|---|---|
| 76 | 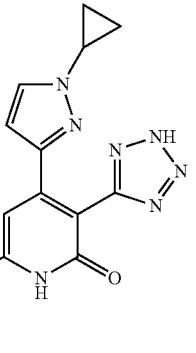<br>4-(1-Cyclopropyl-1H-pyrazol-3-yl)-3-(2H-tetrazol-5-yl)-6-(4-(4,4,4-trifluorobutoxy)phenyl)pyridin-2(1H)-one | $^1$H NMR: δ 7.82 (d, J = 8.4 Hz, 2H), 7.73 (d, J = 2.4 Hz, 1H), 7.09 (d, J = 8.3 Hz, 2H), 7.00 (s, 1H), 6.03 (d, J = 2.4 Hz, 1H), 4.12 (t, J = 6.2 Hz, 2H), 3.64-3.60 (m, 1H), 2.46-2.36 (m, 2H), 2.03-1.88 (m, 2H), 0.93-0.72 (m, 4H). MS(ESI) m/z: 472.5 (M + H)$^+$. | Ex. 13 |
| 77 | 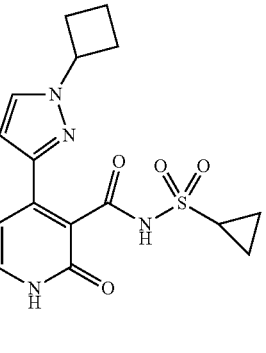<br>4-(1-Cyclobutyl-1H-pyrazol-3-yl)-N-(cyclopropylsulfonyl)-6-(2-fluoro-4-(4,4,4-trifluorobutoxy)phenyl)-2-oxo-1,2-dihydropyridine-3-carboxamide | $^1$H NMR: δ 7.99 (d, J = 2.5 Hz, 1H), 7.64 (t, J = 8.0 Hz, 1H), 7.08 (dd, J = 12.6, 2.4 Hz, 1H), 7.01 (dd, J = 8.7, 2.4 Hz, 1H), 6.94 (bs, 1H), 6.74 (d, J = 2.5 Hz, 1H), 4.93 (q, J = 8.3 Hz, 1H), 4.20 (t, J = 6.3 Hz, 2H), 3.08 (t, J = 6.5 Hz, 1H), 2.55-2.32 (m, 6H), 2.10-2.00 (m, 2H), 1.95-1.73 (m, 2H), 1.20 (t, J = 6.0 Hz, 4H). MS(ESI) m/z: 583.6 (M + H)$^+$. | Ex. 13 |
| 78 | 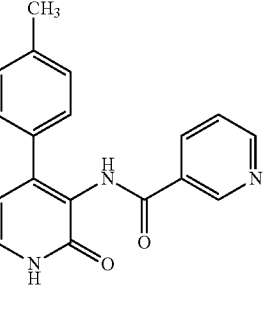<br>N-(2-Oxo-4-(p-tolyl)-6-(4-(4,4,4-trifluorobutoxy)phenyl)-1,2-dihydropyridin-3-yl)nicotinamide | $^1$H NMR: δ 9.73 (s, 1H), 8.96 (br. s., 1H), 8.70 (d, J = 4.27 Hz, 1H), 8.15 (d, J = 7.02 Hz, 1H), 7.78 (d, J = 8.55 Hz, 2H), 7.51 (dd, J = 5.04, 7.78 Hz, 1H), 7.45 (d, J = 8.24 Hz, 2H), 7.20 (d, J = 7.93 Hz, 2H), 7.05 (d, J = 8.85 Hz, 2H), 6.53 (br. s., 1H), 4.10 (t, J = 6.26 Hz, 2H), 2.37-2.46 (m, 2H), 2.27 (s, 3H), 1.90-2.01 (m, 2H). MS(ESI) m/z: 508.2 (M + H)$^+$. | Ex. 15 |

TABLE 2-continued

| Ex. No. | Structure and Name | Analytical Data | Method |
|---|---|---|---|
| 79 | 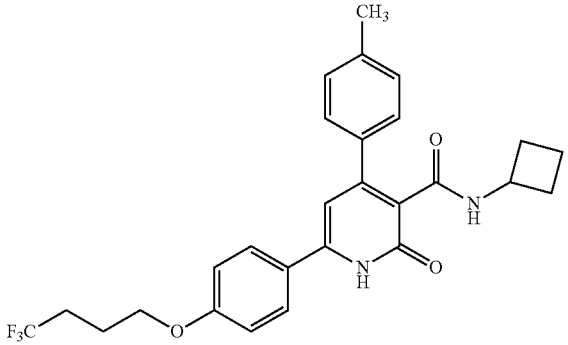 [SMILES: Cc1ccc(-c2cc(-c3ccc(OCCCC(F)(F)F)cc3)[nH]c(=O)c2C(=O)NC2CCC2)cc1]<br>N-Cyclobutyl-2-oxo-4-(p-tolyl)-6-(4-(4,4,4-trifluorobutoxy)phenyl)-1,2-dihydropyridine-3-carboxamide | $^1$H NMR: δ 8.41 (d, J = 7.6 Hz, 1H), 7.79 (d, J = 8.4 Hz, 2H), 7.41 (d, J = 7.8 Hz, 2H), 7.20 (d, J = 7.8 Hz, 2H), 7.04 (d, J = 8.3 Hz, 2H), 6.53 (s, 1H), 4.18-4.08 (m, 1H), 4.10 (t, J = 6.3 Hz, 2H), 2.48-2.36 (m, 2H), 2.33 (s, 3H), 2.12-2.01 (m, 2H), 2.00-1.92 (m, 2H), 1.82-1.66 (m, 2H), 1.63-1.48 (m, 2H). MS(ESI) m/z: 485.6 (M + H)$^+$. | Ex. 13 |
| 80 | 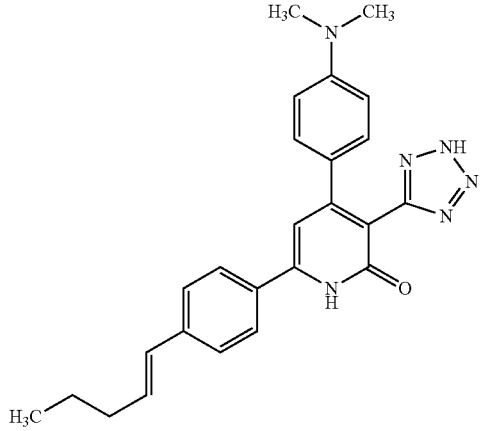 [SMILES: CCC/C=C/c1ccc(-c2cc(-c3ccc(N(C)C)cc3)c(-c3nn[nH]n3)c(=O)[nH]2)cc1]<br>(E)-4-(4-(Dimethylamino)phenyl)-6-(4-(pent-1-en-1-yl)phenyl)-3-(2H-tetrazol-5-yl)pyridin-2(1H)-one | $^1$H NMR: δ 7.82 (d, J = 8.0 Hz, 2H), 7.53 (d, J = 8.0 Hz, 2H), 7.00 (d, J = 8.5 Hz, 2H), 6.72 (s, 1H), 6.60-6.55 (m, 2H), 6.51-6.41 (m, 2H), 2.89 (s, 6H), 2.24-2.12 (m, 2H), 1.58-1.37 (m, 2H), 0.92 (t, J = 7.4 Hz, 3H). MS(ESI) m/z: 427.6 (M + H)$^+$. | Ex. 13 |
| 81 | 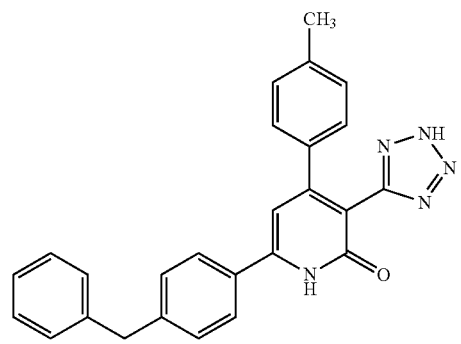 [SMILES: Cc1ccc(-c2cc(-c3ccc(Cc4ccccc4)cc3)[nH]c(=O)c2-c2nn[nH]n2)cc1]<br>6-(4-Benzylphenyl)-3-(2H-tetrazol-5-yl)-4-(p-tolyl)pyridin-2(1H)-one | $^1$H NMR: δ 7.80 (d, J = 7.8 Hz, 2H), 7.38 (d, J = 7.8 Hz, 2H), 7.34-7.24 (m, 4H), 7.24-7.17 (m, 1H), 7.10 (d, J = 7.9 Hz, 2H), 7.06 (d, J = 7.8 Hz, 2H), 6.71 (s, 1H), 4.00 (s, 2H), 2.26 (s, 3H). MS(ESI) m/z: 420.5 (M + H)$^+$. | Ex. 13 |

TABLE 2-continued

| Ex. No. | Structure and Name | Analytical Data | Method |
|---|---|---|---|
| 82 | 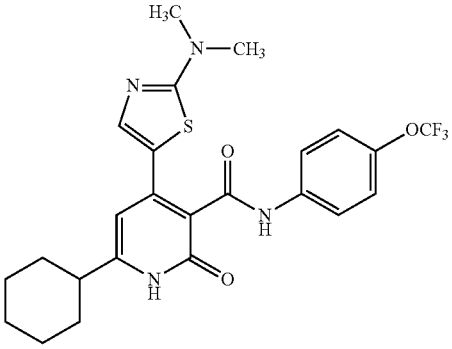 [SMILES: CN(C)c1ncc(-c2cc(C3CCCCC3)[nH]c(=O)c2C(=O)Nc2ccc(OC(F)(F)F)cc2)s1]<br>6-Cyclohexyl-4-(2-(dimethylamino)thiazol-5-yl)-2-oxo-N-(4-(trifluoromethoxy)phenyl)-1,2-dihydropyridine-3-carboxamide, TFA | $^1$H NMR (400 MHz, CDCl$_3$) δ 10.88 (s, 1H), 7.74 (s, 1H), 7.64 (d, J = 9.02 Hz, 2H), 7.20 (d, J = 8.36 Hz, 2H), 6.50 (s, 1H), 3.34 (s, 6H), 2.53-2.66 (m, 1H), 1.86-2.02 (m, 4H), 1.76 (d, J = 12.54 Hz, 2H), 1.20-1.57 (m, 4H). MS(ESI) m/z: 507.6 (M + H)$^+$. | Ex. 5 |
| 83 | 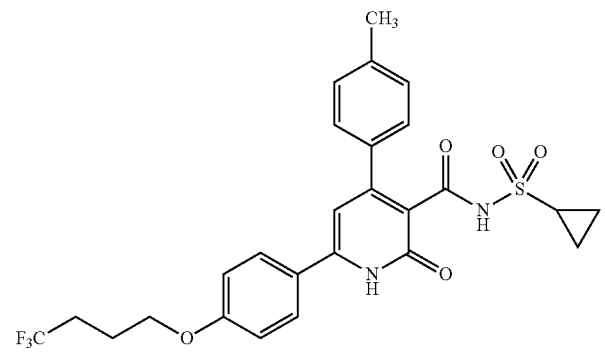 [SMILES: Cc1ccc(-c2cc(-c3ccc(OCCCC(F)(F)F)cc3)[nH]c(=O)c2C(=O)NS(=O)(=O)C2CC2)cc1]<br>N-(Cyclopropylsulfonyl)-2-oxo-4-(p-tolyl)-6-(4-(4,4,4-trifluorobutoxy)phenyl)-1,2-dihydropyridine-3-carboxamide | $^1$H NMR: δ 7.81 (d, J = 8.5 Hz, 2H), 7.36 (d, J = 7.8 Hz, 2H), 7.24 (d, J = 7.6 Hz, 2H), 7.05 (d, J = 8.4 Hz, 2H), 6.60 (s, 1H), 4.10 (t, J = 6.3 Hz, 2H), 2.85-2.76 (m, 1H), 2.46-2.37 (m, 2H), 2.33 (s, 3H), 2.01-1.86 (m, 2H), 1.07-0.90 (m, 4H). MS(ESI) m/z: 535.5 (M + H)$^+$. | Ex. 13 |
| 84 | 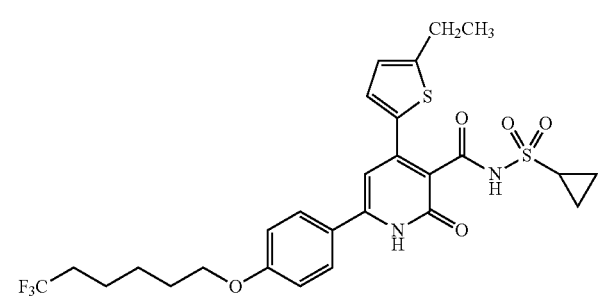 [SMILES: CCc1ccc(-c2cc(-c3ccc(OCCCCCC(F)(F)F)cc3)[nH]c(=O)c2C(=O)NS(=O)(=O)C2CC2)s1]<br>N-(Cyclopropylsulfonyl)-4-(5-ethylthiophen-2-yl)-2-oxo-6-(4-((6,6,6-trifluorohexyl)oxy)phenyl)-1,2-dihydropyridine-3-carboxamide | $^1$H NMR: δ 12.12 (s, 2H), 7.79 (d, J = 8.2 Hz, 2H), 7.39 (d, J = 3.7 Hz, 1H), 7.11-7.01 (m, 2H), 6.94 (d, J = 3.6 Hz, 1H), 6.62 (s, 1H), 4.06 (t, J = 6.4 Hz, 2H), 2.99 (tt, J = 7.7, 5.1 Hz, 1H), 2.86 (q, J = 7.5 Hz, 2H), 2.38-2.20 (m, 2H), 1.80-1.68 (m, 2H), 1.64-1.39 (m, 4H), 1.27 (t, J = 7.5 Hz, 3H), 1.19-1.02 (m, 4H). MS(ESI) m/z: 583.5 (M + H)$^+$. | Ex. 13 |

| Ex. No. | Structure and Name | Analytical Data | Method |
|---|---|---|---|
| 85 | 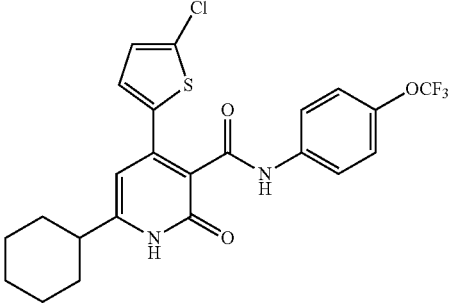 [SMILES: O=C(Nc1ccc(OC(F)(F)F)cc1)c1c(-c2ccc(Cl)s2)cc(C2CCCCC2)[nH]c1=O]<br>4-(5-Chlorothiophen-2-yl)-6-cyclohexyl-2-oxo-N-(4-(trifluoromethoxy)phenyl)-1,2-dihydropyridine-3-carboxamide | $^1$H NMR (400 MHz, CDCl$_3$) δ 11.03-11.51 (m, 1H), 10.41 (br. s., 1H), 7.65 (d, J = 9.02 Hz, 2H), 7.16 (d, J = 8.36 Hz, 2H), 7.06 (d, J = 3.96 Hz, 1H), 6.90 (d, J = 3.74 Hz, 1H), 6.26 (s, 1H), 2.50 (t, J = 11.66 Hz, 1H), 1.95 (d, J = 11.66 Hz, 2H), 1.83 (d, J = 12.76 Hz, 2H), 1.65-1.72 (m, 1H), 1.38-1.51 (m, 2H), 1.14-1.36 (m, 3H). MS(ESI) m/z: 497.3 (M + H)$^+$. | Ex. 5 |
| 86 | 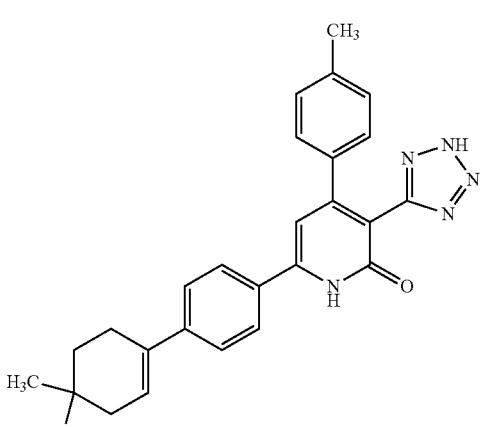<br>6-(4',4'-Dimethyl-2',3',4',5'-tetrahydro-[1,1'-biphenyl]-4-yl)-3-(2H-tetrazol-5-yl)-4-(p-tolyl)pyridin-2(1H)-one | $^1$H NMR: δ 7.91 (d, J = 8.3 Hz, 2H), 7.64 (d, J = 8.1 Hz, 2H), 7.20 (d, J = 7.8 Hz, 2H), 7.15 (d, J = 7.8 Hz, 2H), 6.82 (s, 1H), 6.41-6.28 (m, 1H), 2.54-2.43 (m, 2H), 2.35 (s, 3H), 2.13-2.04 (m, 2H), 1.57 (t, J = 6.4 Hz, 2H), 1.02 (s, 6H). MS(ESI) m/z: 438.6 (M + H)$^+$. | Ex. 13 |
| 87 | 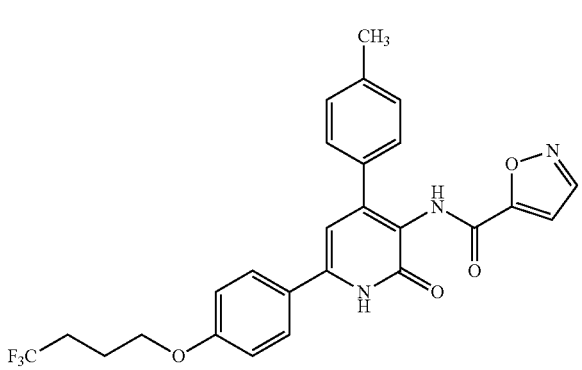 [SMILES: Cc1ccc(-c2cc(-c3ccc(OCCCC(F)(F)F)cc3)[nH]c(=O)c2NC(=O)c2ccno2)cc1]<br>N-(2-Oxo-4-(p-tolyl)-6-(4-(4,4,4-trifluorobutoxy)phenyl)-1,2-dihydropyridin-3-yl)isoxazole-5-carboxamide | $^1$H NMR: δ 10.01 (br.s., 1H), 8.71 (s, 1H), 7.77 (d, J = 8.55 Hz, 2H), 7.42 (d, J = 7.63 Hz, 2H), 7.21 (d, J = 7.93 Hz, 2H), 7.08 (br. s., 1H), 7.04 (d, J = 8.55 Hz, 2H), 6.51 (br. s., 1H), 4.10 (t, J = 6.10 Hz, 2H), 2.34-2.48 (m, 2H), 2.29 (s, 3H), 1.86-2.01 (m, 2H). MS(ESI) m/z: 498.2 (M + H)$^+$. | Ex. 15 |

TABLE 2-continued

| Ex. No. | Structure and Name | Analytical Data | Method |
|---|---|---|---|
| 88 | 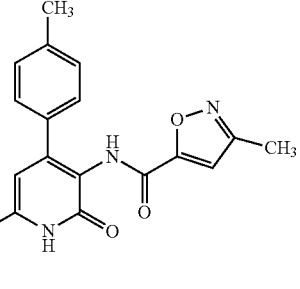<br>3-Methyl-N-(2-oxo-4-(p-tolyl)-6-(4-(4,4,4-trifluorobutoxy)phenyl)-1,2-dihydropyridin-3-yl)isoxazole-5-carboxamide | $^1$H NMR: δ 9.92 (br. s., 1H), 7.77 (d, J = 8.55 Hz, 2H), 7.41 (d, J = 7.93 Hz, 2H), 7.20 (d, J = 7.93 Hz, 2H), 7.04 (d, J = 8.54 Hz, 2H), 6.93 (s, 1H), 6.50 (br. s., 1H), 4.10 (t, J = 6.10 Hz, 2H), 2.35-2.48 (m, 2H), 2.29 (br. s., 3H), 2.28 (br. s., 3H), 1.87-2.00 (m, 2H). MS(ESI) m/z: 512.2 (M+H)$^+$. | Ex. 15 |
| 89 | 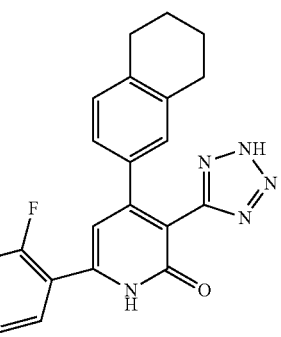<br>6-(2-Fluoro-4-(4,4,4-trifluorobutoxy)phenyl)-4-(5,6,7,8-tetrahydronaphthalen-2-yl)-3-(2H-tetrazol-5-yl)pyridin-2(1H)-one | $^1$H NMR: δ 7.67 (t, J = 8.9 Hz, 1H), 7.00 (d, J = 12.7 Hz, 1H), 6.96-6.88 (m, 3H), 6.75 (d, J = 7.9 Hz, 1H), 6.53 (s, 1H), 4.12 (t, J = 6.0 Hz, 2H), 2.71-2.55 (m, 4H), 2.42 (q, J = 10.5, 10.0 Hz, 2H), 1.99-1.92 (m, 2H), 1.68 (s, 4H). MS(ESI) m/z: 514.6 (M + H)$^+$. | Ex. 13 |
| 90 | 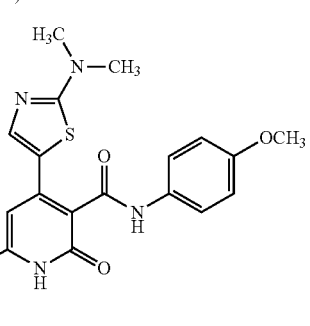<br>4-(2-(Dimethylamino)thiazol-5-yl)-2-oxo-6-(4-(4,4,4-trifluorobutoxy)phenyl)-N-(4-(trifluoromethoxy)phenyl)-1,2-dihydropyridine-3-carboxamide, TFA | $^1$H NMR (400 MHz, CDCl$_3$) δ 10.75 (br. s., 1H), 7.71 (s, 1H), 7.66 (d, J = 7.92 Hz, 2H), 7.56 (d, J = 9.02 Hz, 2H), 7.12 (d, J = 8.36 Hz, 2H), 6.92 (d, J = 8.36 Hz, 2H), 6.69 (s, 1H), 3.94 (t, J = 5.94 Hz, 2H), 3.21 (s, 6H), 2.23-2.39 (m, 2H), 2.02-2.12 (m, 2H). MS(ESI) m/z: 627.5 (M + H)$^+$. | Ex. 5 |
| 91 | 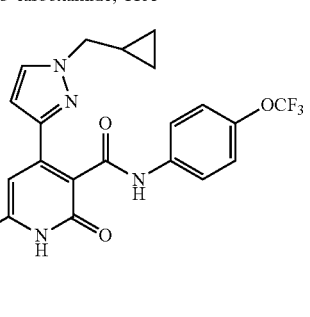<br>4-(1-(Cyclopropylmethyl)-1H-pyrazol-3-yl)-2-oxo-6-(4-(4,4,4-trifluorobutoxy)phenyl)-N-(4-(trifluoromethoxy)phenyl)-1,2-dihydropyridine-3-carboxamide | $^1$H NMR: δ 10.54 (s, 1H), 7.69-7.83 (m, 5H), 7.33 (d, J = 8.54 Hz, 2H), 7.08 (d, J = 8.55 Hz, 2H), 7.00 (br. s., 1H), 6.61 (s, 1H), 4.12 (t, J = 5.95 Hz, 2H), 3.94 (d, J = 7.32 Hz, 2H), 2.36-2.47 (m, 2H), 1.91-2.02 (m, 2H), 1.15 (br. s., 1H), 0.42 (d, J = 7.63 Hz, 2H), 0.28 (d, J = 4.58 Hz, 2H). MS(ESI) m/z: 621.1 (M + H)$^+$. | Ex. 5 |

| Ex. No. | Sructure and Name | Analytical Data | Method |
|---|---|---|---|
| 92 | 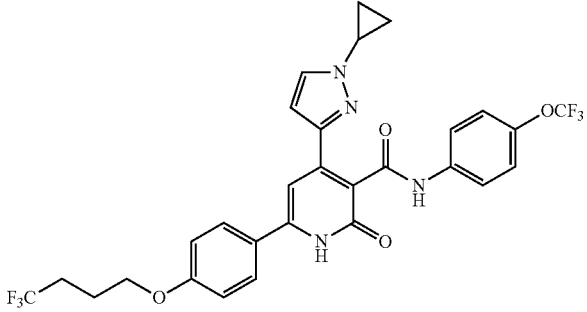 [SMILES: O=C(Nc1ccc(OC(F)(F)F)cc1)c1c(-c2ccn(C3CC3)n2)cc(-c2ccc(OCCCC(F)(F)F)cc2)[nH]c1=O]<br>4-(1-Cyclopropyl-1H-pyrazol-3-yl)-2-oxo-6-(4-(4,4,4-trifluorobutoxy)phenyl)-N-(4-(trifluoromethoxy)phenyl)-1,2-dihydropyridine-3-carboxamide | $^1$H NMR: δ 10.52 (s, 1H), 7.74-7.84 (m, 5H), 7.33 (d, J = 8.54 Hz, 2H), 7.08 (d, J = 8.55 Hz, 2H), 6.97 (br. s., 1H), 6.61 (d, J = 1.83 Hz, 1H), 4.12 (t, J = 6.26 Hz, 2H), 3.73 (td, J = 3.51, 7.02 Hz, 1H), 2.44 (dd, J = 11.44, 16.33 Hz, 2H), 1.93-2.01 (m, 2H), 0.94 (d, J = 3.36 Hz, 2H), 0.87 (d, J = 5.80 Hz, 2H). MS(ESI) m/z: 607.1 (M + H)$^+$. | Ex. 5 |
| 93 | 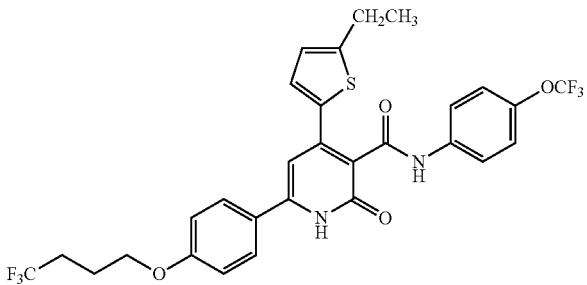 [SMILES: CCc1ccc(-c2cc(-c3ccc(OCCCC(F)(F)F)cc3)[nH]c(=O)c2C(=O)Nc2ccc(OC(F)(F)F)cc2)s1]<br>4-(5-Ethylthiophen-2-yl)-2-oxo-6-(4-(4,4,4-trifluorobutoxy)phenyl)-N-(4-(trifluoromethoxy)phenyl)-1,2-dihydropyridine-3-carboxamide | $^1$H NMR: δ 10.67 (s, 1H), 7.79 (d, J = 8.55 Hz, 2H), 7.76 (d, J = 8.85 Hz, 2H), 7.43 (d, J = 3.66 Hz, 1H), 7.34 (d, J = 8.55 Hz, 2H), 7.07 (d, J = 8.85 Hz, 2H), 6.87 (d, J = 3.36 Hz, 1H), 6.70 (br. s., 1H), 4.12 (t, J = 6.10 Hz, 2H), 2.78 (q, J = 7.32 Hz, 2H), 2.37-2.48 (m, 2H), 1.92-2.01 (m, 2H), 1.19 (t, J = 7.48 Hz, 3H). MS(ESI) m/z: 611.0 (M + H)$^+$. | Ex. 5 |
| 94 | 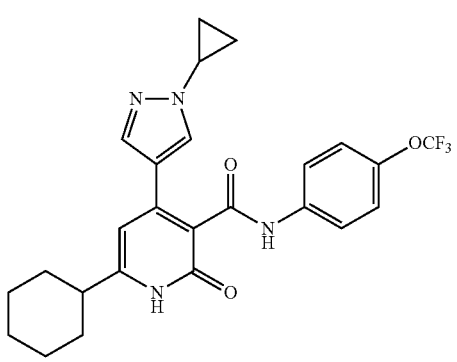 [SMILES: O=C(Nc1ccc(OC(F)(F)F)cc1)c1c(-c2cnn(C3CC3)c2)cc(C2CCCCC2)[nH]c1=O]<br>6-Cyclohexyl-4-(1-cyclopropyl-1H-pyrazol-4-yl)-2-oxo-(trifluoromethoxy)phenyl)-1,2-dihydropyridine-3-carboxamide | $^1$H NMR (400 MHz, DMSO-d$_6$) δ 11.68 (br. s., 1H), 10.55 (s, 1H), 8.19 (s, 1H), 7.78 (d, J = 9.24 Hz, 2H), 7.63 (s, 1H), 7.34 (d, J = 8.58 Hz, 2H), 6.30 (s, 1H), 3.67-3.74 (m, 1H), 1.81 (br. s., 3H), 1.69 (d, J = 10.34 Hz, 1H), 1.43-1.59 (m, 3H), 1.19-1.35 (m, 3H), 0.84-1.01 (m, 5H). MS(ESI) m/z: 487.5 (M + H)$^+$. | Ex. 5 |

TABLE 2-continued

| Ex. No. | Structure and Name | Analytical Data | Method |
|---|---|---|---|
| 95 | 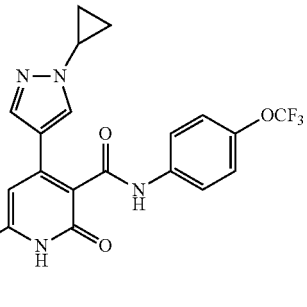<br>4-(1-Cyclopropyl-1H-pyrazol-4-yl)-2-oxo-6-(4-(4,4,4-trifluorobutoxy)phenyl)-N-(4-(trifluoromethoxy)phenyl)-1,2-dihydropyridine-3-carboxamide | $^1$H NMR: δ 10.63 (s, 1H), 8.29 (s, 1H), 7.75-7.86 (m, 4H), 7.72 (s, 1H), 7.36 (d, J = 8.55 Hz, 2H), 7.07 (d, J = 8.54 Hz, 2H), 6.81 (br. s., 1H), 4.12 (t, J = 5.95 Hz, 2H), 3.72 (d, J = 3.97 Hz, 1H), 2.37-2.47 (m, 2H), 1.88-2.00 (m, 2H), 0.81-1.04 (m, 4H). MS(ESI) m/z: 607.1 (M + H)$^+$. | Ex. 5 |
| 96 | 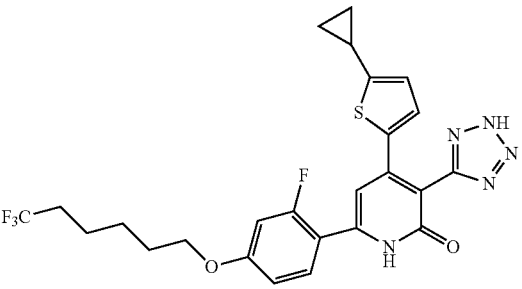 [SMILES: O=c1[nH]c(-c2ccc(OCCCCCC(F)(F)F)cc2F)cc(-c2ccc(C3CC3)s2)c1-c1nn[nH]n1]<br>4-(5-Cyclopropylthiophen-2-yl)-6-(2-fluoro-4-((6,6,6-trifluorohexyl)oxy)phenyl)-3-(2H-tetrazol-5-yl)pyridin-2(1H)-one | $^1$H NMR: δ 7.70 (t, J = 8.8 Hz, 1H), 7.12 (d, J = 3.8 Hz, 1H), 7.06 (dd, J = 12.8, 2.5 Hz, 1H), 7.00 (dd, J = 8.7, 2.4 Hz, 1H), 6.81 (d, J = 4.0 Hz, 1H), 6.79 (s, 1H), 4.14 (t, J = 6.3 Hz, 2H), 2.44-2.24 (m, 2H), 2.20-2.02 (m, 1H), 1.96-1.78 (m, 2H), 1.73-1.48 (m, 4H), 1.16-0.93 (m, 2H), 0.76-0.57 (m, 2H). MS(ESI) m/z: 534.4 (M + H)$^+$. | Ex. 13 |
| 97 | 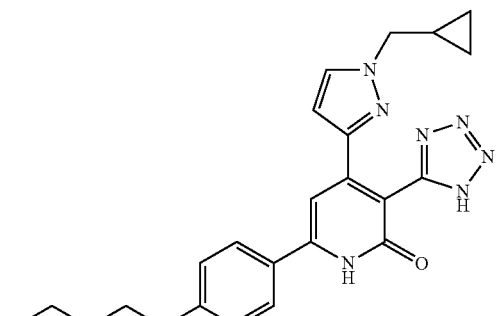<br>4-(1-(Cyclopropylmethyl)-1H-pyrazol-3-yl)-3-1H-tetrazol-5-yl)-6-(4-(4,4,4-trifluorobutoxy)phenyl)pyridin-2(1H)-one | $^1$H NMR (400 MHz, DMSO-d$_6$) δ 12.23 (br. s., 1H), 7.83 (br. s., 2H), 7.71 (d, J = 2.42 Hz, 1H), 7.10 (d, J = 9.02 Hz, 2H), 7.01 (br. s., 1H), 5.86 (s, 1H), 4.14 (t, J = 6.16 Hz, 2H), 3.87 (d, J = 7.26 Hz, 2H), 2.39-2.48 (m, 2H), 1.92-2.03 (m, 2H), 1.04-1.17 (m, 1H), 0.43-0.51 (m, 2H), 0.24-0.32 (m, 2H). MS(ESI) m/z: 486.4 (M + H)$^+$. | Ex. 13 |
| 98 | 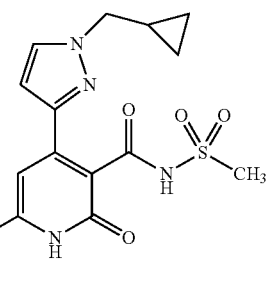<br>4-(1-(Cyclopropylmethyl)-1H-pyrazol-3-yl)-N-(methylsulfonyl)-2-oxo-6-(4-(4,4,4-trifluorobutoxy)phenyl)-1,2-dihydropyridine-3-carboxamide | $^1$H NMR (400 MHz, DMSO-d$_6$) δ 12.05 (s, 2H), 7.90 (d, J = 2.20 Hz, 1H), 7.78 (d, J = 7.48 Hz, 2H), 7.08 (d, J = 9.02 Hz, 2H), 6.92 (br. s., 1H), 6.80 (d, J = 2.42 Hz, 1H), 4.12 (t, J = 6.16 Hz, 2H), 4.02 (d, J = 7.04 Hz, 2H), 3.33 (s, 3H), 2.37-2.48 (m, 2H), 1.92-2.01 (m, 2H), 1.20-1.32 (m, 1H), 0.50-0.56 (m, 2H), 0.35-0.41 (m, 2H). MS(ESI) m/z: 539.4 (M + H)$^+$. | Ex. 13 |

TABLE 2-continued

| Ex. No. | Structure and Name | Analytical Data | Method |
|---|---|---|---|
| 99 | 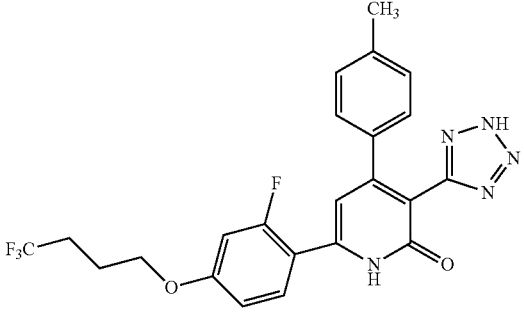 [SMILES: Cc1ccc(-c2cc(-c3ccc(OCCCC(F)(F)F)cc3F)[nH]c(=O)c2-c2nn[nH]n2)cc1]<br>6-(2-Fluoro-4-(4,4,4-trifluorobutoxy)phenyl)-3-(2H-tetrazol-5-yl)-4-(p-tolyl)pyridin-2(1H)-one | $^1$H NMR: δ 7.75 (t, J = 9.0 Hz, 1H), 7.19 (d, J = 7.8 Hz, 2H), 7.15-7.06 (m, 3H), 7.01 (dd, J = 8.8, 2.4 Hz, 1H), 6.59 (s, 1H), 4.21 (d, J = 6.4 Hz, 2H), 2.56-2.42 (m, 2H), 2.34 (s, 3H), 2.03 (dq, J = 12.5, 6.4 Hz, 2H). MS(ESI) m/z: 474.4 (M + H)$^+$. | Ex. 13 |
| 100 | 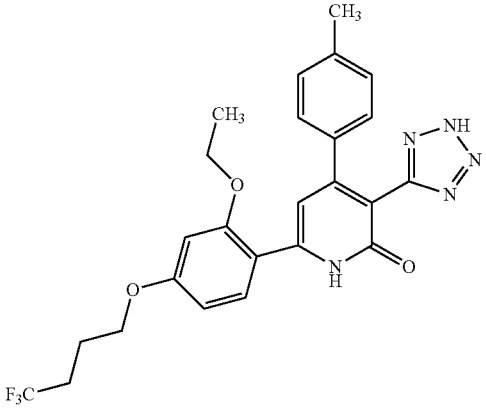 [SMILES: CCOc1cc(OCCCC(F)(F)F)ccc1-c1cc(-c2ccc(C)cc2)c(-c2nn[nH]n2)c(=O)[nH]1]<br>6-(2-Ethoxy-4-(4,4,4-trifluorobutoxy)phenyl)-3-(2H-tetrazol-5-yl)-4-(p-tolyl)pyridin-2(1H)-one | $^1$H NMR: δ 7.45 (d, J = 8.7 Hz, 1H), 7.05 (d, J = 7.9 Hz, 2H), 6.98 (d, J = 7.8 Hz, 2H), 6.63 (s, 1H), 6.58 (d, J = 8.9 Hz, 1H), 6.40 (s, 1H), 4.16-3.96 (m, 4H), 2.42-2.30 (m, 2H), 2.21 (s, 3H), 2.00-1.68 (m, 2H), 1.28 (t, J = 6.8 Hz, 3H). MS(ESI) m/z: 500.4 (M + H)$^+$. | Ex. 13 |
| 101 | 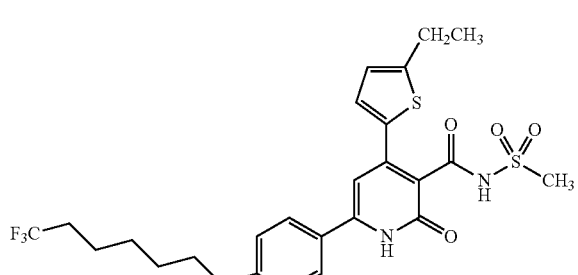<br>4-(5-Ethylthiophen-2-yl)-N-(methylsulfonyl)-2-oxo-6-(4-((6,6,6-trifluorohexyl)oxy)phenyl)-1,2-dihydropyridine-3-carboxamide | $^1$H NMR: δ 7.78 (d, J = 8.2 Hz, 2H), 7.37 (d, J = 3.8 Hz, 1H), 7.04 (d, J = 8.4 Hz, 2H), 6.93 (d, J = 3.7 Hz, 1H), 6.63 (s, 1H), 4.05 (t, J = 6.4 Hz, 2H), 2.86 (q, J = 7.5 Hz, 2H), 2.50 (s, 3H), 2.27 (dt, J = 12.9, 8.2 Hz, 2H), 1.83-1.68 (m, 2H), 1.65-1.42 (m, 4H), 1.26 (t, J = 7.5 Hz, 3H). MS(ESI) m/z: 557.3 (M + H)$^+$. | Ex. 13 |

TABLE 2-continued

| Ex. No. | Structure and Name | Analytical Data | Method |
|---|---|---|---|
| 102 | 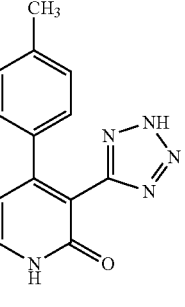<br>6-(2-Fluoro-4-((6,6,6-trifluorohexyl)oxy)phenyl)-3-(2H-tetrazol-5-yl)-4-(p-tolyl)pyridin-2(1H)-one | $^1$H NMR: δ 7.76 (t, J = 9.1 Hz, 1H), 7.19 (d, J = 7.8 Hz, 2H), 7.12 (d, J = 7.8 Hz, 2H), 7.06 (d, J = 13.1 Hz, 1H), 6.99 (d, J = 8.7 Hz, 1H), 6.63 (s, 1H), 4.14 (t, J = 6.3 Hz, 2H), 2.40-2.28 (m, 2H), 2.35 (s, 3H), 1.94-1.75 (m, 2H), 1.70-1.46 (m, 4H). MS(ESI) m/z: 502.5 (M + H)$^+$. | Ex. 13 |
| 103 | 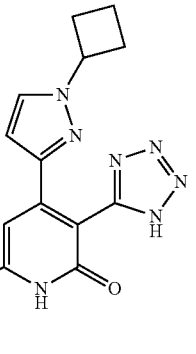<br>4-(1-Cyclobutyl-1H-pyrazol-3-yl)-6-(2-fluoro-4-(5,5,5-trifluoropentyl)phenyl)-3-1H-tetrazol-5-yl)pyridin-2(1H)-one | $^1$H NMR: δ 7.72 (s, 1H), 7.58-7.67 (m, 1H), 7.27 (d, J = 11.90 Hz, 1H), 7.22 (d, J = 7.93 Hz, 1H), 6.94 (br. s., 1H), 5.98 (br. s., 1H), 4.72 (quin, J = 7.86 Hz, 1H), 2.71 (t, J = 7.32 Hz, 2H), 2.17-2.37 (m, 6H), 1.70 (t, J = 7.48 Hz, 4H), 1.45-1.56 (m, 2H). MS(ESI) m/z: 502.2 (M + H)$^+$. | Ex. 13 |
| 104 | 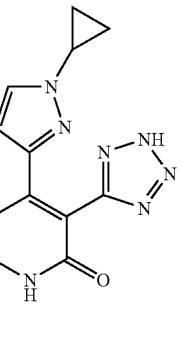<br>4-(1-Cyclopropyl-1H-pyrazol-3-yl)-6-(2-fluoro-4-((6,6,6-trifluorohexyl)oxy)phenyl)-3-(2H-tetrazol-5-yl)pyridin-2(1H)-one | $^1$H NMR: δ 7.75 (d, J = 2.4 Hz, 1H), 7.63 (t, J = 8.7 Hz, 1H), 7.01 (d, J = 12.7 Hz, 1H), 6.93 (d, J = 8.8 Hz, 1H), 6.89 (s, 1H), 5.88 (s, 1H), 4.07 (t, J = 6.4 Hz, 2H), 3.68 (dt, J = 6.9, 3.6 Hz, 1H), 2.28 (dp, J = 15.6, 4.9, 4.5 Hz, 2H), 1.84-1.64 (m, 2H), 1.65-1.44 (m, 4H), 0.96-0.69 (m, 4H). MS(ESI) m/z: 518.4 (M + H)$^+$. | Ex. 13 |

TABLE 2-continued

| Ex. No. | Structure and Name | Analytical Data | Method |
|---|---|---|---|
| 105 | 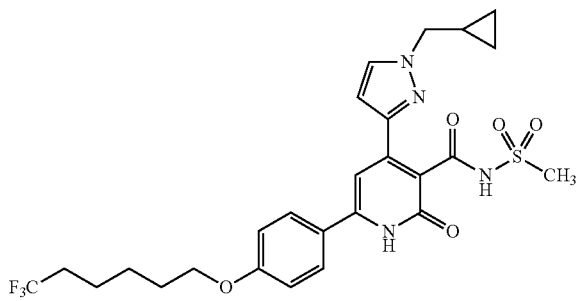 [SMILES: CS(=O)(=O)NC(=O)c1c(-c2ccn(CC3CC3)n2)cc(-c2ccc(OCCCCCC(F)(F)F)cc2)[nH]c1=O]<br>4-(1-(Cyclopropylmethyl)-1H-pyrazol-3-yl)-N-(methylsulfonyl)-2-oxo-6-(4-((6,6,6-trifluorohexyl)oxy)phenyl)-1,2-dihydropyridine-3-carboxamide | $^1$H NMR: δ 7.88 (s, 1H), 7.76 (d, J = 7.02 Hz, 2H), 7.05 (d, J = 8.55 Hz, 2H), 6.93 (br. s., 1H), 6.78 (br. s., 1H), 3.97-4.08 (m, 4H), 2.50 (br. s., 3H), 2.26 (d, J = 8.24 Hz, 2H), 1.71-1.83 (m, 2H), 1.44-1.62 (m, 4H), 1.25 (d, J = 16.78 Hz, 1H), 0.53 (d, J = 7.32 Hz, 2H), 0.38 (d, J = 4.58 Hz, 2H). MS(ESI) m/z: 567.2 (M + H)$^+$. | Ex. 13 |
| 106 | 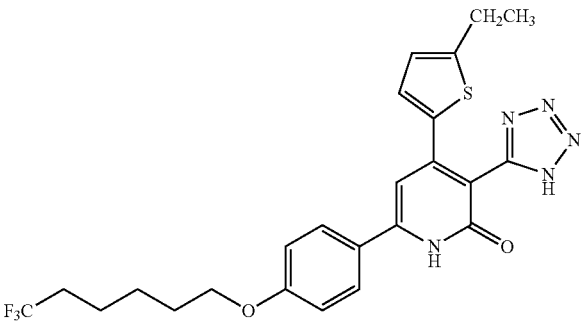 [SMILES: CCc1ccc(-c2cc(-c3ccc(OCCCCCC(F)(F)F)cc3)[nH]c(=O)c2-c2nnn[nH]2)s1]<br>4-(5-Ethylthiophen-2-yl)-3-1H-tetrazol-5-yl)-6-(4-((6,6,6-trifluorohexyl)oxy)phenyl)pyridin-2(1H)-one | $^1$H NMR: δ 7.86 (d, J = 7.63 Hz, 2H), 7.19 (br. s., 1H), 7.07 (d, J = 8.24 Hz, 2H), 6.85 (br. s., 1H), 6.82 (br. s., 1H), 4.07 (t, J = 6.10 Hz, 2H), 2.73 (q, J = 7.43 Hz, 2H), 2.26 (d, J = 8.85 Hz, 2H), 1.73-1.82 (m, 2H), 1.46-1.62 (m, 4H), 1.16 (t, J = 7.48 Hz, 3H). MS(ESI) m/z: 504.2 (M + H)$^+$. | Ex. 13 |
| 107 | 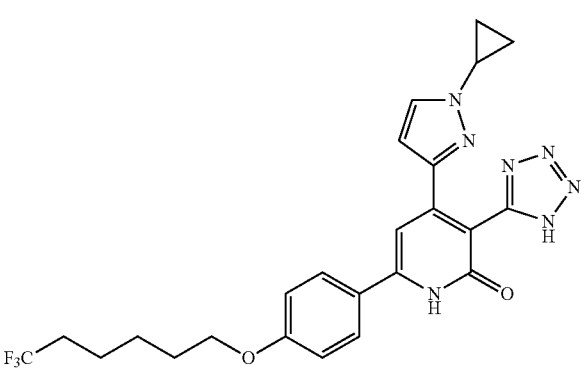 [SMILES: O=c1[nH]c(-c2ccc(OCCCCCC(F)(F)F)cc2)cc(-c2ccn(C3CC3)n2)c1-c1nnn[nH]1]<br>4-(1-Cyclopropyl-1H-pyrazol-3-yl)-3-1H-tetrazol-5-yl)-6-(4-((6,6,6-trifluorohexyl)oxy)phenyl)pyridin-2(1H)-one | $^1$H NMR: δ 7.83 (br. s., 2H), 7.76 (s, 1H), 7.07 (d, J = 8.24 Hz, 2H), 6.99 (br. s., 1H), 6.05 (br. s., 1H), 4.06 (t, J = 6.26 Hz, 2H), 3.67 (br. s., 1H), 2.26 (d, J = 11.90 Hz, 2H), 1.73-1.83 (m, 2H), 1.45-1.62 (m, 4H), 0.79-0.91 (m, 4H). MS(ESI) m/z: 500.2 (M + H)$^+$. | Ex. 13 |

TABLE 2-continued

| Ex. No. | Structure and Name | Analytical Data | Method |
|---|---|---|---|
| 108 | 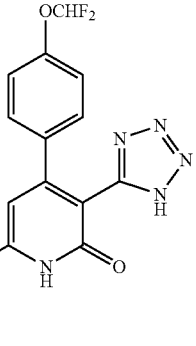<br>4-(4-(Difluoromethoxy)phenyl)-3-(1H-tetrazol-5-yl)-6-(4-((6,6-trifluorohexyl)oxy)phenyl)pyridin-2(1H)-one | $^1$H NMR: δ 7.90 (d, J = 8.80 Hz, 2H), 7.28-7.46 (m, 1H), 7.28 (d, J = 8.53 Hz, 2H), 7.13 (d, J = 8.80 Hz, 2H), 7.05 (d,.J = 9.08 Hz, 2H), 6.77 (br. s., 1H), 4.06 (t, J = 6.33 Hz, 2H), 2.22-2.33 (m, 2H), 1.77 (quin, J = 6.81 Hz, 2H), 1.45-1.64 (m, 4H). MS(ESI) m/z: 536.2 (M + H)$^+$. | Ex. 13 |
| 109 | 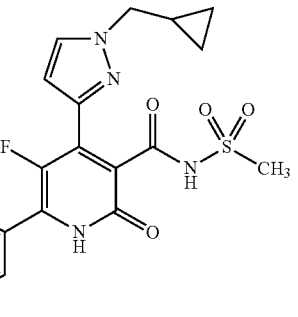<br>4-(1-(Cyclopropylmethyl)-1H-pyrazol-3-yl)-5-fluoro-N-(methylsulfonyl)-2-oxo-6-(4-(4,4,4-trifluorobutoxy)phenyl)-1,2-dihydropyridine-3-carboxamide | $^1$H NMR: δ 7.87 (br. s., 1H), 7.83 (d, J = 7.93 Hz, 2H), 7.08 (d, J = 8.55 Hz, 2H), 6.56 (br. s., 1H), 4.12 (t, J = 5.95 Hz, 2H), 4.01 (d, J = 6.71 Hz, 2H), 2.50 (br. s., 3H), 2.44 (dd, J = 10.83, 16.63 Hz, 2H), 1.90-2.03 (m, 2H), 1.25 (d, J = 12.21 Hz, 1H), 0.52 (d, J = 7.63 Hz, 2H), 0.37 (d, J = 4.27 Hz, 2H). MS(ESI) m/z: 490.1 (M + H)$^+$. | Ex. 19 |
| 110 | 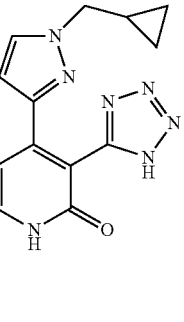<br>4-(1-(Cyclopropylmethyl)-1H-pyrazol-3-yl)-3-(1H-tetrazol-5-yl)-6-(4-((6,6,6-trifluorohexyl)oxy)phenyl)pyridin-2(1H)-one | $^1$H NMR (400 MHz, DMSO-d$_6$) δ 12.25 (br. s., 1H), 7.83 (d, J = 7.92 Hz, 2H), 7.72 (d, J = 2.42 Hz, 1H), 7.08 (d, J = 9.02 Hz, 2H), 6.94-7.05 (m, 1H), 5.91 (br. s., 1H), 4.07 (t, J = 6.38 Hz, 2H), 3.86 (d, J = 7.04 Hz, 2H), 2.21-2.36 (m, 2H), 1.78 (quin, J = 6.60 Hz, 2H), 1.47-1.62 (m, 4H), 1.04-1.17 (m, 1H), 0.44-0.51 (m, 2H), 0.24-0.31 (m, 2H). MS(ESI) m/z: 514.5 (M + H)$^+$. | Ex. 13 |
| 111 | 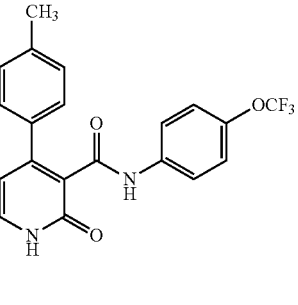<br>2-Oxo-4-(p-tolyl)-6-(4-(4,4,4-trifluorobutoxy)-2-(trifluoromethyl)phenyl)-N-(4-(trifluoromethoxy)phenyl)-1,2-dihydropyridine-3-carboxamide | 1H NMR: δ 10.60 (s, 1H), 7.65 (d, J = 8.7 Hz, 2H), 7.52 (d, J = 8.3 Hz, 1H), 7.46-7.31 (m, 4H), 7.28 (d, J = 8.5 Hz, 2H), 7.19 (d, J = 7.9 Hz, 2H), 6.18 (s, 1H), 4.18 (t, J = 6.2 Hz, 2H), 2.48-2.38 (m, 2H), 2.27 (s, 3H), 2.04-1.89 (m, 2H). MS(ESI) m/z: 661.4 (M + H)$^+$. | Ex. 5 |

TABLE 2-continued

| Ex. No. | Structure and Name | Analytical Data | Method |
|---|---|---|---|
| 112 | 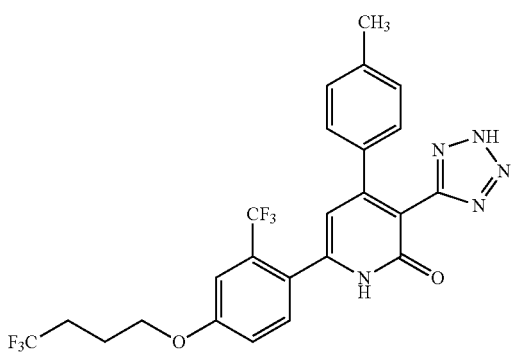 [SMILES: Cc1ccc(-c2cc(-c3ccc(OCCCC(F)(F)F)cc3C(F)(F)F)[nH]c(=O)c2-c2nn[nH]n2)cc1]<br>3-(2H-Tetrazol-5-yl)-4-(p-tolyl)-6-(4-(4,4,4-trifluorobutoxy)-2-(trifluoromethyl)phenyl)pyridin-2(1H)-one | $^1$H NMR: δ 7.71 (d, J = 8.2 Hz, 1H), 7.47-7.39 (m, 2H), 7.17 (d, J = 7.8 Hz, 2H), 7.06 (d, J = 7.7 Hz, 2H), 6.38 (s, 1H), 4.26 (t, J = 6.2 Hz, 2H), 2.55-2.45 (m, 2H), 2.33 (s, 3H), 2.17-1.97 (m, 2H). MS(ESI) m/z: 524.4 (M + H)$^+$. | Ex. 1 |
| 113 | 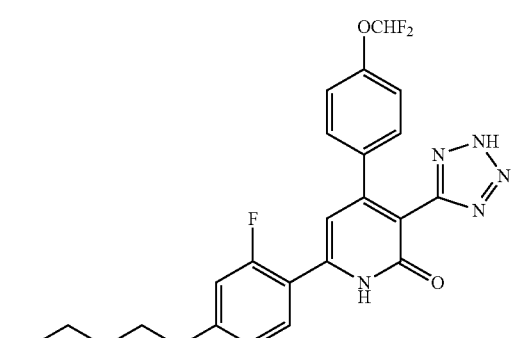<br>4-(4-(Difluoromethoxy)phenyl)-6-(2-fluoro-4-(4,4,4-trifluorobutoxy)phenyl)-3-(2H-tetrazol-5-yl)pyridin-2(1H)-one | $^1$H NMR: δ 7.69 (s, 1H), 7.27 (t, J = 73.9 Hz, 1H), 7.24 (d, J = 8.4 Hz, 2H), 7.12 (d, J = 7.7 Hz, 2H), 7.04 (d, J = 12.7 Hz, 1H), 6.99-6.90 (m, 1H), 6.52 (s, 1H), 4.14 (t, J = 6.3 Hz, 2H), 2.48-2.37 (m, 2H), 2.04-1.83 (m, 2H). MS(ESI) m/z: 526.3 (M + H)$^+$. | Ex. 22 |
| 114 | 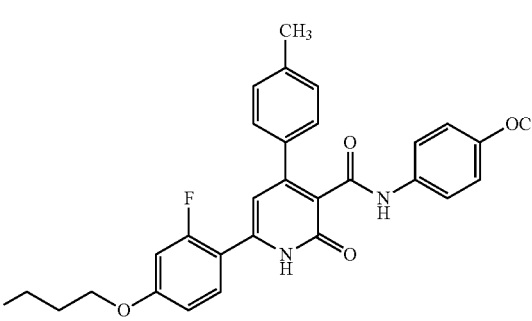<br>N-(4-Ethoxyphenyl)-6-(2-fluoro-4-(4,4,4-trifluorobutoxy)phenyl)-2-oxo-4-(p-tolyl)-1,2-dihydropyridine-3-carboxamide | $^1$H NMR: δ 10.18 (s, 1H), 7.62 (s, 1H), 7.48-7.39 (m, 4H), 7.20 (d, J = 7.9 Hz, 2H), 7.00 (d, J = 12.7 Hz, 1H), 6.92 (d, J = 8.7 Hz, 1H), 6.82 (d, J = 8.5 Hz, 2H), 6.40 (s, 1H), 4.12 (t, J = 6.5 Hz, 2H), 3.96 (q, J = 7.0 Hz, 2H), 2.48-2.35 (m, 2H), 2.29 (s, 3H), 1.96 (t, J = 7.8 Hz, 2H), 1.29 (t, J = 7.0 Hz, 3H). MS(ESI) m/z: 526.3 (M + H)$^+$. | Ex. 5 |

TABLE 2-continued

| Ex. No. | Structure and Name | Analytical Data | Method |
|---|---|---|---|
| 115 | 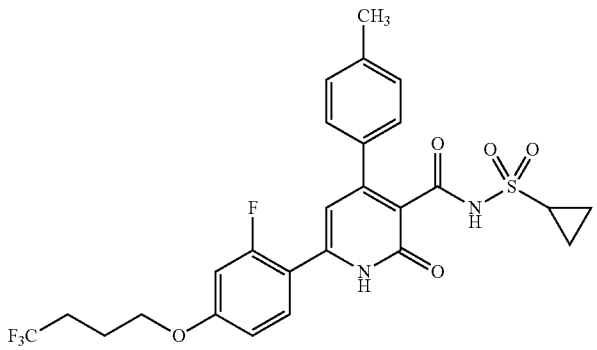 [SMILES: Cc1ccc(-c2cc(-c3ccc(OCCCC(F)(F)F)cc3F)[nH]c(=O)c2C(=O)NS(=O)(=O)C2CC2)cc1]<br>N-(Cyclopropylsulfonyl)-6-(2-fluoro-4-(4,4,4-trifluorobutoxy)phenyl)-2-oxo-4-(p-tolyl)-1,2-dihydropyridine-3-carboxamide | $^1$H NMR: δ 7.57-7.74 (m, 1H), 7.36 (d, J = 7.63 Hz, 2H), 7.26 (d, J = 7.93 Hz, 2H), 7.00 (d, J = 13.12 Hz, 1H), 6.92 (d, J = 8.85 Hz, 1H), 6.42 (br. s., 1H), 4.13 (t, J = 5.95 Hz, 2H), 2.82 (br. s., 1H), 2.38-2.47 (m, 2H), 2.34 (s, 3H), 1.90-2.00 (m, 2H), 1.00 (d, J = 16.78 Hz, 4H). MS(ESI) m/z: 553.1 (M + H)$^+$. | Ex. 13 |
| 116 | 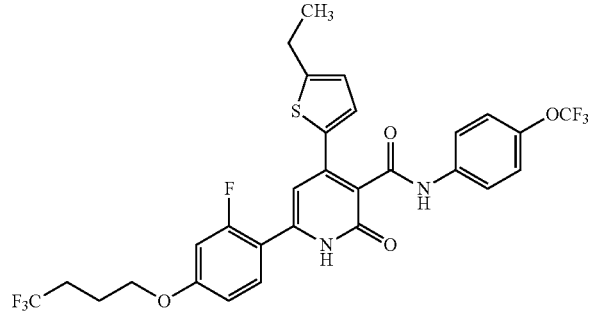 [SMILES: CCc1ccc(-c2cc(-c3ccc(OCCCC(F)(F)F)cc3F)[nH]c(=O)c2C(=O)Nc2ccc(OC(F)(F)F)cc2)s1]<br>4-(5-Ethylthiophen-2-yl)-6-(2-fluoro-4-(4,4,4-trifluorobutoxy)phenyl)-2-oxo-N-(4-(trifluoromethoxy)phenyl)-1,2-dihydropyridine-3-carboxamide | $^1$H NMR: δ 10.69 (s, 1H), 7.76 (d, J = 8.5 Hz, 2H), 7.59 (s, 1H), 7.44-7.36 (m, 1H), 7.34 (d, J = 8.7 Hz, 2H), 7.01 (d, J = 12.7 Hz, 1H), 6.93 (d, J = 8.7 Hz, 1H), 6.90-6.82 (m, 1H), 6.55 (s, 1H), 4.13 (t, J = 6.5 Hz, 2H), 2.78 (q, J = 7.6 Hz, 2H), 2.48-2.28 (m, 2H), 1.96 (t, J = 7.9 Hz, 2H), 1.18 (t, J = 7.6 Hz, 3H). MS(ESI) m/z: 629.5 (M + H)$^+$. | Ex. 11 |
| 117 | 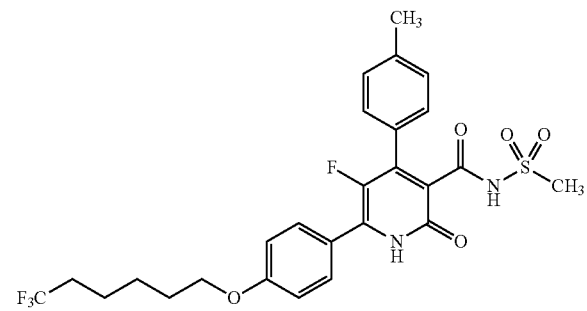<br>5-Fluoro-N-(methylsulfonyl)-2-oxo-4-(p-tolyl)-6-(4-((6,6,6-trifluorohexyl)oxy)phenyl)-1,2-dihydropyridine-3-carboxamide | $^1$H NMR: δ 7.80 (d, J = 7.63 Hz, 2H), 7.26 (br. s., 4H), 7.05 (d, J = 8.54 Hz, 2H), 4.04 (t, J = 6.10 Hz, 2H), 2.94 (br. s., 3H), 2.35 (s, 3H), 2.20-2.31 (m, 2H), 1.72-1.81 (m, 2H), 1.45-1.60 (m, 4H). MS(ESI) m/z: 555.1 (M + 1)$^+$. | Ex. 19 |

TABLE 2-continued

| Ex. No. | Structure and Name | Analytical Data | Method |
|---|---|---|---|
| 118 | 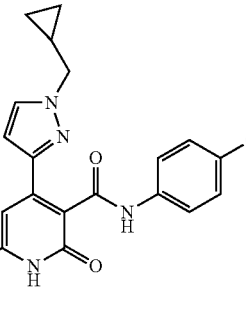<br>4-(1-(Cyclopropylmethyl)-1H-pyrazol-3-yl)-6-(2-fluoro-4-((6,6,6-trifluorohexyl)oxy)phenyl)-2-oxo-N-(4-(trifluoromethoxy)phenyl)-1,2-dihydropyridine-3-carboxamide | $^1$H NMR: δ 10.59 (s, 1H), 7.77-7.88 (m, 3H), 7.45-7.61 (m, 1H), 7.34 (d, J = 7.63 Hz, 2H), 6.99 (d, J = 13.12 Hz, 1H), 6.91 (d, J = 8.54 Hz, 1H), 6.76-6.87 (m, 1H), 6.55 (s, 1H), 4.06 (t, J = 6.10 Hz, 2H), 3.95 (d, J = 7.02 Hz, 2H), 2.27 (br. s., 2H), 1.73-1.82 (m, 2H), 1.53 (dd, J = 7.17, 14.19 Hz, 4H), 1.15 (br. s., 1H), 0.39-0.56 (m, 2H), 0.23-0.39 (m, 2H). MS (ESI) m/z: 667.2 (M + H)$^+$. | Ex. 5 |
| 119 | 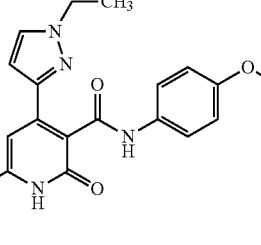<br>N-(4-Ethoxyphenyl)-4-(1-ethyl-1H-pyrazol-3-yl)-6-(2-fluoro-4-(4,4,4-trifluorobutoxy)phenyl)-2-oxo-1,2-dihydropyridine-3-carboxamide | $^1$H NMR: δ 10.24 (s, 1H), 7.75 (s, 1H), 7.66-7.48 (m, 3H), 7.10-6.81 (m, 5H), 6.52 (s, 1H), 4.26-4.08 (m, 4H), 4.00 (q, J = 6.9 Hz, 2H), 2.47-2.37 (m, 2H), 2.10-1.92 (m, 2H), 1.46-1.25 (m, 6H). MS (ESI) m/z: 573.4 (M + H)$^+$. | Ex. 5 |
| 120 | 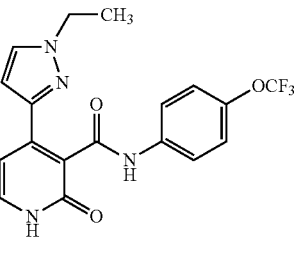<br>4-(1-Ethyl-1H-pyrazol-3-yl)-6-(2-fluoro-4-(4,4,4-trifluorobutoxy)phenyl)-2-oxo-N-(4-(trifluoromethoxy)phenyl)-1,2-dihydropyridine-3-carboxamide | $^1$H NMR: δ 10.65 (s, 1H), 7.93-7.75 (m, 3H), 7.64 (s, 1H), 7.40 (d, J = 8.4 Hz, 2H), 7.15-6.80 (m, 3H), 6.60 (d, J = 23 Hz, 1H), 4.27-4.05 (m, 4H), 2.55-2.40 (m, 2H), 2.11-1.84 (m, 2H), 1.36 (t, J = 7.3 Hz, 3H). MS (ESI) m/z: 613.1 (M + H)$^+$. | Ex. 5 |
| 121 | 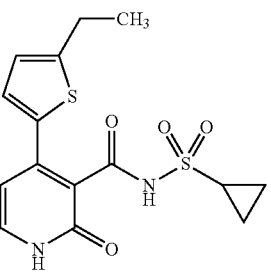<br>N-(Cyclopropylsulfonyl)-4-(5-ethylthiophen-2-yl)-2-oxo-6-(4-(4,4,4-trifluorobutoxy(phenyl)-1,2-dihydropyridine-3-carboxamide | $^1$H NMR: δ 7.79 (d, J = 6.41 Hz, 2H), 7.38 (d, J = 3.05 Hz, 1H), 7.07 (d, J = 8.55 Hz, 2H), 6.94 (br. s., 1H), 6.62 (br. s., 1H), 4.12 (t, J = 6.10 Hz, 2H), 2.99 (br. s., 1H), 2.86 (q, J = 7.32 Hz, 2H), 2.44 (dd, J = 10.99, 16.78 Hz, 2H), 1.91-2.01 (m, 2H), 1.26 (t, J = 7.48 Hz, 3H), 1.02-1.14 (m, 4H). MS (ESI) m/z: 555.1 (M + H)$^+$. | Ex. 13 |

TABLE 2-continued

| Ex. No. | Structure and Name | Analytical Data | Method |
|---|---|---|---|
| 122 | 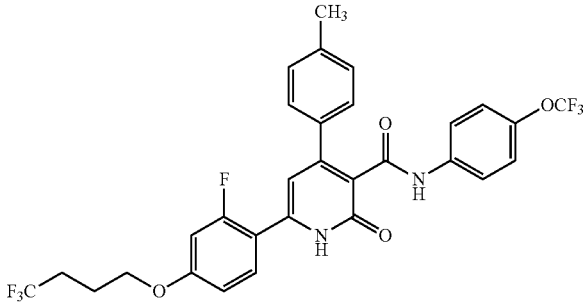 [SMILES: Cc1ccc(-c2cc(-c3ccc(OCCCC(F)(F)F)cc3F)[nH]c(=O)c2C(=O)Nc2ccc(OC(F)(F)F)cc2)cc1]<br>6-(2-Fluoro-4-(4,4,4-trifluorobutoxy)phenyl)-2-oxo-4-(p-tolyl)-N-(4-(trifluorormethoxy)phenyl)-1,2-dihydropyridine-3-carboxamide | $^1$H NMR: δ 12.22 (s, 1H), 10.66 (s, 1H), 7.75-7.58 (m, 3H), 7.44 (d, J = 7.8 Hz, 2H), 7.29 (d, J = 8.6 Hz, 2H), 7.21 (d, J = 7.8 Hz, 2H), 7.01 (dd, J = 13.2, 2.4 Hz, 1H), 6.97-6.90 (m, 1H), 6.40 (s, 1H), 4.14 (t, J = 6.2 Hz, 2H), 2.48-2.38 (m, 2H), 2.30 (s, 3H), 2.00-1.93 (m, 2H). MS (ESI) m/z: 609.4 (M + H)$^+$. | Ex. 11 |
| 123 | 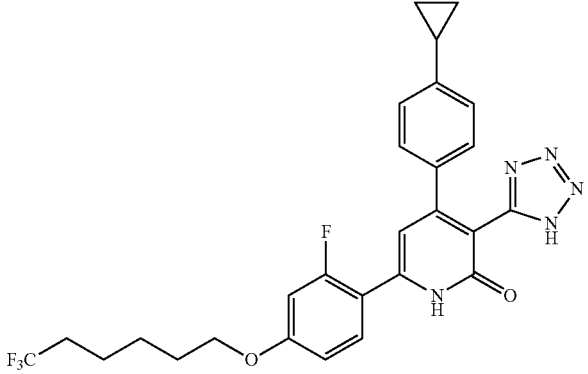 [SMILES: O=c1[nH]c(-c2ccc(OCCCCCC(F)(F)F)cc2F)cc(-c2ccc(C3CC3)cc2)c1-c1nnn[nH]1]<br>4-(4-Cyclopropylphenyl)-6-(2-fluoro-4-((6,6,6-trifluorohexyl)oxy)phenyl)-3-(1H-tetrazol-5-yl)pyridin-2(1H)-one | $^1$H NMR (500MHz, CD$_3$OD) δ 7.60 (t, J = 8.7 Hz, 1H), 7.13-7.05 (m, 2H), 7.03-6.97 (m, 2H), 6.95-6.85 (m, 2H), 6.64 (s, 1H), 4.09 (t, J = 6.2 Hz, 2H), 2.26-2.13 (m, 2H), 2.03 (s, 1H), 1.92-1.80 (m, 2H), 1.70-1.53 (m, 4H), 1.02-0.90 (m, 2H), 0.72-0.63 (m, 2H). MS (ESI) m/z: 528.0 (M + H)$^+$. | Ex. 13 |
| 124 | 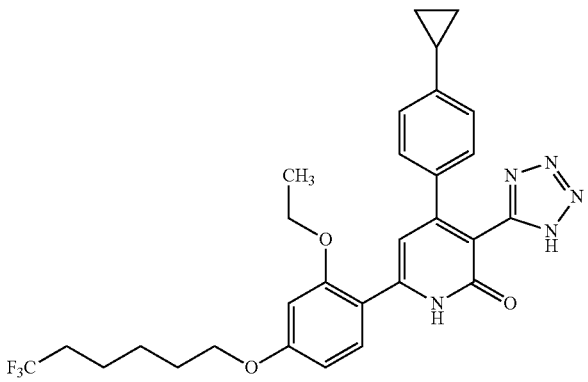 [SMILES: CCOc1cc(OCCCCCC(F)(F)F)ccc1-c1cc(-c2ccc(C3CC3)cc2)c(-c2nnn[nH]2)c(=O)[nH]1]<br>4-(4-Cyclopropylphenyl)-6-(2-ethoxy-4-((6,6,6-trifluorohexyl)oxy)phenyl)-3-(1H-tetrazol-5-yl)pyridin-2(1H)-one | MS (ESI) m/z: 554.1 (M + H)$^+$. | Ex. 13 |

TABLE 2-continued

| Ex. No. | Structure and Name | Analytical Data | Method |
|---|---|---|---|
| 125 | 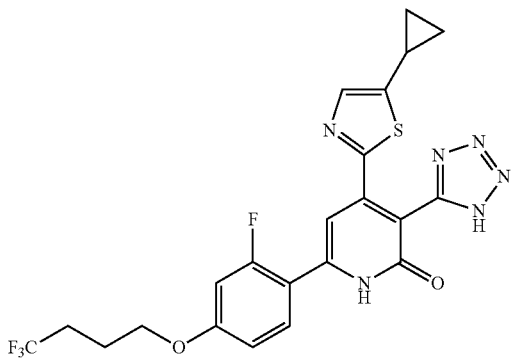 [SMILES: O=c1[nH]c(-c2ccc(OCCCC(F)(F)F)cc2F)cc(-c2ncc(C3CC3)s2)c1-c1nnn[nH]1]<br>4-(5-Cyclopropylthiazol-2-yl)-6-(2-fluoro-4-(4,4,4-trifluorobutoxy)phenyl)-3-(1H-tetrazol-5-yl)pyridin-2(1H)-one | $^1$H NMR: δ 7.68 (t, J = 8.7 Hz, 1H), 7.61 (s, 1H), 7.04 (d, J = 13.1 Hz, 2H), 6.96 (dd, J = 8.7, 2.0 Hz, 1H), 4.14 (t, J = 6.1 Hz, 2H), 2.47-2.38 (m, 2H), 2.17-2.08 (m, 1H), 2.01-1.91 (m, 2H), 1.08-0.99 (m, 2H), 0.70-0.60 (m, 2H). MS (ESI) m/z: 507.1 (M + H)$^+$. | Ex. 20 |
| 126 | 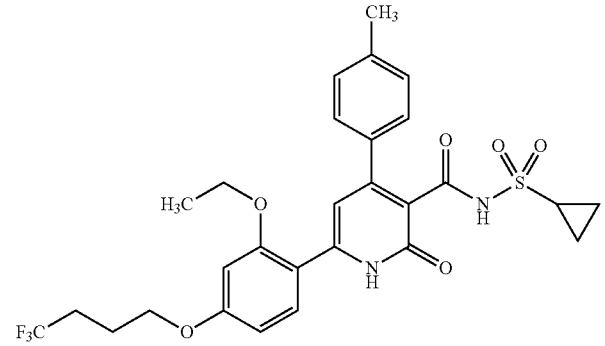 [SMILES: CCOc1cc(OCCCC(F)(F)F)ccc1-c1cc(-c2ccc(C)cc2)c(C(=O)NS(=O)(=O)C2CC2)c(=O)[nH]1]<br>N-(Cyclopropylsulfonyl)-6-(2-ethoxy-4-(4,4,4-trifluorobutoxy)phenyl)-2-oxo-4-(p-tolyl)-1,2-dihydropyridine-3-carboxamide | $^1$H NMR (400 MHz, DMSO-d$_6$) δ 12.30 (br. s., 1H), 12.05 (br. s., 1H), 7.44 (br. s., 1H), 7.34 (d, J = 5.72 Hz, 2H), 7.25 (d, J = 7.26 Hz, 2H), 6.68 (br. s., 1H), 6.63 (d, J = 8.36 Hz, 1H), 6.36 (br. s., 1H), 4.11 (d, J = 4.84 Hz, 4H), 2.83 (br. s., 1H), 2.45 (br. s., 2H), 2.34 (br. s., 3H), 1.95(br.s., 2H), 1.28-1.38 (m, 3H), 1.02 (br. s., 4H). MS (ESI) m/z: 579.3 (M + H)$^+$. | Ex. 13 |
| 127 | 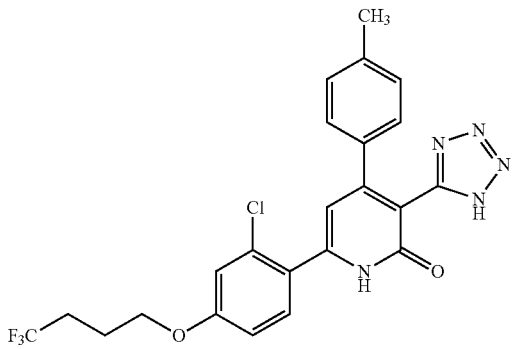 [SMILES: Cc1ccc(-c2cc(-c3ccc(OCCCC(F)(F)F)cc3Cl)[nH]c(=O)c2-c2nnn[nH]2)cc1]<br>6-(2-Chloro-4-(4,4,4-trifluorobutoxy)phenyl)-3-(1H-tetrazol-5-yl)-4-(p-tolyl)pyridin-2(1H)-one | $^1$H NMR: δ 7.58 (d, J = 8.5 Hz, 1H), 7.22 (s, 1H), 7.14-6.97 (m, 5H), 6.41 (br. s., 1H), 4.14 (t, J = 5.6 Hz, 2H), 2.44 (dd, J = 17.2, 10.5 Hz, 2H), 2.27 (s, 3H), 2.00-1.89 (m, 2H). MS (ESI) m/z: 490.1 (M + H)$^+$. | Ex. 13 |

TABLE 2-continued

| Ex. No. | Structure and Name | Analytical Data | Method |
|---|---|---|---|
| 128 | 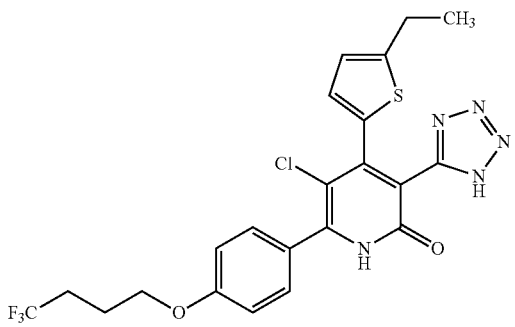 [SMILES: CCc1ccc(-c2c(Cl)c(-c3ccc(OCCCC(F)(F)F)cc3)[nH]c(=O)c2-c2nnn[nH]2)s1]<br>5-Chloro-4-(5-ethylthiophen-2-yl)-3-(1H-tetrazol-5-yl)-6-(4-(4,4,4-trifluorobutoxy)phenyl)pyridin-2(1H)-one | $^1$H NMR: δ 7.61 (d, J = 7.43 Hz, 2H), 7.09 (d, J = 8.25 Hz, 2H), 6.77 (d, J = 3.30 Hz, 1H), 6.73 (br. s., 1H), 4.13 (t, J = 5.91 Hz, 2H), 2.75 (q, J = 7.15 Hz, 2H), 2.40-2.48 (m, 2H), 1.94-2.02 (m, 2H), 1.18 (t, J = 7.43 Hz, 3H). MS(ESI) m/z: 510.1 (M + H)$^+$. | Ex. 19 |
| 129 | 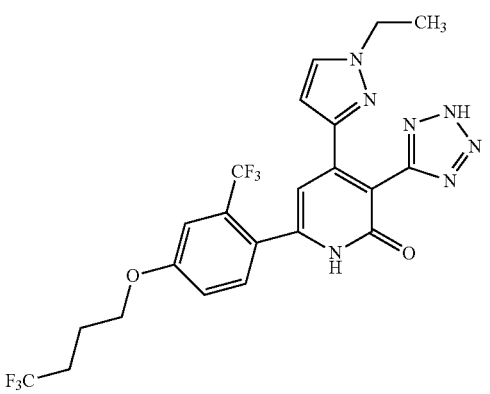 [SMILES: CCn1ccc(-c2cc(-c3ccc(OCCCC(F)(F)F)cc3C(F)(F)F)[nH]c(=O)c2-c2nn[nH]n2)n1]<br>4-(1-Ethyl-1H-pyrazol-3-yl)-3-(2H-tetrazol-5-yl)-6-(4-(4,4,4-trifluorobutoxy)-2-(trifluoromethyl)phenyl)pyridin-2(1H)-one | $^1$H NMR (400 MHz, methanol-d$_4$) δ 7.62 (d, J = 8.5 Hz, 1H), 7.57 (d, J = 2.4 Hz, 1H), 7.44 (d, J = 2.5 Hz, 1H), 7.37 (dd, J = 8.6, 2.6 Hz, 1H), 6.90 (s, 1H), 6.00 (d, J = 2.4 Hz, 1H), 4.23 (t, J = 6.1 Hz, 2H), 4.09 (q, J = 7.3 Hz, 2H), 2.57-2.31 (m, 2H), 2.22-2.05 (m, 2H), 1.34 (t, J = 7.3 Hz, 3H). MS (ESI) m/z: 528.3 (M + H)$^+$. | Ex. 1 |
| 130 | 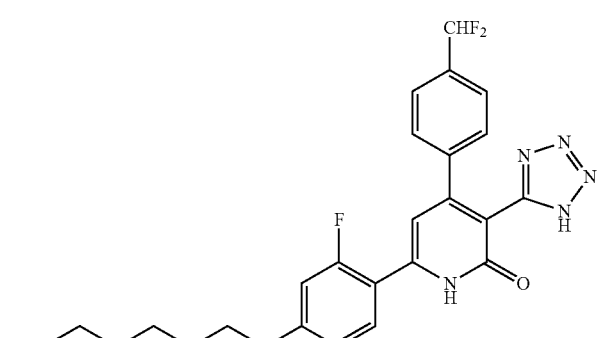<br>4-(4-(Difluoromethyl)phenyl)-6-(2-fluoro-4-((6,6,6-trifluorohexyl)oxy)phenyl)-3-(1H-tetrazol-5-yl)pyridin-2(1H)-one | $^1$H NMR: δ 7.70 (br. s., 1H), 7.53 (d, J = 8.3 Hz, 2H), 7.33 (d, J = 8.3 Hz, 2H), 7.18-6.88 (m, 3H), 6.69-6.43 (m, 1H), 4.08 (t, J = 6.3 Hz, 2H), 2.33-2.21 (m, 2H), 1.77 (quin, J = 6.9 Hz, 2H), 1.60-1.44 (m, 4H). MS (ESI) m/z: 538.0 (M + H)$^+$. | Ex. 13 |

TABLE 2-continued

| Ex. No. | Structure and Name | Analytical Data | Method |
|---|---|---|---|
| 131 | 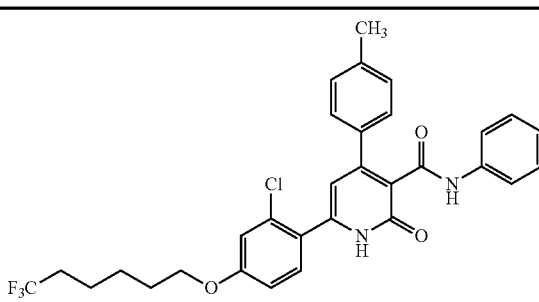<br>6-(2-Chloro-4-((6,6,6-trifluorohexyl)oxy)phenyl)-2-oxo-4-(p-tolyl)-Ar-(4-(trifluoromethoxy)phenyl)-1,2-dihydropyridine-3-carboxamide | $^1$H NMR: δ 10.58 (s, 1H), 7.62 (d, J = 8.85 Hz, 2H), 7.45 (d, J = 8.55 Hz, 1H), 7.41 (d, J = 7.63 Hz, 2H), 7.27 (d, J = 8.54 Hz, 2H), 7.19 (d, J = 7.93 Hz, 2H), 7.14 (s, 1H), 7.01 (d, J = 8.54 Hz, 1H), 6.29 (br. s., 1H), 4.03 (t, J = 6.10 Hz, 2H), 2.26 (s, 3H), 2.15-2.29 (m, 2H), 1.68-1.79 (m, 2H), 1.39-1.58 (m, 4H). MS (ESI) m/z: 563.1 (M + H)$^+$. | Ex. 5 |
| 132 | 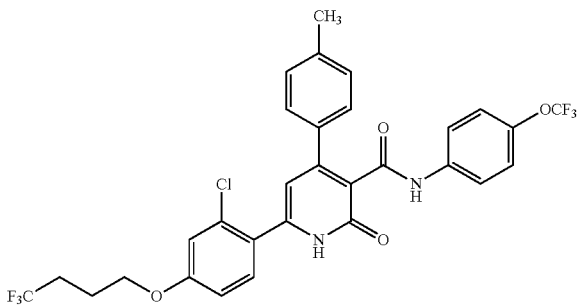 [SMILES: Cc1ccc(-c2cc(-c3ccc(OCCCC(F)(F)F)cc3Cl)[nH]c(=O)c2C(=O)Nc2ccc(OC(F)(F)F)cc2)cc1]<br>6-(2-Chloro-4-(4,4,4-trifluorobutoxy)phenyl)-2-oxo-4-(p-tolyl)-N-(4-(trifluoromethoxy)phenyl)-1,2-dihydropyridine-carboxamide | $^1$H NMR: δ 10.61 (s, 1H), 7.66 (d, J = 8.24 Hz, 2H), 7.49 (d, J = 8.24 Hz, 1H), 7.43 (d, J = 7.32 Hz, 2H), 7.29 (d, J = 8.24 Hz, 2H), 7.15-7.23 (m, 3H), 7.05 (d, J = 8.55 Hz, 1H), 6.29 (br. s., 1H), 4.13 (t, J = 5.95 Hz, 2H), 2.43 (dd, J = 10.68, 17.09 Hz, 2H), 2.28 (s, 3H), 1.95 (d, J = 6.41 Hz, 2H). MS (ESI) m/z: 625.1 (M + H)$^+$. | Ex. 5 |
| 133 | 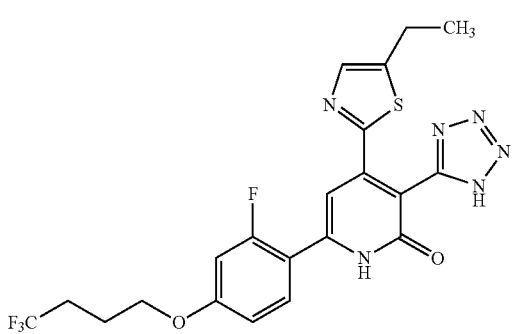<br>4-(5-Ethylthiazol-2-yl)-6-(2-fluoro-4-(4,4,4-trifluorobutoxy)phenyl)-3-(1H-tetrazol-5-yl)pyridin-2(1H)-one | $^1$H NMR (400 MHz, DMSO-d$_6$) δ 12.63 (s, 1H), 7.67 (s, 1H), 7.75-7.65 (bs, 1H), 7.08 (dd, J = 12.9, 2.4 Hz, 1H), 7.03-6.91 (m, 2H), 4.17 (t, J = 6.2 Hz, 2H), 2.83 (q, J = 7.5 Hz, 2H), 2.51-2.35 (m, 2H), 2.09-1.87 (m, 2H), 1.20 (t, J = 7.5 Hz, 3H). MS (ESI) m/z: 495.4 (M + H)$^+$. | Ex. 20 |
| 134 | 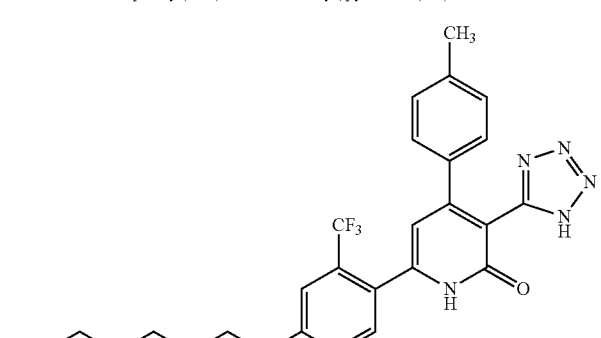<br>3-(2H-Tetrazol-5-yl)-4-(p-tolyl)-6-(4-((6,6,6-trifluorohexyl)oxy)-2-(trifluoromethyl)phenyl)pyridin-2(1H)-one | $^1$H NMR: δ 12.59 (s, 1H), 7.64 (d, J = 8.9 Hz, 1H), 7.39-7.33 (m, 2H), 7.12 (d, J = 7.9 Hz, 2H), 7.03-6.97 (m, 2H), 6.28 (s, 1H), 4.14 (t, J = 6.4 Hz, 2H), 2.26 (s, 3H), 2.34-2.17 (m, 2H), 1.88-1.72 (m, 2H), 1.66-1.40 (m, 4H). MS (ESI) m/z: 552.3 (M + H)$^+$. | Ex. 2 |

TABLE 2-continued

| Ex. No. | Structure and Name | Analytical Data | Method |
|---|---|---|---|
| 135 | 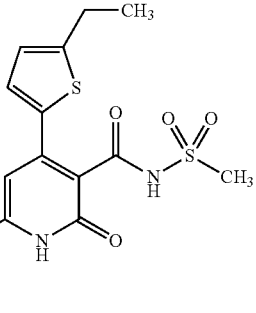… 4-(5-Ethylthiophen-2-yl)-6-(2-fluoro-4-(4,4,4-trifluorobutoxy)phenyl)-N-(methylsulfonyl)-2-oxo-1,2-dihydropyridine-3-carboxamide | $^1$H NMR: δ 7.60 (br. s., 1H), 7.34 (d, J = 336 Hz, 1H), 7.00 (d, J = 12.82 Hz, 1H), 6.86-6.95 (m, 2H), 6.52 (br. s., 1H), 4.12 (t, J = 6.10 Hz, 2H), 2.84 (q, J = 7.32 Hz, 2H), 2.50 (s, 3H), 2.43 (dd, J = 11.14, 16.33 Hz, 2H), 1.90-2.02 (m, 2H), 1.25 (t, J = 7.63 Hz, 3H). MS (ESI) m/z: 547.2 (M + H)$^+$. | Ex. 13 |
| 136 | 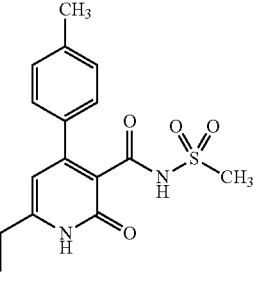… 6-(2-Fluoro-4-((6,6,6-trifluorohexyl)oxy)phenyl)-N-(methylsulfonyl)-2-oxo-4-(p-tolyl)-1,2-dihydropyridine-3-carboxamide | $^1$H NMR: δ 7.62 (br. s., 1H), 7.35 (d, J = 7.93 Hz, 2H), 7.26 (d, J = 7.93 Hz, 2H), 6.97 (d, J = 12.82 Hz, 1H), 6.90 (dd, J = 1.98, 8.70 Hz, 1H), 6.45 (br. s., 1H), 4.05 (t, J = 6.26 Hz, 2H), 3.11 (s, 3H), 2.34 (s, 3H), 2.18-2.30 (m, 2H), 1.71-1.80 (m, 2H), 1.39-1.62 (m, 4H). MS (ESI) m/z: 555.2 (M + H)$^+$. | Ex. 13 |
| 137 | 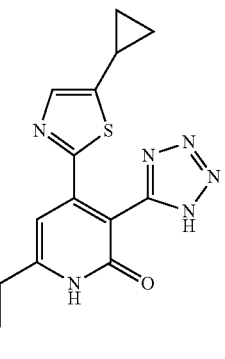… 4-(5-Cyclopropylthiazol-2-yl)-6-(2-ethoxy-4-(4,4,4-trifluorobutoxy)phenyl)-3-(1H-tetrazol-5-yl)pyridin-2(1H)-one | $^1$H NMR: δ 7.59 (s, 1H), 7.54-7.43 (m, 1H), 6.90 (br. s., 1H), 6.75-6.59 (m, 2H), 4.22-4.04 (m, 5H), 2.45 (d, J = 3.3 Hz, 2H), 2.20-2.09 (m, 1H), 2.00-1.87 (m, 2H), 1.35 (t, J = 7.0 Hz, 2H), 1.07-0.99 (m, 2H), 0.72-0.64 (m, 2H). MS (ESI) m/z: 533.3 (M + H)$^+$. | Ex. 20 |

TABLE 2-continued

| Ex. No. | Structure and Name | Analytical Data | Method |
|---|---|---|---|
| 138 | 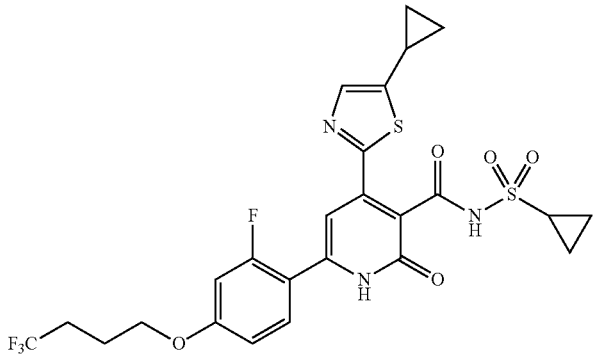 [SMILES: O=C(NS(=O)(=O)C1CC1)c1c(-c2ncc(C3CC3)s2)cc(-c2ccc(OCCCC(F)(F)F)cc2F)[nH]c1=O]<br>N-(Cyclopropylsulfonyl)-4-(5-cyclopropylthiazol-2-yl)-6-(2-fluoro-4-(4,4,4-trifluorobutoxy)phenyl)-2-oxo-1,2-dihydropyridine-3-carboxamide | $^1$H NMR: δ 7.73 (s, 1H), 7.58 (br. s., 1H), 6.97 (d, J = 12.8 Hz, 1H), 6.89 (d, J = 7.0 Hz, 1H), 6.72 (br. s., 1H), 4.08 (t, J = 6.1 Hz, 2H), 2.96 (br. s., 1H), 2.39 (dd, J = 16.5, 11.3 Hz, 2H), 2.23-2.14 (m, 1H), 1.96-1.84 (m, 2H), 1.08 (d, J = 1.5 Hz, 6H), 0.73 (d, J = 4.9 Hz, 2H). MS (ESI) m/z: 586.1 (M + H)$^+$. | Ex. 20 |
| 139 | 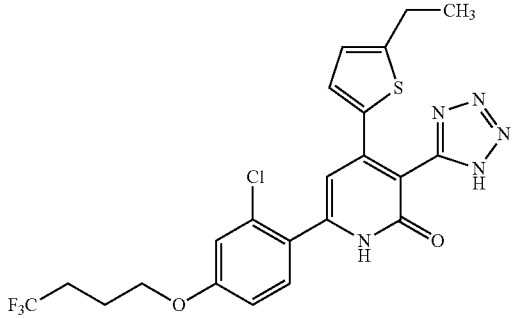 [SMILES: CCc1ccc(-c2cc(-c3ccc(OCCCC(F)(F)F)cc3Cl)[nH]c(=O)c2-c2nnn[nH]2)s1]<br>6-(2-Chloro-4-(4,4,4-trifluorobutoxy)phenyl)-4-(5-ethylthiophen-2-yl)-3-(1H-tetrazol-5-yl)pyridin-2(1H)-one | $^1$H NMR: δ 7.57 (d, J = 8.55 Hz, 1H), 7.23 (d, J = 2.14 Hz, 1H), 7.12 (br. s., 1H), 7.08 (dd, J = 1.98, 8.70 Hz, 1H), 6.81 (d, J = 3.36 Hz, 1H), 6.63 (br. s., 1H), 4.15 (t, J = 6.10 Hz, 2H), 2.71 (q, J = 7.32 Hz, 2H), 2.38-2.48 (m, 2H), 1.90-2.02 (m, 2H), 1.14 (t, J = 7.48 Hz, 3H). MS (ESI) m/z: 510.2 (M + H)$^+$. | Ex. 21 |
| 140 | 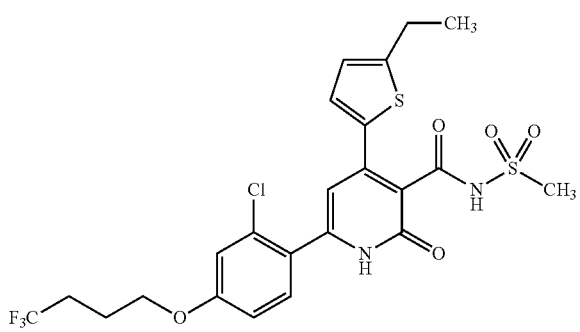<br>6-(2-Chloro-4-(4,4,4-trifluorobutoxy)phenyl)-4-(5-ethylthiophen-2-yl)-N-(methylsulfonyl)-2-oxo-1,2-dihydropyridine-3-carboxamide | 1H NMR: δ 7.46 (d, J = 8.54 Hz, 1H), 7.35 (d, J = 3.36 Hz, 1H), 7.20 (s, 1H), 7.05 (d, J = 7.02 Hz, 1H), 6.93 (d, J = 3.05 Hz, 1H), 6.37 (br. s., 1H), 4.13 (t, J = 5.80 Hz, 2H), 2.84 (q, J = 7.43 Hz, 2H), 2.50 (br. s., 3H), 2.44 (dd, J = 11.14, 16.63 Hz, 2H), 1.88-2.02 (m, 2H), 1.24 (t, J = 7.48 Hz, 3H). MS (ESI) m/z: 563.2 (M + H)$^+$. | Ex. 21 |

TABLE 2-continued

| Ex. No. | Structure and Name | Analytical Data | Method |
|---|---|---|---|
| 141 | 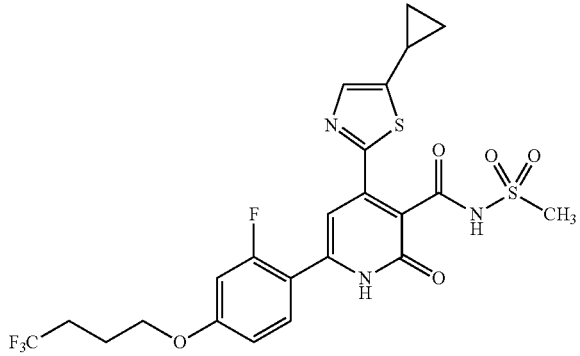 [SMILES: CS(=O)(=O)NC(=O)c1c(-c2ncc(C3CC3)s2)cc(-c2ccc(OCCCC(F)(F)F)cc2F)[nH]c1=O]<br>4-(5-Cyclopropylthiazol-2-yl)-6-(2-fluoro-4-(4,4,4-trifluorobutoxy)phenyl)-N-(methylsulfonyl)-2-oxo-1,2-dihydropyridine-3-carboxamide | $^1$H NMR: δ 7.78 (s, 1H), 7.64 (br. s., 1H), 7.02 (d, J = 13.1 Hz, 1H), 6.94 (dd, J = 8.7, 2.0 Hz, 1H), 6.76 (br. s., 1H), 4.13 (t, J = 6.1 Hz, 2H), 2.54 (s, 3H), 2.46-2.37 (m, 2H), 2.28-2.21 (m, 1H), 2.00-1.89 (m, 2H), 1.16-1.06 (m, 2H), 0.83-0.75 (m, 2H). MS (ESI) m/z: 560.1 (M + H)$^+$. | Ex. 20 |
| 142 | 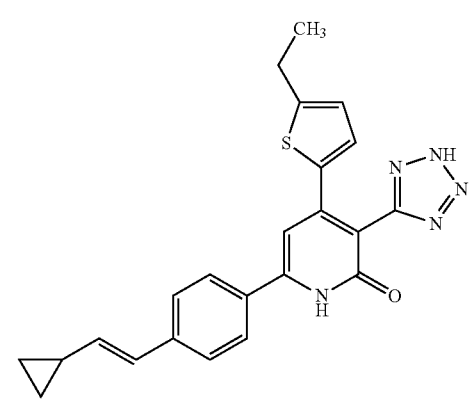 [SMILES: CCc1ccc(-c2cc(-c3ccc(/C=C/C4CC4)cc3)[nH]c(=O)c2-c2nn[nH]n2)s1]<br>(E)-6-(4-(2-Cyclopropylvinyl)phenyl)-4-(5-ethylthiophen-2-yl)-3-(2H-tetrazol-5-yl)pyridin-2(1H)-one | $^1$H NMR: δ 7.82 (d, J = 8.1 Hz, 2H), 7.48 (d, J = 8.2 Hz, 2H), 7.20 (d, J = 3.7 Hz, 1H), 6.94 (s, 1H), 6.81 (d, J = 3.8 Hz, 1H), 6.54 (d, J = 15.8 Hz, 1H), 6.01 (dd, 1H), 2.71 (q, J =7.5 Hz, 2H), 1.62 (tt, J = 8.2, 4.0 Hz, 1H), 1.15 (t, J = 7.5 Hz, 3H), 0.91-0.72 (m, 2H), 0.63-0.47 (m, 2H). MS (ESI) m/z: 416.3 (M + H)$^+$. | Ex. 13 |
| 143 | 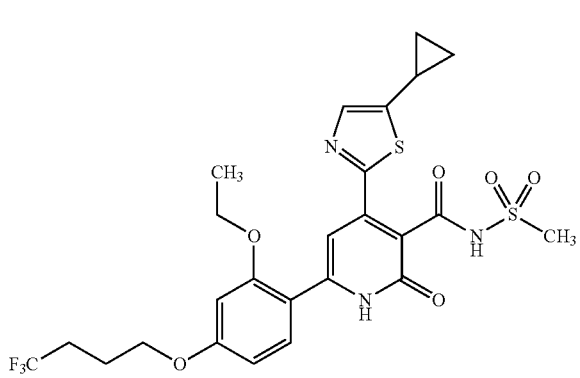 [SMILES: CCOc1cc(OCCCC(F)(F)F)ccc1-c1cc(-c2ncc(C3CC3)s2)c(C(=O)NS(C)(=O)=O)c(=O)[nH]1]<br>4-(5-Cyclopropylthiazol-2-yl)-6-(2-ethoxy-4-(4,4,4-trifluorobutoxy)phenyl)-N-(methylsulfonyl)-2-oxo-1,2-dihydropyridine-3-carboxamide | $^1$H NMR: δ 7.76 (s, 1H), 7.45 (br. s., 1H), 6.74-6.57 (m, 3H), 4.21-4.02 (m, 4H), 2.57-2.37 (m, 5H), 2.29-2.18 (m, 1H), 2.00-1.89 (m, 2H), 1.35 (t, J = 6.9 Hz, 3H), 1.15-1.02 (m, 2H), 0.78 (d, J = 6.1 Hz, 2H). MS (ESI) m/z: 586.2 (M + H)$^+$. | Ex. 20 |

TABLE 2-continued

| Ex. No. | Structure and Name | Analytical Data | Method |
|---|---|---|---|
| 144 | 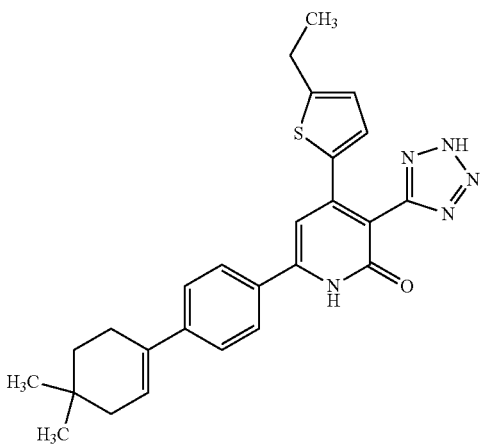 [SMILES: CCc1ccc(-c2cc(-c3ccc(C4=CCC(C)(C)CC4)cc3)[nH]c(=O)c2-c2nn[nH]n2)s1]<br>6-(4',4'-Dimethyl-2',3',4',5'-tetrahydro-[1,1'-biphenyl]-4-yl)-4-(5-ethylthiophen-2-yl)-3-(2H-tetrazol-5-yl)pyridin-2(1H)-one | $^1$H NMR: δ 7.93 (d, J = 8.2 Hz, 2H), 7.65 (d, J = 8.2 Hz, 2H), 7.30 (d, J = 3.9 Hz, 1H), 7.02 (s, 1H), 6.90 (d, J = 3.7 Hz, 1H), 6.41-6.28 (m, 1H), 2.80 (q, J = 7.6 Hz, 2H), 2.55-2.43 (m, 2H), 2.12-1.99 (m, 2H), 1.58 (t, J = 6.4 Hz, 2H), 1.23 (t, J = 7.5 Hz, 3H), 1.02 (s, 6H). MS (ESI) m/z: 458.4 (M + H)$^+$. | Ex. 13 |
| 145 | 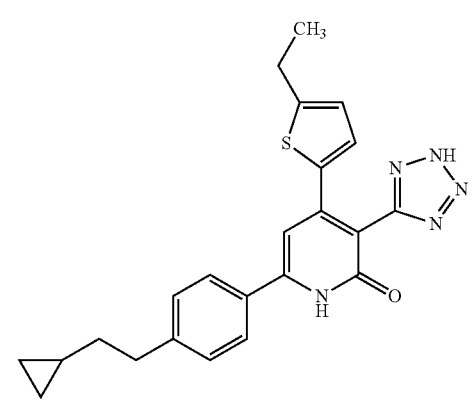 [SMILES: CCc1ccc(-c2cc(-c3ccc(CCC4CC4)cc3)[nH]c(=O)c2-c2nn[nH]n2)s1]<br>6-(4-(2-Cyclopropylethyl)phenyl)-4-(5-ethylthiophen-2-yl)-3-(2H-tetrazol-5-yl)pyridin-2(1H)-one | $^1$H NMR: δ 7.74 (d, J = 7.9 Hz, 2H), 7.30 (d, J = 7.9 Hz, 2H), 7.11 (d, J = 3.8 Hz, 1H), 6.84 (s, 1H), 6.74 (d, J = 3.8 Hz, 1H), 2.77-2.56 (m, 4H), 1.44 (q, J = 7.4 Hz, 2H), 1.08 (t, J =7.5 Hz, 3H), 0.71-0.57 (m, 1H), 0.44-0.26 (m, 2H), 0.07--0.06 (m, 2H). MS (ESI) m/z: 418.4 (M + H)$^+$. | Ex. 18 |
| 146 | 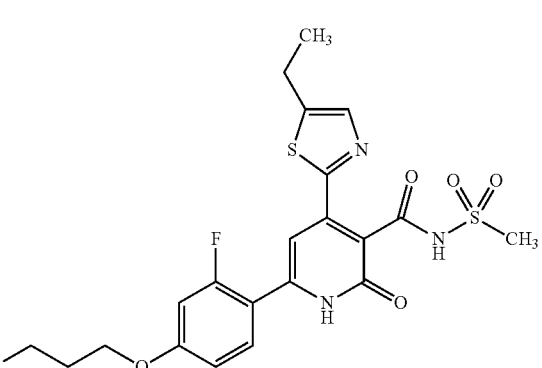<br>4-(5-Ethylthiazol-2-yl)-6-(2-fluoro-4-(4,4,4-trifluorobutoxy) phenyl)-N-(methylsulfonyl)-2-oxo-1,2-dihydropyridine-3-carboxamide | $^1$H NMR: δ 7.78 (s, 1H), 7.66 (s, 1H), 7.03 (dd, J = 13.0, 2.5 Hz, 1H), 6.94 (dd, J = 8.6, 2.4 Hz, 1H), 6.77 (s, 1H), 4.14 (t, J = 6.3 Hz, 2H), 2.92 (q, J = 7.5 Hz, 2H), 2.50 (s, 3H), 2.47-2.39 (m, 2H), 2.01-1.91 (m, 2H), 1.28 (t, J = 7.5 Hz, 3H). MS (ESI) m/z: 548.2 (M + H)$^+$. | Ex. 20 |

TABLE 2-continued

| Ex. No. | Structure and Name | Analytical Data | Method |
|---|---|---|---|
| 147 | 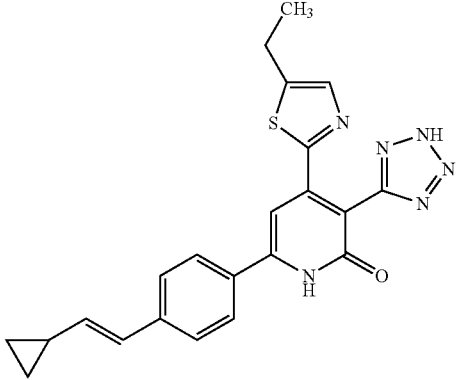 [SMILES: CCc1cnc(-c2cc(-c3ccc(/C=C/C4CC4)cc3)[nH]c(=O)c2-c2nn[nH]n2)s1]<br>(E)-6-(4-(2-Cyclopropylvinyl)phenyl)-4-(5-ethylthiazol-2-yl)-3-(2H-tetrazol-5-yl)pyridin-2(1H)-one | $^1$H NMR (400 MHz, DMSO-$d_6$) δ 12.60 (s, 1H), 7.99-7.76 (m, 2H), 7.67 (s, 1H), 7.60-7.42 (m, 2H), 7.11 (s, 1H), 6.57 (d, J = 15.8 Hz, 1H), 6.04 (dd, J = 15.8, 9.3 Hz, 1H), 2.84 (q, J = 7.5 Hz, 2H), 1.74-1.52 (m, 1H), 1.21 (t, J = 7.5 Hz, 3H), 0.93-0.78 (m, 2H), 0.66-0.51 (m, 2H). MS (ESI) m/z: 417.1 (M + H)$^+$. | Ex. 13 |
| 148 | 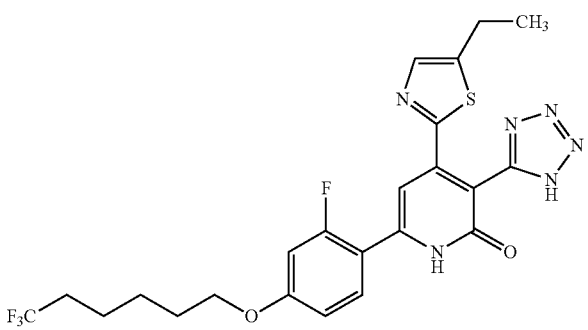 [SMILES: CCc1cnc(-c2cc(-c3ccc(OCCCCCC(F)(F)F)cc3F)[nH]c(=O)c2-c2nnn[nH]2)s1]<br>4-(5-Ethylthiazol-2-yl)-6-(2-fluoro-4-((6,6,6-trifluorohexyl)oxy)phenyl)-3-(1H-tetrazol-5-yl)pyridin-2(1H)-one | $^1$H NMR: δ 7.77-7.56 (m, 2H), 7.15-6.99 (m, 2H), 6.98-6.88 (m, 1H), 4.08 (t, J = 6.4 Hz, 2H), 2.81 (q, J = 7.5 Hz, 2H), 2.39-2.18 (m, 2H), 1.86-1.73 (m, 2H), 1.66-1.43 (m, 4H), 1.18 (t, J = 7.5 Hz, 3H). MS (ESI) m/z: 523.3 (M + H)$^+$. | Ex. 20 |
| 149 | 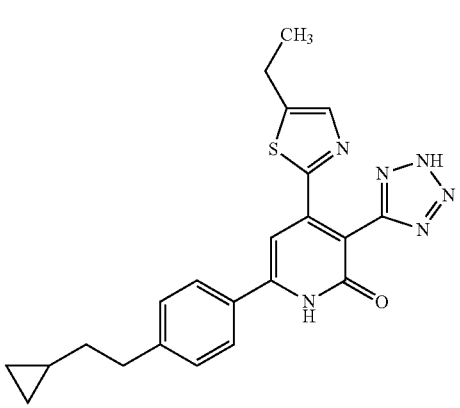 [SMILES: CCc1cnc(-c2cc(-c3ccc(CCC4CC4)cc3)[nH]c(=O)c2-c2nn[nH]n2)s1]<br>6-(4-(2-Cyclopropylethyl)phenyl)-4-(5-ethylthiazol-2-yl)-3-(2H-tetrazol-5-yl)pyridin-2(1H)-one | $^1$H NMR (400 MHz, DMSO-$d_6$) δ 12.52 (s, 1H), 7.82-7.62 (m, 2H), 7.57 (s, 1H), 7.37-7.26 (m, 2H), 7.01 (s, 1H), 2.74 (q, J = 7.5 Hz, 2H), 2.67 (dd, J = 8.9, 6.7 Hz, 2H), 1.44 (dt, J = 9.5, 7.0 Hz, 2H), 1.11 (t, J = 7.5 Hz, 3H), 0.64 (dd, J = 8.6, 3.9 Hz, 1H), 0.46-0.25 (m, 2H), 0.05--0.09 (m, 2H). MS (ESI) m/z: 419.2 (M + H)$^+$. | Ex. 18 |

TABLE 2-continued

| Ex. No. | Structure and Name | Analytical Data | Method |
|---|---|---|---|
| 150 | 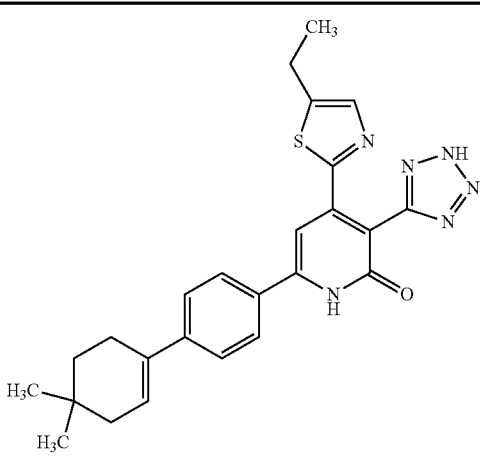<br>6-(4',4'-Dimethyl-2',3',4',5'-tetrahydro-[1,1'-biphenyl]-4-yl)-4-(5-ethylthiazol-2-yl)-3-(2H-tetrazol-5-yl)pyridin-2(1H)-one | $^1$H NMR (400 MHz, methanol-$d_4$) δ 7.80 (d, J = 8.2 Hz, 2H), 7.65 (d, J = 8.2 Hz, 2H), 7.61 (s, 1H), 7.24 (s, 1H), 6.34-6.25 (m, 1H), 2.91 (q, J = 7.8 Hz, 2H), 2.58-2.49 (m, 2H), 2.18-2.03 (m, 2H), 1.61 (t, J = 6.3 Hz, 2H), 1.31 (t, J = 7.5 Hz, 3H), 1.03 (s, 6H). MS (ESI) m/z: 459.1 (M + H)$^+$. | Ex. 13 |
| 151 | 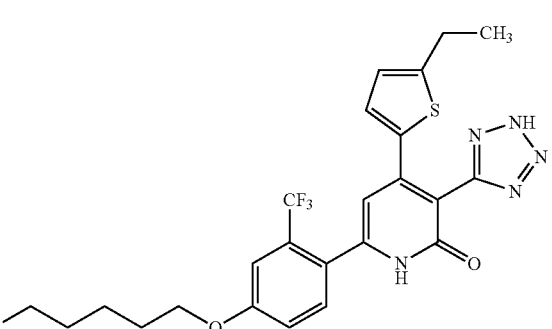<br>4-(5-Ethylthiophen-2-yl)-3-(2H-tetrazol-5-yl)-6-(4-((6,6,6-trifluorohexyl)oxy)-2-(trifluoromethyl)phenyl)pyridin-2(1H)-one | $^1$H NMR: δ 7.62 (d, J = 9.3 Hz, 1H), 7.42-7.32 (m, 2H), 6.99 (d, J = 3.8 Hz, 1H), 6.77 (d, J = 3.7 Hz, 1H), 6.53 (s, 1H), 4.15 (t, J = 6.3 Hz, 2H), 2.71 (q, J = 8.0 Hz, 2H), 2.39-2.20 (m, 2H), 1.88-1.73 (m, 2H), 1.65-1.43 (m, 4H), 1.15 (t, J = 7.5 Hz, 3H). MS (ESI) m/z: 572.3 (M + H)$^+$. | Ex. 21 |
| 152 | 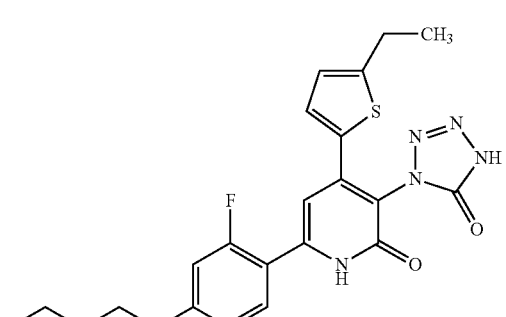<br>4-(5-Ethylthiophen-2-yl)-6-(2-fluoro-4-(4,4,4-trifluorobutoxy)phenyl)-3-(5-oxo-4,5-dihydro-1H-tetrazol-1-yl)pyridin-2(1H)-one | $^1$H NMR: δ 7.57-7.70 (m, 2H), 7.03 (dd, J = 1.98, 12.66 Hz, 1H), 6.90-6.98 (m, 2H), 6.85 (br. s., 1H), 4.14 (t, J = 6.10 Hz, 2H), 2.79 (q, J = 7.63 Hz, 2H), 2.35-2.47 (m, 2H), 1.89-2.00 (m, 2H), 1.19 (t, J = 7.48 Hz, 3H). MS (ESI) m/z: 510.2 (M + H)$^+$. | Ex. 22 |

TABLE 2-continued

| Ex. No. | Structure and Name | Analytical Data | Method |
|---|---|---|---|
| 153 | 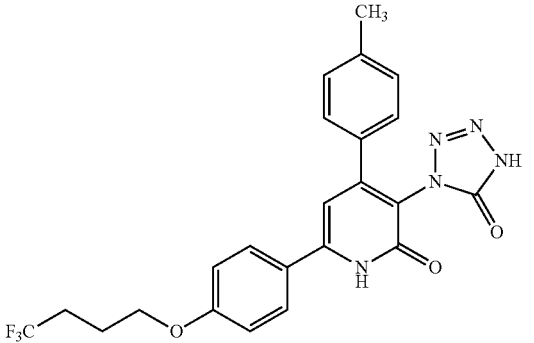 [SMILES: Cc1ccc(-c2cc(-c3ccc(OCCCC(F)(F)F)cc3)[nH]c(=O)c2-n2nn[nH]c2=O)cc1]<br>3-(5-Oxo-4,5-dihydro-1H-tetrazol-1-yl)-4-(p-tolyl)-6-(4-(4,4,4-trifluorobutoxy)phenyl)pyridin-2(1H)-one | $^1$H NMR: δ 7.84 (d, J = 7.93 Hz, 2H), 7.26-7.32 (m, 2H), 7.19-7.25 (m, 2H), 7.08 (d, J = 8.85 Hz, 2H), 6.63 (br. s., 1H), 4.12 (t, J = 6.10 Hz, 2H), 2.37-2.47 (m, 2H), 2.31 (s, 3H), 1.91-2.02 (m, 2H). MS (ESI) m/z: 472.4 (M + H)$^+$. | Ex. 22 |
| 154 | 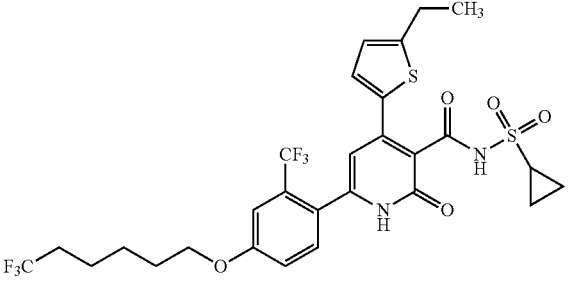 [SMILES: CCc1ccc(-c2cc(-c3ccc(OCCCCCC(F)(F)F)cc3C(F)(F)F)[nH]c(=O)c2C(=O)NS(=O)(=O)C2CC2)s1]<br>N-(Cyclopropanesulfonyl)-4-(5-ethylthiophen-2-yl)-2-oxo-6-{4-[(6,6,6-trifluorohexyl)oxy]-2-(trifluoromethyl)phenyl}-1,2-dihydropyridine-3-carboxamide | $^1$H NMR: δ 7.48 (d, J = 9.2 Hz, 1H), 7.37-7.22 (m, 3H), 6.92 (d, J = 3.7 Hz, 1H), 6.27 (s, 1H), 4.10 (t, J = 6.3 Hz, 2H), 3.09-2.91 (m, 1H), 2.82 (q, J = 7.5 Hz, 2H), 2.36-2.15 (m, 2H), 1.83-1.69 (m, 2H), 1.68-1.40 (m, 4H), 1.22 (t, J = 7.5 Hz, 3H), 1.17-1.00 (m, 4H). MS (ESI) m/z: 651.4 (M + H)$^+$. | Ex. 21 |
| 155 | 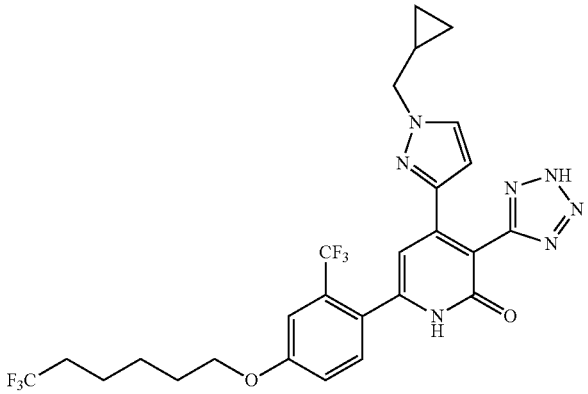 [SMILES: O=c1[nH]c(-c2ccc(OCCCCCC(F)(F)F)cc2C(F)(F)F)cc(-c2ccn(CC3CC3)n2)c1-c1nn[nH]n1]<br>4-[1-(Cyclopropylmethyl)-1H-pyrazol-3-yl]-3-(2H-1,2,3,4-tetrazol-5-yl)-6-{4-[(6,6,6-trifluorohexyl)oxy]-2-(trifluoromethyl)phenyl}-1,2-dihydropyridin-2-one | $^1$H NMR: δ 7.70 (d, J = 2.4 Hz, 1H), 7.62 (d, J = 9.0 Hz, 1H), 7.44-7.32 (m, 2H), 6.75 (s, 1H), 5.67 (s, 1H), 4.16 (t, J = 6.4 Hz, 2H), 3.86 (d, J = 7.2 Hz, 2H), 2.45-2.18 (m, 2H), 1.98-1.73 (m, 2H), 1.71-1.41 (m, 4H), 1.20-1.01 (m, 1H), 0.58-0.40 (m, 2H), 0.38-0.16 (m, 2H). MS (ESI) m/z: 598.5 (M + H)$^+$. | Ex. 21 |

| Ex. No. | Structure and Name | Analytical Data | Method |
|---|---|---|---|
| 156 | 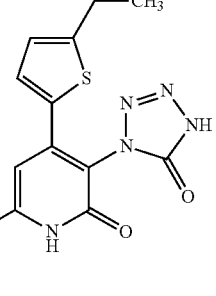<br>4-(5-Ethylthiophen-2-yl)-3-(5-oxo-4,5-dihydro-1H-1,2,3,4-tetrazol-1-yl)-6-{4-[(6,6,6-trifluorohexyl)oxy]phenyl}-1,2-dihydropyridin-2-one | $^1$H NMR: δ 12.63 (br. s., 1H), 8.11 (s, 1H), 7.67 (br. s., 1H), 7.01 (d, J = 12.93 Hz, 1H), 6.93 (dd, J = 2.34, 8.67 Hz, 1H), 6.80 (br. s., 1H), 4.07 (t, J = 6.46 Hz, 2H), 3.87 (d, J = 7.15 Hz, 2H), 2.22-2.34 (m, 2H), 1.77 (quin, J = 6.88 Hz, 2H), 1.44-1.61 (m, 4H), 1.03-1.19 (m, 1H), 0.47-0.54 (m, 2H), 0.31 (q, J = 4.86 Hz, 2H). MS (ESI) m/z: 520.2 (M + H)$^+$. | Ex. 22 |
| 157 | 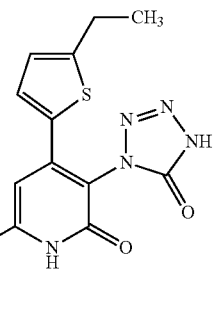<br>4-(5-Ethylthiophen-2-yl)-6-{2-fluoro-4-[(6,6,6-trifluorohexyl)oxy]phenyl}-3-(5-oxo-4,5-dihydro-1H-1,2,3,4-tetrazol-1-yl)-1,2-dihydropyridin-2-one | $^1$H NMR: δ 7.59-7.68 (m, 2H), 7.01 (d, J = 12.82 Hz, 1H), 6.94-6.97 (m, 1H), 6.90-6.94 (m, 1H), 6.85 (br. s., 1H), 4.07 (t, J = 6.26 Hz, 2H), 2.80 (q, J = 7.32 Hz, 2H), 2.20-2.33 (m, 2H), 1.71-1.82 (m, 2H), 1.53 (td, J = 7.10, 14.50 Hz, 4H), 1.20 (t, J = 7.48 Hz, 3H). MS (ESI) m/z: 538.1 (M + H)$^+$. | Ex. 22 |
| 158 | 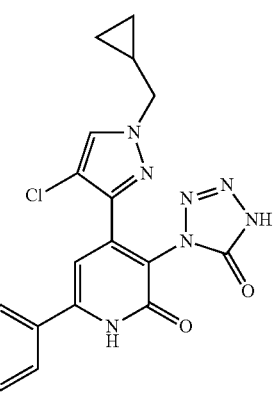<br>4-[4-Chloro-1-(cyclopropylmethyl)-1H-pyrazol-3-yl]-3-(5-oxo-4,5-dihydro-1H-1,2,3,4-tetrazol-1-yl)-6-{4-[(6,6,6-trifluorohexyl)oxy]phenyl}-1,2-dihydropyridin-2-one | $^1$H NMR (400 MHz, CD$_3$OD) δ 7.86 (s, 1H), 7.73 (d, J = 8.80 Hz, 2H), 7.10 (d, J = 8.80 Hz, 2H), 7.04 (s, 1H), 4.10 (t, J = 6.27 Hz, 2H), 3.90 (d, J = 7.04 Hz, 2H), 2.12-2.27 (m, 2H), 1.81-1.91 (m, 2H), 1.55-1.72 (m, 4H), 1.16-1.28 (m, 1H), 0.56-0.63 (m, 2H), 0.32-0.38 (m, 2H). MS (ESI) m/z: 564.4 (M + H)$^+$. | Ex. 22 |

TABLE 2-continued

| Ex. No. | Structure and Name | Analytical Data | Method |
|---|---|---|---|
| 159 | 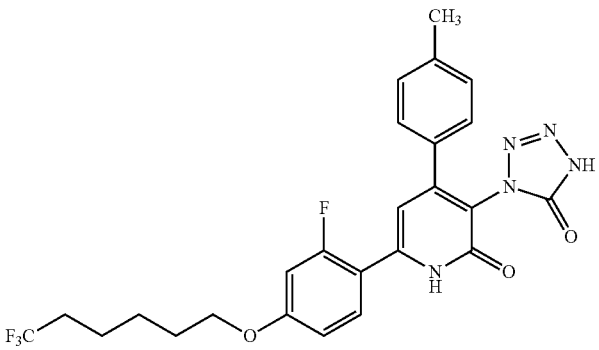 [SMILES: Cc1ccc(-c2cc(-c3ccc(OCCCCCC(F)(F)F)cc3F)[nH]c(=O)c2-n2nn[nH]c2=O)cc1]<br>6-{2-Fluoro-4-[(6,6,6-trifluorohexyl)oxy]phenyl}-4-(4-methylphenyl)-3-(5-oxo-4,5-dihydro-1H-1,2,3,4-tetrazol-1-yl)-1,2-dihydropyridin-2-one | $^1$H NMR (400 MHz, CD$_3$OD) δ 7.86 (s, 1H), 7.73 (d, J = 8.80 Hz, 2H), 7.10 (d, J = 8.80 Hz, 2H), 7.04 (s, 1H), 4.10 (t, J = 6.27 Hz, 2H), 3.90 (d, J = 7.04 Hz, 2H), 2.12-2.27 (m, 2H), 1.81-1.91 (m, 2H), 1.55-1.72 (m, 4H), 1.16-1.28 (m, 1H), 0.56-0.63 (m, 2H), 0.32-0.38 (m, 2H). MS (ESI) m/z: 518.2 (M + H)$^+$. | Ex. 22 |
| 160 | 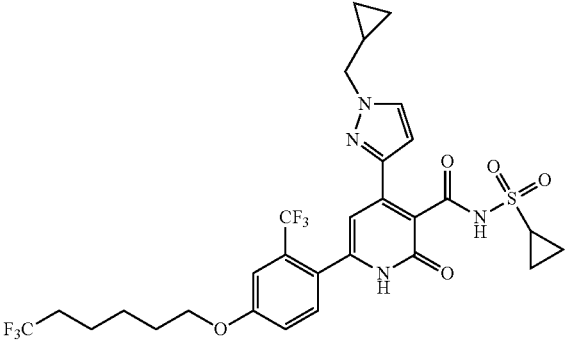 [SMILES: O=C(NS(=O)(=O)C1CC1)c1c(-c2ccn(CC3CC3)n2)cc(-c2ccc(OCCCCCC(F)(F)F)cc2C(F)(F)F)[nH]c1=O]<br>N-(Cyclopropanesulfonyl)-4-[1-(cyclopropylmethyl)-1H-pyrazol-3-yl]-2-oxo-6-{4-[(6,6,6-trifluorohexyl)oxy]-2-(trifluoromethyl)phenyl}-1,2-dihydropyridine-3-carboxamide | 1H NMR: δ 12.10 (s, 2H), 7.88 (d, J = 2.4 Hz, 1H), 7.48 (d, J = 9.3 Hz, 1H), 7.38-7.29 (m, 2H), 6.67 (d, J = 2.4 Hz, 1H), 6.62 (s, 1H), 4.13 (t, J = 6.4 Hz, 2H), 4.00 (d, J = 7.2 Hz, 2H), 3.15-2.90 (m, 1H), 2.38-2.16 (m, 2H), 1.91-1.73 (m, 2H), 1.66-1.38 (m, 4H), 1.34-1.19 (m, 1H), 1.14 (t, J = 6.9 Hz, 4H), 0.59-0.48 (m, 2H), 0.45-0.27 (m, 2H). MS (ESI) m/z: 661.2 (M + H)$^+$. | Ex. 21 |
| 161 | 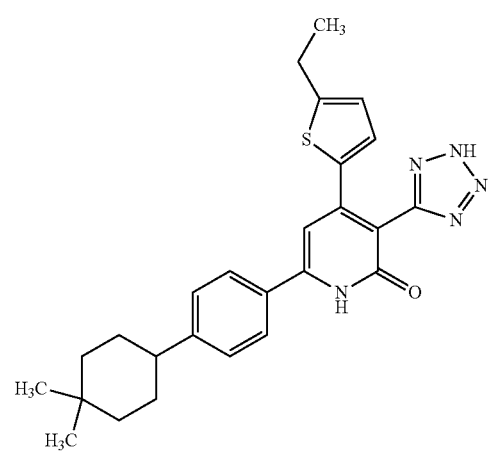 [SMILES: CCc1ccc(-c2cc(-c3ccc(C4CCC(C)(C)CC4)cc3)[nH]c(=O)c2-c2nn[nH]n2)s1]<br>6-[4-(4,4-Dimethylcyclohexyl)phenyl]-4-(5-ethylthiophen-2-yl)-3-(2H-1,2,3,4-tetrazol-5-yl)-1,2-dihydropyridin-2-one | $^1$H NMR (400 MHz, DMSO-d$_6$) δ 12.34 (s, 1H), 7.83 (d, J = 7.9 Hz, 2H), 7.48-7.39 (m, 2H), 7.23 (d, J = 3.8 Hz, 1H), 6.90 (s, 1H), 6.87-6.79 (m, 1H), 2.83-2.70 (m, 2H), 1.80-1.58 (m, 4H), 1.58-1.45 (m, 2H), 1.43-1.30 (m, 2H), 1.17 (t, J = 7.5 Hz, 3H), 1.01 (s, 3H), 0.97 (s, 3H). MS (ESI) m/z: 460.5 (M + H)$^+$. | Ex. 13 |

TABLE 2-continued

| Ex. No. | Structure and Name | Analytical Data | Method |
|---|---|---|---|
| 162 | 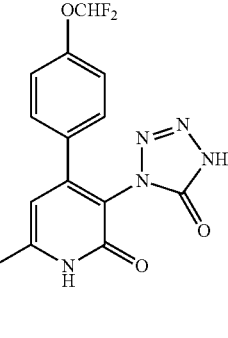<br>4-[4-(Difluoromethoxy)phenyl]-3-(5-oxo-4,5-dihydro-1H-1,2,3,4-tetrazol-1-yl)-6-{4-[(6,6,6-trifluorohexyl)oxy]phenyl}-1,2-dihydropyridin-2-one | $^1$H NMR: δ 7.84 (d, J = 7.93 Hz, 2H), 7.46 (d, J = 8.85 Hz, 2H), 7.24 (d, J = 8.54 Hz, 2H), 7.12-7.44 (m, 1H), 7.06 (d, J = 8.85 Hz, 2H), 6.66 (br. s., 1H), 4.06 (t, J = 6.26 Hz, 2H), 2.19-2.33 (m, 2H), 1.70-1.82 (m, 2H), 1.41-1.61 (m, 4H). MS (ESI) m/z: 552.4 (M + H)$^+$. | Ex. 22 |
| 163 | 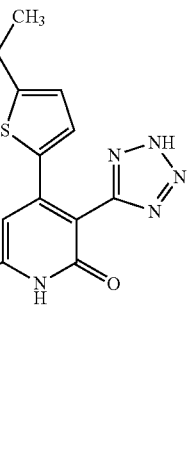<br>6-[4-(4-tert-Butylcyclohex-1-en-1-yl)phenyl]-4-(5-ethylthiophen-2-yl)-3-(2H-1,2,3,4-tetrazol-5-yl)-1,2-dihydropyridin-2-one | $^1$H NMR: δ 7.87 (d, J = 8.2 Hz, 2H), 7.57 (d, J = 8.1 Hz, 2H), 7.22 (d, J = 3.7 Hz, 1H), 6.96 (s, 1H), 6.84 (d, J = 3.8 Hz, 1H), 6.35 (s, 1H), 2.74 (q, J = 7.6 Hz, 2H), 2.46-2.35 (m, 1H), 2.31-2.21 (m, 1H), 1.90-2.03 (m, 2H), 1.46-1.23 (m, 3H), 1.17 (t, J = 7.5 Hz, 3H), 0.92 (s, 9H). MS (ESI) m/z: 486.4 (M + H)$^+$. | Ex. 13 |
| 164 | 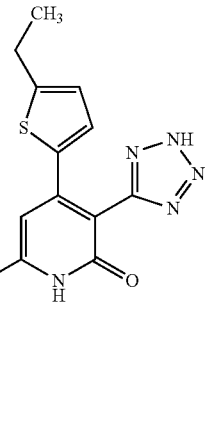<br>4-(5-Ethylthiophen-2-yl)-6-[4-(4-propylcyclohex-1-en-1-yl)phenyl]-3-(2H-1,2,3,4-tetrazol-5-yl)-1,2-dihydropyridin-2-one | $^1$H NMR: δ 7.81 (d, J = 8.2 Hz, 2H), 7.53 (d, J = 8.1 Hz, 2H), 7.17 (d, J = 3.9 Hz, 1H), 6.91 (s, 1H), 6.79 (d, J = 3.9 Hz, 1H), 6.27 (s, 1H), 2.69 (q, J = 7.4 Hz, 2H), 2.45-2.36 (m, 1H), 2.35-2.24 (m, 1H), 1.93-1.72 (m, 2H), 1.65-1.16 (m, 7H), 1.12 (t, J = 7.5 Hz, 3H), 0.87 (t, J = 7.1 Hz, 3H). MS (ESI) m/z: 472.5 (M + H)$^+$. | Ex. 13 |

TABLE 2-continued

| Ex. No. | Structure and Name | Analytical Data | Method |
|---|---|---|---|
| 165 | 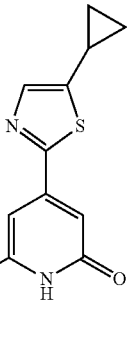<br>4-(5-Cyclopropyl-1,3-thiazol-2-yl)-6-{2-fluoro-4-[(6,6,6-trifluorohexyl)oxy]phenyl}-1,2-dihydropyridin-2-one | $^1$H NMR: δ 7.75 (s, 1H), 7.61 (t, J = 8.39 Hz, 1H), 6.83-6.99 (m, 3H), 6.74 (s, 1H), 4.04 (t, J = 6.41 Hz, 2H), 2.18-2.31 (m, 3H), 1.71-1.79 (m, 2H), 1.52 (td, J = 7.25, 14.80 Hz, 4H), 1.06-1.15 (m, 2H), 0.71-0.82 (m, 2H). MS (ESI) m/z: 467.2 (M + H)$^+$. | Ex. 22 |
| 166 | 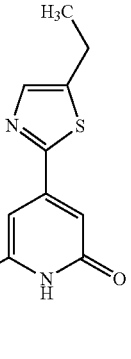<br>4-(5-Ethyl-1,3-thiazol-2-yl)-6-{2-fluoro-4-[(6,6,6-trifluorohexyl)oxy]phenyl}-1,2-dihydropyridin-2-one | $^1$H NMR: δ 7.76 (s, 1H), 7.62 (t, J = 8.54 Hz, 1H), 6.83-7.01 (m, 3H), 6.77 (s, 1H), 4.05 (t, J = 6.41 Hz, 2H), 2.91 (q, J = 7.53 Hz, 2H), 2.18-2.33 (m, 2H), 1.69-1.81 (m, 2H), 1.44-1.60 (m, 4H), 1.28 (t, J = 7.48 Hz, 3H). MS (ESI) m/z: 455.4 (M + H)$^+$. | Ex. 22 |
| 167 | 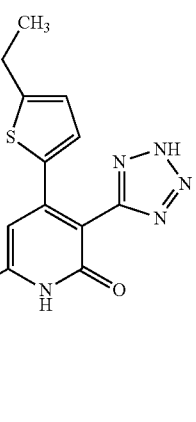<br>4-(5-Ethylthiophen-2-yl)-6-[4-(4-propylcyclohexyl)phenyl]-3-(2H-1,2,3,4-tetrazol-5-yl)-1,2-dihydropyridin-2-one | $^1$H NMR: δ 7.87 (d, J = 8.0 Hz, 2H), 7.48 (d, J = 8.0 Hz, 2H), 7.20 (d, J = 3.4 Hz, 1H), 6.96 (s, 1H), 6.87 (d, J = 3.7 Hz, 1H), 2.79 (q, J = 7.5 Hz, 2H), 2.71 (s, 1H), 1.85-1.60 (m, 9H), 1.54-1.32 (m, 4H), 1.23 (t, J = 7.5 Hz, 3H), 0.98 (t, J = 7.1 Hz, 3H). MS (ESI) m/z: 474.4 (M + H)$^+$. | Ex. 13 |

TABLE 2-continued

| Ex. No. | Structure and Name | Analytical Data | Method |
|---|---|---|---|
| 168 | 4-[1-(Cyclopropylmethyl)-1H-pyrazol-3-yl]-6-{2-fluoro-4-[(6,6,6-trifluorohexyl)oxy]phenyl}-3-(5-oxo-4,5-dihydro-1H-1,2,3,4-tetrazol-1-yl)-1,2-dihydropyridin-2-one | $^1$H NMR: δ 12.27 (br. s., 1H), 7.81 (d, J = 2.20 Hz, 1H), 7.61 (t, J = 8.80 Hz, 1H), 7.02 (dd, J = 2.20, 12.93 Hz, 1H), 6.88-6.96 (m, 2H), 6.13 (br. s., 1H), 4.08 (t, J = 6.46 Hz, 2H), 3.96 (d, J = 7.15 Hz, 2H), 2.22-2.35 (m, 2H), 1.78 (quin, J = 6.81 Hz, 2H), 1.42-1.62 (m, 4H), 1.15-1.25 (m, 1H), 0.47-0.53 (m, 2H), 0.30-0.37 (m, 2H). MS (ESI) m/z: 548.2 (M + H)$^+$. | Ex. 22 |
| 169 | 4-[4-Chloro-1-(cyclopropylmethyl)-1H-pyrazol-3-yl]-6-{2-fluoro-4-[(6,6,6-trifluorohexyl)oxy]phenyl}-3-(5-oxo-4,5-dihydro-1H-1,2,3,4-tetrazol-1-yl)-1,2-dihydropyridin-2-one | $^1$H NMR: δ 12.63 (br. s., 1H), 8.11 (s, 1H), 7.67 (br. s., 1H), 7.01 (d, J = 12.93 Hz, 1H), 6.93 (dd, J = 2.34, 8.67 Hz, 1H), 6.80 (br. s., 1H), 4.07 (t, J = 6.46 Hz, 2H), 3.87 (d, J = 7.15 Hz, 2H), 2.22-2.34 (m, 2H), 1.77 (quin, J = 6.88 Hz, 2H), 1.44-1.61 (m, 4H), 1.03-1.19 (m, 1H), 0.47-0.54 (m, 2H), 0.31 (q, J = 4.86 Hz, 2H). MS (ESI) m/z: 582.2 (M + H)$^+$. | Ex. 22 |
| 170 | 4-[1-(Cyclopropylmethyl)-1H-pyrazol-3-yl]-6-[4-(4,4-dimethylcyclohex-1-en-1-yl)phenyl]-3-(2H-1,2,3,4-tetrazol-5-yl)-1,2-dihydropyridin-2-one | $^1$H NMR: δ 7.84 (d, J = 8.2 Hz, 2H), 7.72 (d, J = 2.4 Hz, 1H), 7.60 (d, J = 8.2 Hz, 2H), 7.13 (s, 1H), 6.40-6.16 (m, 1H), 5.90 (d, J = 2.4 Hz, 1H), 3.87 (d, J = 7.3 Hz, 2H), 2.51-2.35 (m, 2H), 2.12-1.87 (m, 2H), 1.52 (t, J = 6.4 Hz, 2H), 1.23-1.04 (m, 1H), 0.96 (s, 6H), 0.62-0.39 (m, 2H), 0.35-0.17 (m, 2H). MS (ESI) m/z: 468.5 (M + H)$^+$. | Ex. 13 |

TABLE 2-continued

| Ex. No. | Structure and Name | Analytical Data | Method |
|---|---|---|---|
| 171 | 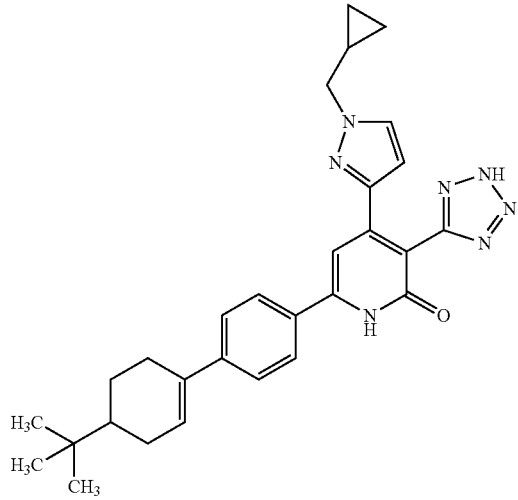 [SMILES: CC(C)(C)C1CC=C(c2ccc(-c3cc(-c4ccn(CC5CC5)n4)c(-c4nn[nH]n4)c(=O)[nH]3)cc2)CC1]<br>6-[4-(4-tert-Butylcyclohex-1-en-1-yl)phenyl]-4-[1-(cyclopropylmethyl)-1H-pyrazol-3-yl]-3-(2H-1,2,3,4-tetrazol-5-yl)-1,2-dihydropyridin-2-one | $^1$H NMR: δ 7.89 (d, J = 8.2 Hz, 2H), 7.78 (d, J = 2.4 Hz, 1H), 7.64 (d, J = 8.2 Hz, 2H), 7.19 (s, 1H), 6.43-6.38 (m, 1H), 5.94 (s, 1H), 3.93 (d, J = 7.2 Hz, 2H), 2.56-2.42 (m, 1H), 2.37-2.29 (m, 1H), 2.05 (s, 2H), 1.43-1.28 (m, 2H), 1.23-1.14 (m, 1H), 0.99-0.95 (m, 10H), 0.57-0.50 (m, 2H), 0.37-0.32 (m, 2H). MS (ESI) m/z: 496.6 (M + H)$^+$. | Ex. 13 |
| 172 | 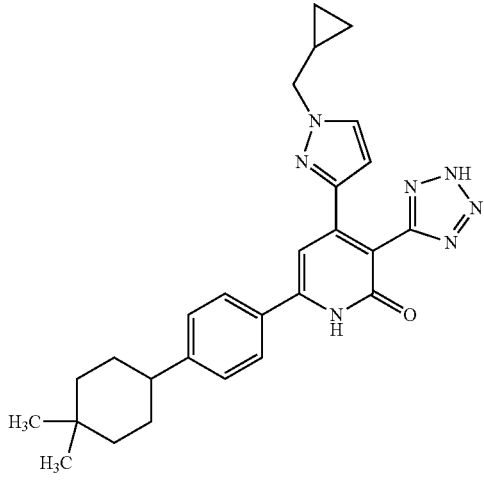 [SMILES: CC1(C)CCC(c2ccc(-c3cc(-c4ccn(CC5CC5)n4)c(-c4nn[nH]n4)c(=O)[nH]3)cc2)CC1]<br>4-[1-(Cyclopropylmethyl)-1H-pyrazol-3-yl]-6-[4-(4,4-dimethylcyclohexyl)phenyl]-3-(2H-1,2,3,4-tetrazol-5-yl)-1,2-dihydropyridin-2-one | $^1$H NMR: δ 7.80 (d, J = 7.9 Hz, 2H), 7.72 (d, J = 2.4 Hz, 1H), 7.44 (d, J = 8.1 Hz, 2H), 7.08 (s, 1H), 5.89 (s, 1H), 3.87 (d, J = 7.1 Hz, 2H), 1.75-1.58 (m, 4H), 1.57-1.45 (m, 2H), 1.44-1.29 (m, 2H), 1.19-1.05 (m, 1H), 1.00 (s, 3H), 0.97 (s, 3H), 0.55-0.41 (m, 2H), 0.35-0.20 (m, 2H). MS (ESI) m/z: 470.6 (M + H)$^+$. | Ex. 13 |

TABLE 2-continued

| Ex. No. | Structure and Name | Analytical Data | Method |
|---|---|---|---|
| 173 | 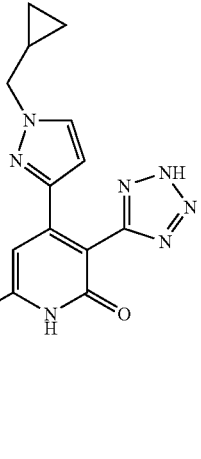<br>4-[1-(Cyclopropylmethyl)-1H-pyrazol-3-yl]-6-[4-(4-propylcyclohex-1-en-1-yl)phenyl]-3-(2H-1,2,3,4-tetrazol-5-yl)-1,2-dihydropyridin-2-one | $^1$H NMR: δ 7.87 (d, J = 8.2 Hz, 2H), 7.68 (d, J = 2.4 Hz, 1H), 7.64 (d, J = 8.2 Hz, 2H), 7.24 (s, 1H), 6.37 (s, 1H), 5.51 (s, 1H), 3.97 (d, J = 7.5 Hz, 2H), 2.56-2.47 (m, 2H), 2.48-2.36 (m, 1H), 2.06-1.82 (m, 2H), 1.77-1.54 (m, 1H), 1.53-1.29 (m, 5H), 1.26-1.13 (m, 1H), 0.97 (t, J = 7.2 Hz, 3H), 0.67-0.45 (m, 2H), 0.42-0.28 (m, 2H). MS (ESI) m/z: 482.6 (M + H)$^+$. | Ex. 13 |

What is claimed is:

1. A compound of Formula (I):

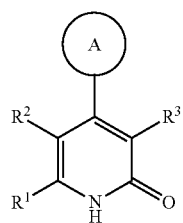

or a stereoisomer, a tautomer, or a pharmaceutically acceptable salt thereof, wherein:

ring A is independently a 5- to 10-membered heteroaryl comprising carbon atoms and 1-4 heteroatoms selected from N, NR$^e$ O and S; wherein said heteroaryl is substituted with 0-1 R$^6$ and 0-3 R$^7$;

R$^1$ is independently selected from: —(CH$_2$)$_m$—C$_{3-6}$ carbocycle substituted with 0-2 R$^b$ and 0-2 R$^g$), R$^2$ is independently selected from: H, halogen, C$_{3-4}$ cycloalkyl, phenyl substituted with 0-2 R$^h$, and C$_{1-12}$ hydrocarbon chain substituted with 0-3 R$^a$; wherein said hydrocarbon chain may be straight or branched, saturated or unsaturated;

R$^3$ is independently selected from: CO$_2$H, —(CH$_2$)$_n$—X—(CH$_2$)$_m$R$^4$, —CONHSO$_2$R$^i$, —NHCOX$_1$SO$_2$R$^i$, a 5- to 6-membered heterocycle comprising carbon atoms and 1-4 heteroatoms selected from N, NR$^e$ O, and S; wherein said heterocycle is substituted with 0-2 R$^d$;

X is independently selected from: CONH and NHCO;

X$_1$ is independently C$_{1-4}$ hydrocarbon chain optionally substituted with C$_{1-4}$ alkyl or C$_{3-4}$ cycloalkyl;

R$^4$ is independently selected from: C$_{3-6}$ cycloalkyl substituted with 0-2 R$^d$, C$_{3-6}$ cycloalkenyl substituted with 0-2 R$^d$, —(CH$_2$)$_m$-(phenyl substituted with 0-3 R$^d$), and a 5- to 6-membered heterocycle comprising carbon atoms and 1-4 heteroatoms selected from N, NR$^e$ O, and S; wherein said heterocycle is substituted with 0-2 R$^d$;

R$^6$ is independently selected from: halogen, C$_{1-6}$ alkyl substituted with 0-2 R$^h$, C$_{1-4}$ alkoxy, C$_{1-4}$ haloalkyl, C$_{1-4}$ haloalkoxy, —(CH$_2$)$_m$—C$_{3-6}$ cycloalkyl, —(CH$_2$)$_m$—NR$^f$R$^i$, CN, OR$^i$, SR$^i$, and a 4- to 6-membered heterocycle comprising carbon atoms and 1-4 heteroatoms selected from N, NR$^e$ O, and S;

R$^7$ is independently selected from: halogen, C$_{1-4}$ alkyl, C$_{1-4}$ alkoxy, C$_{1-4}$ haloalkyl, and C$_{1-4}$ haloalkoxy;

R$^a$ is, at each occurrence, independently selected from: halogen, OH, C$_{1-6}$ alkoxy, C$_{1-6}$ haloalkyl, C$_{1-6}$ haloalkoxy, N(C$_{1-4}$ alkyl)$_2$, and —(CH$_2$)N—(X)$_t$—R$^c$;

R$^b$ is, at each occurrence, independently selected from: halogen, OH, C$_{1-10}$ alkyl, C$_{2-8}$ alkenyl, C$_{1-10}$ alkoxy, C$_{1-10}$ haloalkyl, C$_{1-10}$ haloalkoxy, C$_{1-10}$ alkylthio, C$_{1-10}$ haloalkylthio, N(C$_{1-4}$ alkyl)$_2$, —CONH(C$_{4-20}$ alkyl), —CONH(C$_{4-20}$ haloalkyl), —O(CH$_2$)$_s$O(C$_{1-6}$ alkyl), —O(CH$_2$)$_s$O(C$_{1-6}$ haloalkyl), —(CH═CH)(C$_{3-6}$ cycloalkyl), R$^c$, and —(CH$_2$)$_n$—(O)$_t$—(CH$_2$)$_m$R$^c$;

R$^c$ is, at each occurrence, independently selected from: C$_{3-6}$ cycloalkyl substituted with 0-2 R$^d$, C$_{4-8}$ cycloalkenyl substituted with 0-2 R$^d$, phenyl substituted with 0-3 R$^d$, and a 5- to 6-membered heterocycle comprising carbon atoms and 1-4 heteroatoms selected from N, NR$^e$, O, and S; wherein said heterocycle is substituted with 0-2 R$^d$;

R$^d$ is, at each occurrence, independently selected from: ═O, halogen, OH, CN, NO$_2$, C$_{1-4}$ alkyl, C$_{1-4}$ alkoxy, C$_{1-4}$ haloalkyl, C$_{1-4}$ haloalkoxy, tetrazolyl, OBn and phenyl;

R$^e$ is, at each occurrence, independently selected from: H, C$_{1-8}$ alkyl, C$_{1-8}$ haloalkyl, —(CH$_2$)$_n$—C$_{3-6}$ carbocycle, CO(C$_{1-4}$ alkyl) and COBn;

R$^f$ is, at each occurrence, independently selected from: H and C$_{1-4}$ alkyl;

R$^g$ is independently selected from: halogen, OH, C$_{1-4}$ alkyl, C$_{1-4}$ alkoxy, C$_{1-4}$ haloalkyl, and C$_{1-4}$ haloalkoxy;

$R^h$ is independently selected from: halogen, $C_{1-4}$ alkoxy, $C_{1-4}$ haloalkoxy, and $C_{1-12}$ hydrocarbon chain substituted with 0-3 $R^a$; wherein said hydrocarbon chain may be straight or branched, saturated or unsaturated;

$R^i$ is, at each occurrence, independently selected from: $C_{1-4}$ alkyl, $C_{3-4}$ cycloalkyl and phenyl;

n, at each occurrence, is independently 0 or 1;

m, at each occurrence, is independently 0, 1, 2, 3, or 4;

s, at each occurrence, is independently 1, 2, or 3; and t, at each occurrence, is independently 0 or 1;

provided that:
when $R^1$ is phenyl, 4-halo-Ph, or 3,4-diCl-Ph, then $R^3$ is other than $CO_2H$.

2. A compound according to claim 1, or a stereoisomer, a tautomer, or a pharmaceutically acceptable salt thereof, wherein:
$R^1$ is independently selected from: $-(CH_2)_m-(C_{3-6}$ carbocycle substituted with 1 $R^b$ and 0-2 $R^g$).

3. A compound according to claim 2, or a stereoisomer, a tautomer, or a pharmaceutically acceptable salt thereof, wherein:
ring A is independently a heteroaryl substituted with 0-1 $R^6$; wherein said heteroaryl is selected from: furanyl, thienyl, 1-$R^e$-pyrrolyl, thiazolyl, 1-$R^e$-pyrazolyl, and benzothienyl;

$R^1$ is independently selected from: $C_{3-6}$ cycloalkyl substituted 0-1 $R^g$, $C_{5-6}$ cycloalkenyl substituted 0-1 $R^g$, phenyl substituted with 1 $R^b$ and 0-1 $R^g$;

$R^2$ is independently selected from: H, halogen, $C_{1-4}$ alkyl, $C_{2-4}$ alkenyl, $C_{1-4}$ alkoxy, and phenyl substituted with 0-1 $C_{1-6}$ alkyl;

$R^3$ is independently selected from: tetrazolyl, tetrazolone, $-NHCO$(tetrazolyl), $-CONH$(pyridyl), $-CONH(C_{3-6}$ cycloalkyl), $-CONH$(phenyl substituted with 0-1 $R^d$), $-CONHSO_2(C_{1-4}$ alkyl), $-CONHSO_2(C_{3-6}$ cycloalkyl), $-CONHSO_2$ (isoxazolyl substituted with 0-1 $C_{1-4}$ alkyl), and $-CONHSO_2N(C_{1-4}$ alkyl)$_2$;

$R^6$ is independently selected from: $C_{1-4}$ alkyl, $C_{1-4}$ alkoxy, $C_{1-4}$ haloalkoxy, $N(C_{1-4}$ alkyl)$_2$, and $-(CH_2)_{1-4}(C_{3-6}$ cycloalkyl);

$R^7$ is independently selected from: halogen and $C_{1-4}$ alkyl;

$R^b$ is independently selected from: $C_{1-6}$ alkyl, $C_{2-6}$ alkenyl, $C_{1-6}$ alkoxy, $C_{1-8}$ haloalkyl, $C_{1-8}$ haloalkoxy, $-CONH(CH_2)_{6-20}H$, $C_{3-6}$ cycloalkyl substituted with 0-2 $C_{1-4}$ alkyl, $C_{4-8}$ cycloalkenyl substituted with 0-2 $C_{1-4}$ alkyl, $-(O)_t-(CH_2)_m(C_{3-6}$ cycloalkyl), $-(CH=CH)(C_{3-6}$ cycloalkyl), Ph, Bn, phenoxy, benzoxy, pyrimidinyl, pyrazinyl and $-O$-pyrimidinyl;

$R^d$ is, at each occurrence, independently selected from: halogen, $C_{1-4}$ alkyl, $C_{1-4}$ alkoxy, $C_{1-4}$ haloalkyl, and $C_{1-4}$ haloalkoxy;

$R^e$ is independently selected from: H, $C_{1-6}$ alkyl, $C_{1-8}$ haloalkyl, and $-(CH_2)_n-(C_{3-6}$ cycloalkyl); and $R^g$ is independently selected from: halogen, OH, $C_{1-4}$ alkyl and $C_{1-4}$ alkoxy.

4. A compound according to claim 3, or a stereoisomer, a tautomer, or a pharmaceutically acceptable salt thereof, wherein:
ring A is independently selected from:

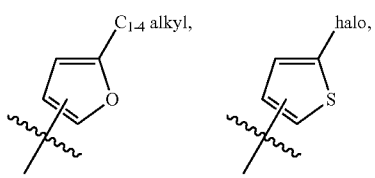

-continued

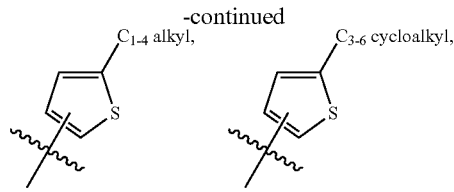

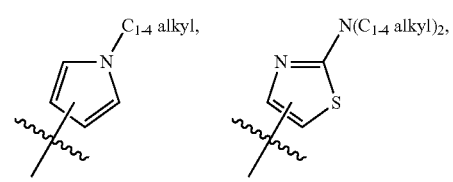

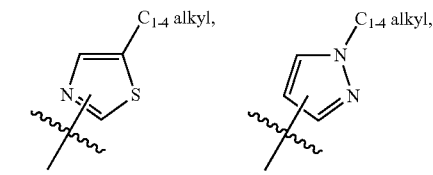

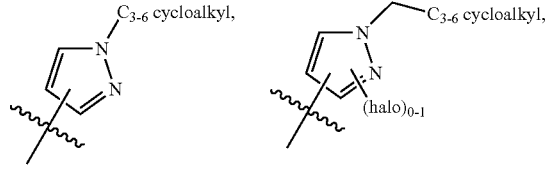

and

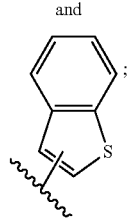

$R^1$ is independently selected from: $C_{3-6}$ cycloalkyl, $C_{5-6}$ cycloalkenyl, 1-halo-$C_{3-6}$ cycloalkyl, 1-OH—$C_{3-6}$ cycloalkyl, 4-$R^b$-Ph;

$R^2$ is independently selected from: H, halogen, $C_{1-4}$ alkyl, $C_{2-4}$ alkenyl, $C_{1-4}$ alkoxy, and phenyl substituted with 0-1 $C_{1-6}$ alkyl;

$R^3$ is independently selected from: tetrazolyl, tetrazolone, $-NHCO$(tetrazolyl), $-CONH(C_{3-6}$ cycloalkyl), $-CONHPh$, $-CONH(4-C_{1-4}$ alkoxy-Ph), $-CONH(4-C_{1-4}$ haloalkoxy-Ph), $-CONH$(pyrid-3-yl), $-CONHSO_2(C_{1-4}$ alkyl), $-CONHSO_2(C_{3-6}$ cycloalkyl), $-CONHSO_2$ (isoxazolyl substituted with 0-1 $C_{1-4}$ alkyl), and $-CONHSO_2N(C_{1-4}$ alkyl)$_2$;

$R^6$ is independently selected from: $C_{1-4}$ alkyl, $C_{1-4}$ alkoxy, $C_{1-4}$ haloalkoxy, $N(C_{1-4}$ alkyl)$_2$, and $-(CH_2)_{1-4}(C_{3-6}$ cycloalkyl);

$R^7$ is independently selected from: halogen and $C_{1-4}$ alkyl; and $R^b$ is independently selected from: $C_{2-6}$ alkyl, $C_{2-6}$ alkenyl, $-(CH_2)_{1-6}CF_3$, $-O(CH_2)_{1-6}CF_3$, $-(O)_{0-1}-(CH_2)_{1-4}(C_{3-6}$ cycloalkyl), $-(CH=CH)(C_{3-6}$ cycloalkyl), $C_{3-6}$ cycloalkyl substituted with 0-2 $C_{1-4}$ alkyl, $C_{5-6}$ cycloalkenyl substituted with 0-2 $C_{1-4}$ alkyl, and Bn.

5. A compound according to claim 1, or a stereoisomer, a tautomer, or a pharmaceutically acceptable salt thereof, wherein:
- $R^1$ is independently selected from: $C_{3-6}$ cycloalkyl substituted 0-1 $R^g$, $C_{5-6}$ cycloalkenyl substituted 0-1 $R^g$, phenyl substituted with 1 $R^b$ and 0-1 $R^g$;
- $R^2$ is independently selected from: H, halogen, $C_{1-4}$ alkyl, $C_{2-4}$ alkenyl, $C_{1-4}$ alkoxy, and phenyl substituted with 0-1 $C_{1-6}$ alkyl;
- $R^3$ is independently selected from: tetrazolyl, tetrazolone, —CONH(pyridyl), and —CONH(phenyl substituted with 0-1 $C_{1-4}$ alkoxy);
- $R^6$ is independently selected from: $C_{1-4}$ alkyl, $N(C_{1-4}$ alkyl)$_2$, and $C_{3-6}$ cycloalkyl;
- $R^7$ is independently selected from: halogen and $C_{1-4}$ alkyl;
- $R^b$ is independently selected from: $C_{1-6}$ alkyl, $C_{2-6}$ alkenyl, $C_{1-6}$ alkoxy, $C_{1-8}$ haloalkyl, $C_{1-8}$ haloalkoxy, —CONH(CH$_2$)$_{6-20}$H, $C_{3-6}$ cycloalkyl, $C_{4-8}$ cycloalkenyl, —O(CH$_2$)$_m$($C_{3-6}$ cycloalkyl), —(CH=CH)($C_{3-6}$ cycloalkyl), Ph, Bn, phenoxy, and benzoxy; and
- $R^g$ is independently selected from: halogen, OH, $C_{1-4}$ alkyl and $C_{1-4}$ alkoxy.

6. A compound according to claim 5, or a stereoisomer, a tautomer, or a pharmaceutically acceptable salt thereof, wherein:
$R^1$ is

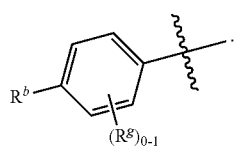

7. A compound selected from the group consisting of:

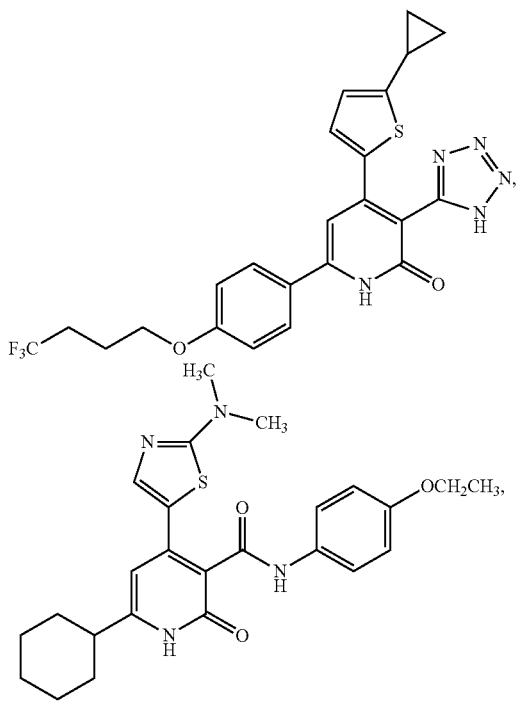

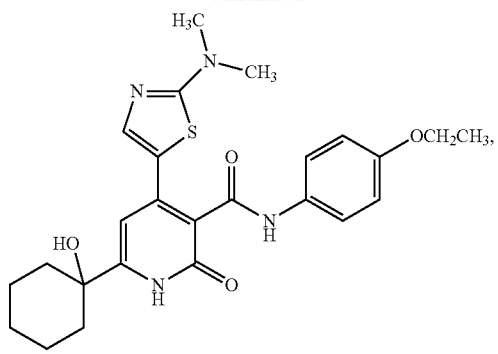

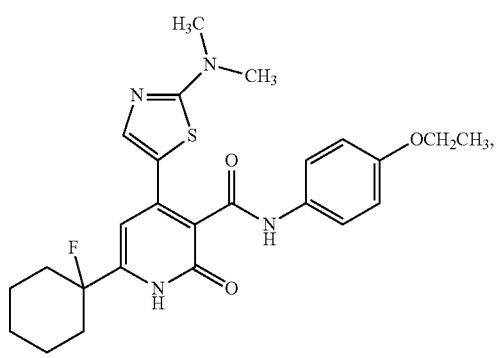

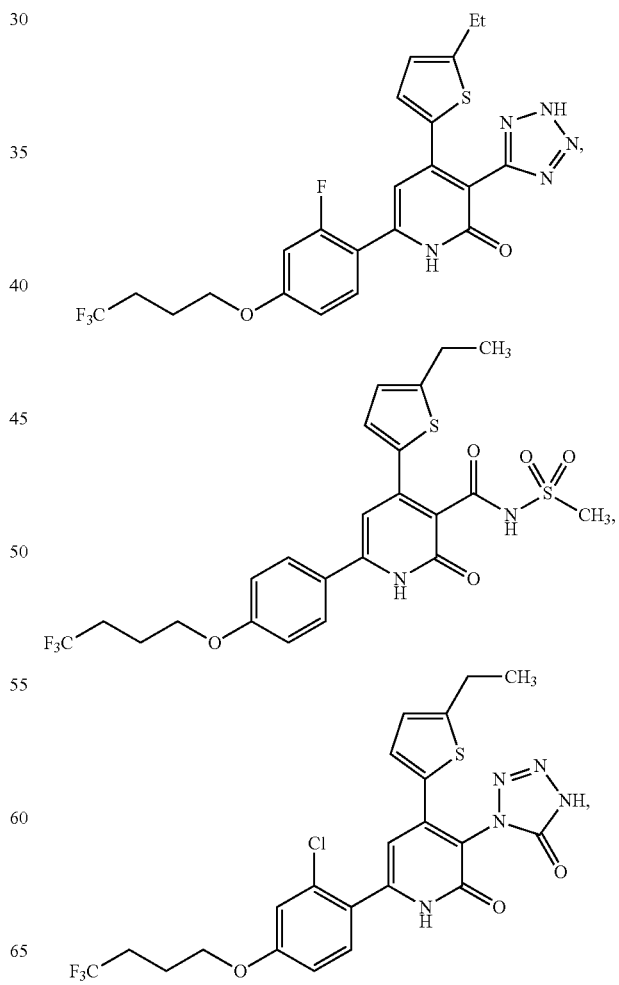

173
-continued
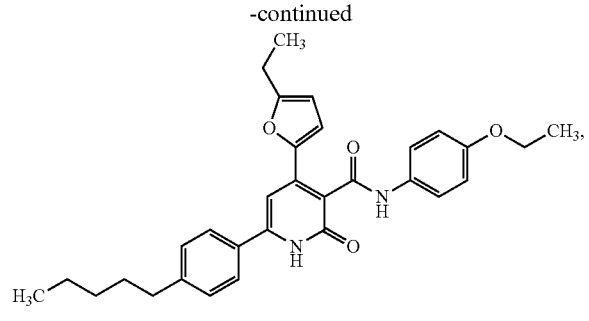
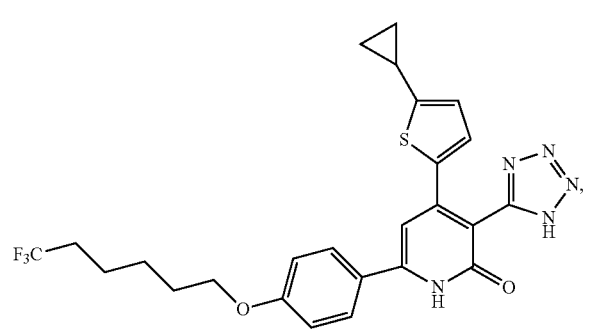
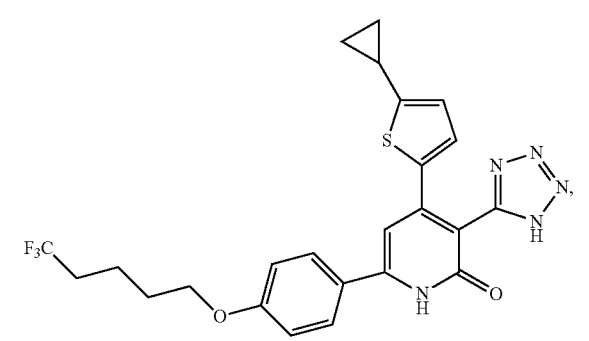
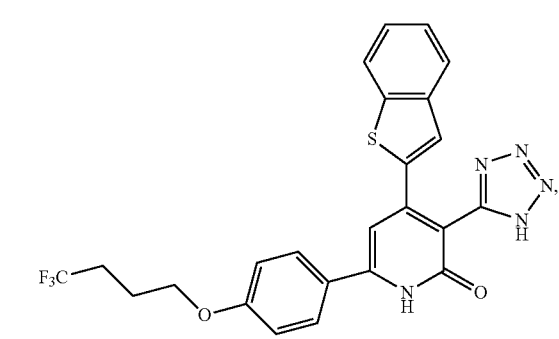
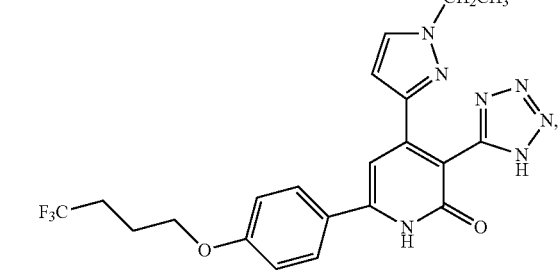
174
-continued
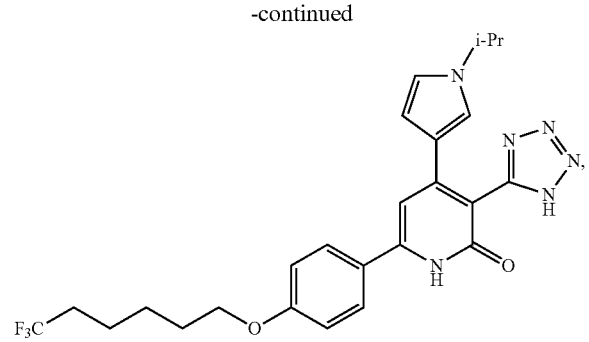
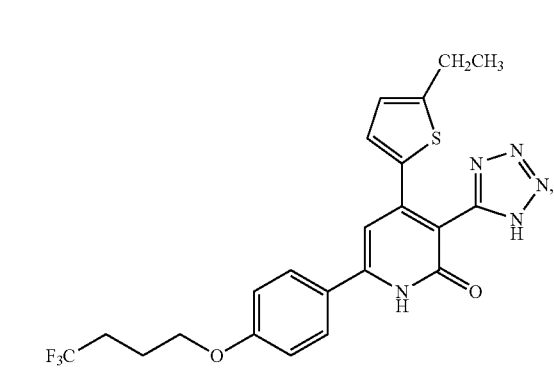
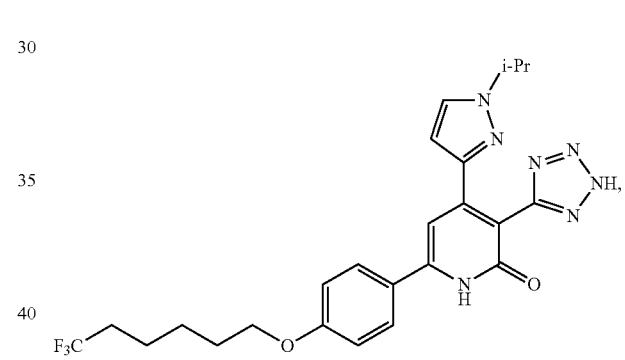
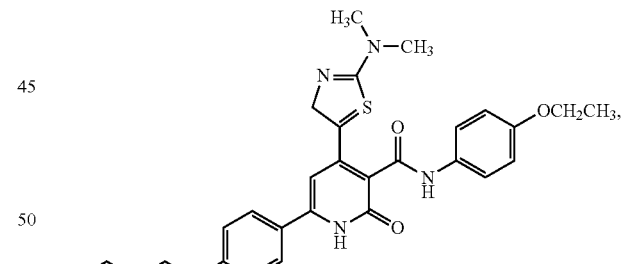
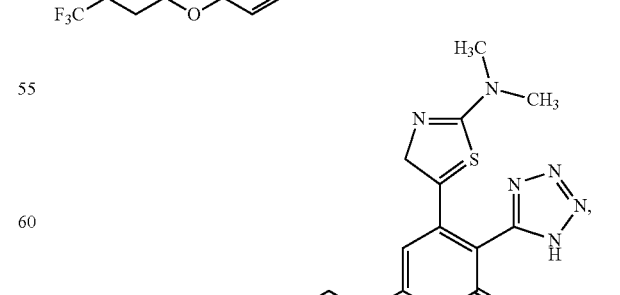
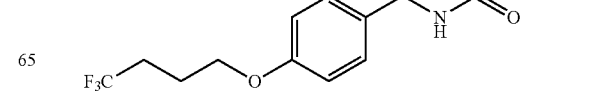

-continued
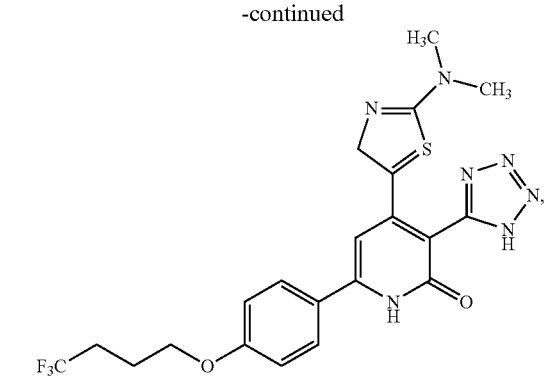
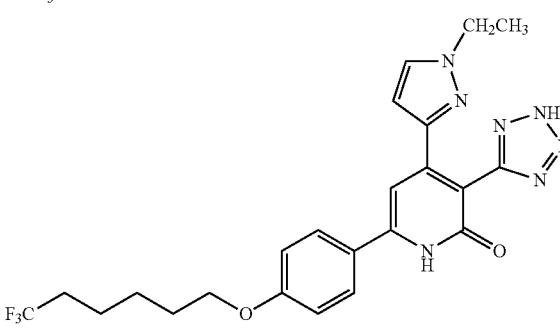
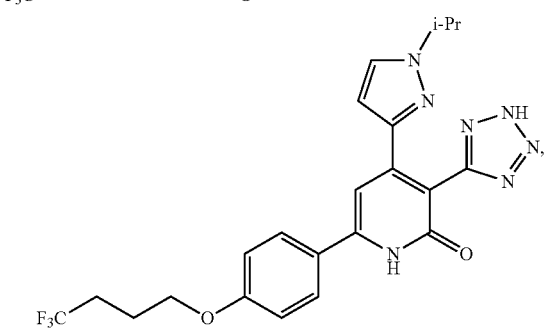
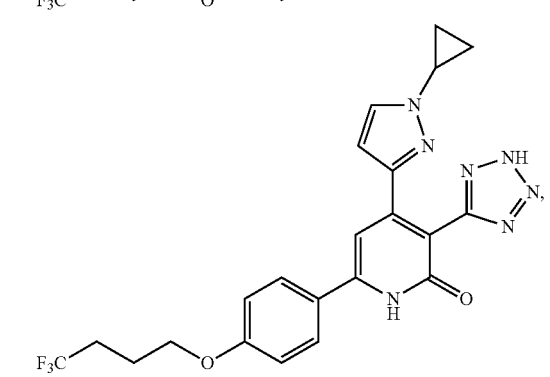
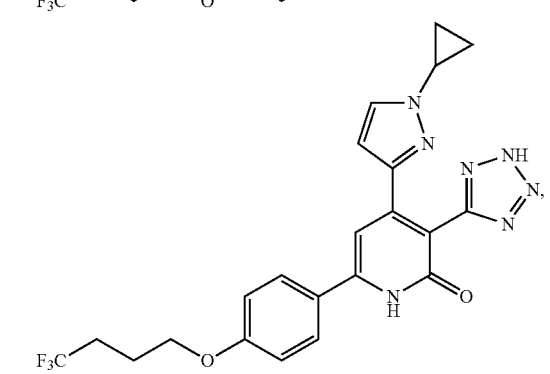
-continued
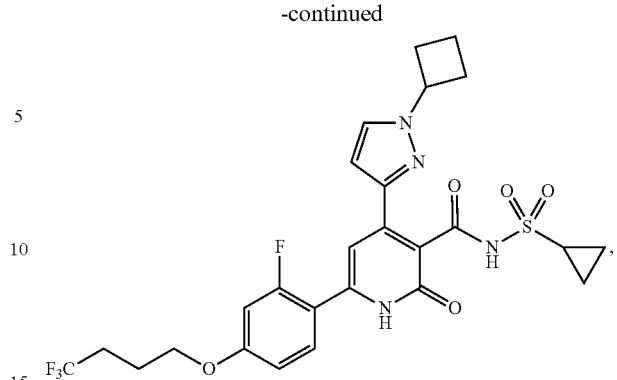
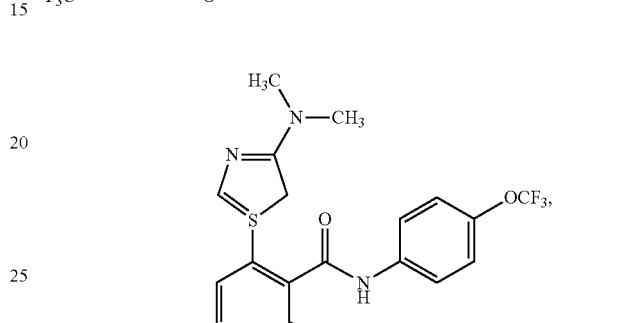
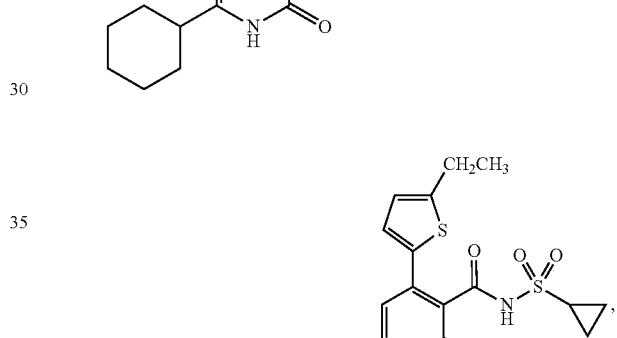
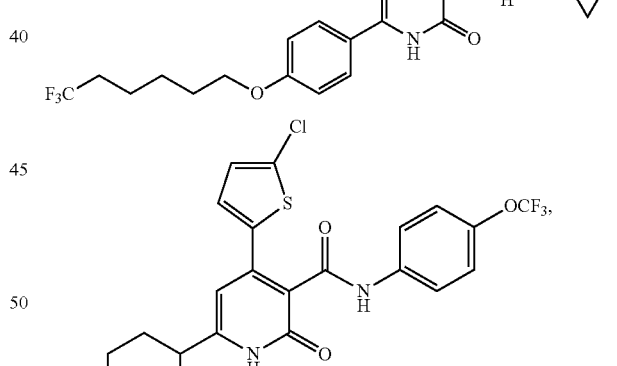
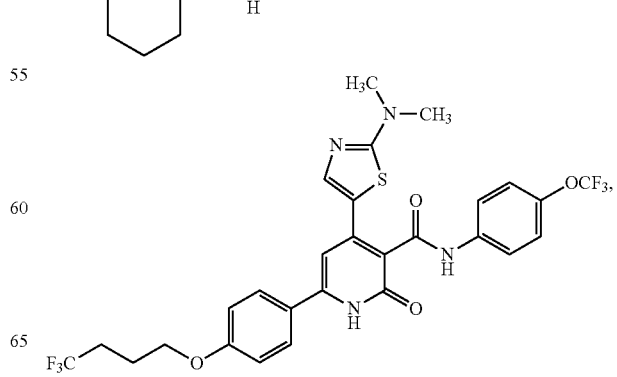

177
-continued
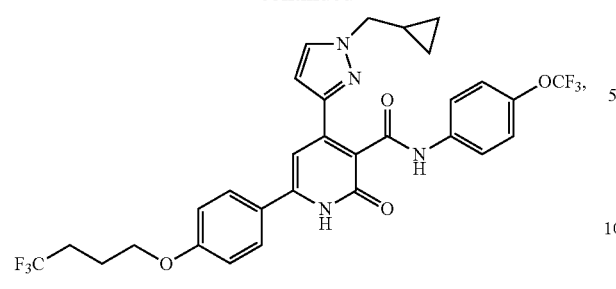
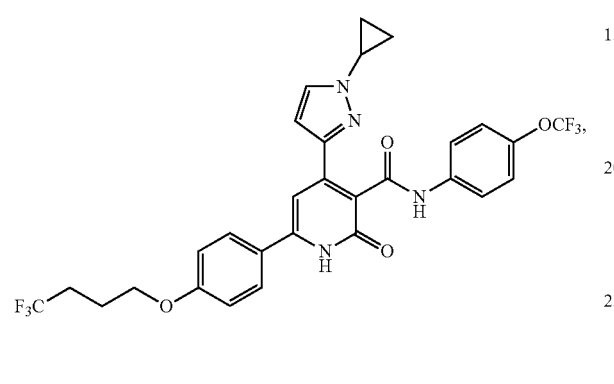
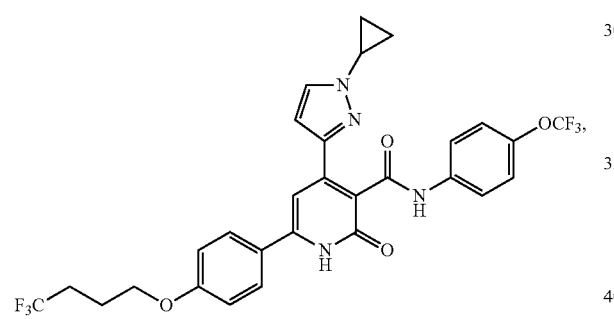
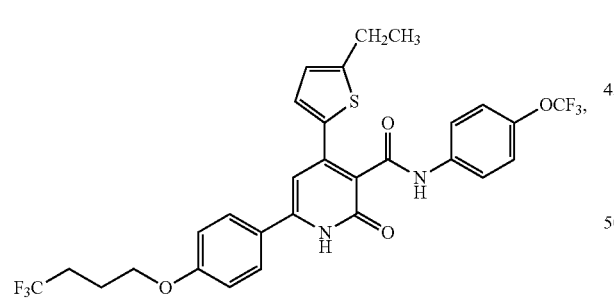
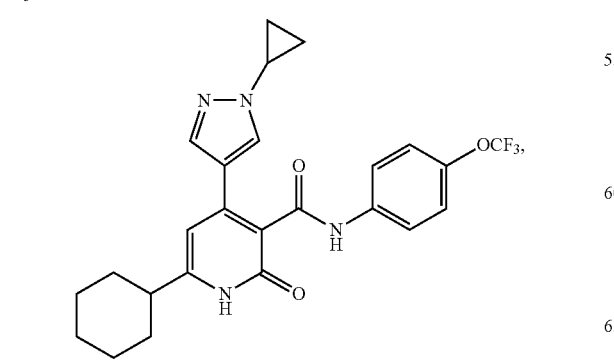
178
-continued
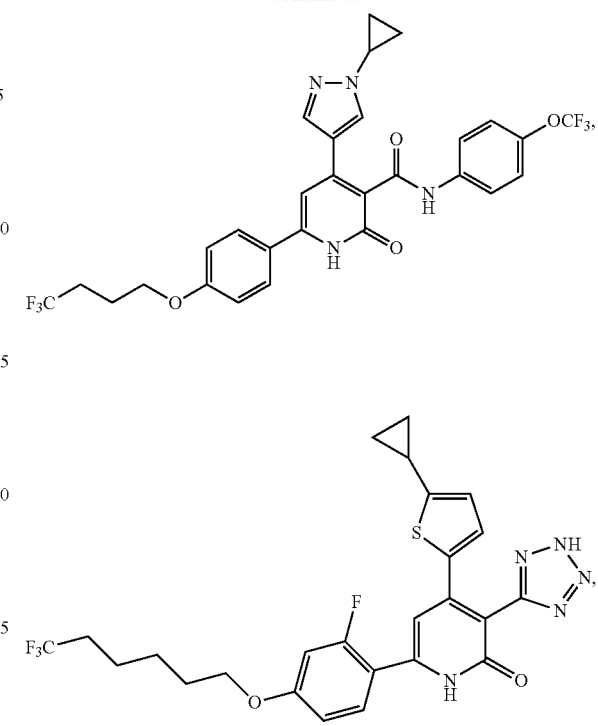
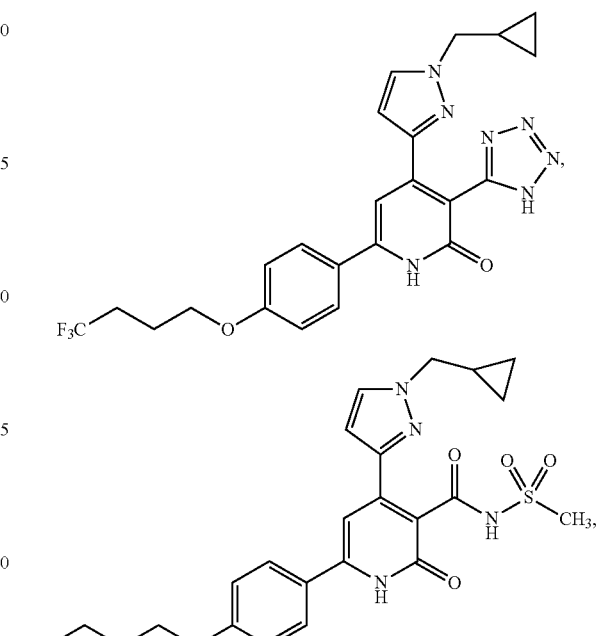
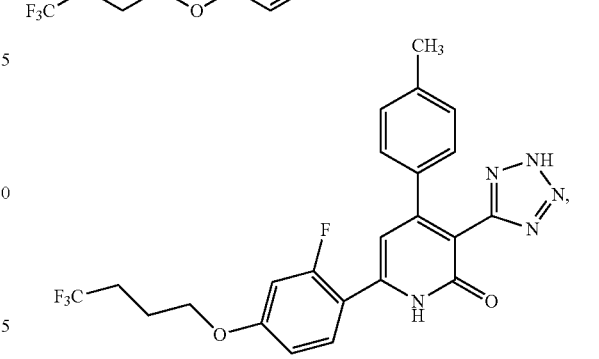

179
-continued
180
-continued
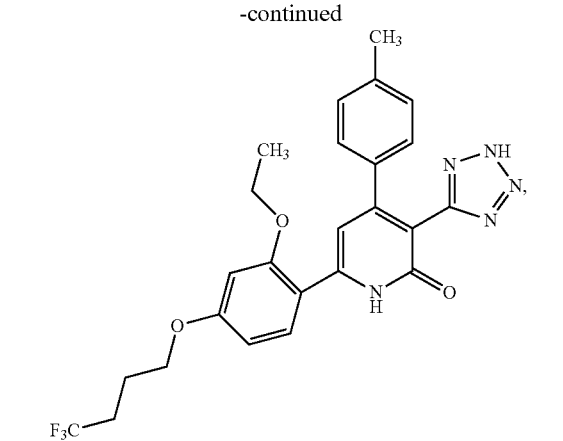
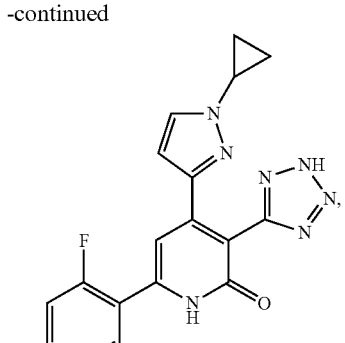
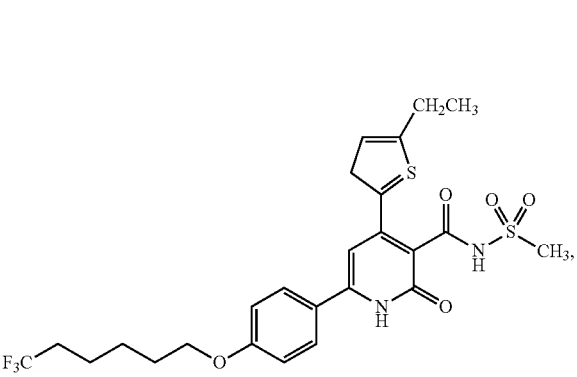
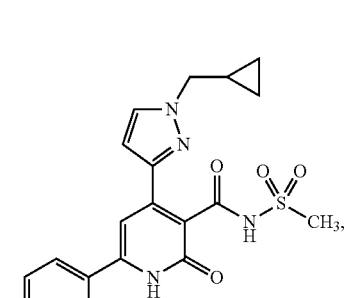
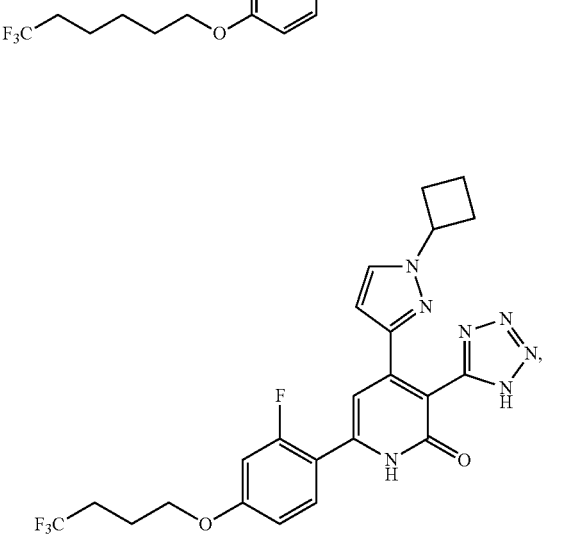
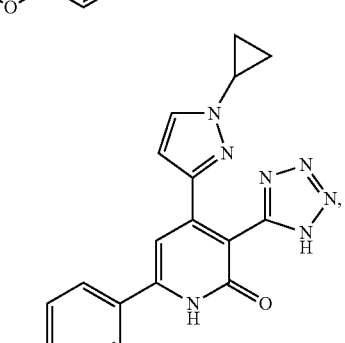
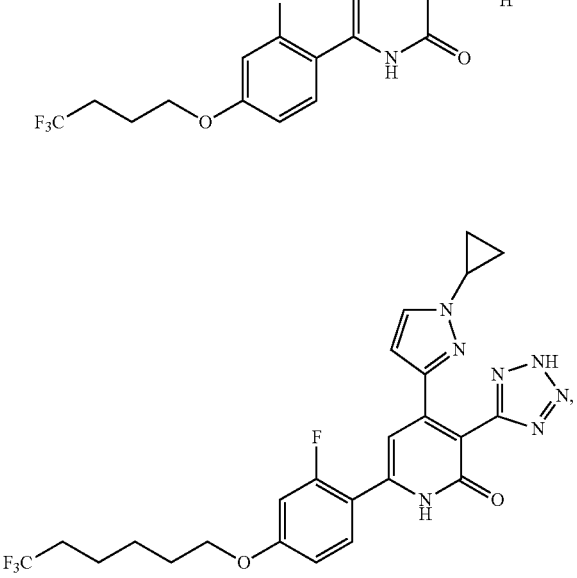
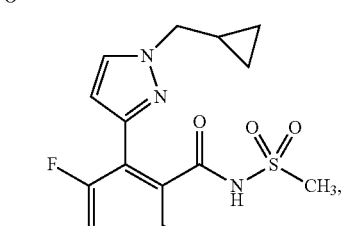

181
-continued
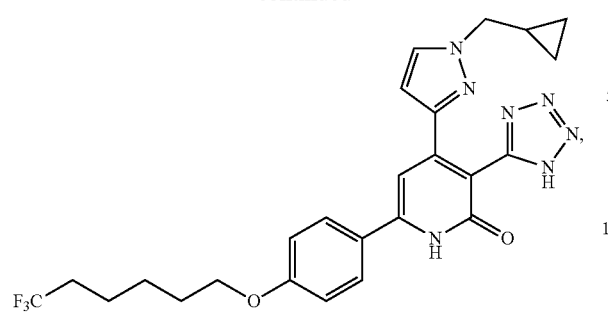
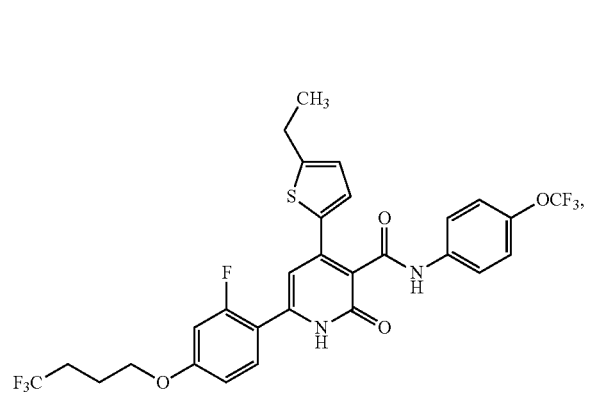
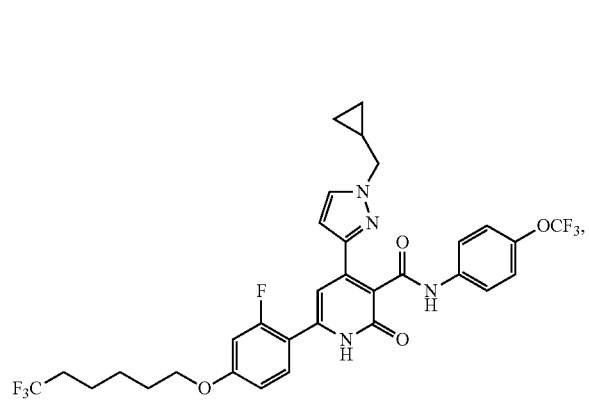
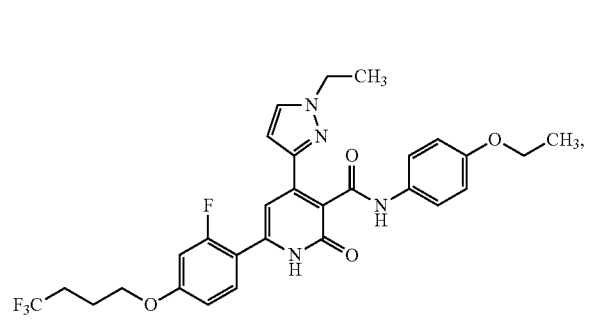
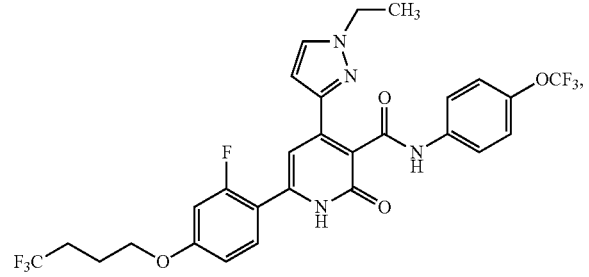
182
-continued
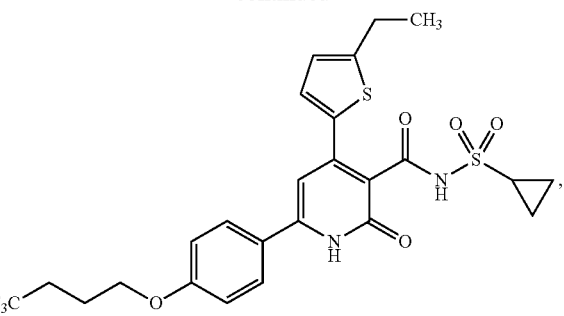
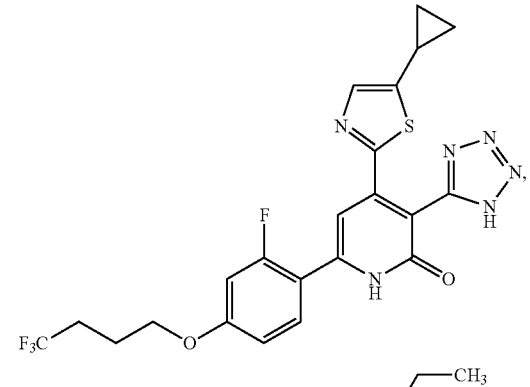
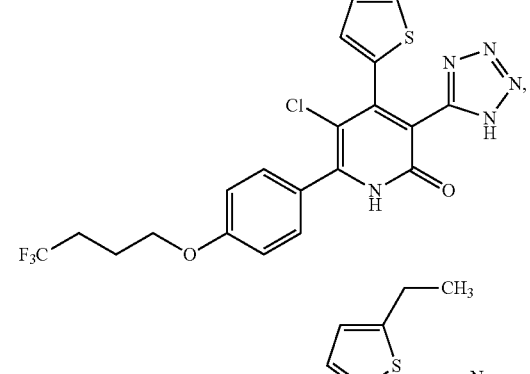
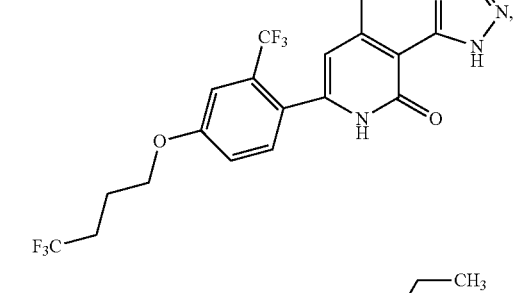
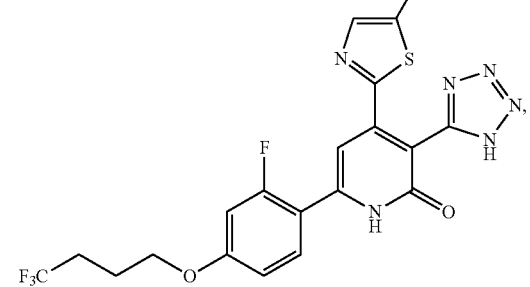

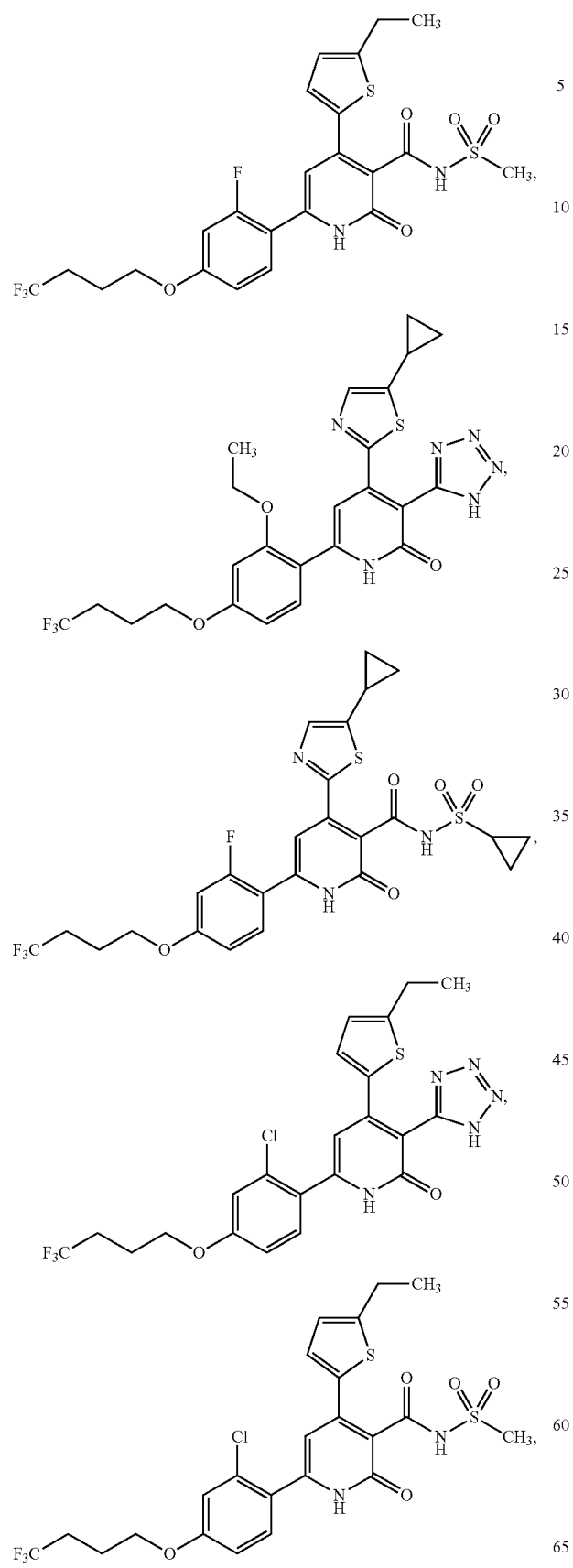
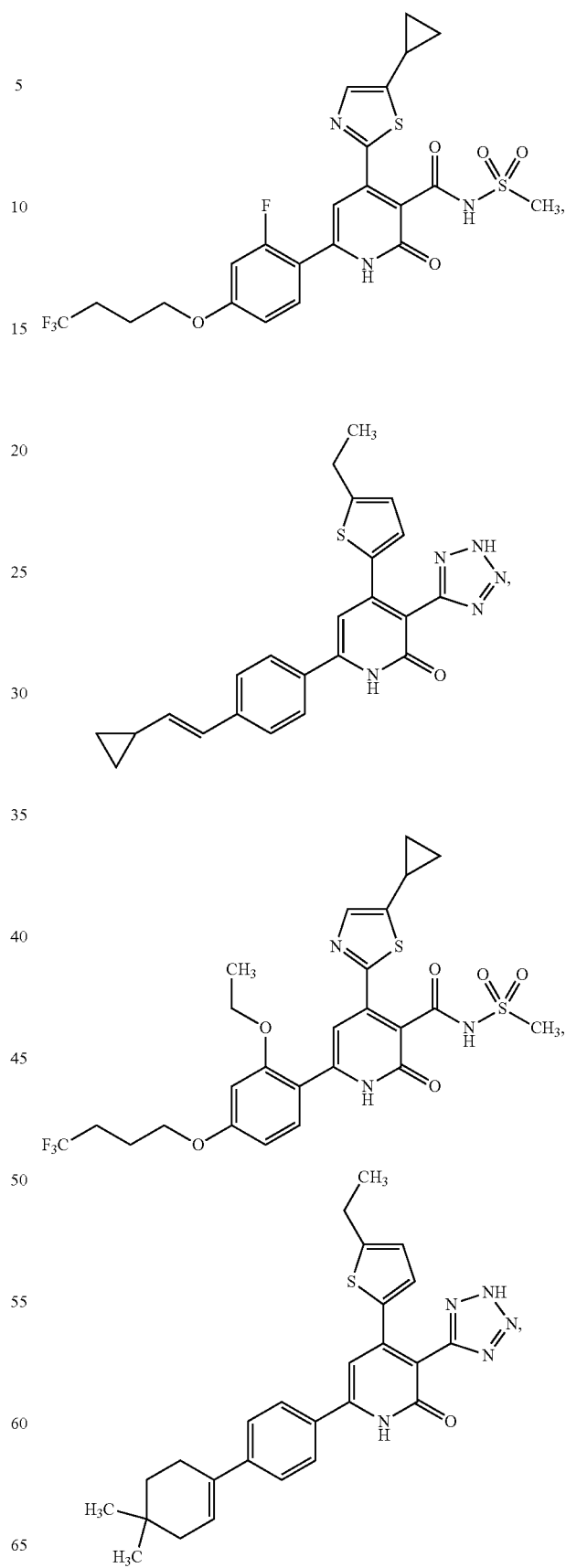

-continued
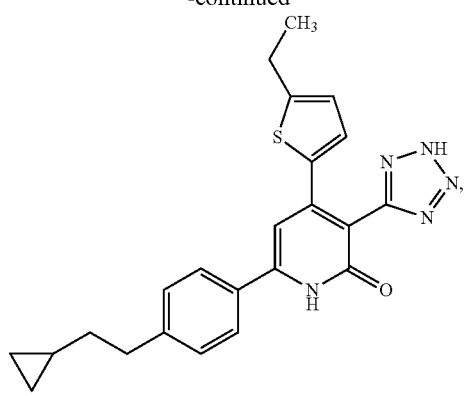
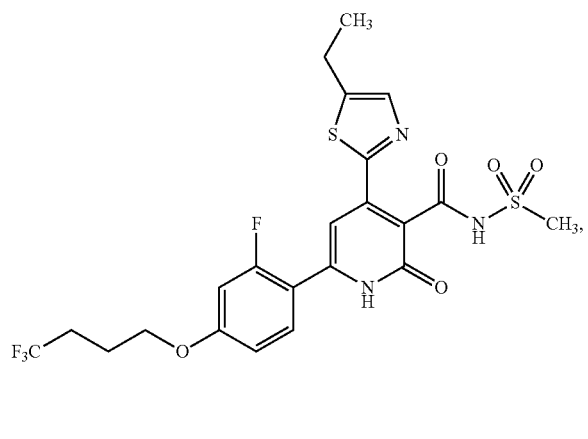
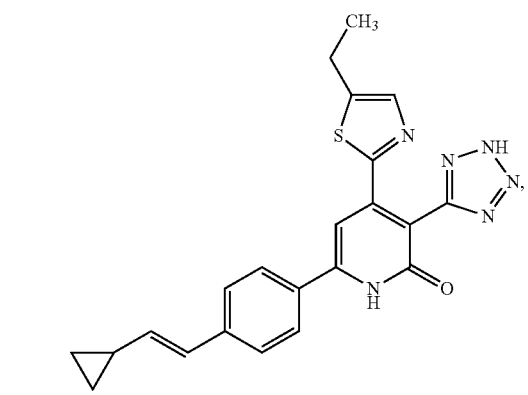
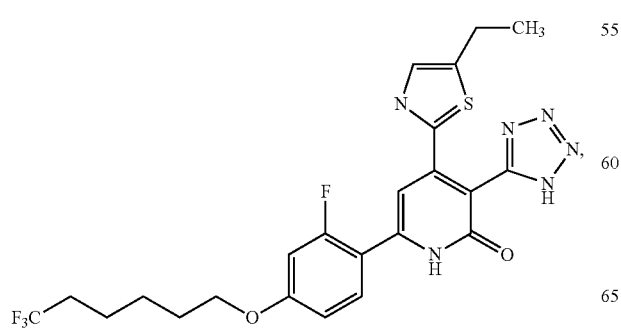
-continued
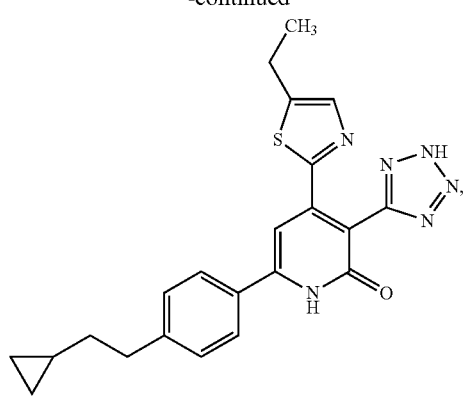
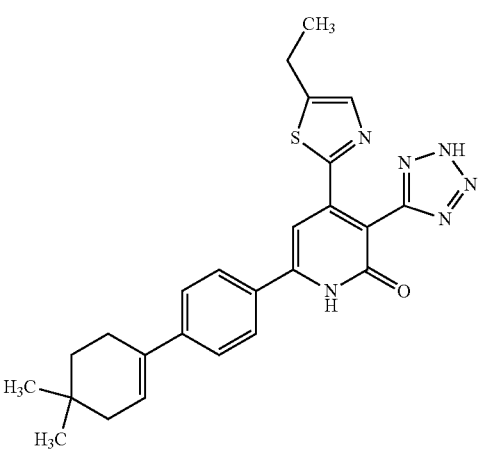
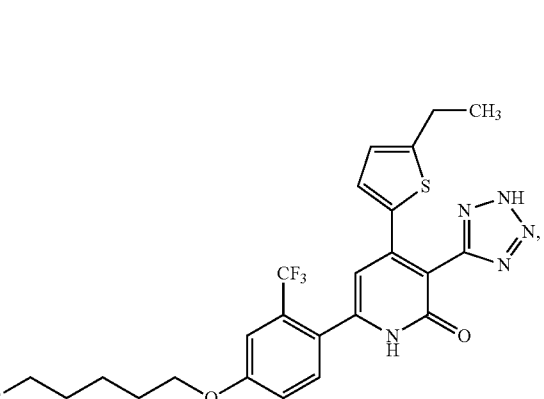
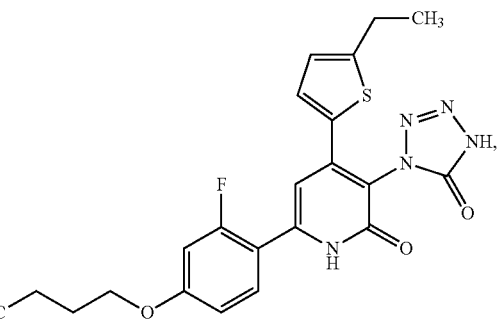

187
-continued
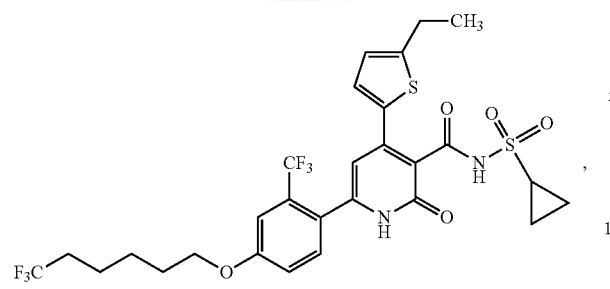
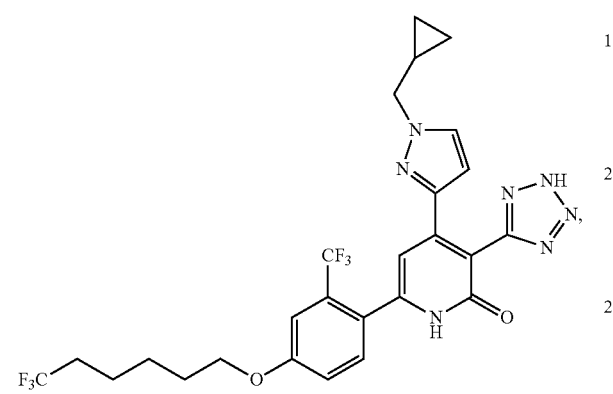
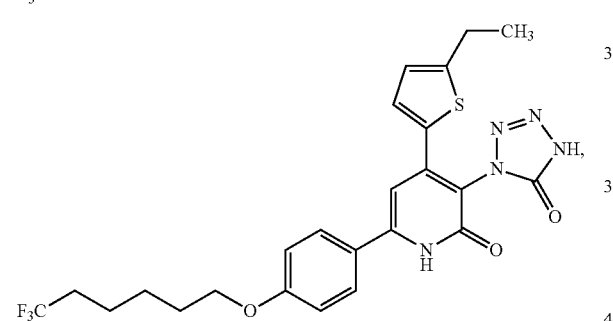
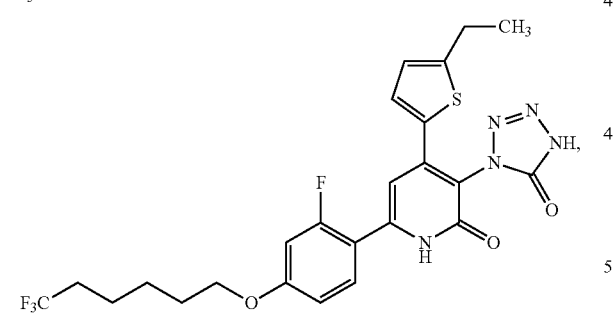
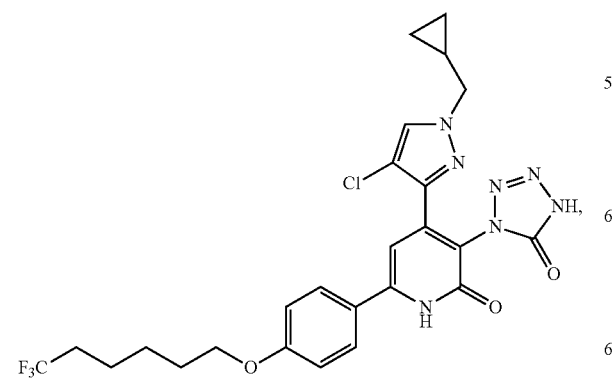
188
-continued
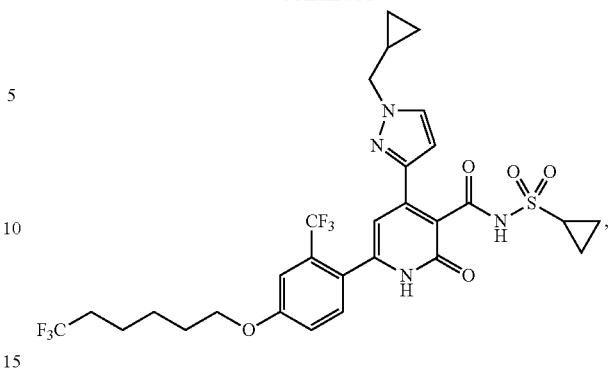
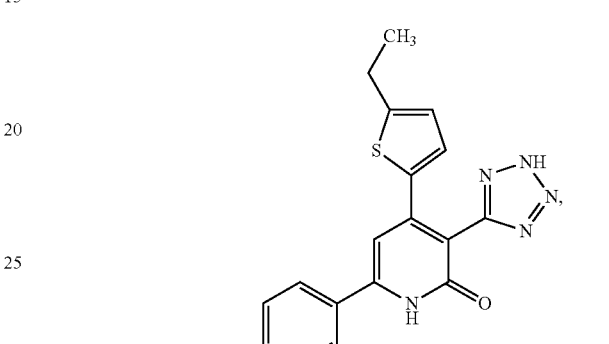
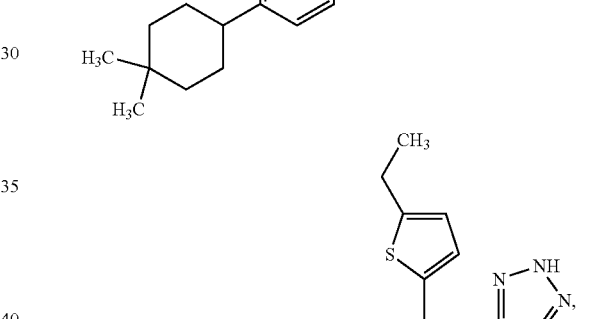
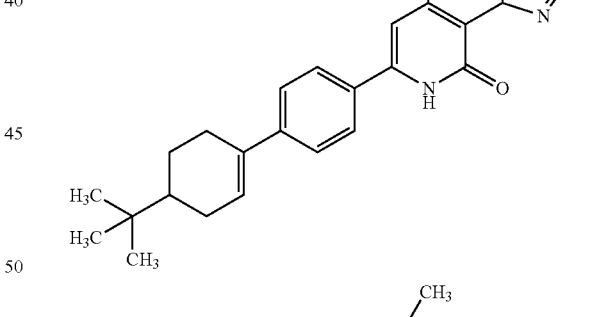
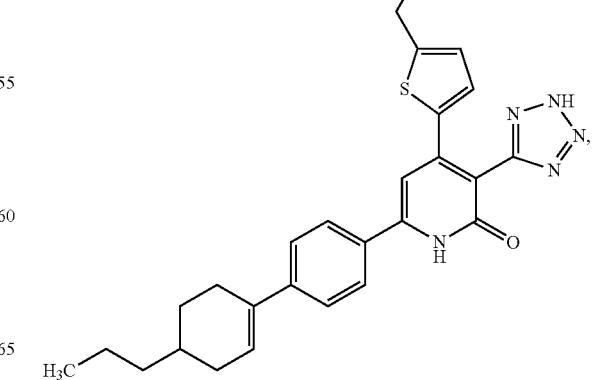

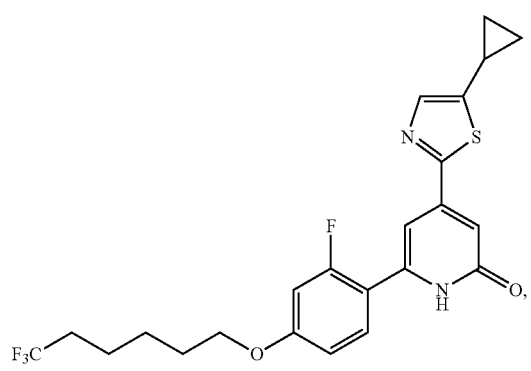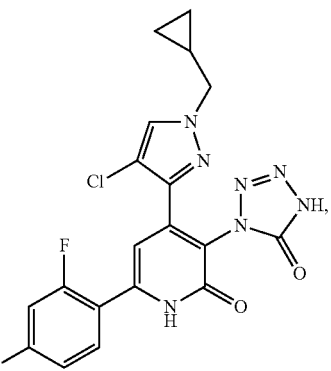

-continued

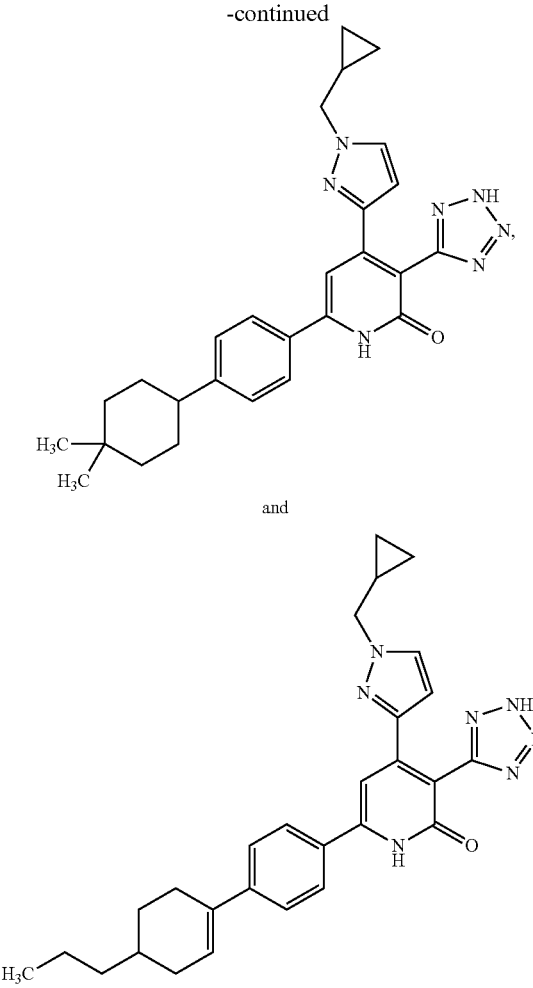

or a stereoisomer, a tautomer, or a pharmaceutically acceptable salt thereof.

8. A pharmaceutical composition, comprising a pharmaceutically acceptable carrier and a compound of claim 1, optionally in combination with one or more additional therapeutic agents wherein the additional therapeutic agent is selected from: "anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

9. The pharmaceutical composition according to claim 8, further comprising one or more additional therapeutic agents selected from: a dipeptidyl peptidase-IV inhibitor, a sodium-glucose transporter-2 inhibitor and a 11b-HSD-1 inhibitor.

10. A method for the treatment of diabetes, hyperglycemia, impaired glucose tolerance, gestational diabetes, insulin resistance, hyperinsulinemia, nonalcoholic fatty liver disease (NAFLD), nonalcoholic steatohepatitis (NASH), delayed wound healing, Metabolic Syndrome, obesity, dyslipidemia, hyperlipidemia, hypertriglyceridemia, or glaucoma, comprising administering to a patient in need of such treatment a therapeutically effective amount of a compound according to claim 1.

11. A pharmaceutical composition, comprising a pharmaceutically acceptable carrier and a compound of claim 7, optionally in combination with one or more additional therapeutic agents wherein the additional therapeutic agent is selected from: "anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

12. The pharmaceutical composition according to claim 11, further comprising one or more additional therapeutic agents selected from: a dipeptidyl peptidase-IV inhibitor, a sodium-glucose transporter-2 inhibitor and a 11b-HSD-1 inhibitor.

13. A method for the treatment of diabetes, hyperglycemia, impaired glucose tolerance, gestational diabetes, insulin resistance, hyperinsulinemia, nonalcoholic fatty liver disease (NAFLD), nonalcoholic steatohepatitis (NASH), delayed wound healing, Metabolic Syndrome, obesity, dyslipidemia, hyperlipidemia, hypertriglyceridemia, or glaucoma, comprising administering to a patient in need of such treatment a therapeutically effective amount of a compound according to claim 7.

14. A pharmaceutical composition, comprising a pharmaceutically acceptable carrier and a compound of claim 4, optionally in combination with one or more additional therapeutic agents wherein the additional therapeutic agent is selected from: "anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

15. The pharmaceutical composition according to claim 14, further comprising one or more additional therapeutic agents selected from: a dipeptidyl peptidase-IV inhibitor, a sodium-glucose transporter-2 inhibitor and a 11b-HSD-1 inhibitor.

16. A method for the treatment of diabetes, hyperglycemia, impaired glucose tolerance, gestational diabetes, insulin resistance, hyperinsulinemia, nonalcoholic fatty liver disease (NAFLD), nonalcoholic steatohepatitis (NASH), delayed wound healing, Metabolic Syndrome, obesity, dyslipidemia, hyperlipidemia, hypertriglyceridemia, or glaucoma, comprising administering to a patient in need of such treatment a therapeutically effective amount of a compound according to claim 4.

* * * * *

UNITED STATES PATENT AND TRADEMARK OFFICE
CERTIFICATE OF CORRECTION

PATENT NO. : 9,974,778 B2
APPLICATION NO. : 15/316853
DATED : May 22, 2018
INVENTOR(S) : Devasthale et al.

Page 1 of 5

It is certified that error appears in the above-identified patent and that said Letters Patent is hereby corrected as shown below:

On the Title Page

Item (*), after "0 days." delete "days.".

In the Specification

Column 167
Line 59, after "NR$^e$" insert -- , --.

Column 168
Line 29, after "NR$^e$" insert -- , --; and
Line 37, after "NR$^e$" insert -- , --.

Column 174
Line 43-53,

" 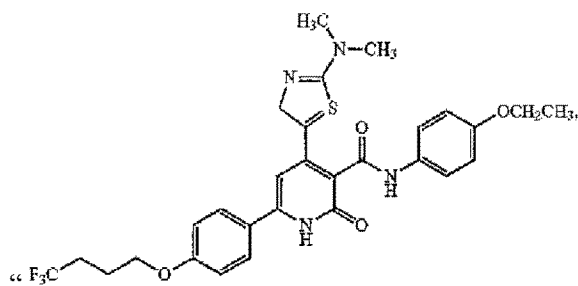 " should read

Signed and Sealed this
Twenty-eighth Day of August, 2018

Andrei Iancu
*Director of the United States Patent and Trademark Office*

CERTIFICATE OF CORRECTION (continued)
U.S. Pat. No. 9,974,778 B2

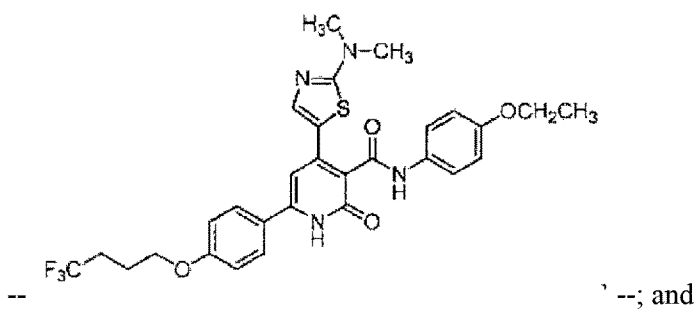

-- ' --; and

Line 53-66,

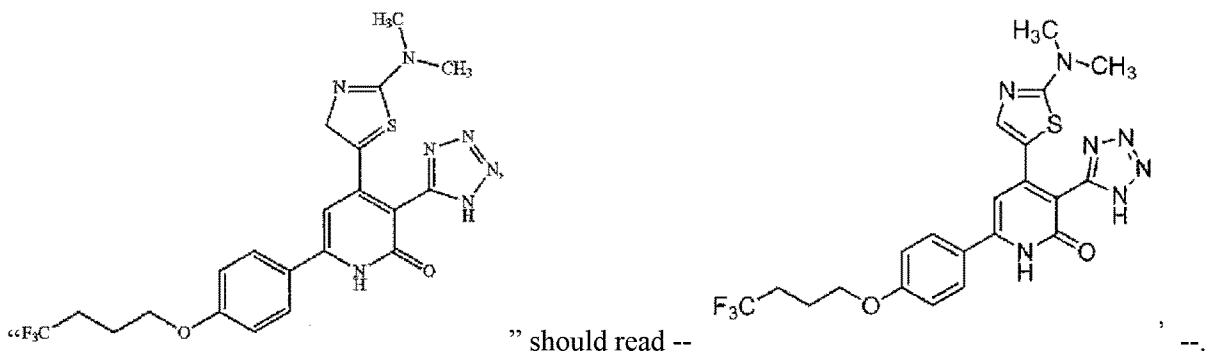

" should read --

Column 175

Line 1-14, delete the duplicate " 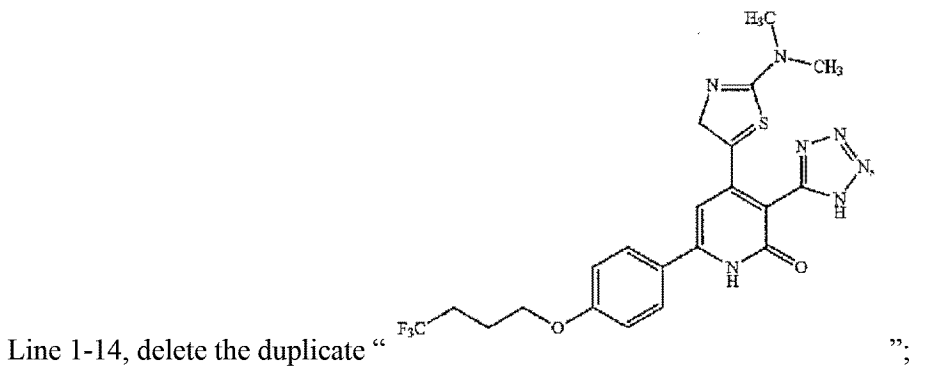 ";

Line 26-39,

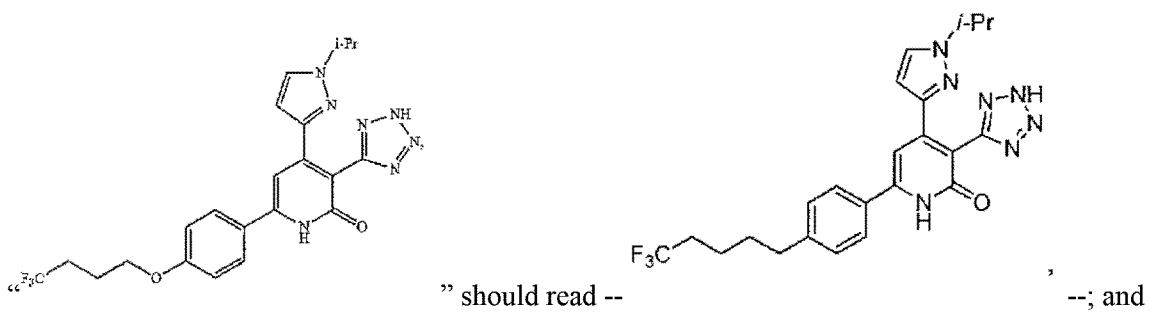

" should read -- --; and

CERTIFICATE OF CORRECTION (continued)
U.S. Pat. No. 9,974,778 B2

Line 53-65, delete the duplicate " 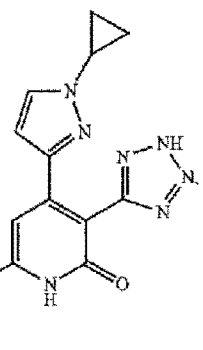 ".

Column 176
Line 17-30,

" 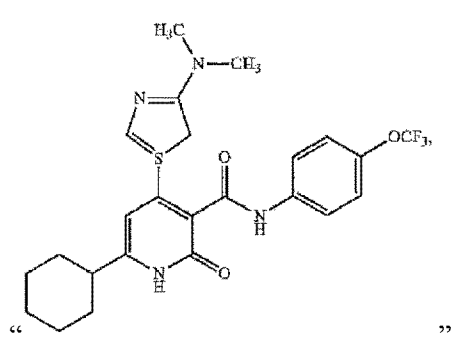 " should read -- 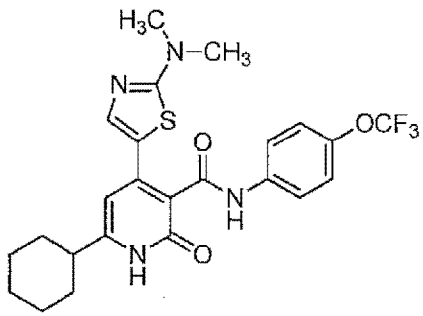 --.

Column 177

Line 29-41, delete the duplicate " 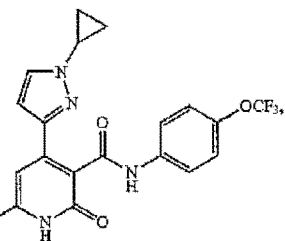 ".

Column 178

Line 55-66, delete " 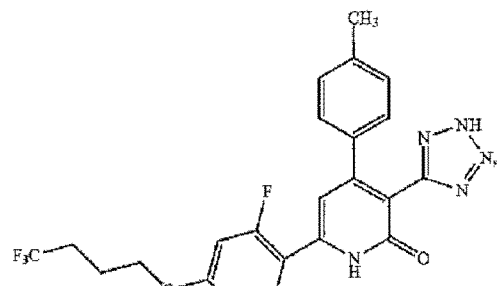 ".

CERTIFICATE OF CORRECTION (continued)

Column 179

Line 1-17, delete " 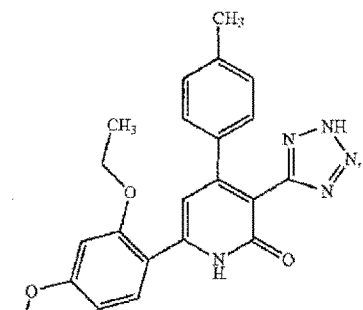 "; and

Line 36-49, " 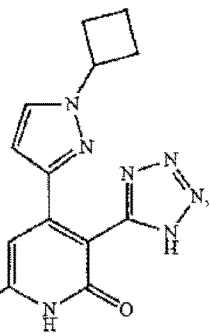 " should read " 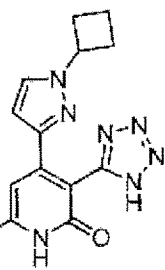 ".

Column 180

Line 1-15, delete the duplicate " 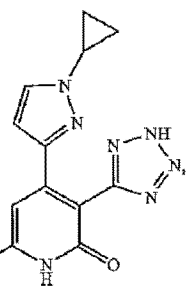 ".

CERTIFICATE OF CORRECTION (continued)
U.S. Pat. No. 9,974,778 B2

Column 182
Line 40-54,

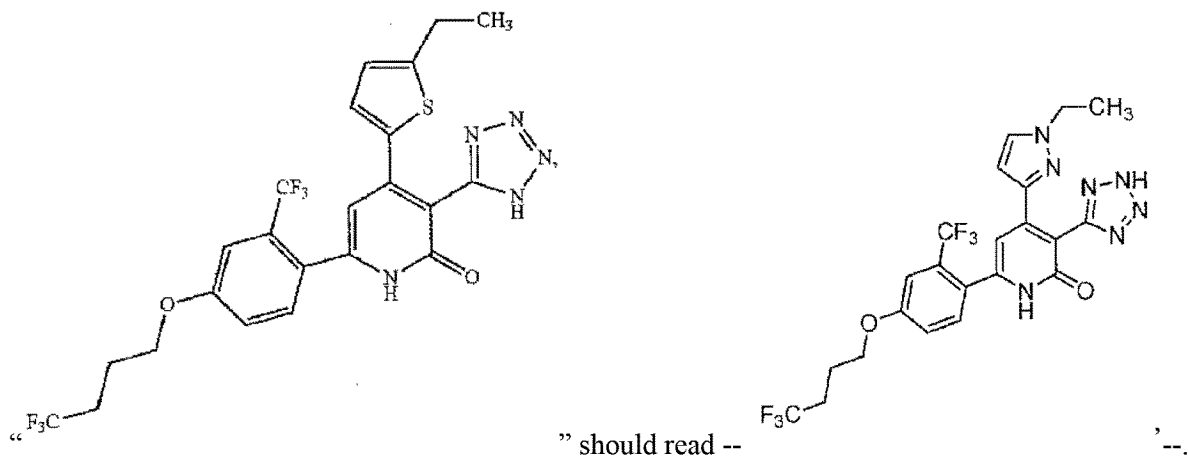

Column 191
Line 46, ""anti-" should read -- anti- --.

Column 192
Line 10, ""anti-" should read -- anti- --; and
Line 38, ""anti-" should read -- anti- --.